United States Patent
Tentori et al.

(10) Patent No.: US 12,249,085 B2
(45) Date of Patent: Mar. 11, 2025

(54) SAMPLE HANDLING APPARATUS AND IMAGE REGISTRATION METHODS

(71) Applicant: 10x Genomics, Inc., Pleasanton, CA (US)

(72) Inventors: Augusto Manuel Tentori, Dublin, CA (US); Hanyoup Kim, Foster City, CA (US); Siyuan Xing, Newark, CA (US); Felice Alessio Bava, Pleasanton, CA (US); Rajiv Bharadwaj, Pleasanton, CA (US); Cedric Uytingco, Pleasanton, CA (US); Erica Graziosa, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 18/185,599

(22) Filed: Mar. 17, 2023

(65) Prior Publication Data

US 2023/0267625 A1    Aug. 24, 2023

Related U.S. Application Data

(63) Continuation of application No. PCT/US2021/050929, filed on Sep. 17, 2021.
(Continued)

(51) Int. Cl.
*G06V 10/24* (2022.01)
*G06T 7/33* (2017.01)
(Continued)

(52) U.S. Cl.
CPC .............. *G06T 7/33* (2017.01); *G06V 10/25* (2022.01); *G01N 1/30* (2013.01);
(Continued)

(58) Field of Classification Search
CPC . G06T 2207/10056; G06T 2207/30024; G06T 7/11; G06T 7/33;
(Continued)

(56) References Cited

U.S. PATENT DOCUMENTS

| 4,514,388 A | 4/1985 | Psaledakis |
| 4,557,903 A | 12/1985 | McCormick |

(Continued)

FOREIGN PATENT DOCUMENTS

| CA | 3054046 | 3/2020 |
| CN | 1425133 | 6/2003 |

(Continued)

OTHER PUBLICATIONS

Wong et al., "ST Spot Detector: A Web-Based Application for Automatic Spot and Tissue Detection for Spatial Transcriptomics Image Datasets", Bioinformatics, Jun. 1, 2018, 34(11):1966-1968.

(Continued)

*Primary Examiner* — Ian L Lemieux
(74) *Attorney, Agent, or Firm* — Fish & Richardson P.C.

(57) ABSTRACT

A method for aligning a sample to an array is provided. An image of sample image of a sample can be received by a data processor. The sample image having a first resolution. An array image including an overlay of an array with the sample and an array fiducial can be received by the data processor. The array image having a second resolution lower than the first resolution of the sample image. The sample image can be registered to the array image by aligning the sample image and the array image. An aligned image can be generated based on the registering. The aligned image can include an overlay of the sample image with the array. The aligned image can be provided by the data processor. A method for detecting fiducials associated with an array is (Continued)

provided. Systems and non-transitory computer readable mediums performing the method are also provided.

27 Claims, 82 Drawing Sheets

Related U.S. Application Data

(60) Provisional application No. 63/155,173, filed on Mar. 1, 2021, provisional application No. 63/080,547, filed on Sep. 18, 2020.

(51) Int. Cl.
  *G06V 10/25* (2022.01)
  *G01N 1/30* (2006.01)

(52) U.S. Cl.
  CPC .............. *G06T 2207/10056* (2013.01); *G06T 2207/10064* (2013.01); *G06T 2207/20132* (2013.01); *G06T 2207/30024* (2013.01); *G06T 2207/30072* (2013.01); *G06T 2207/30204* (2013.01)

(58) Field of Classification Search
  CPC . G06T 2207/10064; G06T 2207/30072; G06T 2207/30204; G06T 7/136; G06T 3/0075; G06T 3/608; G06T 7/0014; G06T 7/0012; G06T 7/194; G06T 2207/20021; G06T 2207/20081; G06T 2207/20092; G06T 2207/20104; G06T 2207/20132; G06T 2207/30004; G06T 7/73; G06T 11/60; G06T 7/37; G06T 1/0007; G06T 2207/20036; G06T 2207/20076; G06T 7/13; G06T 7/155; G06V 20/695; G06V 10/945; G06V 20/698; C12Q 1/6837; C12Q 2565/514; C12Q 2565/501
  See application file for complete search history.

(56) References Cited

U.S. PATENT DOCUMENTS

| | | |
|---|---|---|
| 4,574,729 A | 3/1986 | Wells |
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 5,002,882 A | 3/1991 | Lunnen |
| 5,061,049 A | 10/1991 | Hornbeck |
| 5,130,238 A | 7/1992 | Malek |
| 5,183,053 A | 2/1993 | Yeh et al. |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,559,032 A | 9/1996 | Pomeroy |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,716,825 A | 2/1998 | Hancock et al. |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 6,013,440 A | 1/2000 | Lipshutz |
| 6,027,889 A | 2/2000 | Barany et al. |
| 6,060,240 A | 5/2000 | Kamb et al. |
| 6,083,761 A | 7/2000 | Kedar et al. |
| 6,130,073 A | 10/2000 | Eggerding |
| 6,136,592 A | 10/2000 | Leighton |
| 6,143,496 A | 11/2000 | Brown |
| 6,153,389 A | 11/2000 | Haarer |
| 6,157,432 A | 12/2000 | Helbing |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,221,654 B1 | 4/2001 | Quake |
| 6,258,568 B1 | 7/2001 | Nyren |
| 6,266,459 B1 | 7/2001 | Walt |
| 6,274,320 B1 | 8/2001 | Rothberg |
| 6,291,180 B1 | 9/2001 | Chu |
| 6,300,063 B1 | 10/2001 | Lipshutz et al. |
| 6,309,824 B1 | 10/2001 | Drmanac |
| 6,337,472 B1 | 1/2002 | Garner et al. |
| 6,344,316 B1 | 2/2002 | Lockhart |
| 6,348,990 B1 | 2/2002 | Igasaki et al. |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,485,982 B1 | 11/2002 | Charlton |
| 6,503,713 B1 | 1/2003 | Rana |
| 6,506,561 B1 | 1/2003 | Cheval et al. |
| 6,544,732 B1 | 4/2003 | Chee |
| 6,544,790 B1 | 4/2003 | Sabatini |
| 6,565,727 B1 | 5/2003 | Shenderov |
| 6,620,584 B1 | 9/2003 | Chee |
| 6,632,641 B1 | 10/2003 | Brennan |
| 6,673,620 B1 | 1/2004 | Loeffler |
| 6,737,236 B1 | 5/2004 | Pieken et al. |
| 6,770,441 B2 | 8/2004 | Dickinson |
| 6,773,566 B2 | 8/2004 | Shenderov |
| 6,773,886 B2 | 8/2004 | Kaufman |
| 6,787,308 B2 | 9/2004 | Balasubramanian |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,859,570 B2 | 2/2005 | Walt |
| 6,864,052 B1 | 3/2005 | Drmanac |
| 6,897,023 B2 | 5/2005 | Fu |
| 6,911,132 B2 | 6/2005 | Pamula |
| 6,911,345 B2 | 6/2005 | Quake |
| 6,913,921 B2 | 7/2005 | Fischer |
| 6,942,968 B1 | 9/2005 | Dickinson et al. |
| 6,969,488 B2 | 11/2005 | Bridgham |
| 6,977,033 B2 | 12/2005 | Becker |
| 7,001,792 B2 | 2/2006 | Sauer et al. |
| 7,052,244 B2 | 5/2006 | Fouillet |
| 7,057,026 B2 | 6/2006 | Barnes |
| 7,098,041 B2 | 8/2006 | Kaylor et al. |
| 7,115,400 B1 | 10/2006 | Adessi |
| 7,118,883 B2 | 10/2006 | Inoue |
| 7,163,612 B2 | 1/2007 | Sterling |
| 7,166,431 B2 | 1/2007 | Chee et al. |
| 7,211,414 B2 | 5/2007 | Hardin |
| 7,223,371 B2 | 5/2007 | Hayenga et al. |
| 7,244,559 B2 | 7/2007 | Rothberg |
| 7,255,994 B2 | 8/2007 | Lao |
| 7,258,976 B2 | 8/2007 | Mitsuhashi |
| 7,264,929 B2 | 9/2007 | Rothberg |
| 7,297,518 B2 | 11/2007 | Quake |
| 7,328,979 B2 | 2/2008 | Decre |
| 7,329,492 B2 | 2/2008 | Hardin |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |

(56) References Cited

U.S. PATENT DOCUMENTS

| | | | |
|---|---|---|---|
| 7,407,757 | B2 | 8/2008 | Brenner |
| 7,456,012 | B2 | 11/2008 | Ryttsen et al. |
| 7,462,449 | B2 | 12/2008 | Quake |
| 7,501,245 | B2 | 3/2009 | Quake |
| 7,537,897 | B2 | 5/2009 | Brenner |
| 7,547,380 | B2 | 6/2009 | Velev |
| 7,561,336 | B2 | 7/2009 | Osaka et al. |
| 7,563,576 | B2 | 7/2009 | Chee |
| 7,582,420 | B2 | 9/2009 | Oliphant et al. |
| 7,595,883 | B1 | 9/2009 | El Gamal |
| 7,601,492 | B2 | 10/2009 | Fu et al. |
| 7,601,498 | B2 | 10/2009 | Mao |
| 7,635,566 | B2 | 12/2009 | Brenner |
| 7,641,779 | B2 | 1/2010 | Becker |
| 7,674,752 | B2 | 3/2010 | He |
| 7,709,198 | B2 | 5/2010 | Luo et al. |
| 7,776,567 | B2 | 8/2010 | Mao |
| 7,785,869 | B2 | 8/2010 | Belgrader et al. |
| 7,803,943 | B2 | 9/2010 | Mao |
| 7,858,321 | B2 | 12/2010 | Glezer |
| 7,910,304 | B2 | 3/2011 | Drmanac |
| 7,955,794 | B2 | 6/2011 | Shen et al. |
| 7,960,119 | B2 | 6/2011 | Chee |
| 8,003,354 | B2 | 8/2011 | Shen et al. |
| 8,131,476 | B2 * | 3/2012 | Cline .................. G01N 1/30 435/7.1 |
| 8,148,068 | B2 | 4/2012 | Brenner |
| 8,206,917 | B2 | 6/2012 | Chee |
| 8,278,034 | B2 | 10/2012 | Muraca |
| 8,288,103 | B2 | 10/2012 | Oliphant |
| 8,330,087 | B2 | 12/2012 | Domenicali |
| 8,460,865 | B2 | 6/2013 | Chee |
| 8,481,257 | B2 | 7/2013 | Van Eijk |
| 8,603,743 | B2 | 12/2013 | Liu et al. |
| 8,604,182 | B2 | 12/2013 | Luo et al. |
| 8,637,242 | B2 | 1/2014 | Shen |
| 8,778,849 | B2 | 7/2014 | Bowen |
| 8,815,512 | B2 | 8/2014 | Van Eijk |
| 8,835,358 | B2 | 9/2014 | Fodor |
| 8,900,529 | B2 | 12/2014 | Shaikh et al. |
| 8,911,945 | B2 | 12/2014 | Van Eijk |
| 8,951,726 | B2 | 2/2015 | Luo et al. |
| 8,951,781 | B2 | 2/2015 | Reed |
| 9,062,348 | B1 | 6/2015 | Van Eijk |
| 9,194,001 | B2 | 11/2015 | Brenner |
| 9,201,063 | B2 | 12/2015 | Sood et al. |
| 9,290,808 | B2 | 3/2016 | Fodor |
| 9,290,809 | B2 | 3/2016 | Fodor |
| 9,328,383 | B2 | 5/2016 | Van Eijk |
| 9,334,536 | B2 | 5/2016 | Van Eijk |
| 9,371,598 | B2 | 6/2016 | Chee |
| 9,416,409 | B2 | 8/2016 | Hayden |
| 9,506,061 | B2 | 11/2016 | Brown et al. |
| 9,557,330 | B2 | 1/2017 | Siciliano et al. |
| 9,582,877 | B2 | 2/2017 | Fu |
| 9,593,365 | B2 | 3/2017 | Frisen et al. |
| 9,644,204 | B2 | 5/2017 | Hindson et al. |
| 9,671,344 | B2 * | 6/2017 | Staker ................ G01N 21/6452 |
| 9,694,361 | B2 | 7/2017 | Bharadwaj |
| 9,702,004 | B2 | 7/2017 | Van Eijk |
| 9,727,810 | B2 | 8/2017 | Fodor et al. |
| 9,777,324 | B2 | 10/2017 | Van Eijk |
| 9,783,841 | B2 | 10/2017 | Nolan et al. |
| 9,834,814 | B2 | 12/2017 | Peter et al. |
| 9,850,536 | B2 | 12/2017 | Oliphant et al. |
| 9,868,979 | B2 | 1/2018 | Chee et al. |
| 9,879,313 | B2 | 1/2018 | Chee et al. |
| 9,975,122 | B2 | 5/2018 | Masquelier et al. |
| 10,002,316 | B2 | 6/2018 | Fodor et al. |
| 10,023,907 | B2 | 7/2018 | Van Eijk |
| 10,030,261 | B2 | 7/2018 | Frisen et al. |
| 10,032,064 | B2 | 7/2018 | Hoyt |
| 10,041,949 | B2 | 8/2018 | Bendall et al. |
| 10,053,723 | B2 | 8/2018 | Hindson et al. |
| 10,059,990 | B2 | 8/2018 | Boyden et al. |
| 10,071,377 | B2 | 9/2018 | Bharadwaj et al. |
| 10,246,700 | B2 | 4/2019 | Dunaway et al. |
| 10,266,888 | B2 | 4/2019 | Daugharthy et al. |
| 10,273,541 | B2 | 4/2019 | Hindson et al. |
| 10,308,982 | B2 | 6/2019 | Chee |
| 10,357,771 | B2 | 7/2019 | Bharadwaj |
| 10,472,669 | B2 | 11/2019 | Chee |
| 10,480,022 | B2 | 11/2019 | Chee |
| 10,480,029 | B2 | 11/2019 | Bent et al. |
| 10,494,667 | B2 | 12/2019 | Chee |
| 10,495,554 | B2 | 12/2019 | Deisseroth et al. |
| 10,550,429 | B2 | 2/2020 | Harada et al. |
| 10,590,244 | B2 | 3/2020 | Delaney et al. |
| 10,662,468 | B2 | 5/2020 | Chee |
| 10,685,210 | B2 * | 6/2020 | Wimberger-Friedl ..................... G06T 7/0014 |
| 10,724,078 | B2 | 7/2020 | Van Driel et al. |
| 10,725,027 | B2 | 7/2020 | Bell |
| 10,774,372 | B2 | 9/2020 | Chee et al. |
| 10,774,374 | B2 | 9/2020 | Frisen et al. |
| 10,787,701 | B2 | 9/2020 | Chee |
| 10,858,702 | B2 | 12/2020 | Lucero et al. |
| 10,913,975 | B2 | 2/2021 | So et al. |
| 10,914,730 | B2 | 2/2021 | Chee et al. |
| 10,927,403 | B2 | 2/2021 | Chee et al. |
| 10,961,566 | B2 | 3/2021 | Chee |
| 11,001,879 | B1 * | 5/2021 | Chee .................. G01N 33/5308 |
| 11,008,607 | B2 | 5/2021 | Chee |
| 11,046,996 | B1 | 6/2021 | Chee et al. |
| 11,067,567 | B2 | 7/2021 | Chee |
| 11,156,603 | B2 | 10/2021 | Chee |
| 11,162,132 | B2 | 11/2021 | Frisen et al. |
| 11,208,684 | B2 | 12/2021 | Chee |
| 11,214,796 | B2 | 1/2022 | Shirai et al. |
| 11,286,515 | B2 | 3/2022 | Chee et al. |
| 11,293,917 | B2 | 4/2022 | Chee |
| 11,299,774 | B2 | 4/2022 | Frisen et al. |
| 11,313,856 | B2 | 4/2022 | Chee |
| 11,332,790 | B2 | 5/2022 | Chell et al. |
| 11,352,659 | B2 | 6/2022 | Frisen et al. |
| 11,352,667 | B2 | 6/2022 | Hauling et al. |
| 11,359,228 | B2 | 6/2022 | Chee et al. |
| 11,365,442 | B2 | 6/2022 | Chee |
| 11,371,086 | B2 | 6/2022 | Chee |
| 11,384,386 | B2 | 7/2022 | Chee |
| 11,390,912 | B2 | 7/2022 | Frisen et al. |
| 11,401,545 | B2 | 8/2022 | Chee |
| 11,407,992 | B2 | 8/2022 | Dadhwal |
| 11,408,029 | B2 | 8/2022 | Katiraee et al. |
| 11,434,524 | B2 | 9/2022 | Ramachandran Iyer et al. |
| 11,479,809 | B2 | 10/2022 | Frisen et al. |
| 11,479,810 | B1 | 10/2022 | Chee |
| 11,492,612 | B1 | 11/2022 | Dadhwal |
| 11,501,440 | B2 | 11/2022 | Weisenfeld et al. |
| 11,505,828 | B2 | 11/2022 | Chell et al. |
| 11,512,308 | B2 | 11/2022 | Gallant et al. |
| 11,519,022 | B2 | 12/2022 | Chee |
| 11,519,033 | B2 | 12/2022 | Schnall-Levin et al. |
| 11,530,438 | B2 | 12/2022 | Persson et al. |
| 11,535,887 | B2 | 12/2022 | Gallant et al. |
| 11,542,543 | B2 | 1/2023 | Chee |
| 11,549,138 | B2 | 1/2023 | Chee |
| 11,560,587 | B2 | 1/2023 | Chee |
| 11,560,592 | B2 | 1/2023 | Chew et al. |
| 11,560,593 | B2 | 1/2023 | Chell et al. |
| 11,592,447 | B2 | 2/2023 | Uytingco et al. |
| 11,608,498 | B2 | 3/2023 | Gallant et al. |
| 11,608,520 | B2 | 3/2023 | Galonska et al. |
| 11,613,773 | B2 | 3/2023 | Frisen et al. |
| 11,618,897 | B2 | 4/2023 | Kim et al. |
| 11,618,918 | B2 | 4/2023 | Chee et al. |
| 11,624,063 | B2 | 4/2023 | Dadhwal |
| 11,624,086 | B2 | 4/2023 | Uytingco et al. |
| 11,634,756 | B2 | 4/2023 | Chee |
| 11,649,485 | B2 | 5/2023 | Yin et al. |
| 11,661,626 | B2 | 5/2023 | Katiraee et al. |
| 11,680,260 | B2 | 6/2023 | Kim et al. |
| 11,692,218 | B2 | 7/2023 | Engblom et al. |
| 11,702,693 | B2 | 7/2023 | Bharadwaj |

(56) References Cited

U.S. PATENT DOCUMENTS

| | | |
|---|---|---|
| 11,702,698 B2 | 7/2023 | Stoeckius |
| 11,713,480 B2 | 8/2023 | Lee |
| 11,732,292 B2 | 8/2023 | Chee |
| 11,732,299 B2 | 8/2023 | Ramachandran Iyer |
| 11,732,300 B2 | 8/2023 | Bava |
| 11,733,238 B2 | 8/2023 | Chee |
| 11,739,372 B2 | 8/2023 | Frisen et al. |
| 11,739,381 B2 | 8/2023 | Chew et al. |
| 11,753,673 B2 | 9/2023 | Chew et al. |
| 11,753,674 B2 | 9/2023 | Chee et al. |
| 11,753,675 B2 | 9/2023 | Ramachandran Iyer |
| 11,761,030 B2 | 9/2023 | Chee |
| 11,761,038 B1 | 9/2023 | Stoeckius |
| 11,767,550 B2 | 9/2023 | Chee |
| 11,768,175 B1 | 9/2023 | Kim et al. |
| 11,773,433 B2 | 10/2023 | Gallant et al. |
| 11,781,130 B2 | 10/2023 | Dadhwal |
| 11,788,122 B2 | 10/2023 | Frisen et al. |
| 11,795,498 B2 | 10/2023 | Frisen et al. |
| 11,795,507 B2 | 10/2023 | Chell et al. |
| 11,808,769 B2 | 11/2023 | Uytingco et al. |
| 11,821,024 B2 | 11/2023 | Chee et al. |
| 11,821,035 B1 | 11/2023 | Bent et al. |
| 11,827,935 B1 | 11/2023 | Ramachandran Iyer et al. |
| 11,835,462 B2 | 12/2023 | Bava |
| 11,840,687 B2 | 12/2023 | Gallant et al. |
| 11,840,724 B2 | 12/2023 | Chew et al. |
| 11,845,979 B2 | 12/2023 | Engblom et al. |
| 11,859,178 B2 | 1/2024 | Gallant et al. |
| 11,866,767 B2 | 1/2024 | Uytingco et al. |
| 11,866,770 B2 | 1/2024 | Chee |
| 11,873,482 B2 | 1/2024 | Kim et al. |
| 11,891,654 B2 | 2/2024 | Alvarado Martinez et al. |
| 11,898,205 B2 | 2/2024 | Bava |
| 11,926,822 B1 | 3/2024 | Gohil et al. |
| 11,926,863 B1 | 3/2024 | Boutet |
| 11,926,867 B2 | 3/2024 | Yin et al. |
| 11,933,957 B1 | 3/2024 | Tentori et al. |
| 11,952,627 B2 | 4/2024 | Stoeckius |
| 11,959,076 B2 | 4/2024 | Kim et al. |
| 11,959,130 B2 | 4/2024 | Galonska et al. |
| 11,965,213 B2 | 4/2024 | Williams |
| 11,970,739 B2 | 4/2024 | Chew et al. |
| 11,981,958 B1 | 5/2024 | Galonska |
| 11,981,960 B1 | 5/2024 | Lin et al. |
| 11,981,965 B2 | 5/2024 | Chell et al. |
| RE50,065 E | 7/2024 | Frisen et al. |
| 12,024,741 B2 | 7/2024 | Tentori et al. |
| 12,031,177 B1 | 7/2024 | Tentori et al. |
| 12,060,604 B2 | 8/2024 | Katiraee et al. |
| 12,071,655 B2 | 8/2024 | Sukovich et al. |
| 12,076,701 B2 | 9/2024 | Bava |
| 12,098,417 B2 | 9/2024 | Engblom et al. |
| 12,098,985 B2 | 9/2024 | Cox et al. |
| 12,110,541 B2 | 10/2024 | Bava |
| 12,117,439 B2 | 10/2024 | Delaney et al. |
| 2002/0022261 A1 | 2/2002 | Anderson et al. |
| 2002/0040275 A1 | 4/2002 | Cravatt |
| 2002/0045272 A1 | 4/2002 | McDevitt et al. |
| 2002/0150909 A1* | 10/2002 | Stuelpnagel ....... G01N 21/6428 435/7.1 |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0108726 A1* | 6/2003 | Schembri ............ B82Y 30/00 428/203 |
| 2003/0113713 A1 | 6/2003 | Glezer |
| 2003/0148335 A1 | 8/2003 | Shen et al. |
| 2003/0162216 A1 | 8/2003 | Gold |
| 2003/0175844 A1 | 9/2003 | Nadler et al. |
| 2003/0175947 A1 | 9/2003 | Liu et al. |
| 2003/0190744 A1 | 10/2003 | McGarry et al. |
| 2003/0205632 A1 | 11/2003 | Kim et al. |
| 2003/0211489 A1 | 11/2003 | Shen et al. |
| 2003/0215936 A1 | 11/2003 | Kallioniemi et al. |
| 2003/0224419 A1 | 12/2003 | Corcoran |
| 2003/0232348 A1 | 12/2003 | Jones et al. |
| 2003/0232382 A1 | 12/2003 | Brennan |
| 2004/0033499 A1 | 2/2004 | Ilsley et al. |
| 2004/0050699 A1 | 3/2004 | Goncalves |
| 2004/0067492 A1 | 4/2004 | Peng et al. |
| 2004/0082058 A1 | 4/2004 | Schleifer et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0112442 A1 | 6/2004 | Maerkl |
| 2004/0121456 A1 | 6/2004 | Fischer |
| 2004/0219588 A1 | 11/2004 | Furuta |
| 2004/0248287 A1 | 12/2004 | Hu et al. |
| 2005/0037393 A1 | 2/2005 | Gunderson et al. |
| 2005/0048580 A1 | 3/2005 | Labaer |
| 2005/0095627 A1 | 5/2005 | Kolman et al. |
| 2005/0100900 A1 | 5/2005 | Kawashima et al. |
| 2005/0106617 A1 | 5/2005 | Besemer et al. |
| 2005/0116161 A1 | 6/2005 | Hafeman et al. |
| 2005/0130173 A1 | 6/2005 | Leamon et al. |
| 2005/0136414 A1 | 6/2005 | Gunderson et al. |
| 2005/0170373 A1 | 8/2005 | Monforte |
| 2005/0179746 A1 | 8/2005 | Roux et al. |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0226780 A1 | 10/2005 | Sandell et al. |
| 2005/0227271 A1 | 10/2005 | Kwon |
| 2005/0239192 A1 | 10/2005 | Nasarabadi et al. |
| 2005/0260653 A1 | 11/2005 | LaBaer |
| 2006/0039823 A1 | 2/2006 | Yamakawa et al. |
| 2006/0041384 A1* | 2/2006 | Kermani ............... G06T 7/0012 702/19 |
| 2006/0041385 A1 | 2/2006 | Bauer et al. |
| 2006/0063160 A1 | 3/2006 | West et al. |
| 2006/0127946 A1 | 6/2006 | Montagu et al. |
| 2006/0134669 A1 | 6/2006 | Casasanta |
| 2006/0164490 A1 | 7/2006 | Kim et al. |
| 2006/0194331 A1 | 8/2006 | Pamula et al. |
| 2006/0211001 A1 | 9/2006 | Yu et al. |
| 2006/0216775 A1 | 9/2006 | Burkart et al. |
| 2006/0263789 A1 | 11/2006 | Kincaid |
| 2007/0020640 A1 | 1/2007 | McCloskey et al. |
| 2007/0023292 A1 | 2/2007 | Kim et al. |
| 2007/0036511 A1 | 2/2007 | Lundquist et al. |
| 2007/0054288 A1 | 3/2007 | Su et al. |
| 2007/0099208 A1 | 5/2007 | Drmanac et al. |
| 2007/0116612 A1 | 5/2007 | Williamson, IV |
| 2007/0128071 A1 | 6/2007 | Shea et al. |
| 2007/0128624 A1 | 6/2007 | Gormley et al. |
| 2007/0128656 A1 | 6/2007 | Agrawal |
| 2007/0166725 A1 | 7/2007 | McBride et al. |
| 2007/0172873 A1 | 7/2007 | Brenner et al. |
| 2007/0184456 A1 | 8/2007 | Chee et al. |
| 2007/0207482 A1 | 9/2007 | Church et al. |
| 2007/0215466 A1 | 9/2007 | Okada |
| 2007/0243634 A1 | 10/2007 | Pamula et al. |
| 2007/0254305 A1 | 11/2007 | Paik et al. |
| 2007/0264656 A1 | 11/2007 | Kawamura |
| 2007/0269805 A1 | 11/2007 | Hogers |
| 2008/0009420 A1 | 1/2008 | Schroth et al. |
| 2008/0043235 A1 | 2/2008 | Oldham et al. |
| 2008/0108804 A1 | 5/2008 | Hayashizaki et al. |
| 2008/0145616 A1 | 6/2008 | Gharib et al. |
| 2008/0160580 A1 | 7/2008 | Adessi et al. |
| 2008/0218838 A1 | 9/2008 | Rey-Mermet |
| 2008/0220434 A1 | 9/2008 | Thomas |
| 2008/0261204 A1 | 10/2008 | Lexow |
| 2008/0286795 A1 | 11/2008 | Kawashima et al. |
| 2009/0005252 A1 | 1/2009 | Drmanac et al. |
| 2009/0006002 A1 | 1/2009 | Honisch et al. |
| 2009/0011943 A1 | 1/2009 | Drmanac et al. |
| 2009/0018024 A1 | 1/2009 | Church et al. |
| 2009/0023148 A1 | 1/2009 | Moyle et al. |
| 2009/0026082 A1 | 1/2009 | Rothberg et al. |
| 2009/0068667 A1 | 3/2009 | Meisner et al. |
| 2009/0082212 A1 | 3/2009 | Williams |
| 2009/0099041 A1 | 4/2009 | Church et al. |

(56) References Cited

U.S. PATENT DOCUMENTS

| | | |
|---|---|---|
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0169089 A1 | 7/2009 | Hunt et al. |
| 2009/0192044 A1 | 7/2009 | Fouillet |
| 2009/0197326 A1 | 8/2009 | El Gamal et al. |
| 2009/0233802 A1 | 9/2009 | Bignell et al. |
| 2009/0239232 A1 | 9/2009 | Kurn |
| 2009/0253163 A1 | 10/2009 | Xie et al. |
| 2009/0253581 A1 | 10/2009 | van Eijk et al. |
| 2009/0253582 A1 | 10/2009 | Pena et al. |
| 2009/0270273 A1 | 10/2009 | Burns et al. |
| 2009/0291854 A1 | 11/2009 | Weisinger-Mayr et al. |
| 2009/0312193 A1 | 12/2009 | Kim et al. |
| 2009/0321262 A1 | 12/2009 | Adachi et al. |
| 2010/0009871 A1 | 1/2010 | Reed et al. |
| 2010/0031757 A1 | 2/2010 | Hoyer |
| 2010/0035249 A1 | 2/2010 | Hayashizaki et al. |
| 2010/0096266 A1 | 4/2010 | Kim et al. |
| 2010/0111768 A1 | 5/2010 | Banerjee et al. |
| 2010/0120097 A1 | 5/2010 | Matz et al. |
| 2010/0120098 A1 | 5/2010 | Grunenwald et al. |
| 2010/0126862 A1 | 5/2010 | Sabin et al. |
| 2010/0145037 A1 | 6/2010 | Brive et al. |
| 2010/0151511 A1 | 6/2010 | Greenizen et al. |
| 2010/0210475 A1 | 8/2010 | Lee et al. |
| 2010/0267590 A1 | 10/2010 | Grudzien et al. |
| 2010/0273219 A1 | 10/2010 | May et al. |
| 2010/0273679 A1 | 10/2010 | Cuppoletti et al. |
| 2010/0282617 A1 | 11/2010 | Rothberg et al. |
| 2011/0028685 A1 | 2/2011 | Purkayastha et al. |
| 2011/0048951 A1 | 3/2011 | Wu |
| 2011/0059436 A1 | 3/2011 | Hardin et al. |
| 2011/0177518 A1 | 7/2011 | Kartalov et al. |
| 2011/0244448 A1 | 10/2011 | Shirai et al. |
| 2011/0245111 A1 | 10/2011 | Chee |
| 2012/0135871 A1 | 5/2012 | van Eijk et al. |
| 2012/0160683 A1 | 6/2012 | Ye et al. |
| 2012/0177543 A1 | 7/2012 | Battrell |
| 2012/0195810 A1 | 8/2012 | Cohen et al. |
| 2012/0202698 A1 | 8/2012 | van Eijk et al. |
| 2012/0270305 A1 | 10/2012 | Reed et al. |
| 2012/0279954 A1 | 11/2012 | Ceremony et al. |
| 2013/0052331 A1 | 2/2013 | Kram et al. |
| 2013/0053273 A1 | 2/2013 | Juncker et al. |
| 2013/0065788 A1 | 3/2013 | Glezer et al. |
| 2013/0096033 A1 | 4/2013 | Routenberg |
| 2013/0146459 A1 | 6/2013 | Bazant et al. |
| 2013/0203100 A1 | 8/2013 | Otter et al. |
| 2013/0252847 A1 | 9/2013 | McKenna et al. |
| 2013/0260372 A1 | 10/2013 | Buermann et al. |
| 2013/0296174 A1 | 11/2013 | Peumans |
| 2014/0011707 A1 | 1/2014 | Ye et al. |
| 2014/0066318 A1 | 3/2014 | Frisen et al. |
| 2014/0155295 A1 | 6/2014 | Hindson et al. |
| 2014/0270435 A1 | 9/2014 | Dunn |
| 2014/0274731 A1 | 9/2014 | Raymond et al. |
| 2014/0323330 A1* | 10/2014 | Bergo .............. G01N 33/6851 506/18 |
| 2014/0378350 A1 | 12/2014 | Hindson et al. |
| 2015/0148239 A1 | 5/2015 | Peter et al. |
| 2015/0219618 A1 | 8/2015 | Krishnan et al. |
| 2015/0292988 A1 | 10/2015 | Bharadwaj et al. |
| 2015/0298091 A1 | 10/2015 | Weitz et al. |
| 2015/0344942 A1* | 12/2015 | Frisen ................ C12Q 1/6841 506/30 |
| 2016/0033496 A1 | 2/2016 | Chou et al. |
| 2016/0138091 A1 | 5/2016 | Chee et al. |
| 2016/0145677 A1 | 5/2016 | Chee et al. |
| 2016/0253584 A1 | 9/2016 | Fodor et al. |
| 2016/0289669 A1 | 10/2016 | Fan et al. |
| 2016/0289740 A1 | 10/2016 | Fu et al. |
| 2016/0291006 A1* | 10/2016 | Trau .................. C40B 30/04 |
| 2016/0298180 A1 | 10/2016 | Chee |
| 2016/0299165 A1 | 10/2016 | Zhou |
| 2017/0016053 A1 | 1/2017 | Beechem et al. |
| 2017/0159109 A1 | 6/2017 | Zheng et al. |
| 2017/0220733 A1 | 8/2017 | Zhuang et al. |
| 2017/0342405 A1 | 11/2017 | Fu et al. |
| 2017/0349940 A1 | 12/2017 | Morin et al. |
| 2018/0052082 A1 | 2/2018 | Groll et al. |
| 2018/0057873 A1 | 3/2018 | Zhou et al. |
| 2018/0074039 A1 | 3/2018 | Soper et al. |
| 2018/0080876 A1 | 3/2018 | Rockel et al. |
| 2018/0095067 A1 | 4/2018 | Huff et al. |
| 2018/0104694 A1 | 4/2018 | Huff et al. |
| 2018/0104964 A1 | 4/2018 | Uemura et al. |
| 2018/0112261 A1 | 4/2018 | Van Driel et al. |
| 2018/0127817 A1 | 5/2018 | Borchert et al. |
| 2018/0201980 A1 | 7/2018 | Chee et al. |
| 2018/0216162 A1 | 8/2018 | Belhocine et al. |
| 2018/0217094 A1 | 8/2018 | Herr et al. |
| 2018/0245142 A1 | 8/2018 | So et al. |
| 2018/0251833 A1 | 9/2018 | Daugharthy et al. |
| 2018/0257075 A1 | 9/2018 | Yellen et al. |
| 2018/0291439 A1 | 10/2018 | van Eijk et al. |
| 2018/0305681 A1 | 10/2018 | Jovanovich et al. |
| 2019/0064173 A1 | 2/2019 | Bharadwaj et al. |
| 2019/0099754 A1 | 4/2019 | Dupouy et al. |
| 2019/0113532 A1 | 4/2019 | Tan et al. |
| 2019/0126280 A1 | 5/2019 | Gach et al. |
| 2019/0155835 A1 | 5/2019 | Daugharthy et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0201891 A1 | 7/2019 | Pallas et al. |
| 2019/0203275 A1 | 7/2019 | Frisen et al. |
| 2019/0218276 A1 | 7/2019 | Regev et al. |
| 2019/0233878 A1 | 8/2019 | Delaney et al. |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0338353 A1 | 11/2019 | Belgrader et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0047010 A1 | 2/2020 | Lee et al. |
| 2020/0048690 A1 | 2/2020 | Chee |
| 2020/0049599 A1 | 2/2020 | Alexander et al. |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0109443 A1 | 4/2020 | Chee |
| 2020/0173985 A1 | 6/2020 | Dong et al. |
| 2020/0256867 A1 | 8/2020 | Hennek et al. |
| 2020/0277663 A1 | 9/2020 | Iyer |
| 2020/0277664 A1 | 9/2020 | Frenz |
| 2020/0298241 A1 | 9/2020 | Kabaha et al. |
| 2020/0299757 A1 | 9/2020 | Chee et al. |
| 2020/0325531 A1 | 10/2020 | Chee |
| 2020/0363408 A1 | 11/2020 | Chou et al. |
| 2020/0370095 A1 | 11/2020 | Farmer et al. |
| 2020/0393343 A1 | 12/2020 | Kennedy-Darling et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0069709 A1* | 3/2021 | Chou .................. B01L 7/52 |
| 2021/0095331 A1 | 4/2021 | Fan et al. |

(56) References Cited

U.S. PATENT DOCUMENTS

| | | |
|---|---|---|
| 2021/0123040 A1 | 4/2021 | Macosko et al. |
| 2021/0130881 A1 | 5/2021 | Cox |
| 2021/0140982 A1 | 5/2021 | Uytingco et al. |
| 2021/0155982 A1* | 5/2021 | Yin ............................ G06T 7/13 |
| 2021/0158522 A1 | 5/2021 | Weisenfeld et al. |
| 2021/0172007 A1 | 6/2021 | Chee et al. |
| 2021/0189475 A1* | 6/2021 | Tentori ................. C12Q 1/6841 |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0278654 A1* | 9/2021 | Gedraitis ............... G02B 27/32 |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0049294 A1 | 2/2022 | Uytingco et al. |
| 2022/0064630 A1 | 3/2022 | Bent et al. |
| 2022/0081728 A1 | 3/2022 | Williams |
| 2022/0088561 A1* | 3/2022 | Brenan ............... G01N 35/1011 |
| 2022/0090058 A1 | 3/2022 | Frisen et al. |
| 2022/0090175 A1 | 3/2022 | Uytingco et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0220544 A1 | 7/2022 | Ach et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0017773 A1 | 1/2023 | Kim et al. |
| 2023/0416807 A1 | 1/2023 | Chee |
| 2023/0416808 A1 | 1/2023 | Sukovich et al. |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081232 A1* | 3/2023 | Weisenfeld ............ G16H 50/30 |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0126825 A1 | 4/2023 | Nagendran et al. |
| 2023/0129552 A1 | 4/2023 | Ramachandran Iyer |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0147726 A1 | 5/2023 | Hadrup et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |
| 2023/0203478 A1 | 6/2023 | Kim et al. |
| 2023/0183684 A1 | 7/2023 | Gallant et al. |
| 2023/0212650 A1 | 7/2023 | Chew et al. |
| 2023/0212655 A1 | 7/2023 | Chee |
| 2023/0220368 A1 | 7/2023 | Kim |
| 2023/0220454 A1 | 7/2023 | Bent et al. |
| 2023/0220455 A1 | 7/2023 | Galonska et al. |
| 2023/0227811 A1 | 7/2023 | Dadhwal |
| 2023/0228762 A1 | 7/2023 | Uytingco et al. |
| 2023/0242973 A1 | 8/2023 | Frisen et al. |
| 2023/0242976 A1 | 8/2023 | Tentori et al. |
| 2023/0265488 A1 | 8/2023 | Gohil et al. |
| 2023/0265489 A1 | 8/2023 | Uytingco et al. |
| 2023/0265491 A1 | 8/2023 | Tentori et al. |
| 2023/0279474 A1 | 9/2023 | Katiraee |
| 2023/0279477 A1 | 9/2023 | Kvastad et al. |
| 2023/0279481 A1 | 9/2023 | Marrache et al. |
| 2023/0287399 A1 | 9/2023 | Gallant et al. |
| 2023/0287475 A1 | 9/2023 | Chell et al. |
| 2023/0287481 A1 | 9/2023 | Katsori et al. |
| 2023/0295699 A1 | 9/2023 | Sukovich et al. |

(56) References Cited

U.S. PATENT DOCUMENTS

| | | |
|---|---|---|
| 2023/0295722 A1 | 9/2023 | Bharadwaj |
| 2023/0304072 A1 | 9/2023 | Gohil et al. |
| 2023/0304074 A1 | 9/2023 | Chee et al. |
| 2023/0304078 A1 | 9/2023 | Frisen et al. |
| 2023/0313279 A1 | 10/2023 | Giacomello et al. |
| 2023/0323340 A1 | 10/2023 | Dadhwal |
| 2023/0323434 A1 | 10/2023 | Yin et al. |
| 2023/0323436 A1 | 10/2023 | Chee |
| 2023/0323447 A1 | 10/2023 | Schnall-Levin et al. |
| 2023/0323453 A1 | 10/2023 | Stoeckius |
| 2023/0332138 A1 | 10/2023 | Kim et al. |
| 2023/0332211 A1 | 10/2023 | Chee |
| 2023/0332212 A1 | 10/2023 | Chew et al. |
| 2023/0332227 A1 | 10/2023 | Ramachandran Iyer |
| 2023/0332247 A1 | 10/2023 | Singh et al. |
| 2023/0351619 A1* | 11/2023 | Tentori .................. G06V 10/25 |
| 2023/0358733 A1 | 11/2023 | Chee |
| 2023/0366008 A1 | 11/2023 | Chew et al. |
| 2023/0383285 A1 | 11/2023 | Kim et al. |
| 2023/0383344 A1 | 11/2023 | Stoeckius |
| 2023/0392204 A1 | 12/2023 | Chell et al. |
| 2023/0393071 A1 | 12/2023 | Bava |
| 2023/0407404 A1 | 12/2023 | Baumgartner et al. |
| 2023/0416850 A1 | 12/2023 | Singh et al. |
| 2024/0002931 A1 | 1/2024 | Bava |
| 2024/0011081 A1 | 1/2024 | Chee |
| 2024/0011090 A1 | 1/2024 | Chew et al. |
| 2024/0018572 A1 | 1/2024 | Mignardi |
| 2024/0018575 A1 | 1/2024 | Gallant et al. |
| 2024/0018589 A1 | 1/2024 | Schnall-Levin et al. |
| 2024/0026445 A1 | 1/2024 | Ramachandran Iyer et al. |
| 2024/0033743 A1 | 2/2024 | Tentori et al. |
| 2024/0035937 A1 | 2/2024 | Cox et al. |
| 2024/0043908 A1 | 2/2024 | Chew et al. |
| 2024/0043925 A1 | 2/2024 | Bent et al. |
| 2024/0052343 A1 | 2/2024 | Gallant et al. |
| 2024/0053351 A1 | 2/2024 | Uytingco et al. |
| 2024/0060115 A1 | 2/2024 | Chee et al. |
| 2024/0067953 A1 | 2/2024 | Mikkelsen et al. |
| 2024/0068016 A1 | 2/2024 | Frisen et al. |
| 2024/0068017 A1 | 2/2024 | Lundeberg et al. |
| 2024/0076723 A1 | 3/2024 | Mignardi |
| 2024/0080346 A1 | 3/2024 | Engblom et al. |
| 2024/0084365 A1 | 3/2024 | Frisen et al. |
| 2024/0084366 A1 | 3/2024 | Chee |
| 2024/0084383 A1 | 3/2024 | Ramachandran Iyer et al. |
| 2024/0093274 A1 | 3/2024 | Frisen et al. |
| 2024/0093290 A1 | 3/2024 | Stahl et al. |
| 2024/0110228 A1 | 4/2024 | Uytingco et al. |
| 2024/0124933 A1 | 4/2024 | Chell et al. |
| 2024/0125772 A1 | 4/2024 | Delaney et al. |
| 2024/0141327 A1 | 5/2024 | Kim et al. |
| 2024/0158838 A1 | 5/2024 | Alvarado Martinez et al. |
| 2024/0175080 A1 | 5/2024 | Galonska et al. |
| 2024/0182968 A1 | 6/2024 | Bava |
| 2024/0191286 A1 | 6/2024 | Boutet et al. |
| 2024/0200121 A1 | 6/2024 | Boutet |
| 2024/0209425 A1 | 6/2024 | Yin et al. |
| 2024/0218427 A1 | 7/2024 | Sukovich et al. |
| 2024/0218432 A1 | 7/2024 | Mielinis |
| 2024/0219701 A1 | 7/2024 | Tentori et al. |
| 2024/0253036 A1 | 8/2024 | Kim et al. |
| 2024/0263218 A1 | 8/2024 | Katiraee et al. |
| 2024/0271190 A1 | 8/2024 | Stoeckius et al. |
| 2024/0271195 A1 | 8/2024 | Mikhaiel et al. |
| 2024/0279747 A1 | 8/2024 | Williams |
| 2024/0287600 A1 | 8/2024 | Iyer et al. |
| 2024/0294971 A1 | 9/2024 | Galonska |
| 2024/0294974 A1 | 9/2024 | Galonska et al. |
| 2024/0294975 A1 | 9/2024 | Lin et al. |
| 2024/0301488 A1 | 9/2024 | Stoeckius |
| 2024/0301489 A1 | 9/2024 | Chew et al. |

FOREIGN PATENT DOCUMENTS

| | | |
|---|---|---|
| CN | 1680604 | 10/2005 |
| CN | 1981188 | 6/2007 |
| CN | 202548048 | 11/2012 |
| CN | 102851369 | 1/2013 |
| CN | 104513785 | 4/2015 |
| EP | 0961110 | 12/1999 |
| EP | 0901631 | 8/2004 |
| EP | 1 782 737 A1 | 5/2007 |
| EP | 1878502 | 1/2008 |
| EP | 1923471 | 5/2008 |
| EP | 2002017 | 12/2008 |
| EP | 2130913 | 12/2009 |
| EP | 2881465 | 6/2015 |
| EP | 3013984 | 5/2016 |
| EP | 2350648 | 7/2017 |
| EP | 3511423 | 7/2019 |
| EP | 3541956 | 9/2019 |
| WO | WO 1989/010977 | 11/1989 |
| WO | WO 1991/006678 | 5/1991 |
| WO | WO 1995/025116 | 9/1995 |
| WO | WO 1995/035505 | 12/1995 |
| WO | WO 1999/063385 | 12/1999 |
| WO | WO 2000/063437 | 10/2000 |
| WO | WO 2002/040874 | 5/2002 |
| WO | WO 2002/059355 | 8/2002 |
| WO | WO 2002/077283 | 10/2002 |
| WO | WO 2003/002979 | 1/2003 |
| WO | WO 2003/010176 | 2/2003 |
| WO | WO 2003/106973 | 12/2003 |
| WO | WO 2004/028955 | 4/2004 |
| WO | WO-2004/108268 A1 | 12/2004 |
| WO | WO 2005/007814 | 1/2005 |
| WO | WO 2006/056861 | 6/2006 |
| WO | WO 2007/073171 | 6/2007 |
| WO | WO 2007/076726 | 7/2007 |
| WO | WO 2007/120241 | 10/2007 |
| WO | WO 2007/123744 | 11/2007 |
| WO | WO 2007/145612 | 12/2007 |
| WO | WO 2008/075086 | 6/2008 |
| WO | WO 2008/157801 | 12/2008 |
| WO | WO 2009/032167 | 3/2009 |
| WO | WO 2009/152928 | 12/2009 |
| WO | WO 2010/088517 | 8/2010 |
| WO | WO 2010/126614 | 11/2010 |
| WO | WO 2011/068088 | 6/2011 |
| WO | WO 2011/094669 | 8/2011 |
| WO | WO 2011/102903 | 8/2011 |
| WO | WO 2011/127099 | 10/2011 |
| WO | WO 2012/058096 | 5/2012 |
| WO | WO 2012/140224 | 10/2012 |
| WO | WO 2012/159089 | 11/2012 |
| WO | WO 2012/168003 | 12/2012 |
| WO | WO 2013/123442 | 8/2013 |
| WO | WO 2013/131962 | 9/2013 |
| WO | WO 2013/138510 | 9/2013 |
| WO | WO 2013/150082 | 10/2013 |
| WO | WO 2013/150083 | 10/2013 |
| WO | WO 2014/060483 | 4/2014 |
| WO | WO 2014/128129 | 8/2014 |
| WO | WO 2014/142841 | 9/2014 |
| WO | WO 2014/163886 | 10/2014 |
| WO | WO 2014/210223 | 12/2014 |
| WO | WO 2014/210225 | 12/2014 |
| WO | WO 2014/210233 | 12/2014 |
| WO | WO 2015/031691 | 3/2015 |
| WO | WO 2015/161173 | 10/2015 |
| WO | WO 2016/007839 | 1/2016 |
| WO | WO 2016/057552 | 4/2016 |
| WO | WO-2016/126882 A1 | 8/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/027367 | 2/2017 |

(56) References Cited

FOREIGN PATENT DOCUMENTS

| | | |
|---|---|---|
| WO | WO 2017/027368 | 2/2017 |
| WO | WO 2017/048871 | 3/2017 |
| WO | WO 2017/075293 | 5/2017 |
| WO | WO 2017/112957 | 6/2017 |
| WO | WO 2017/096158 | 7/2017 |
| WO | WO 2017/144338 | 8/2017 |
| WO | WO 2017/147483 | 8/2017 |
| WO | WO 2017/222453 | 12/2017 |
| WO | WO 2018/022809 | 2/2018 |
| WO | WO 2018/045181 | 3/2018 |
| WO | WO 2018/045186 | 3/2018 |
| WO | WO 2018/057999 | 3/2018 |
| WO | WO 2018/064640 | 4/2018 |
| WO | WO-2018/075436 A1 | 4/2018 |
| WO | WO 2018/091676 | 5/2018 |
| WO | WO 2018/107054 | 6/2018 |
| WO | WO 2018/136856 | 7/2018 |
| WO | WO-2018/144582 A1 | 8/2018 |
| WO | WO 2018/148471 | 8/2018 |
| WO | WO 2018/175779 | 9/2018 |
| WO | WO 2019/012005 | 1/2019 |
| WO | WO 2019/068880 | 4/2019 |
| WO | WO 2019/075091 | 4/2019 |
| WO | WO 2019/104337 | 5/2019 |
| WO | WO 2019/113457 | 6/2019 |
| WO | WO 2019/140334 | 7/2019 |
| WO | WO 2019/213254 | 11/2019 |
| WO | WO 2019/213294 | 11/2019 |
| WO | WO 2020/028194 | 2/2020 |
| WO | WO 2020/047002 | 3/2020 |
| WO | WO 2020/047004 | 3/2020 |
| WO | WO 2020/047010 | 3/2020 |
| WO | WO 2020/076979 | 4/2020 |
| WO | WO 2020/099640 | 5/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO-2020123320 A2 * 6/2020 .......... B01L 3/50853 | |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/219901 | 10/2020 |
| WO | WO 2020/243579 | 12/2020 |
| WO | WO 2021/016379 | 1/2021 |
| WO | WO 2021/041974 | 3/2021 |
| WO | WO 2021/067246 | 4/2021 |
| WO | WO 2021/067514 | 4/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/247593 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/051152 | 3/2022 |
| WO | WO 2022/060798 | 3/2022 |
| WO | WO 2022/060953 | 3/2022 |
| WO | WO 2022/061150 | 3/2022 |
| WO | WO 2022/061152 | 3/2022 |
| WO | WO 2022/087273 | 4/2022 |
| WO | WO 2022/098810 | 5/2022 |
| WO | WO 2022/099037 | 5/2022 |
| WO | WO 2022/103712 | 5/2022 |
| WO | WO 2022/109181 | 5/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/122033 | 6/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |

OTHER PUBLICATIONS

Final Office Action mailed on Jan. 31, 2022, for U.S. Appl. No. 17/172,926, filed Feb. 10, 2021, 33 pages.
Final Office Action mailed on Sep. 14, 2022, for U.S. Appl. No. 17/172,926, filed Feb. 10, 2021, 30 pages.
Final Office Action mailed on Jan. 26, 2023, for U.S. Appl. No. 17/172,926, filed Feb. 10, 2021, 24 pages.
Final Office Action mailed on Sep. 20, 2022, for U.S. Appl. No. 17/665,169, filed Feb. 4, 2022, 7 pages.
Forster, S.C. et al. (Feb. 2019, e-published Feb. 4, 2019). "A human gut bacterial genome and culture collection for improved metagenomic analyses," *Nature Biotechnology* 37(2):186-192.
Gabbatiss, J. et al. (Apr. 24, 2018). "New form of DNA discovered inside living human cells," *The Independent*, 2 pages.
"Human Genome" Wikipedia .com located at <https://en.wikipedia.org/wiki/Human_genome#:~: text=The%20human%20genome%

(56) References Cited

OTHER PUBLICATIONS

20is%20a,genome%20and%20the%20mitochondrial%20genome> last accessed Feb. 7, 2024, 33 pages.
International Preliminary Report on Patentability mailed on Jun. 8, 2021, for PCT Application No. PCT/US2019/065100, filed Dec. 6, 2019, 13 pages.
International Search Report mailed on Jun. 23, 2020, for PCT Application No. PCT/US2019/065100, filed Dec. 6, 2019, 8 pages.
International Preliminary Report on Patentability mailed on Sep. 28, 2021, for PCT Application No. PCT/US2020/029843, filed Apr. 24, 2020, 14 pages.
International Search Report mailed on Oct. 7, 2020, for PCT Application No. PCT/US2020/029843, filed Apr. 24, 2020, 6 pages.
Liu, H. et al. (Dec. 15, 2010, e-published Jul. 30, 2010). "An integrated and sensitive detection platform for biosensing application based on Fe@Au magnetic nanoparticles as bead array carries," *Biosensors and Bioelectronics* 26(4):1442-1448.
Non-Final Office Action mailed on May 10, 2021, for U.S. Appl. No. 17/172,926, filed Feb. 10, 2021, 33 pages.
Non-Final Office Action mailed on May 12, 2022, for U.S. Appl. No. 17/665,169, filed Feb. 4, 2022, 8 pages.
Non-Final Office Action mailed on Aug. 3, 2023, for U.S. Appl. No. 17/665,169, filed Feb. 4, 2022, 6 pages.
Non-Final Office Action mailed on Nov. 27, 2023, for U.S. Appl. No. 17/665,169, filed Feb. 4, 2022, 8 pages.
Non-Final Office Action mailed on May 22, 2023, for U.S. Appl. No. 18/049,094, filed Oct. 24, 2022, 32 pages.
Sah, R. et al. (Mar. 12, 2020). "Complete Genome Sequence of a 2019 Novel Coronavirus (SARS-CoV-2) Strain Isolated in Nepal," *Microbiology Resource Announcements* 9(11):e00169-20.
Sumitomo, K. et al. (Jan. 15, 2012, e-published Nov. 15, 2011). "Ca2+ ion transport through channels formed by α-hemolysin analyzed using a microwell array on a Si substrate," *Biosensors and Bioelectronics* 31(1):445-450.
Wu, L. et al. (Jun. 18, 2010). "Detection DNA point mutation with rolling-circle amplification chip," Bioinformatics and Biomedical Engineering (ICBBE), 2010 4$^{th}$ International Conference, IEEE, Piscataway, NJ, USA pp. 1-4.
Zeberg, H. et al. (Nov. 2020, e-published Sep. 30, 2020). "The major genetic risk factor for severe COVID-19 is inherited from Neanderthals," *Nature* 587(7835):610-612.
Anonymous, "ST Spot Detector Usage Guide. A Guide to Using the Spatial Transcriptomics Spot Detector 2.0", GitHub, Jun. 15, 2018, 1 page.
Anonymous, "Visium Spatial Gene Expression Imaging Guidelines", 10x Genomics Inc., Dec. 13, 2021, 11 pages.
Asp et al., "Spatially Resolved Transcriptomes-Next Generation Tools for Tissue Exploration", Bioessays, May 4, 2020, 42(10):1900221(16 pages).
Cardona et al., "TrakEM2 0.9a User Manual", https://www.ini.uzh.ch/-acardona/trakem2manual.html, Sep. 8, 2011, 38 pages.
Chen, K.H. et al. (Apr. 24, 2015). "Spatially resolved, highly multiplexed RNA profiling in single cells," *Science* 348(6233):aaa6090.
Dedeoglu, G. et al. (2005). "On the Source of Asymmetry in Image Registration Problems," Technical Report, located at <https://www.ri.cmu.edu/pub_files/pub4/dedeoglu_goksel_2005_1/dedeoglu_goksel_2005_1.pdf> 18 pages.
Navarro et al., "ST Viewer: A Tool for Analysis and Visualization of Spatial Transcriptomics Datasets", Bioinformatics, Mar. 15, 2019, 35(6): 1058-1060.
Strell, C. et al. (Apr. 2019, e-published Mar. 31, 2018). "Placing RNA in context and space—methods for spatially resolved transcriptomics," *FEBS Journal* 286(8):1468-1481.
Wilbrey-Clark et al., "Cell Atlas Technologies and Insights Into Tissue Architecture", The Biochemical Journal, Apr. 27, 2020, 477(8):1427-1442.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
10xGenomics.com, [online], "Visium Spatial Gene Expression Reagent Kits—Tissue Optimization—User Guide," Feb. 2022, retrieved on Mar. 29, 2024, retrieved from URL<https://cdn.10xgenomics.com/image/upload/v1660261286/support-documents/CG000238_VisiumSpatialTissueOptimizationUserGuide_RevE.pdf>, 46 pages.
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jan. 2022, retrieved on Jun. 27, 2024, retrieved from URL<https://web.archive.org/web/20230326192142/https://www.10xgenomics.com/support/spatial-gene-expression-fresh-frozen/documentation/steps/library-construction/visium-spatial-gene-expression-reagent-kits-user-guide>, 71 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 70 pages.
Adessi et al., "Solid phase DNA amplification: characterisation of primer attachment and amplification mechanisms," Nucl. Acids Res., 2000, 28(20):E87, 8 pages.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal G.T Mismatches in DNA," Biochemistry, 1996, 36(34):10581-10594.
Andor.com [online], "Discover new ways of seeing," Next Generation Digital Illumination, Mosaic 3, 2020, 11 pages.
Armani et al, "2D-PCR: a method of mapping DNA in tissue sections," Lab Chip, 2009, 9(24):3526-34.
Asp et al., "A spatiotemporal organ-wide gene expression and cell atlas of the developing human heart," Cell, Dec. 12, 2019, 179(7):1647-1660.

(56) References Cited

OTHER PUBLICATIONS

Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Barnes, "PCR amplification of up to 35-kb DNA with high fidelity and high yield from lambda bacteriophage templates," Proc. Natl. Acad. Sci USA, 1994, 91(6):2216-2220.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bergenstråhle et al., "Seamless integration of image and molecular analysis for spatial transcriptomics workflows," BMC Genomics, Jul. 2020, 21(1):482, 7 pages.
Birney et al., "Identification and analysis of functional elements in 1% of the human genome by the ENCODE pilot project," Nature, 2007, 447(7146):799-816.
Blair et al., "Microarray temperature optimization using hybridization kinetics," Methods Mol Biol., 2009, 529:171-96.
Blanchard et al., "High-density oligonucleotide arrays," Biosensors & Bioelectronics, 1996, 11(6-7):687-690.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolotin et al., "MiXCR: software for comprehensive adaptive immunity profiling," Nat Methods., May 2015, 12(5):380-1.
Borm et al., "High throughput human embryo spatial transcriptome mapping by surface transfer of tissue RNA," Abstracts Selected Talks, Single Cell Genomics mtg, (SCG2019), 2019, 1 pages (Abstract Only).
Borm et al., "Scalable in situ single-cell profiling by electrophoretic capture of mRNA," bioRxiv, Jan. 2022, 32 pages.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Calvert, "Materials science. Printing cells," Science, Oct. 2007, 318(5848):208-209.
Carter et al., "Stabilization of an optical microscope to 0.1 nm in three dimensions," Applied Optics, 2007, 46:421-427.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "DNA hybridization detection in a microfluidic Channel using two fluorescently labelled nucleic acid probes," Biosensors and Bioelectronics, 2008, 23(12):1878-1882.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "Spatial Transcriptomics and In Situ Sequencing to Study Alzheimer's Disease," Cell, Aug. 2020, 182(4):976-991.
Chen et al., "μCB-seq: microfluidic cell barcoding and sequencing for high-resolution imaging and sequencing of single cells," Lab Chip, Nov. 2020, 20(21):3899-3913.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Cockroft et al., "A single-molecule nanopore device detects DNA polymerase activity with single-nucleotide resolution," J Am Chem Soc., Jan. 2008, 130(3):818-20.
Codeluppi et al., "Spatial organization of the somatosensory cortex revealed by osmFISH," Nature Methods, Nov. 2018, 15:932-935.
Constantine et al., "Use of genechip high-density oligonucleotide arrays for gene expression monitoring," Life Science News, Amersham Life Science, 1998, pp. 11-14.
Crosetto et al., "Spatially resolved transcriptomics and beyond," Nature Review Genetics, 2015, 16(1):57-66.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by Nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Dhindsa et al., "Virtual Electrowetting Channels: Electronic Liquid Transport with Continuous Channel Functionality," Lab Chip, 2010, 10:832-836.
Duncan et al., "Affinity chromatography of a sequence-specific DNA binding protein using Teflon-linked oligonucleotides," Anal. Biochem., 1988, 169(1):104-108.
Eastburn, "Microfluidic droplet enrichment for targeted sequencing," Nucleic Acids Research, 2015, 43(13):1-8.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Transcriptome-scale super-resolved imaging in tissues by RNA seqFISH+," Nature, Apr. 2019, 568(7751):235-239, 37 pages.
Ertsey et al., "Coverslip Mounted-Immersion Cycled in Situ RT-PCR for the Localization of mRNA in Tissue Sections," Biotechniques, 1998, 24(1):92-100.
Fahy et al., "Design and synthesis of polyacrylamide-based oligonucleotide supports for use in nucleic acid diagnostics," Nucleic Acids Res., Apr. 1993, 21(8):1819-26.
Fire et al., "Rolling replication of short DNA circles," Proc. Natl. Acad. Sci., 1995, 92(10):4641-4645.

(56) References Cited

OTHER PUBLICATIONS

Fluidigm, "Hyperion Imaging System: Visualize a new path forward," Feb. 2018, retrieved from URL <https://www.fluidigm.com/binaries/content/documents/fluidigm/search/hippo%3Aresultset/hyperion-imaging-system-br-400326/fluidigm%3Afile>, 27 pages.

Fluidigm, "Immuno-Oncology Research with the Hyperion Imaging System: A high-parameter imaging solution at subcellular resolution to characterize the immune repertoire in the tumor microenvironment," Apr. 2018, retrieved from URL <https://www.fluidigm.com/binaries/content/documents/fluidigm/search/hippo%3Aresultset/application-note-immuno-oncology-research-with-the-hyperion%E2%84%A2-imaging-system/fluidigm%3Afile>, 6 pages.

Fluidigm, "Immuno-Oncology Research with the Hyperion Imaging System: A high-parameter imaging solution at subcellular resolution to characterize the immune repertoire in the tumor microenvironment," Aug. 2018, retrieved from URL <https://www.fluidigm.com/binaries/content/documents/fluidigm/marketing/immuno-oncology-research-with-the-hyperion-imaging-system-appnote-400332/immuno-oncology-research-with-the-hyperion-imaging-system-appnote-400332/fluidigm%3Afile>, 6 pages.

Fluidigm, "Maxpar Antibodies for Imaging Mass Cytometry," Mar. 2018, retrieved from URL <https://www.fluidigm.com/binaries/content/documents/fluidigm/search/hippo%3Aresultset/hyperion-antibodies-for-imaging-mass-cytometry-br-101-7115/fluidigm%3Afile>, 2 pages.

Fodor et al., "Light-directed, spatially addressable parallel chemical synthesis," Science, 1995, 251(4995):767-773.

Forcucci et al., "All-plastic miniature fluorescence microscope for point-of-care readout of bead-based bioassays.," J. Biomed Opt., 2015, 20(10):105010, 15 pages.

Frese et al., "Formylglycine aldehyde Tag—protein engineering through a novel post-translational modification," ChemBioChem., 2009, 10(3):425-27.

Fu et al., "Continuous Polony Gels for Tissue Mapping with High Resolution and RNA Capture Efficiency," bioRxiv, 2021, 20 pages.

Fu et al., "Counting individual DNA molecules by the stochastic attachment of diverse labels," PNAS, 2011, 108(22):9026-9031.

Fullwood et al., "Next-generation DNA sequencing of paired-end tags (PET) for transcriptome and genome analyses," Genome Res., 2009, 19(4):521-532.

Gamper et al., "Gene expression profile of bladder tissue of patients with ulcerative interstitial cystitis," BMC Genomics, Apr. 28, 2009, 10(199):1-17.

Ganguli et al., "Pixelated spatial gene expression analysis from tissue," Nat Commun., Jan. 2018, 9(1):202, 9 pages.

Gao et al., "Q&A: Expansion microscopy," BMC Biology, 15:50, 9 pages, 2017.

Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.

Gnanapragasam, "Unlocking the molecular archive: the emerging use of formalin-fixed paraffin-embedded tissue for biomarker research in urological cancer," BJU International, 2009, 105(2):274-278.

Goh et al., "Highly Specific Multiplexed RNA Imaging In Tissues With Split-FISH," Nat Methods, Jun. 15, 2020, 17(7):689-693, 21 pages.

Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.

Gracia Villacampa et al., "Genome-wide Spatial Expression Profiling in FFPE Tissues," bioRxiv, Cell Genomics, posted Jul. 25, 2020, published Dec. 8, 2021, 1(3):100065, 38 pages.

Gunderson et al., "Decoding randomly ordered DNA arrays," Genome Research, 2004, 14(5):870-877.

Guo et al., "Direct fluorescence analysis of genetic polymorphisms by hybridization with oligonucleotide arrays on glass supports," Nucleic Acids Res., Dec. 1994, 22(24):5456-65.

Gupta et al., "Single-cell isoform RNA sequencing characterizes isoforms in thousands of cerebellar cells," Nature Biotechnol., Oct. 2018, 36:1197-1202.

Hamaguchi et al., "Direct reverse transcription-PCR on oligo(dT)-immobilized polypropylene microplates after capturing total mRNA from crude cell lysates," Clin Chem., Nov. 1998, 44(11):2256-63.

Hattersley et al., "Development of a microfluidic device for the maintenance and interrogation of viable tissue biopsies," Lab Chip., Nov. 2008, 8(11):1842-6.

Hayes et al., "Electrophoresis of proteins and nucleic acids: I-Theory," BMJ, Sep. 1989, 299(6703):843-6.

He et al., "In situ synthesis of protein arrays," Current Opinion in Biotechnology, 2008, 19(1):4-9.

He, "Cell-free protein synthesis: applications in proteomics and biotechnology," New Biotechnology, 2008, 25(2-3):126-132.

Hejatko et al., "In situ hybridization technique for mRNA detection in whole mount *Arabidopsis* samples," Nature Protocols, 2006, 1(4):1939-1946.

Hiatt et al., "Parallel, tag-directed assembly of locally derived short sequence reads," Nature Methods, 2010, 7(2):119-25.

Hoyer et al., "Electrostatic spraying: a novel technique for preparation of polymer coatings on electrodes," Anal Chem, Nov. 1996, 68(21):3840-4.

Jamur et al., "Permeabilization of cell membranes.," Method Mol. Biol., 2010, 588:63-66.

Jemt et al., "An automated approach to prepare tissue-derived spatially barcoded RNA-sequencing libraries," Scientific Reports, 2016, 6:37137, 10 pages.

Kapteyn et al., "Incorporation of non-natural nucleotides into template-switching oligonucleotides reduces background and improves cDNA synthesis from very small RNA samples," BMC Genomics, Jul. 2010, 11:413, 9 pages.

Kim et al., "Replication of DNA Microarrays Prepared by In Situ Oligonucleotide Polymerization and Mechanical Transfer," Anal Chem., 2007, 79:7267-7274.

Kim, "Development of Microdevices for Applications to Bioanalysis," Dissertation for the degree of Doctor of Philosophy, University of Texas at Austin, Aug. 2007, 176 pages.

Korbel et al., "Paired-end mapping reveals extensive structural variation in the human genome," Science, 2007, 318(5849):420-426.

Kozlov et al., "A highly scalable peptide-based assay system for proteomics," PLoS ONE, 2012, 7(6):e37441, 10 pages.

Kristensen et al., "High-Throughput Methods for Detection of Genetic Variation," BioTechniques, Feb. 2001, 30(2):318-332.

Kuhn et al., "A novel, high-performance random array platform for quantitative gene expression profiling," Genome Res, 2004, 14:2347-2356.

Kurz et al., "cDNA—protein fusions: covalent protein—gene conjugates for the in vitro selection of peptides and proteins," ChemBioChem., 2001, 2(9):666-72.

Kwok, "High-throughput genotyping assay approaches," Pharmocogenomics, Feb. 2000, 1(1):95-100.

Lage et al., "Whole genome analysis of genetic alterations in small DNA samples using hyperbranched strand displacement amplification and array-CGH," Genome Research, 2003, 13(2):294-307.

Lamture et al., "Direct detection of nucleic acid hybridization on the surface of a charge coupled device," Nucleic Acid Res., Jun. 1994, 22(11):2121-5.

Landegren et al., "Reading bits of genetic information: methods for single-nucleotide polymorphism analysis," Genome Res., Aug. 1998, 8(8):769-76.

Langdale et al., "A rapid method of gene detection using DNA bound to Sephacryl," Gene, 1985, 36(3):201-210.

Lee et al., "Fluorescent in situ sequencing (FISSEQ) of RNA for gene expression profiling in intact cells and tissues," Nature Protocols, 2015, 10(3):442-458.

Leriche et al., "Cleavable linkers in chemical biology," Bioorganic & Medicinal Chemistry, 2012, 20:571-582.

Levene et al., "Zero-Mode Waveguides for Single-Molecule Analysis at High Concentrations," Science, 2003, 299:682-686.

Li et al., "DNA molecules and configurations in a solid-state nanopore microscope," Nat Mater., Sep. 2003, 2(9):611-5.

(56) References Cited

OTHER PUBLICATIONS

Lin et al., "Microfluidic cell trap array for controlled positioning of single cells on adhesive micropatterns," Lab Chip, Feb. 2013, 13(4):714-721.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Lizardi et al., "Mutation detection and single-molecule counting using isothermal rolling-circle amplification," Nat. Genet., 1998, 19(3):225-232.
Lu et al., "A microfluidic electroporation device for cell lysis," Lab Chip., Jan. 2005, 5(1):23-29.
Lundberg et al., "Multiplexed homogeneous proximity ligation assays for high-throughput protein biomarker research in serological material," Mol Cell Proteomics, 2011, 10(4):M110.004978, 11 pages.
Lundquist et al., "Parallel confocal detection of single molecules in real time," Opt. Lett., 2008, 33:1026-1028.
MacBeath et al., "Printing proteins as microarrays for high-throughput function determination," Science, Sep. 2000, 289(5485):1760-1763.
Marx, "Method of the Year: spatially resolved transcriptomics," Nature Methods, 2021, 18(1):9-14.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Mizusawa et al., "A bacteriophage lambda vector for cloning with BamHI and Sau3A," Gene, 1982, 20(3):317-322.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Nikiforov et al., "The use of 96-well polystyrene plates for DNA hybridization-based assays: an evaluation of different approaches to oligonucleotide immobilization," Anal Biochem, May 1995, 227(1):201-9.
Nowak, "Entering the Postgenome Era," Science, 1995, 270(5235):368-71.
PCT International Preliminary Report on Patentability in International Appln. No. PCT/US2021/050929, dated Mar. 21, 2023, 19 pages.
PCT International Search Report and Written Opinion in International Appln. No. PCT/US2021/050929, dated Feb. 3, 2022, 26 pages.
PCT Invitation to Pay Additional Fees in International Appln. No. PCT/US2021/050929, dated Jan. 5, 2022, 25 pages.
Pemov et al., "DNA analysis with multiplex microarray-enhanced PCR," Nucl. Acids Res., Jan. 2005, 33(2):e11, 9 pages.
Perler et al., "Intervening sequences in an Archaea DNA polymerase gene," Proc Natl Acad Sci USA, Jun. 1992, 89(12):5577-5581.
Petterson et al., "Generations of sequencing technologies," Genomics, 2009, 93(2):105-111.
Polsky-Cynkin et al., "Use of DNA immobilized on plastic and agarose supports to detect DNA by sandwich hybridization," Clin. Chem., 1985, 31(9):1438-1443.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Rountenberg et al., "Microfluidic probe: a new tool for integrating microfluidic environments and electronic wafer-orobina," Lab Chip, Oct. 2009, 10: 123-127.
Salmén et al., "Barcoded solid-phase RNA capture for Spatial Transcriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Shalon et al., "A Dna microarray system for analyzing complex DNA samples using two-color fluorescent probe hybridization," Genome Res., Jul. 1996, 6(7):639-45.
Soni and Meller, "Progress toward ultrafast DNA sequencing using solid-state nanopores," Clin Chem., 2007, 53:1996-2001.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Sun et al., "Statistical Analysis of Spatial Expression Pattern for Spatially Resolved Transcriptomic Studies," Nature Methods, Jan. 27, 2020, 17(2): 193-200.
Svensson et al., "SpatialDE: identification of spatially variable genes," Nature Methods, May 2018, 15:343-346, 15 pages.
Takei et al., "Integrated Spatial Genomics Reveals Global Architecture of Single Nuclei," Nature, Jan. 27, 2021, 590(7845):344-350, 53 pages.
Taylor et al., "Microfluidic local perfusion chambers for the visualization and manipulation of synapses," Neuron., Apr. 2010, 66(1):57-68, 25 pages.
Thomas et al., "A chamber for the perfusion of in vitro tissue with multiple solutions," J. Neurophysiol., Jul. 2013, 110:269-277.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Toy et al., "A Simple Plastic Perfusion Chamber for Continuous Maintenance and Cinematography of Tissue Cultures," Experimental Cell Research, 1958, 14:97-103.

(56) References Cited

OTHER PUBLICATIONS

Trejo et al., "Extraction-free whole transcriptome gene expression analysis of FFPE sections and histology-directed subareas of tissue," PLoS ONE, Feb. 2019, 14(2):e0212031, 22 pages.
Twyman et al., "Techniques Patents for SNP Genotyping," Pharmacogenomics, Jan. 2003, 4(1):67-79.
Valley et al., "Optoelectronic tweezers as a tool for parallel single-cell manipulation and stimulation," IEEE Trans Biomed Circuits Syst., Dec. 2009, 3(6):424-31.
Van Gelder et al., "Amplified RNA synthesized from limited quantities of heterogeneous cDNA," Proc. Natl. Acad. Sci. USA, 1990, 87(5):1663-1667.
Vasiliskov et al., "Fabrication of microarray of gel-immobilized compounds on a chip by copolymerization," Biotechniques, Sep. 1999, 27(3):592-606.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vogelstein et al., "Digital PCR," Proceedings of the National Academy of Sciences, Aug. 1999, 96(16):9236-9241.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "High-fidelity mRNA amplification for gene profiling," Nature Biotechnology, Apr. 2000, 18(4):457-459.
Wang et al., "Imaging-based pooled CRISPR screening reveals regulators of lncRNA localization," Proc Natl Acad Sci USA, May 2019, 116(22):10842-10851.
Wheeler et al., "Microfluidic device for single-cell analysis," Analytical Chemistry, Jul. 2003, 75(14):3581-3586.
Worthington et al., "Cloning of random oligonucleotides to create single-insert plasmid libraries," Anal Biochem, 2001, 294(2):169-175.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Yershov et al., "DNA analysis and diagnostics on oligonucleotide microchips," Proc. Natl. Acad. Sci. USA, May 1996, 93(10):4913-4918.
Yoda et al., "Site-specific gene expression analysis using an automated tissue micro-dissection punching system," Sci Rep., Jun. 2017, 7(1):4325, 11 pages.
Zhu et al., "Reverse transcriptase template switching: a SMART approach for full-length cDNA library construction," Biotechniques, Apr. 2001, 30(4):892-897.

* cited by examiner

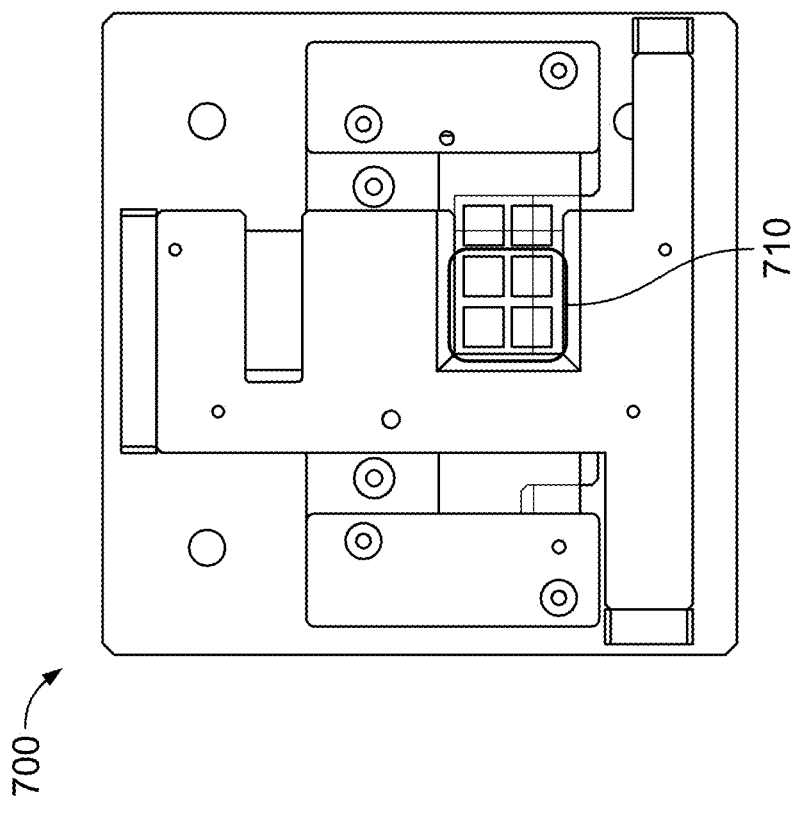
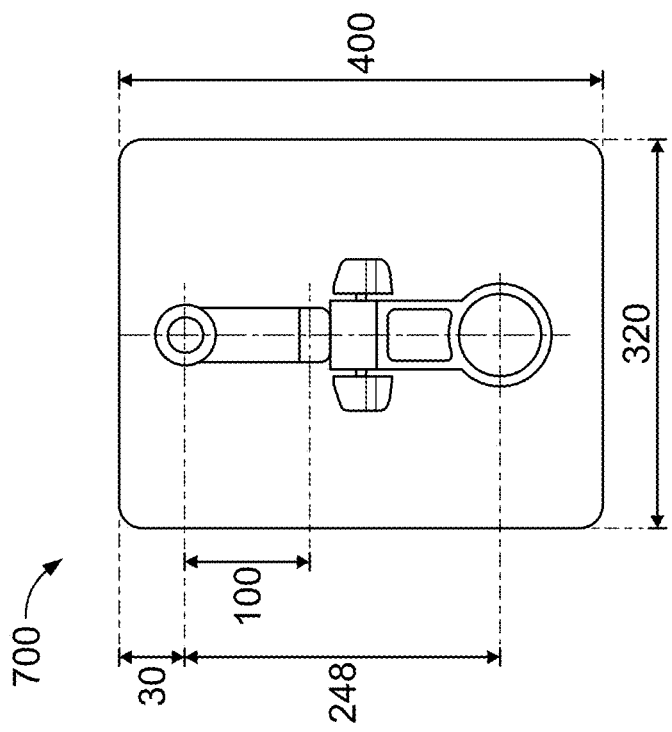
FIG. 7

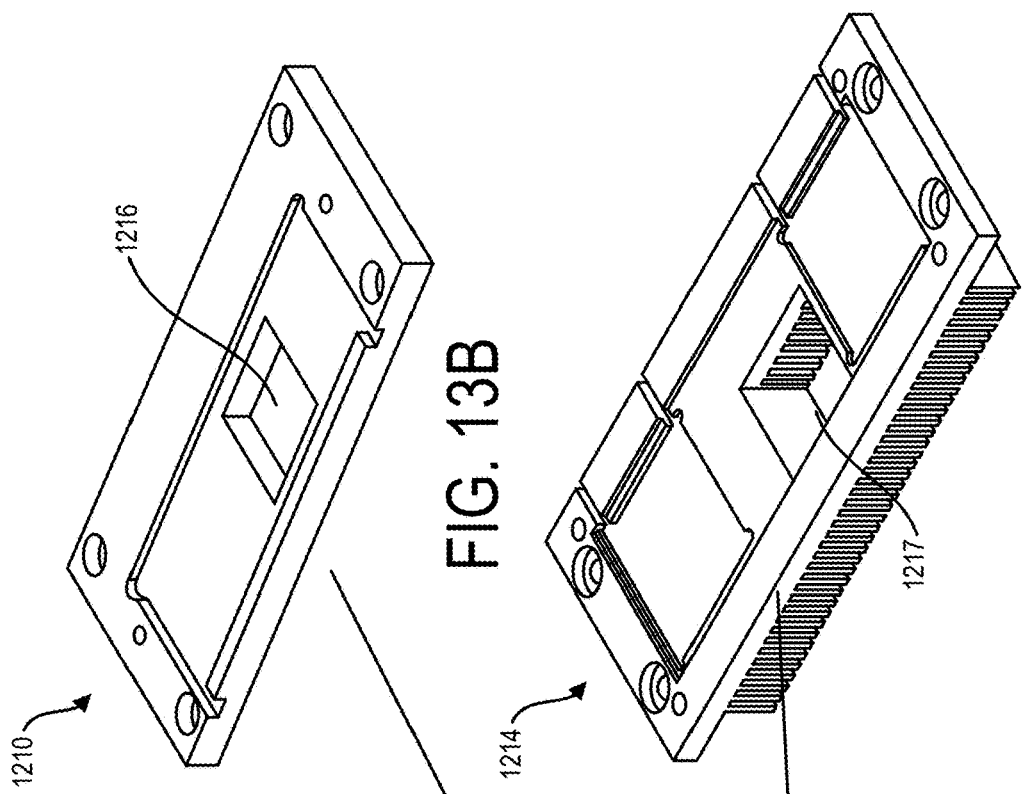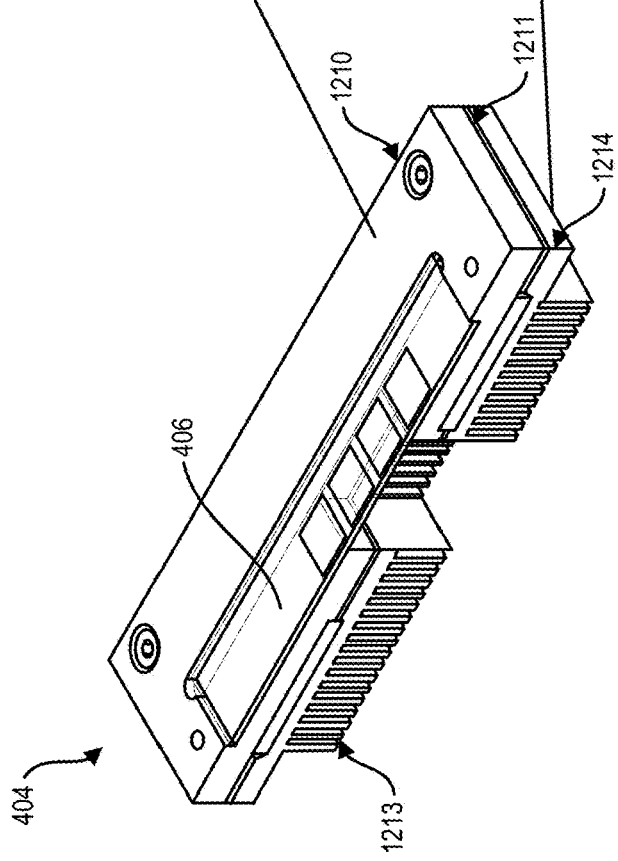

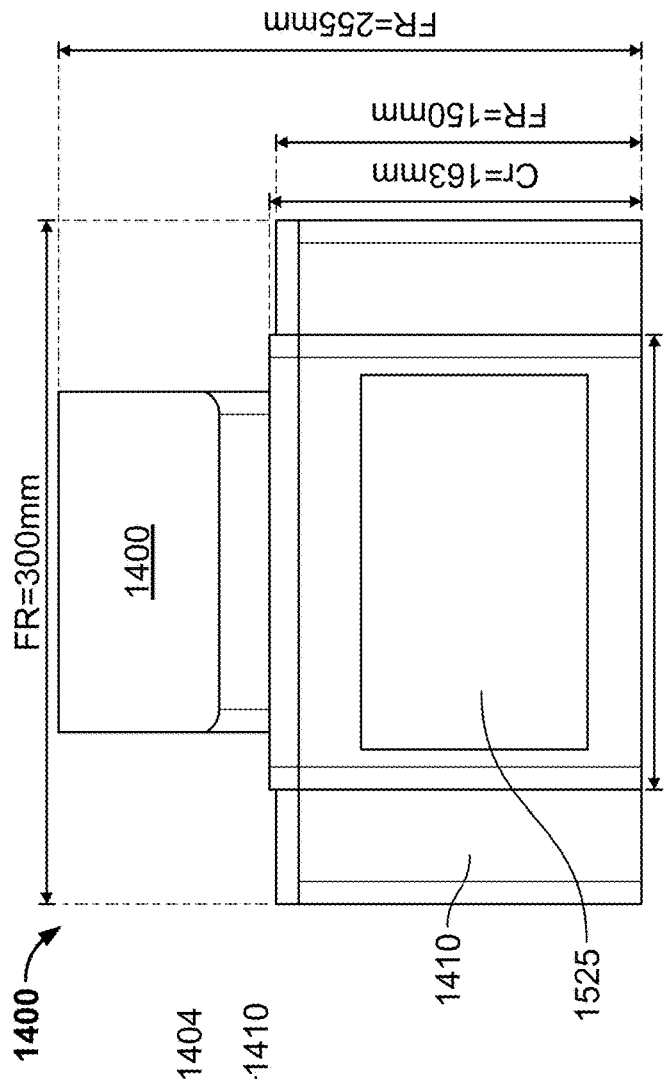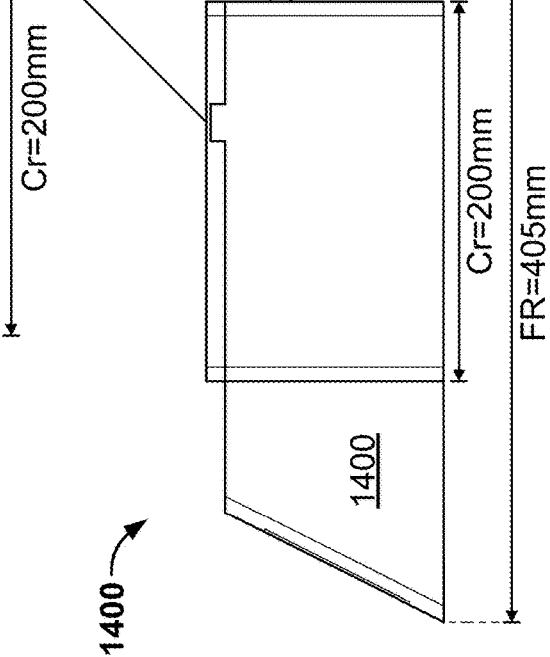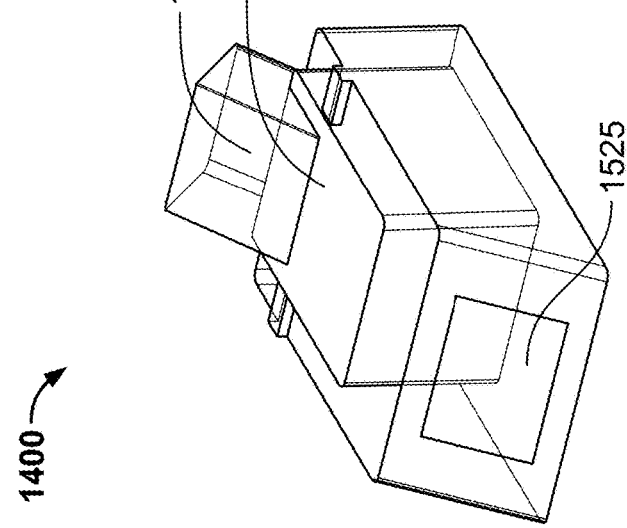
FIG. 16B
FIG. 16C
FIG. 16A

2100

FIG. 33A    FIG. 33B
FIG. 33C    FIG. 33D    FIG. 33E

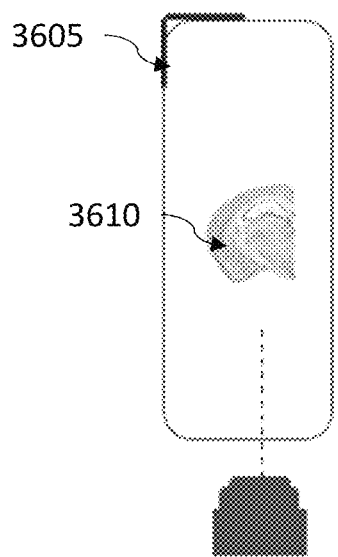
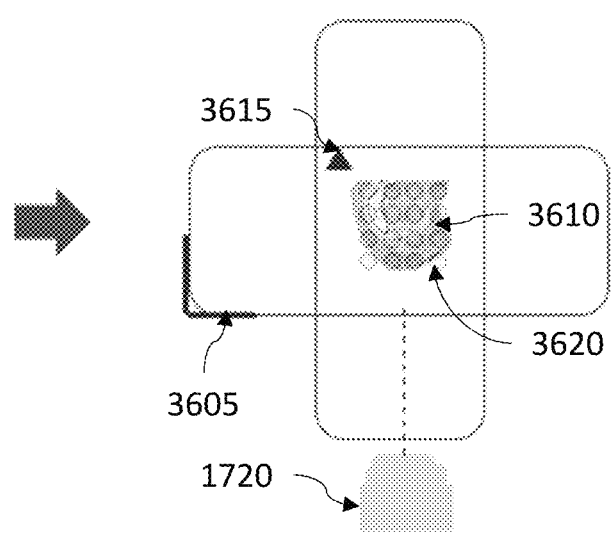
FIG. 36A   FIG. 36B

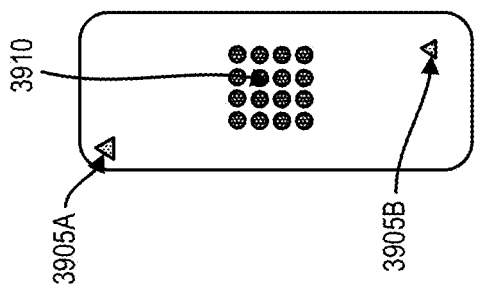
FIG. 39C
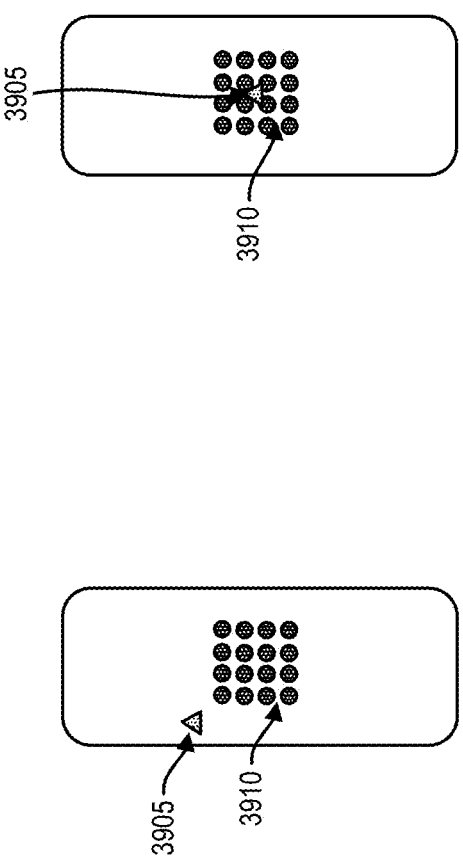
FIG. 39B
FIG. 39A
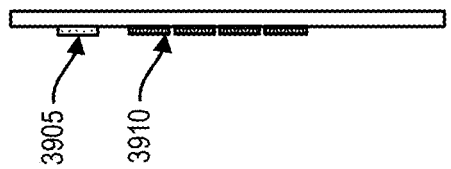
FIG. 39E
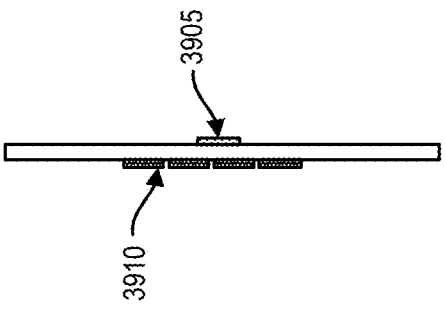
FIG. 39D

4100

4110 — Receiving sample image data comprising a sample image of a sample and a sample fiducial, the sample image having a first resolution 4120 — Receiving instrument fiducial data comprising an instrument fiducial image of a first instrument fiducial and a second instrument fiducial 4130 — Receiving array image data comprising an array image having a second resolution lower than the first resolution of the sample image, the array image comprising the array and an array fiducial overlaid atop the sample and the sample fiducial 4140 — Registering the instrument fiducial image to the array image by aligning the first instrument fiducial and the array fiducial 4150 — Registering the instrument fiducial image to the sample image by aligning the second instrument fiducial and the sample fiducial 4160 — Generating an aligned image based on registering the instrument fiducial to the sample image and registering the instrument fiducial image to the array image 4170 — Providing the aligned image

FIG. 41

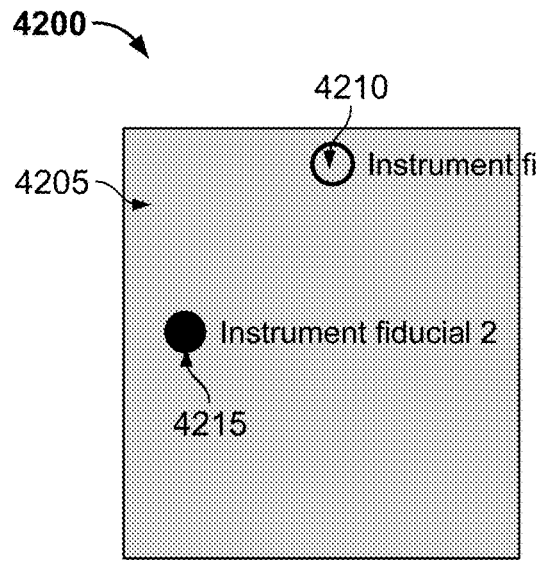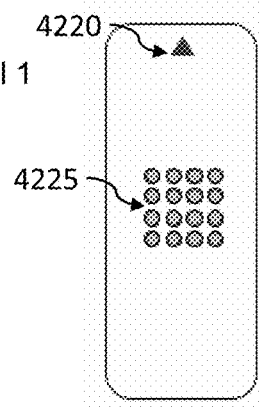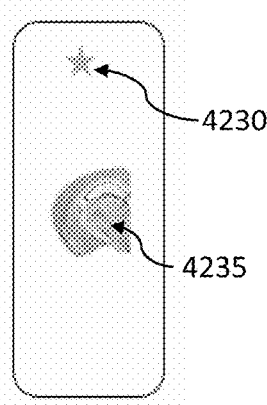
FIG. 42A  FIG. 42B  FIG. 42C
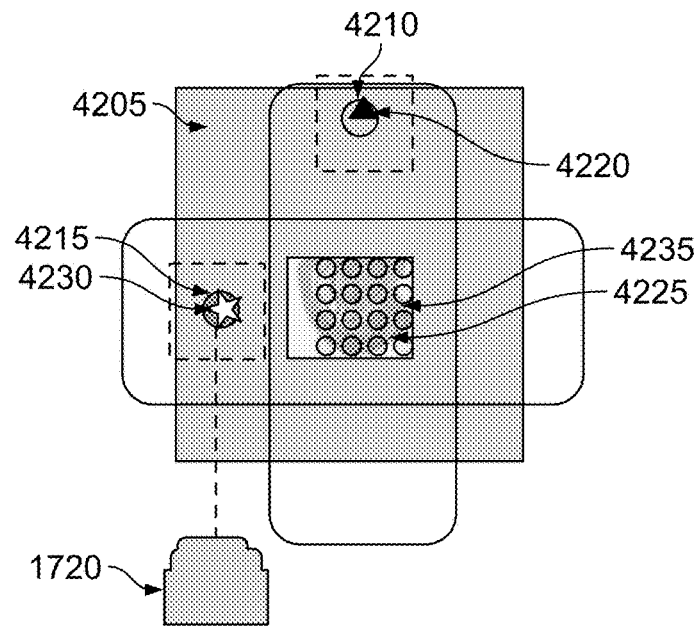
FIG. 42D

4600

4610 — Determining a plurality of array portion images in the array image

4620 — Registering one or more array portion images in the array image to a corresponding portion of the sample in the sample image

FIG. 46

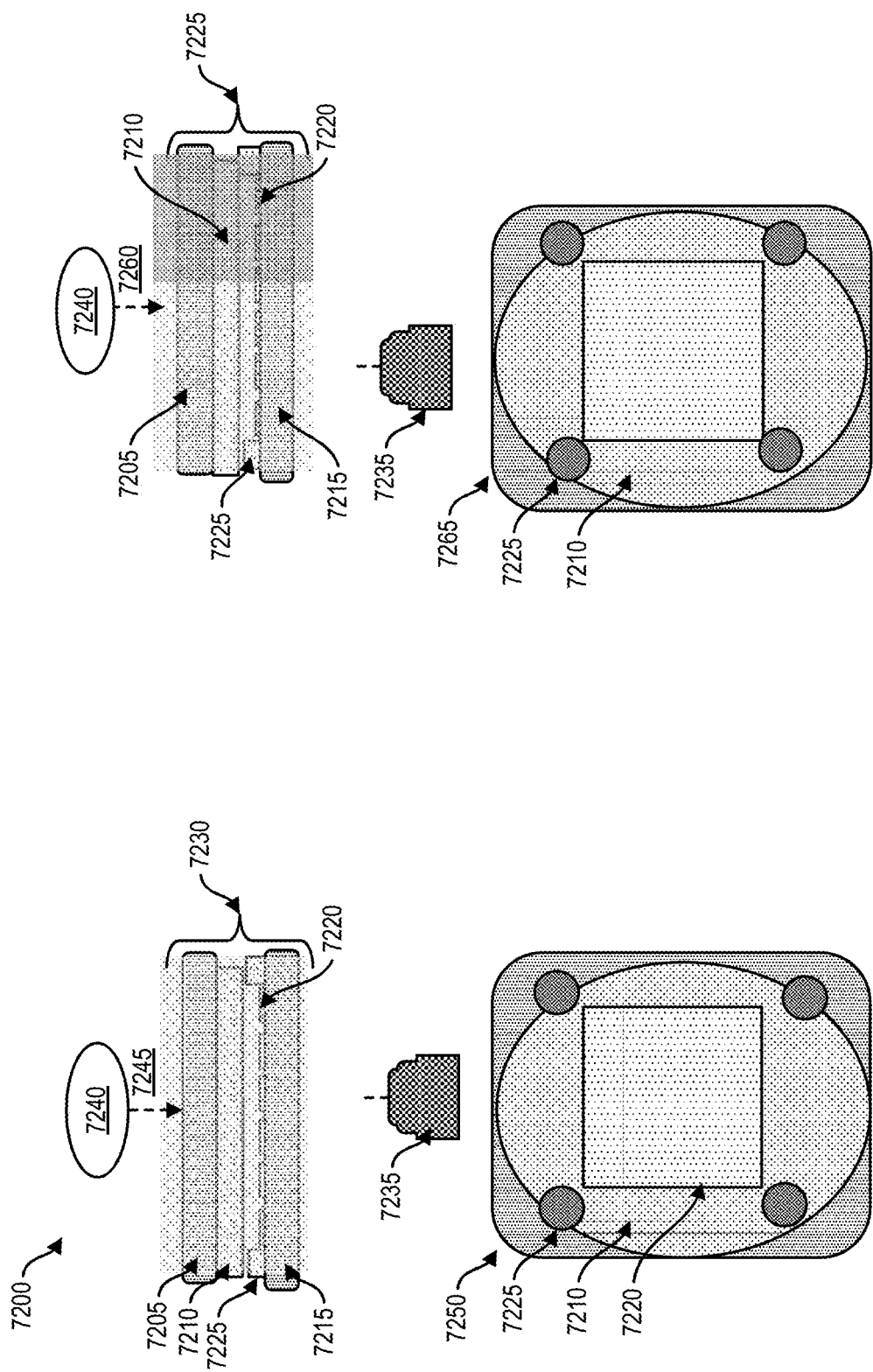

SAMPLE HANDLING APPARATUS AND IMAGE REGISTRATION METHODS

CROSS-REFERENCE TO RELATED APPLICATIONS

This application is a continuation of and claims priority to WO Application No. PCT/US2021/050929 filed on Sep. 17, 2021, which claims the benefit of U.S. Provisional Patent Application No. 63/080,547 filed Sep. 18, 2020 and U.S. Provisional Patent Application No. 63/155,173 filed Mar. 1, 2021, the contents of each of which are hereby incorporated by reference in their entirety.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provide a lot of analyte data for single cells, but fail to provide information regarding the position of the single cell in a parent biological sample (e.g., tissue sample).

Analytes from a biological sample can be captured onto a reagent array while preserving spatial context of the analytes. The captured analytes can be used to generate a sequence data that can be mapped to an image of the biological sample. There exists a need for improved methods and systems for registering the image data with the sequence data.

Image data can be utilized to assess the spatial heterogeneity of analyte levels for cells and tissues. To accurately determine the degree of spatial heterogeneity and transcriptomic activity within a cell or tissue, image data associated with a sample of a cell or a tissue can be aligned with image data associated with a reagent array configured to capture analytes from the cell or tissue sample. The alignment can be determined using image registration to provide accurate spatial mapping of the transcriptomic activity within a sample. Various methods of performing image registration on biological samples are described herein.

SUMMARY

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Analytes within a biological sample are generally released through disruption (e.g., permeabilization) of the biological sample. Various methods of disrupting a biological sample are known, including permeabilization of the cell membrane of the biological sample. Described herein are methods of delivering a fluid to the biological sample, systems for sample analysis, and sample alignment methods.

In one aspect, a method for aligning a sample to an array is provided. The method includes receiving, by a data processor, sample image data comprising a sample image of the sample. The sample image can have a first resolution. The method further includes receiving, by the data processor, array image data including an array image including an overlay of an array with the sample and an array fiducial. The array image can have a second resolution lower than the first resolution of the sample image. The method also includes registering, by the data processor, the sample image to the array image by aligning the sample image and the array image. The method further includes generating, by the data processor, an aligned image based on the registering. The aligned image can include an overlay of the sample image with the array. The method also includes providing, by the data processor, the aligned image.

In some variations, one or more features disclosed herein including the following features may optionally be included in any feasible combination. For example, the sample image data can be received from a user or from a computing device remote from the data processor. The aligned image can include the array fiducial aligned with the sample. The sample image can include a sample fiducial delineating a sample area into which the sample is placed.

In some embodiments, the sample image can be of the sample on a first substrate. In some embodiments, the sample can be located on a first substrate and the array can be located on a second substrate. The array and the array fiducial can be located on a first side of a second substrate. In some embodiments, the array fiducial can be located on the second substrate adjacent to, within, or distanced from a reagent configured on the second substrate. In some embodiments, the array image can include a portion of the array overlaid top a portion of the sample based on allocation of the array fiducial.

In some embodiments, the sample image can include a plurality of sample portion images and each sample portion image can be associated with a portion of the sample. In some embodiments, a size of each sample portion image can be less than a size of a single field of view of the sample image.

In some embodiments, registering the sample image to the array image can include cropping, by the data processor, the sample image to determine the plurality of sample portion images and registering one or more sample portion images in the sample image to a corresponding portion of the sample in the array image. In some embodiments, registering the one or more sample portion images in the sample image to the corresponding portion of the sample in the array image can be performed after registering the sample image to the array image. In some embodiments, the array image can include a plurality of array portion images. Each array portion image can be associated with a portion of the array. A size of each array portion image can be less than a size of a single field of view of the array image.

In some embodiments, the registering can include determining, by the data processor, the plurality of array portion images in the array image and registering, by the data processor, one or more array portion images in the array image to a corresponding portion of the sample in the sample image.

In another aspect, a system for aligning a sample to an array is provided. The system can include a sample holder including a first retaining mechanism configured to retain a first substrate within the first retaining mechanism. The first substrate can include a sample. The sample holder can also include a second retaining mechanism configured to retain a second substrate received within the second retaining mechanism. The second substrate can include an array. The sample holder can be configured to adjust a location of the first substrate relative to the second substrate to cause all or a portion of the sample to be aligned with the array. The system can further include a microscope operatively coupled to the sample holder. The microscope can be configured to view the first substrate and the second substrate within the sample holder and can acquire image data associated with the sample and/or the array. The system can also include a first computing device communicatively coupled to the microscope and to the sample holder. The computing device can include a display, a data processor, and a non-transitory computer readable storage medium storing computer readable and executable instructions, which when executed can cause the data processor to perform operations including receiving sample image data comprising a sample image of the sample. The sample image can have a first resolution. The operations can also include receiving array image data including an array image having a second resolution lower than the first resolution of the sample image. The array image can include the array and an array fiducial overlaid atop the sample. The operations can further include registering the sample image to the array image by aligning the sample image and the array image. The operations can also include generating an aligned image based on the registering. The aligned image can include the sample aligned with the array and providing the aligned image.

In some variations, one or more features disclosed herein including the following features may optionally be included in any feasible combination. For example, the sample image data can be received from a user or from a computing device remote from the data processor. The aligned image can further include the array fiducial aligned with the sample. The sample image can further include a sample fiducial delineating a sample area into which the sample can be placed on the first substrate. The sample image can be of the sample on the first substrate.

The array fiducial can be located on the second substrate adjacent to, within, or distanced from a reagent configured on the second substrate. The sample image can include a plurality of sample portion images. Each sample portion image can be associated with a portion of the sample. A size of each sample portion image can be less than a size of a single field of view of the sample image.

In some embodiments, the registering can include cropping, by the data processor, the sample image to determine the plurality of sample portion images and registering one or more sample portion images in the sample image to a corresponding portion of the sample in the array image.

In some embodiments, the array image can include a plurality of array portion images. Each array portion image can be associated with a portion of the array. A size of each array portion image can be less than a size of a single field of view of the array image. In some embodiments, the registering can include determining the plurality of array portion images in the array image and registering one or more array portion images in the array image to a corresponding portion of the sample in the sample image.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIG. 7 depicts a diagram of a close-up bottom view of the first member coupled to the second member and an overlap area where the first substrate overlaps with the second substrate in accordance with some example implementations.

FIG. 13A is a perspective cross-section view of an example first member in accordance with some example implementations.

FIG. 13B is a perspective view of the example holder plate of FIG. 13A in accordance with some example implementations.

FIG. 13C is a perspective view of the example heat sink block of FIG. 13A in accordance with some example implementations.

FIG. 16A is a perspective view of the example sample handling apparatus in accordance with some example implementations.

FIG. 16B is a front view of the example sample handling apparatus showing example dimensions of the apparatus in accordance with some example implementations.

FIG. 16C is a side view of the example sample handling apparatus showing example dimensions of the apparatus in accordance with some example implementations.

FIGS. 33A-33E depict a workflow for registering a sample image to an array image according to some implementations of the current subject matter.

FIGS. 36A-36B depict a workflow for registering a sample image to an array image based on aligning an edge of a sample substrate and an array fiducial according to some implementations of the current subject matter.

FIGS. 39A-39E are diagrams illustrating embodiments of configurations of array fiducials according to some implementations of the current subject matter.

FIG. 41 is a process flow diagram illustrating an example process for generating an aligned image based on registering a sample image to an array image using multiple instrument fiducials according to some implementations of the current subject matter.

FIGS. 42A-42D depict a workflow for generating an aligned image based on registering a sample image to an array image using multiple instrument fiducials according to some implementations of the current subject matter.

FIG. 46 is a process flow diagram illustrating an example process for registering array portion images of an array image to corresponding portions of the sample in a sample image according to some implementations of the current subject matter.

FIGS. 72A-72B depict a workflow for detecting array fiducials overlapped with a sample in image data acquired and registered at multiple illuminations using a sample handling apparatus including spacers in accordance with some example implementations.

DETAILED DESCRIPTION

I. Introduction

Figure 1:
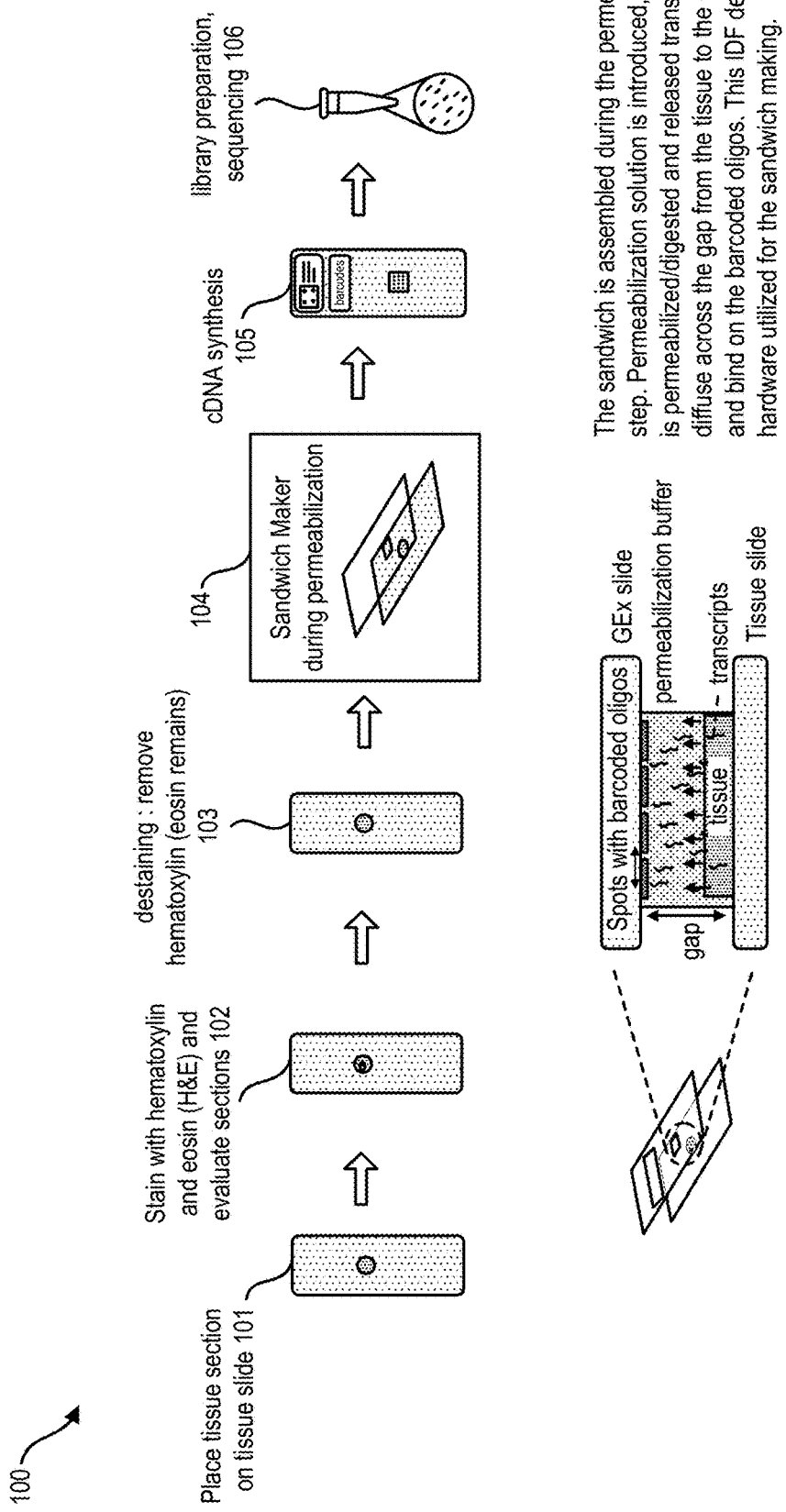
FIG. 1 shows an exemplary spatial analysis workflow in accordance with some example implementations.

This disclosure describes apparatus, systems, methods, and compositions for spatial analysis of biological samples. This section describes certain general terminology, analytes, sample types, and preparative steps that are referred to in later sections of the disclosure. For example, the terms and phrases: spatial analysis, barcode, nucleic acid, nucleotide, probe, target, oligonucleotide, polynucleotide, subject, genome, adaptor, adapter, tag, hybridizing, hybridize, annealing, anneal, primer, primer extension, proximity ligation, nucleic acid extension, polymerase chain reaction (PCR) amplification, antibody, affinity group, label, detectable label, optical label, template switching oligonucleotide, splint oligonucleotide, analytes, biological samples, general spatial array-based analytical methodology, spatial analysis methods, immunohistochemistry and immunofluorescence, capture probes, substrates, arrays, analyte capture, partitioning, analysis of captured analytes, quality control, multiplexing, and/or the like are described in more detail in PCT Patent Application Publication No. WO2020/123320, the entire contents of which are incorporated herein by reference.

Tissues and cells can be obtained from any source. For example, tissues and cells can be obtained from single-cell or multicellular organisms (e.g., a mammal). The relationship between cells and their relative locations within a tissue sample may be critical to understanding disease pathology. Spatialomic (e.g., spatial transcriptomic) technology may allow scientists to measure all the gene activity in a tissue sample and map where the activity is occurring. This technology and embodiments described herein may lead to new discoveries that may prove instrumental in helping scientists gain a better understanding of biological processes and disease.

Tissues and cells obtained from a mammal, e.g., a human, often have varied analyte levels (e.g., gene and/or protein expression) which can result in differences in cell morphology and/or function. The position of a cell or a subset of cells (e.g., neighboring cells and/or non-neighboring cells) within a tissue can affect, e.g., the cell's fate, behavior, morphology, and signaling and cross-talk with other cells in the tissue. Information regarding the differences in analyte levels (gene and/or protein expression) within different cells in a tissue of a mammal can also help physicians select or administer a treatment that will be effective and can allow researchers to identify and elucidate differences in cell morphology and/or cell function in the single-cell or multicellular organisms (e.g., a mammal) based on the detected differences in analyte levels within different cells in the tissue. Differences in analyte levels within different cells in a tissue of a mammal can also provide information on how tissues (e.g., healthy and diseased tissues) function and/or develop. Differences in analyte levels within different cells in a tissue of a mammal can also provide information of different mechanisms of disease pathogenesis in a tissue and mechanism of action of a therapeutic treatment within a tissue.

The spatial analysis methodologies herein provide for the detection of differences in an analyte level (e.g., gene and/or protein expression) within different cells in a tissue of a mammal or within a single cell from a mammal. For example, spatial analysis methodologies can be used to detect the differences in analyte levels (e.g., gene and/or protein expression) within different cells in histological slide samples, the data from which can be reassembled to generate a three-dimensional map of analyte levels (e.g., gene and/or protein expression) of a tissue sample obtained from a mammal, e.g., with a degree of spatial resolution (e.g., single-cell resolution).

Spatial heterogeneity in developing systems has typically been studied via RNA hybridization, immunohistochemistry, fluorescent reporters, or purification or induction of pre-defined subpopulations and subsequent genomic profiling (e.g., RNA-seq). Such approaches, however, rely on a relatively small set of pre-defined markers, therefore introducing selection bias that limits discovery. These prior approaches also rely on a priori knowledge. RNA assays traditionally relied on staining for a limited number of RNA species. In contrast, single-cell RNA-sequencing allows for deep profiling of cellular gene expression (including non-coding RNA), but the established methods separate cells from their native spatial context.

Spatial analysis methodologies described herein provide a vast amount of analyte level and/or expression data for a variety of multiple analytes within a sample at high spatial resolution, e.g., while retaining the native spatial context.

The binding of an analyte to a capture probe can be detected using a number of different methods, e.g., nucleic acid sequencing, fluorophore detection, nucleic acid amplification, detection of nucleic acid ligation, and/or detection of nucleic acid cleavage products. In some examples, the detection is used to associate a specific spatial barcode with a specific analyte produced by and/or present in a cell (e.g., a mammalian cell).

Capture probes can be, e.g., attached to a surface, e.g., a solid array, a bead, or a coverslip. In some examples, capture probes are not attached to a surface. In some examples, capture probes can be encapsulated within, embedded within, or layered on a surface of a permeable composition (e.g., any of the substrates described herein).

Non-limiting aspects of spatial analysis methodologies are described in WO 2011/127099, WO 2014/210233, WO 2014/210225, WO 2016/162309, WO 2018/091676, WO 2012/140224, WO 2014/060483, U.S. Pat. Nos. 10,002,316, 9,727,810, U.S. Patent Application Publication No. 2017/0016053, Rodrigues et al., *Science* 363(6434):1463-1467, 2019; WO 2018/045186, Lee et al., *Nat. Protoc.* 10(3):442-458, 2015; WO 2016/007839, WO 2018/045181, WO 2014/163886, Trejo et al., *PLoS ONE* 14(2):e0212031, 2019, U.S. Patent Application Publication No. 2018/0245142, Chen et al., *Science* 348(6233):aaa6090, 2015, Gao et al., *BMC Biol.* 15:50, 2017, WO 2017/144338, WO 2018/107054, WO 2017/222453, WO 2019/068880, WO 2011/094669, U.S. Pat. Nos. 7,709,198, 8,604,182, 8,951,726, 9,783,841, 10,041,949, WO 2016/057552, WO 2017/147483, WO 2018/022809, WO 2016/166128, WO 2017/027367, WO 2017/027368, WO 2018/136856, WO 2019/075091, U.S. Pat. No. 10,059,990, WO 2018/057999, WO 2015/161173, and Gupta et al., *Nature Biotechnol.* 36:1197-1202, 2018, the entire contents of which are incorporated herein by reference and can be used herein in any combination. Further non-limiting aspects of spatial analysis methodologies are described herein.

Embodiments described herein may map the spatial gene expression of complex tissue samples (e.g., on tissue slides) with slides (e.g., gene expression slides) that utilize analyte and/or mRNA transcript capture and spatial barcoding technology for library preparation. A tissue (e.g., fresh-frozen, formalin fixed paraffin-embedded (FFPE), or the like may be sectioned and placed in proximity to a slide with thousands of barcoded spots, each containing millions of capture oligonucleotides with spatial barcodes unique to that spot. Once tissue sections are fixed, stained, and permeabilized, they release mRNA which binds to capture oligos from a proximal location on the tissue. A reverse transcription reaction may occur while the tissue is still in place, generating a cDNA library that incorporates the spatial barcodes and preserves spatial information. Barcoded cDNA libraries are mapped back to a specific spot on a capture area of the barcoded spots. This gene expression data may be subsequently layered over a high-resolution microscope image of the tissue section, making it possible to visualize the expression of any mRNA, or combination of mRNAs, within the morphology of the tissue in a spatially-resolved manner.

FIG. 1 shows an exemplary spatial analysis workflow 100 in accordance with some example implementations. The workflow 100 includes preparing a biological sample on a slide (e.g., a pathology slide) 101, fixing the sample, and/or staining 102 the biological sample for imaging. The stained sample can be then imaged on the slide using brightfield (to image the sample hematoxylin and eosin stain) and/or fluorescence (to image features) modalities. The imaging may include high-resolution imaging (e.g., images that can disclose pathological and histological features). Optionally, at 103, the sample can be destained prior to permeabilization. At 104, a permeabilization solution may be applied to biological sample while the pathology slide is aligned in a "sandwich" configuration with a slide comprising a spatially barcoded array (e.g., on an array slide). The permeabilization solution allowing the analyte and/or mRNA transcripts to migrate away from the sample, diffuse across the permeabilization solution, and toward the array. The analyte and/or mRNA transcripts interacts with a capture probe on the slide.

At 105, the capture probes can be optionally cleaved from the array, and the captured analytes can be spatially-barcoded by performing a reverse transcriptase first strand cDNA reaction. A first strand cDNA reaction can be optionally performed using template switching oligonucleotides. At 106, the first strand cDNA can be amplified (e.g., using polymerase chain reaction (PCR)), where the forward and reverse primers flank the spatial barcode and analyte regions of interest, generating a library associated with a particular spatial barcode. In some embodiments, the cDNA comprises a sequencing by synthesis (SBS) primer sequence. The library amplicons may be sequenced and analyzed to decode spatial information.

Figure 2:
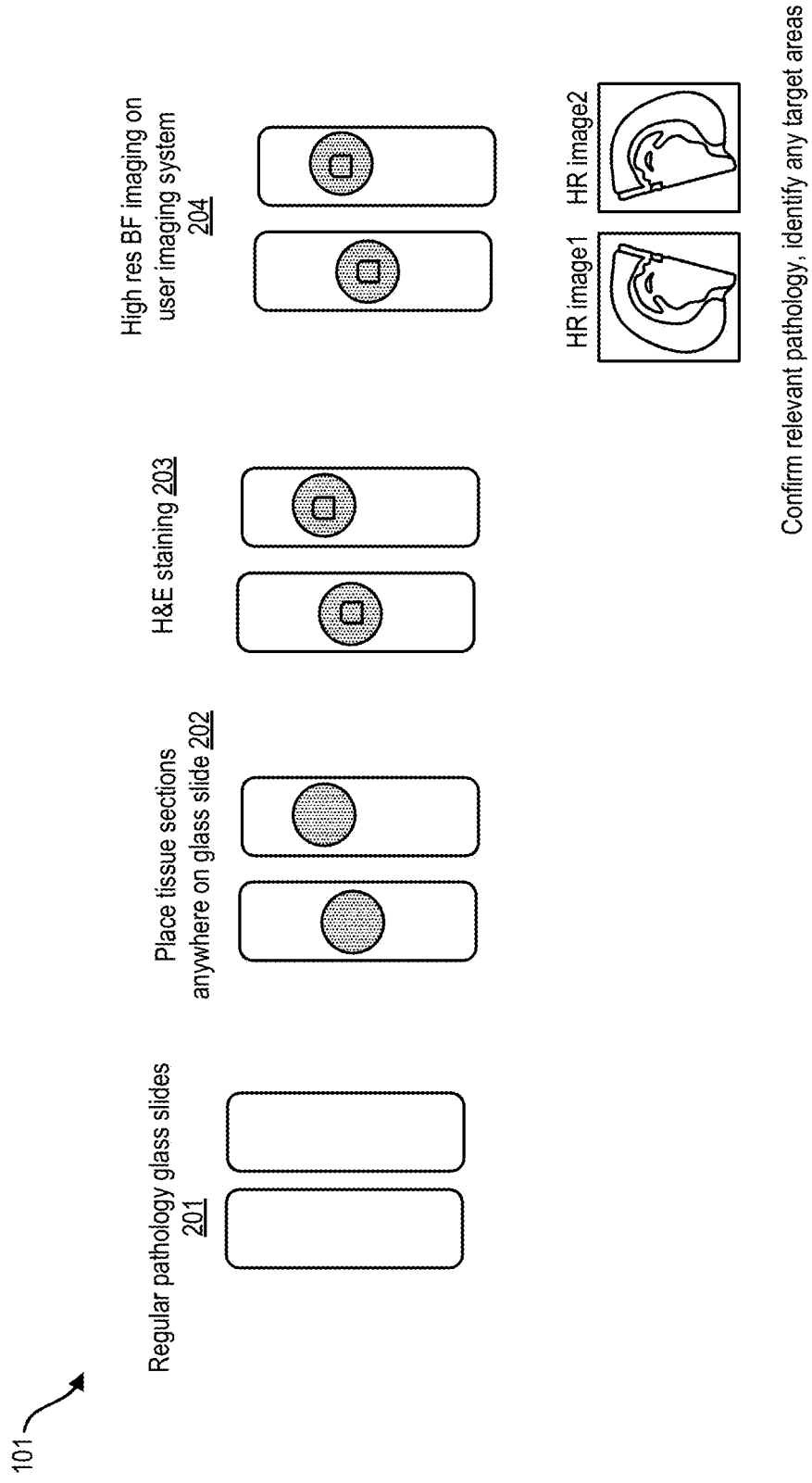
FIG. 2 depicts an example workflow for preparing the biological sample on a slide in accordance with some example implementations.

FIG. 2 depicts an example workflow 101 for preparing the biological sample on the slide (e.g., a pathology slide) in accordance with some example implementations. Preparing the biological sample on the slide may include selecting a pathology glass slide 201. The workflow 101 further includes placing tissue sections on the glass slide 202. Placing tissue sections on the glass slide may include placing the tissue anywhere on the glass slide including placing the tissue on or in relation to a fiducial disposed on the glass slide. The fiducial may include any marking to aid in placement of the tissue on the slide and/or aid in the alignment of the tissue slide relative to the gene expression slide. The workflow 101 further includes staining the tissue with hematoxylin and eosin 203 or another staining agent or method. The workflow 101 further includes imaging the tissue 204 on the slide using brightfield (e.g., to image the sample hematoxylin and eosin stain) or another imaging technique. The imaging may include high-resolution imaging on a user imaging system. The imaging may also include imaging performed using an image capture device configured in the sample handling apparatuses described herein. In some embodiments, the imaging performed using the image capture device can include low-resolution or high-resolution imaging. The imaging may allow the user to confirm the relevant pathology and/or identify any target areas for analysis. The imaging can be performed in one or more image capture modes using the image capture device and sample handling apparatus described herein.

Embodiments described herein relating to preparing the biological sample on the slide may beneficially allow a user to confirm pathology or relevant regions on a tissue section, to confirm selection of best or undamaged tissue sections for analysis, to improve array-tissue alignment by allowing placement anywhere on the pathology slide. Further, workflows for preparing the biological sample on the slide may empower user or scientists to choose what to sequence (e.g., what tissue section(s) to sequence).

Figure 3:
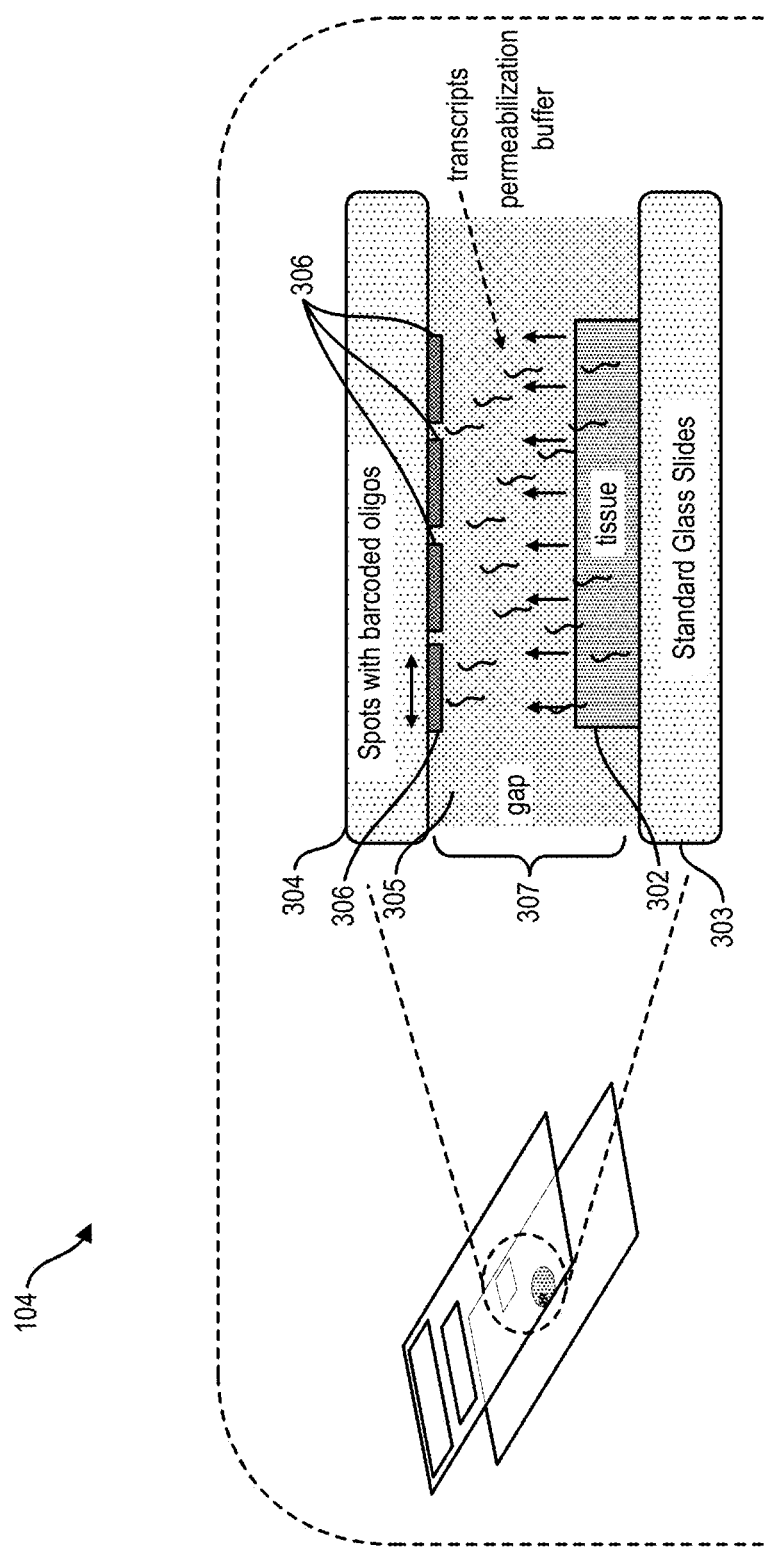
FIG. 3 is a schematic diagram depicting an exemplary permeabilization solution interaction between a tissue slide and a gene expression slide in a sandwich configuration in accordance with some example implementations.

FIG. 3 is a schematic diagram depicting an exemplary sandwiching process (e.g., permeabilization solution interaction) 104 between a first substrate comprising a biological sample such as a tissue section (e.g., a tissue slide) and a second substrate comprising a spatially barcoded array, (e.g., a gene expression slide) in a sandwich configuration in accordance with some example implementations. During an exemplary sandwiching process, the first substrate is aligned with the second substrate, such that at least a portion of the biological sample is aligned with at least a portion of the array (e.g., aligned in a sandwich configuration). In the exemplary configuration, a sample (a tissue or biological sample) 302 is disposed on the pathology slide 303 and is sandwiched between the pathology slide 303 and a slide 304 (e.g., gene expression slide) that is populated with spatially-barcoded capture probes 306. As shown, the slide 304 is in a superior position to the pathology slide 303. In some embodiments, the pathology slide 303 may be positioned superior to the glass slide 304. When a permeabilization solution 305 is applied to a gap 307 between the pathology slide 303 and the slide 304, the permeabilization solution 305 creates a permeabilization buffer which permeabilizes or digests the sample 302 and the analytes (e.g., mRNA transcripts) 308 of the tissue sample 302 may release, diffuse across the gap 307 toward the capture probes 306, and bind on the capture probes 306. In some embodiments, analyte capture agents that have bound to analytes in the sample (or portions of such analyte capture agents) may release, actively or passively migrate across the gap and bind on the capture probes.

After the analytes (e.g., transcripts) 308 bind on the capture probes 306, an extension reaction (e.g., a reverse transcription reaction) may occur, generating a spatially barcoded library. For example, in the case of mRNA transcripts, reverse transcription may occur, thereby generating a cDNA library associated with a particular spatial barcode. Barcoded cDNA libraries may be mapped back to a specific spot on a capture area of the capture probes 306. This gene expression data may be subsequently layered over a high-resolution microscope image of the tissue section ((e.g., taken at 204 of FIG. 2), making it possible to visualize the expression of any mRNA, or combination of mRNAs, within the morphology of the tissue in a spatially-resolved manner.

In some embodiments, the extension reaction can be performed separately from the sample handling apparatus described herein that is configured to perform the exemplary sandwiching process 104. The sandwich configuration of the sample 302, the pathology slide 303 and the slide 304 may provide advantages over other methods of spatial analysis and/or analyte capture. For example, the sandwich configuration may reduce a burden of users to develop in house tissue sectioning and/or tissue mounting expertise. Further, the sandwich configuration may decouple sample preparation/tissue imaging from the barcoded array (e.g., spatially-barcoded capture probes 306) and enable selection of a particular region of interest of analysis (e.g., for a tissue section larger than the barcoded array). The sandwich configuration also beneficially enables spatial analysis without having to place a tissue section 302 directly on the gene expression slide (e.g., slide 304).

The sandwich configuration described herein further provides the beneficial ability to quality check or select specific sections of tissue prior to committing additional time and resources to the analysis workflow. This can be advantageous to reduce costs and risk or mistakes or issues that can arise during sample preparation. Additionally, the sandwich configuration can enable the ability to select which area of a sample to sequence when a sample section is larger than an array. Another benefit of using the sandwich configuration described herein is the ability to separate fiducial imaging and high-resolution sample imaging. This can enable the separation of expertise required to perform histology workflows and molecular biology workflows and can further enable the assay and the sample to be moved between different laboratories. Additionally, the sandwich configuration described herein can provide great flexibility and more options in sample preparation conditions since there are no oligos on the sample substrate or slide. This can reduce the likelihood a sample may fall off the substrate and can reduce the likelihood that oligos are damaged due to high temperatures or interactions with other reagents during sample preparation. The sandwich configuration described herein can also improve the sensitivity and spatial resolution by vertically confining target molecules within the diffusion distance.

II. Systems for Sample Analysis

The methods described above for analyzing biological samples, such as the sandwich configuration described above, can be implemented using a variety of hardware components. In this section, examples of such components are described. However, it should be understood that in general, the various steps and techniques discussed herein can be performed using a variety of different devices and system components, not all of which are expressly set forth.

Figure 4:
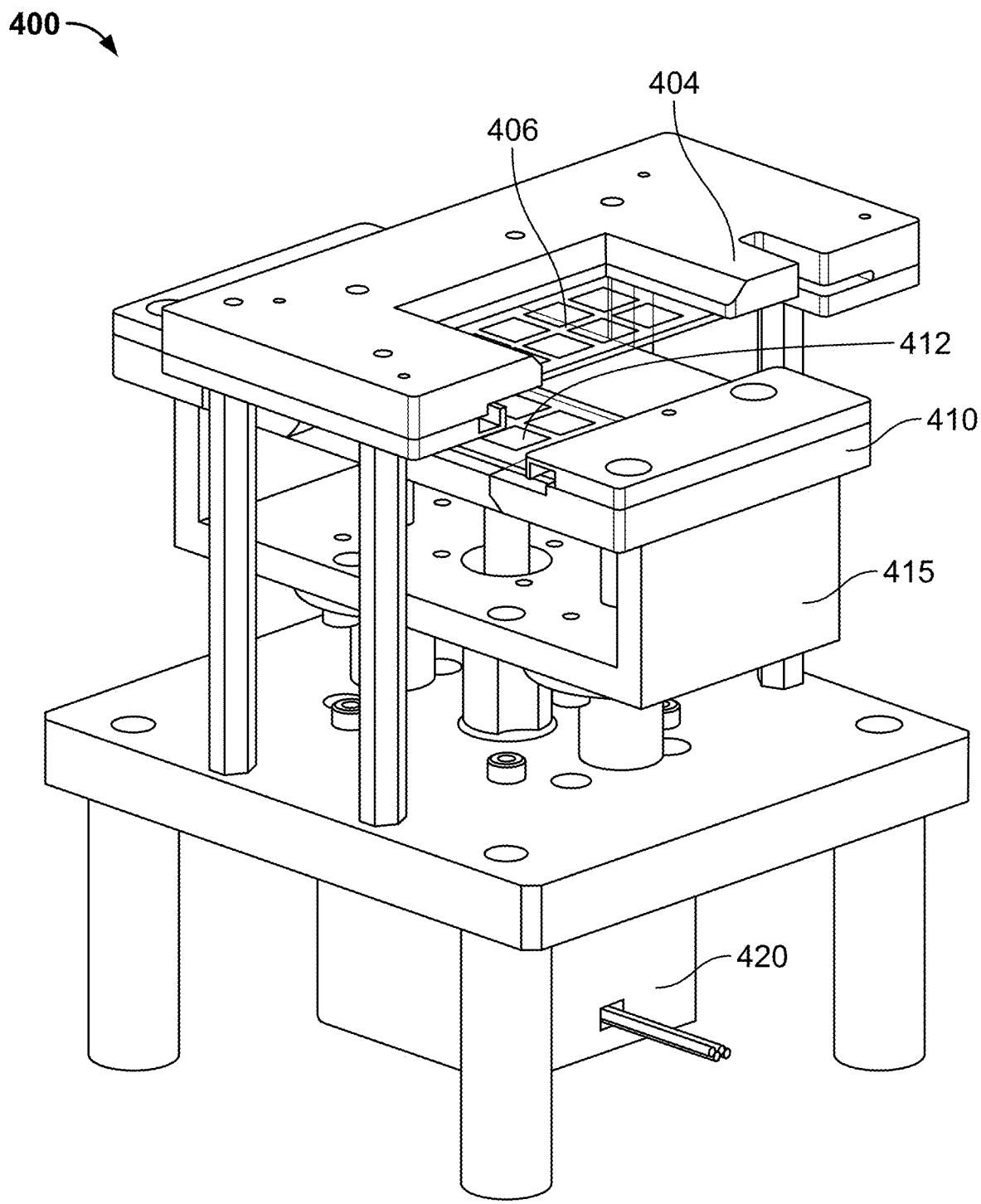
FIG. 4 is a schematic diagram showing an example sample handling apparatus in accordance with some example implementations.

FIG. 4 is a schematic diagram showing an example sample handling apparatus 400 in accordance with some example implementations. Sample handling apparatus 400, also referred to as sample holder 400, includes a first member 404 that holds a first substrate 406 on which a sample 302 may be positioned. The first member 404 may include a first retaining mechanism configured to retain the first substrate 406 in a fixed position along an axis and disposed in a first plane. As shown, the sample handling apparatus 400 also includes a second member 410 that holds a second substrate 412. The second member 410 may include a second retaining mechanism configured to retain the second substrate 412 disposed in a second plane. The second substrate 412 may include a barcoded array (e.g., spatially-barcoded capture probes 306), as described above. As shown, the sample handling apparatus 400 also includes an adjustment mechanism 415 configured to move the second member 410. The adjustment mechanism 415 may be coupled to the second member 410 and includes a linear actuator 420 configured to move the second member 410 along a z axis orthogonal to the second plane. In some aspects, the adjustment mechanism 415 may be alternatively or additionally coupled to the first member 404.

Figure 5A:
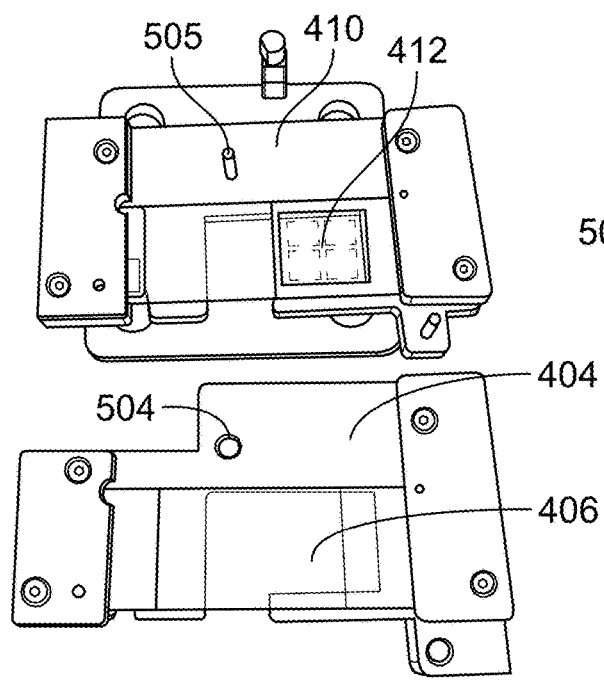
FIG. 5A depicts an example first member and an example second member in accordance with some example implementations.

FIG. 5A depicts an example first member 404 and an example second member 410 in accordance with some example implementations. As shown, the second member 410 includes a pin 505. As further shown, the first member 404 includes an aperture 504. The aperture 504 may be sized and configured to mate with the pin 505. In some aspects, the adjustment mechanism 415 (not shown) may include the pin 505 and the aperture 504. The pin 505 and the aperture 504 mating may result in the first member 404 being aligned relative to the second member 410.

Figure 5B:
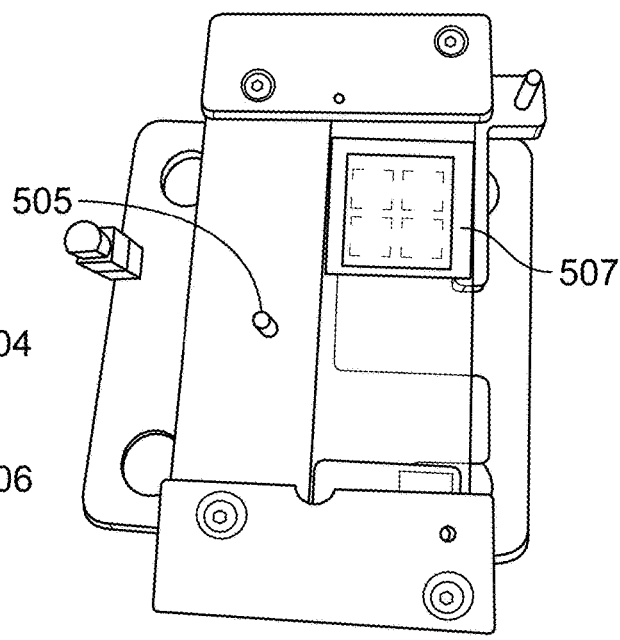
FIG. 5B depicts an example of the first member coupled to the second member in accordance with some example implementations.

FIG. 5B depicts an example of the first member 404 coupled or otherwise mechanically attached to the second member 410 in a sandwich configuration (e.g., via the pin 505 and the aperture 504) in accordance with some example implementations. As shown, the second substrate 412 includes a spacer 507 at least partially surrounding the barcoded array of the second substrate 412. The spacer 507 may be configured to contact and maintain a minimum spacing between the first substrate 406 and the second substrate 412. While the spacer 507 is shown as disposed on the second substrate 412, the spacer 507 may additionally or alternatively be disposed on the first substrate 406.

Figure 5C:
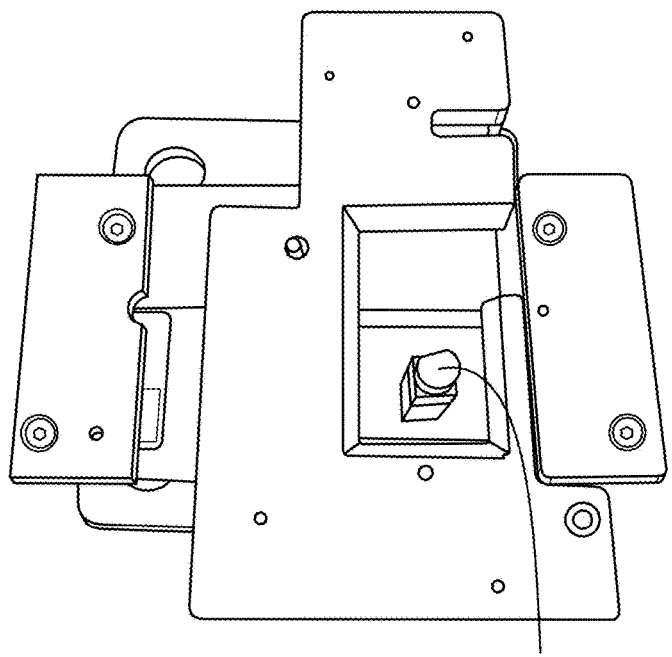
FIG. 5C depicts an example of the first member coupled to the second member including a coupling member coupled to the first substrate and the second substrate in accordance with some example implementations.

FIG. 5C depicts an example of the first member 404 coupled to the second member 410 in a sandwich configuration including a coupling member 509 coupled to the first substrate 406 and the second substrate 412 and configured to inhibit movement between the first substrate 406 and the second substrate 412 in accordance with some example implementations. In some aspects, the coupling member 509 includes a magnet that urges the first substrate 406 toward the second substrate 412 or vice versa (e.g., via a magnetic force).

Figure 6:
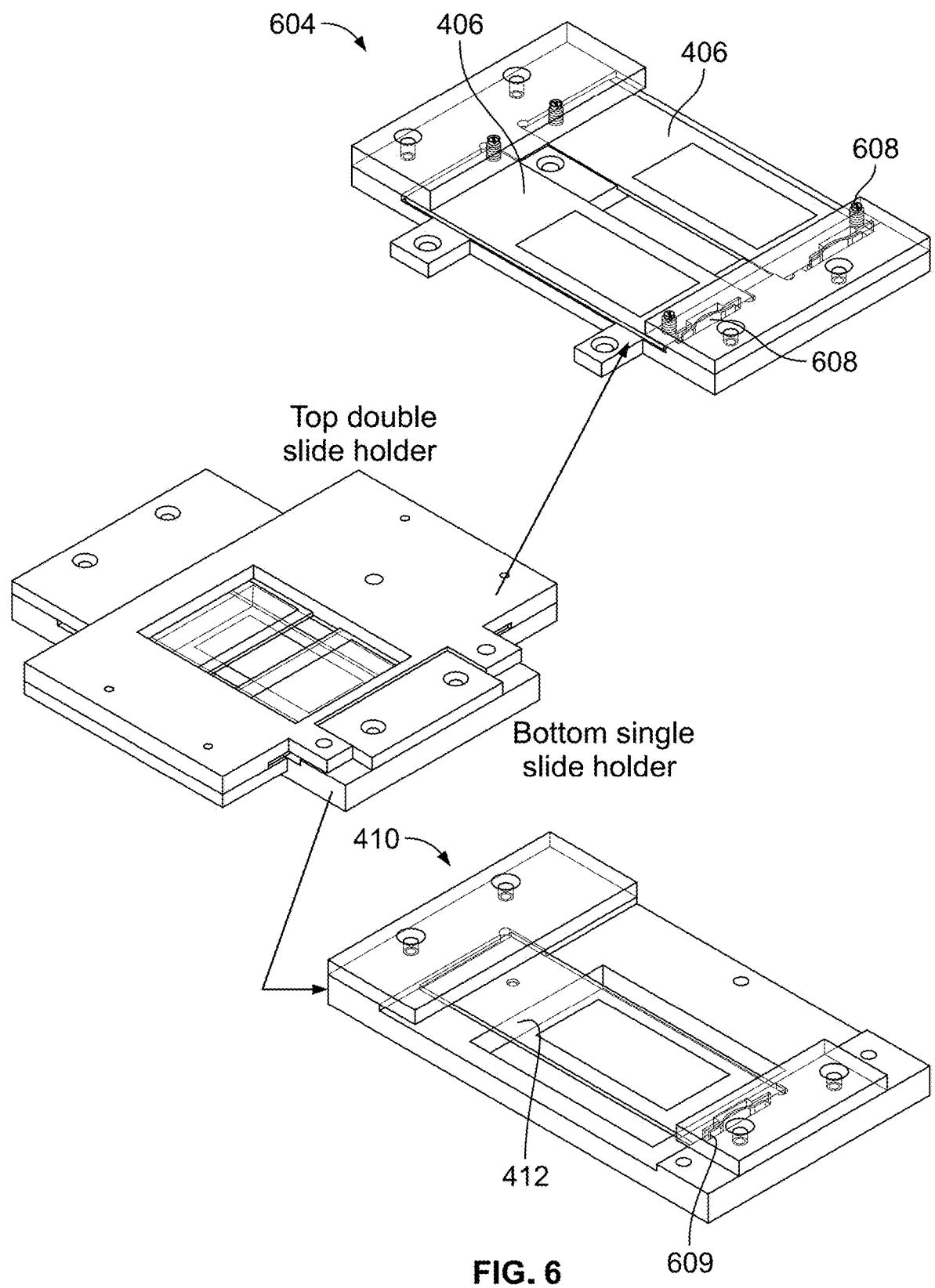
FIG. 6 is a diagram of an example first member and an example second member in accordance with some example implementations.

FIG. 6 is a diagram of an example first member 604 and an example second member 410 in accordance with some example implementations. As shown in the left-hand side of FIG. 6, the first member 604 is coupled to the second member 410. The top right-hand side of FIG. 6 depicts the first member 604. As shown, the first member 604 is configured to retain two first substrates 406. As further shown, the two first substrates 406 are disposed substantially parallel to each other along a common plane (e.g., an xy-plane) within the first member 604. The first member includes a first retaining mechanism 608 configured to retain a first substrate 406. The first retaining mechanism 608 may include spring plungers configured to push the first substrate 406 to a position, may include a spring loaded clamp design configured to apply a force to the first substrate 406 to maintain contact between the first substrate 406 and the first member 604, or the like to retain the first substrate 406 in a position in the first member 604. The bottom-right hand side of FIG. 6 depicts the second member 410. The second member 410 includes a second retaining mechanism 609 configured to retain the second substrate 412. The second retaining mechanism 609 may include spring plungers configured to push the second substrate 412 to a position, may include a spring loaded clamp design configured to apply a force to the second substrate 412 to maintain contact between the second substrate 412 and the second member 410, or the like to retain the second substrate 412 in a position in the second member 410.

FIG. 7 depicts a diagram 700 of a close-up bottom view of the first member 404 coupled to the second member 410 and an overlap area 710 where the first substrate 406 overlaps with the second substrate 412 in accordance with some example implementations. The overlap may occur along an axis orthogonal to the first substrate 406 and/or orthogonal to the second substrate 412. In some aspects, a camera may capture an image of the overlap area 710 that may be used as part of the spatial analysis further described herein. In some embodiments, the diagram 700 depicts an assembly of the first member 404 coupled to the second member 410 having dimensions of 113 mm long and 112 mm wide, although other dimensions are possible.

Figure 8:
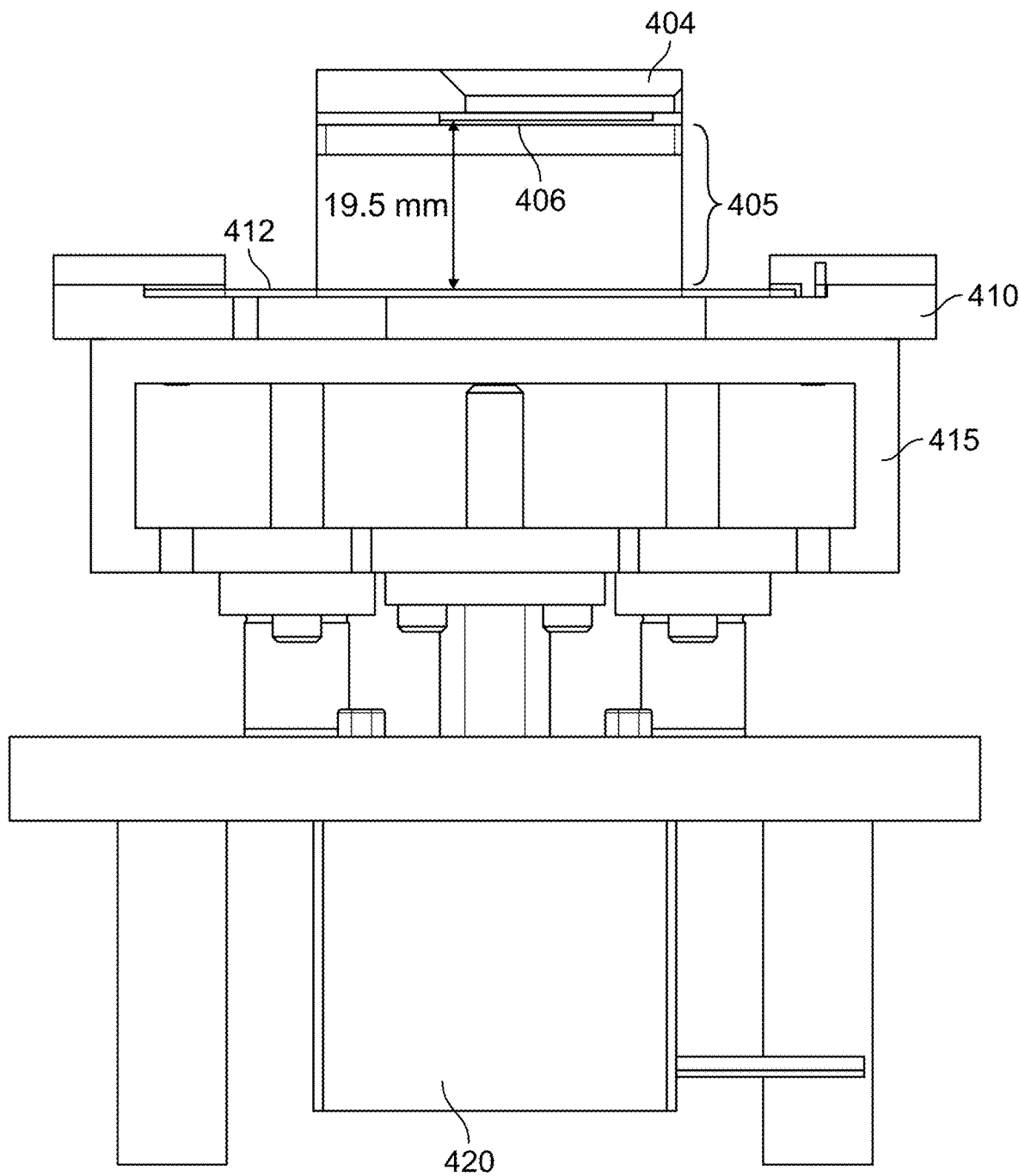
FIG. 8 depicts a front cross-sectional view of the example sample handling apparatus in accordance with some example implementations.

FIG. 8 depicts a front cross-sectional view of the sample handling apparatus 400 in accordance with some example implementations. As shown, the first member 404 and the second member 410 may be configured to maintain a separation distance 405 between the first substrate 406 and the second substrate 412. The separation distance 405 may be 19.5 mm in an initial or open position. In some aspects, the adjustment mechanism 415 may be configured to adjust the separation distance 405.

Figure 9:
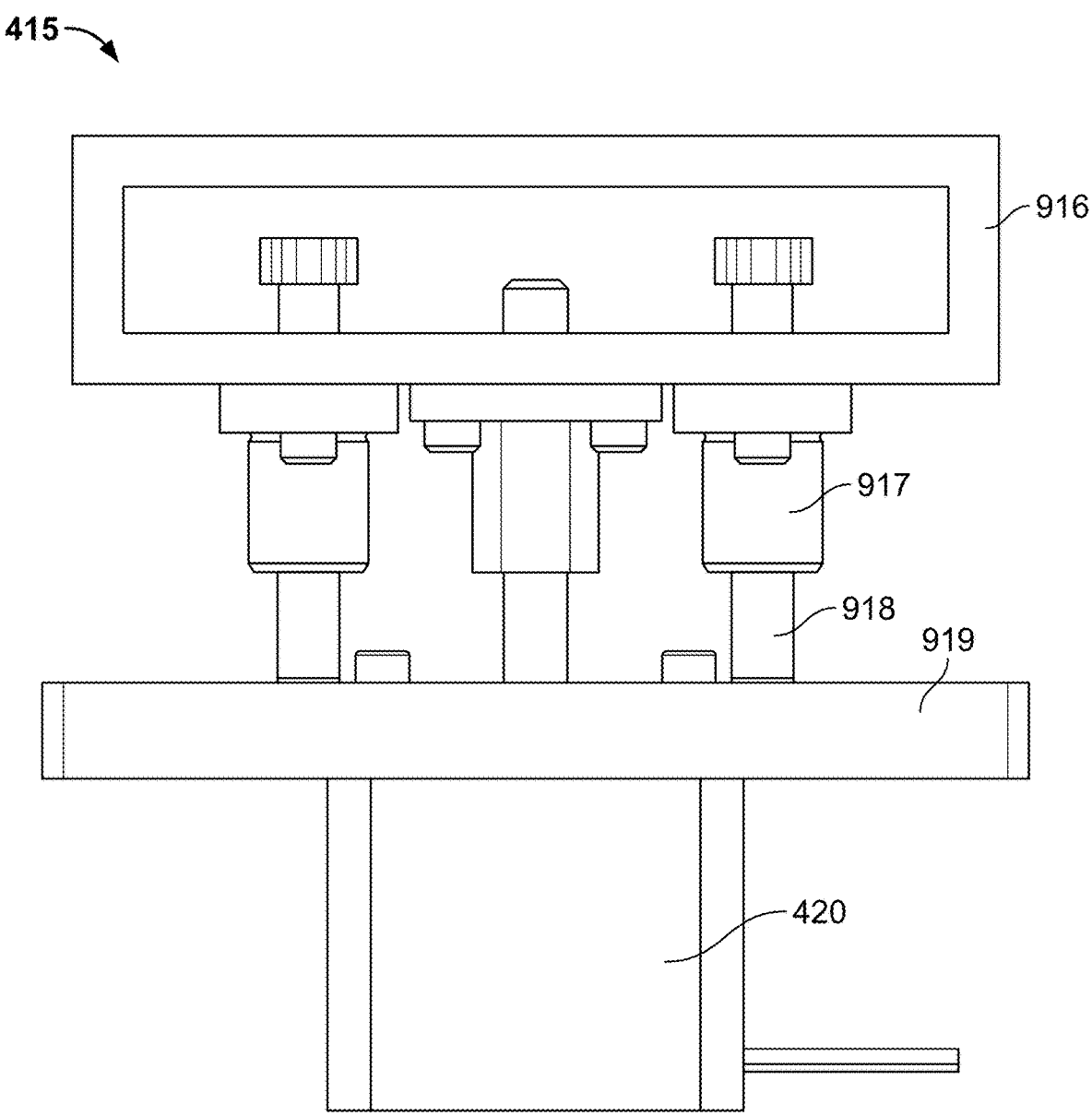
FIG. 9 is diagram of an example adjustment mechanism in accordance with some example implementations.

FIG. 9 is diagram of an example adjustment mechanism 415 in accordance with some example implementations. The adjustment mechanism 415 may include a moving plate 916, a bushing 917, a shoulder screw 918, a motor bracket 919, and the linear actuator 420. The moving plate 916 may be coupled to the second member 410 and adjust the separation distance 405 along a z axis (e.g., orthogonal to the second substrate 412) by moving the moving plate 916 up in a superior direction toward the first substrate 406. The movement of the moving plate 906 may be accomplished by the linear actuator 420 configured to move the second member 410 along the axis orthogonal to the second plane at a velocity. The velocity may be controlled by a controller communicatively coupled to the linear actuator 420. For example, the velocity may be configured to move the moving plate between at least 0.1 mm/sec to 2 mm/sec. In some aspects, the velocity of the moving plate (e.g., closing the sandwich) may affect bubble generation or trapping within the permeabilization solution 305. Further, the linear actuator may be configured to move the moving plate 906 with an amount of force (e.g., between 0.1-4.0 pounds of force). The controller may be configured to adjust the velocity and/or the amount of force of the linear actuator 420 to accomplish a desired combination of velocity and force for the moving plate 906.

In some aspects, the velocity of the moving plate (e.g., closing the sandwich) may affect bubble generation or trapping within the permeabilization solution 305. In some embodiments, the closing speed is selected to minimize bubble generation or trapping within the permeabilization solution 305. In some embodiments, the closing speed is selected to reduce the time it takes the flow front of a reagent medium from an initial point of contact with the first and second substrate to sweep across the sandwich area (also referred to herein as "closing time"). In some embodiments, the closing speed is selected to reduce the closing time to less than about 1100 ms. In some embodiments, the closing speed is selected to reduce the closing time to less than about 1000 ms. In some embodiments, the closing speed is selected to reduce the closing time to less than about 900 ms. In some embodiments, the closing speed is selected to reduce the closing time to less than about 750 ms. In some embodiments, the closing speed is selected to reduce the closing time to less than about 600 ms. In some embodiments, the closing speed is selected to reduce the closing time to about 550 ms or less. In some embodiments, the closing speed is selected to reduce the closing time to about 370 ms or less. In some embodiments, the closing speed is selected to reduce the closing time to about 200 ms or less. In some embodiments, the closing speed is selected to reduce the closing time to about 150 ms or less.

Figure 10:
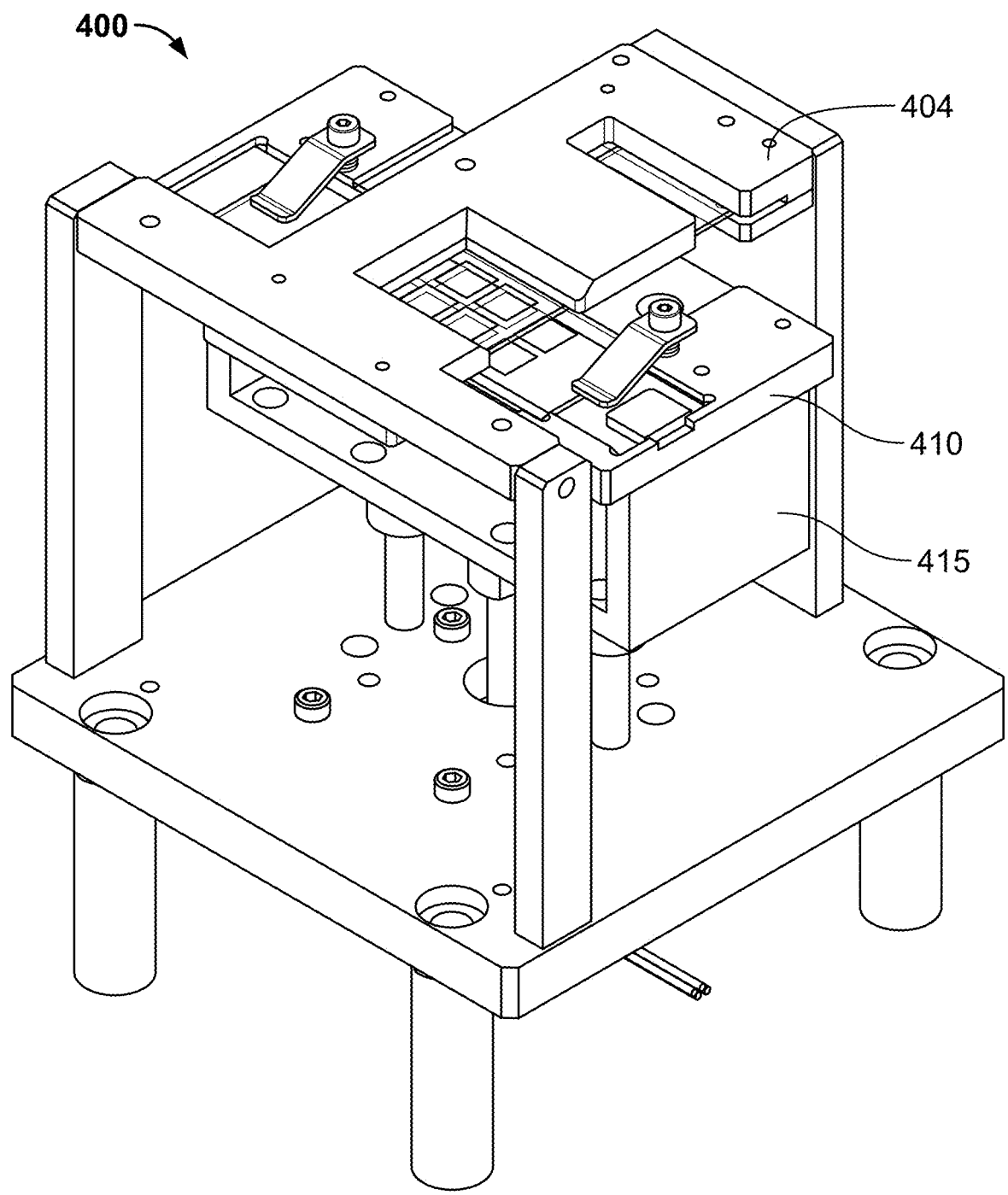
FIG. 10 is a perspective view of an example sample handling apparatus including an automated second member in accordance with some example implementations.

FIG. 10 is a perspective view of an example sample handling apparatus 400 including an automated second member 410 in accordance with some example implementations. As shown, the sample handling apparatus 400 includes the adjustment mechanism 415. The adjustment mechanism 415 may be automated such that one or more of the moving plate 916, the bushing 917, the shoulder screw 918, the motor bracket 919, and the linear actuator 420 may be controlled by a controller (not shown) communicatively coupled to the adjustment mechanism 415. The controller may be configured to adjust a position of the second member 410 relative to the first member 404 (e.g., separation distance 405). The first member 404 may be fixed with respect to one or more axes (e.g., the z axis).

Figure 11A:
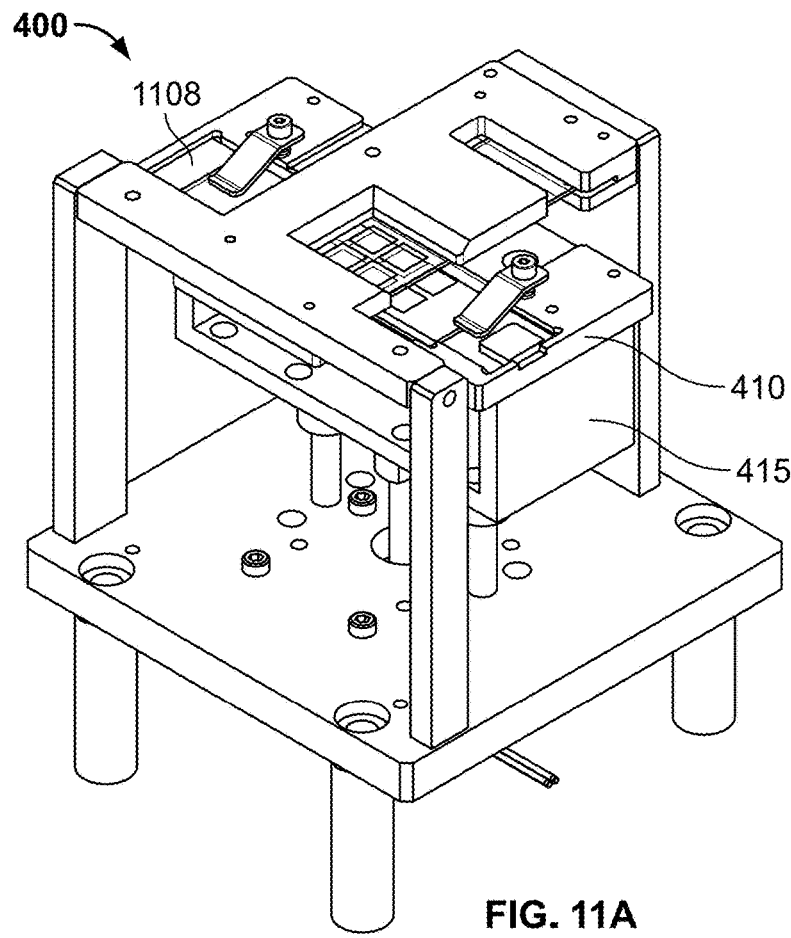
FIG. 11A is a perspective view of an example sample handling apparatus including a heater in accordance with some example implementations.

FIG. 11A is a perspective view of the example sample handling apparatus 400 including a heater 1108 in accordance with some example implementations. As shown, the sample handling apparatus 400 includes the heater 1108 as part of the second member 410.

Figure 11B:
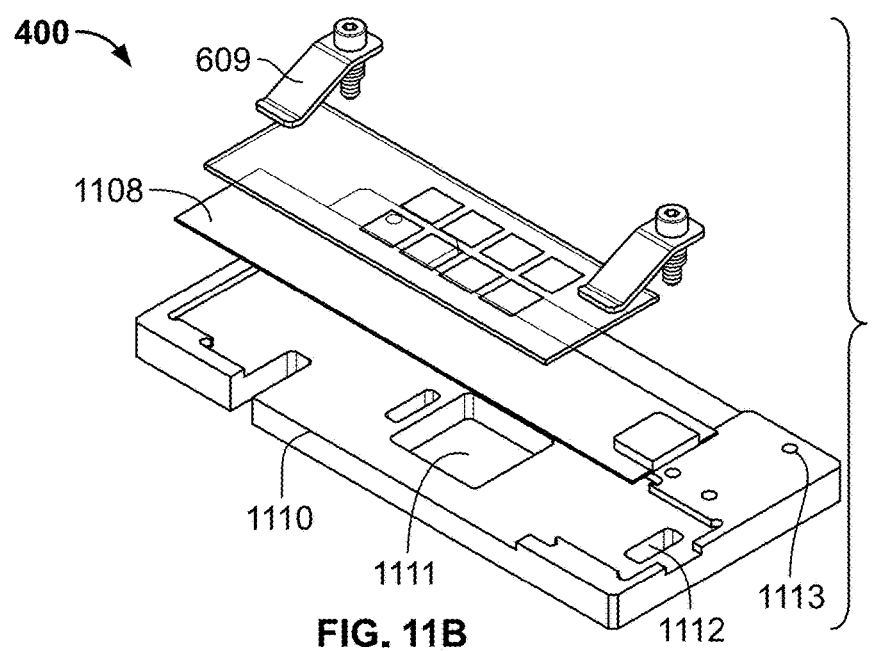
FIG. 11B is a exploded view of an example second member including the heater in accordance with some example implementations.

FIG. 11B is a exploded view of an example second member 410 including the heater 1108 in accordance with some example implementations. As shown, the heater 1108 is positioned below or inferior to the second substrate 412 and above (superior to) the second member holder 1110. The heater 1108 may be configured to heat the second substrate 412 to a desired or target temperature. The second member holder 1110 includes a cutout window 1111 for the overlap area 710. The second member holder 1110 further includes an epoxy pocket 1112 for the heater 1108 and screw holes 1113 for the first substrate 406 and the second substrate 412 parallel alignment. As further shown, the second member 410 includes the second retaining mechanism 609. The second retaining mechanism 609 may include a swing clamp, a spring-loaded clamp, or the like to retain the second substrate 412 in a position within the second member 410.

Figure 11C:
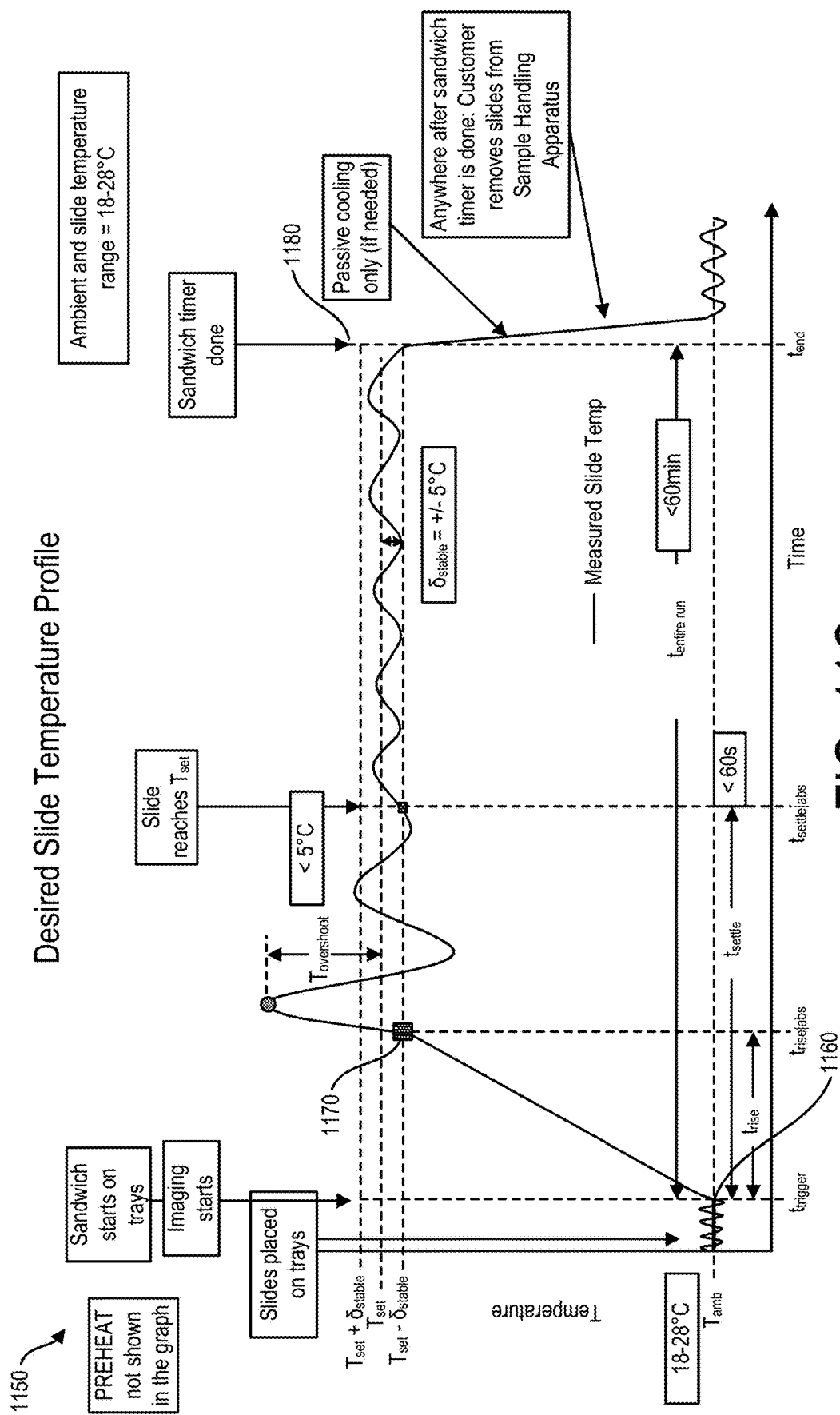
FIG. 11C is a graph of an example desired substrate (e.g., slide) temperature profile over time in accordance with some example implementations.

FIG. 11C is a graph 1150 of an example desired substrate (e.g., slide) temperature profile over time in accordance with some example implementations. As shown in the graph 1150, the temperature of the slide may hover close to an ambient temperature (e.g., between 18-28° C.) until a trigger time 1160 (e.g., when imaging starts or when sandwiching of the substrates starts). After the trigger time 1160, the heater 1108 may heat the slide and the slide temperature may rise linearly until the slide temperature reaches a threshold temperature to the desired slide temperature at 1170. After the threshold temperature is reached, the slide temperature may fluctuate sinusoidally around the desired slide temperature, $T_{set}$, and may settle within a threshold amplitude around the desired temperature $T_{set}$. At 1180, the sandwich timer may complete and the slide temperature may begin to lower and return to the ambient temperature. In some aspects, the desired temperature may be based on the tissue sample 302, the permeabilization solution 305, a starting temperature of the first substrate or the second substrate, or the like.

Figure 12A:
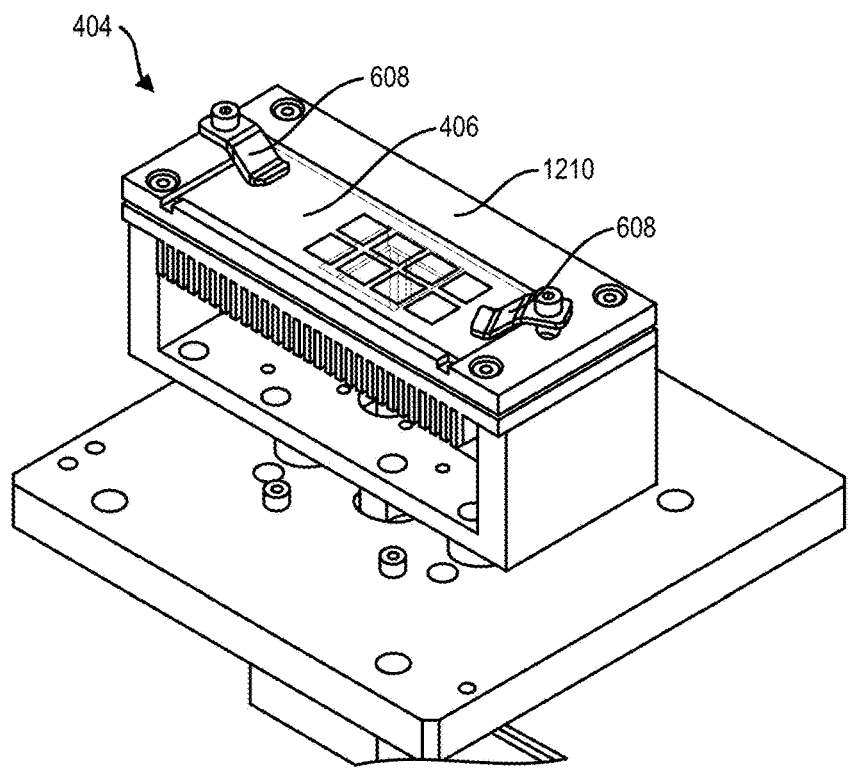
FIG. 12A is a perspective view of an example first member in accordance with some example implementations.

FIG. 12A is a perspective view of an example first member 404 in accordance with some example implementations. As shown, the first member 404 includes a holder plate 1210 and the first retaining mechanism 608 retaining the first substrate 406 within the first member 404.

Figure 12B:
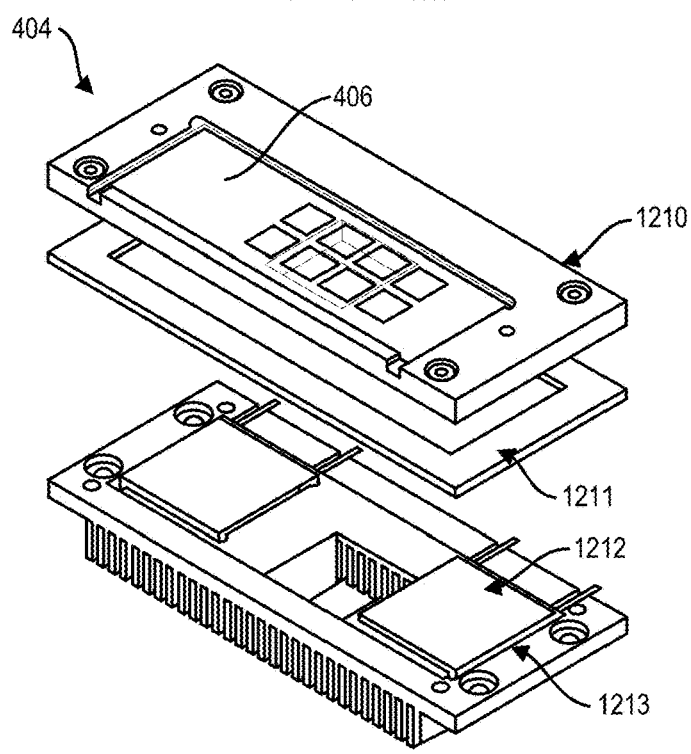
FIG. 12B is an exploded view of the example first member of FIG. 12A in accordance with some example implementations.

FIG. 12B is an exploded view of the example first member 404 of FIG. 12A in accordance with some example implementations. As shown, the first member 404 includes the holder plate 1210, an insulation gasket 1211, a thermal pad 1212, and a thermoelectric cooler (TEC) 1213. The holder plate 1210 may be configured to receive and retain the first substrate 406. The insulation gasket 1211, the thermal pad 1212, and/or the TEC 1213 may be configured to adjust and/or maintain a desired or target temperature for the first substrate 406.

FIG. 13A is a perspective cross-section view of an example first member 404 in accordance with some example implementations. As shown, the first member 404 of FIG. 13A includes the holder plate 1210, the insulation gasket 1211, the TEC 1213, and a heat sink block 1214.

FIG. 13B is a perspective view of the example holder plate 1210 of FIG. 13A in accordance with some example implementations. As shown, the holder plate 1210 includes a cutout window 1216 for the overlap area 710.

FIG. 13C is a perspective view of the example heat sink block 1214 of FIG. 13A in accordance with some example implementations. As shown, the heat sink block 1214 includes a cut out window 1217 for the overlap area 710.

Figure 14A:
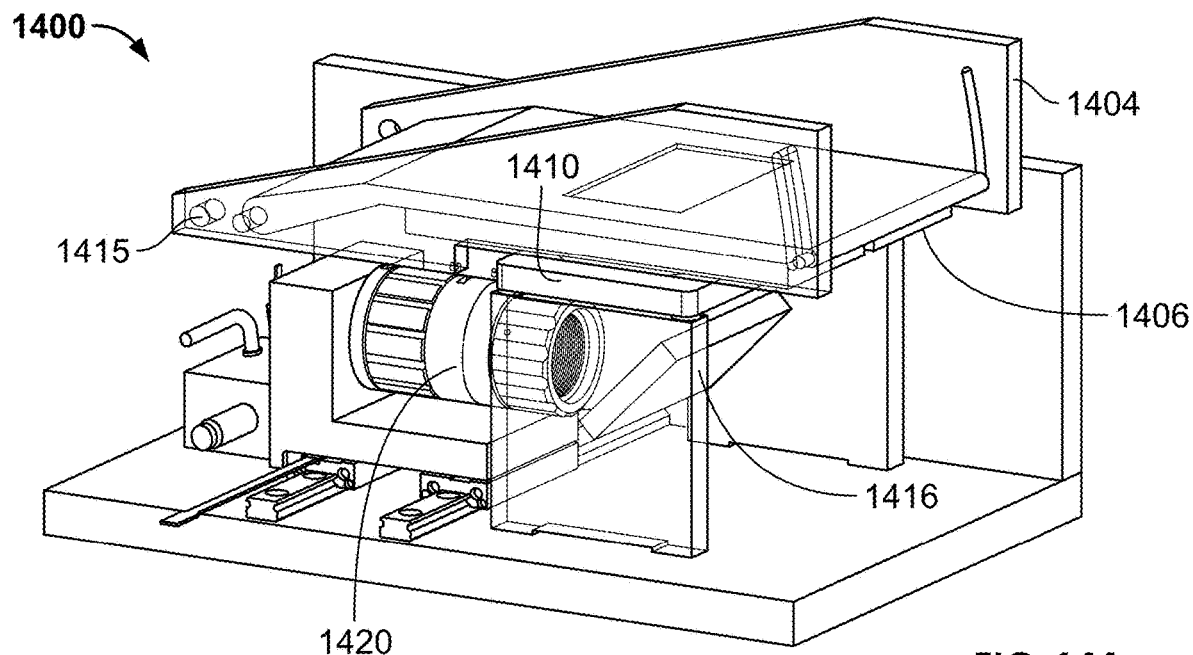
FIG. 14A is a perspective view of an example sample handling apparatus in a closed position in accordance with some example implementations.

FIG. 14A is a perspective view of an example sample handling apparatus 1400 in a closed position in accordance with some example implementations. As shown, the sample handling apparatus 1400 includes a first member 1404, a second member 1410, an image capture device 1420, a first substrate 1406, a hinge 1415, and a mirror 1416. The hinge 1415 may be configured to allow the first member 1404 to be positioned in an open or closed configuration by opening and/or closing the first member 1404 in a clamshell manner along the hinge 1415.

Figure 14B:
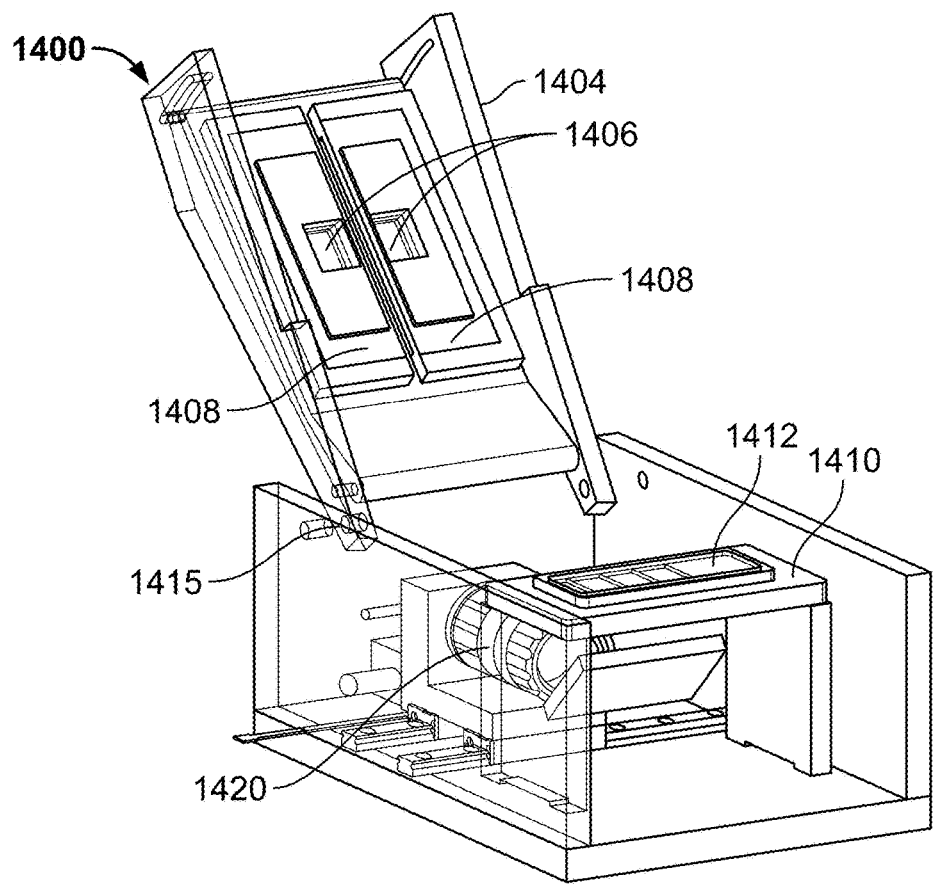
FIG. 14B is a perspective view of the example sample handling apparatus in an open position in accordance with some example implementations.

FIG. 14B is a perspective view of the example sample handling apparatus 1400 in an open position in accordance with some example implementations. As shown, the sample handling apparatus 1400 includes one or more first retaining mechanisms 1408 configured to retain one or more first substrates 1406. In the example of FIG. 14B, the first member 1404 is configured to retain two first substrates 1406, however the first member 1404 may be configured to retain more or fewer first substrates 1406.

In some aspects, when the sample handling apparatus 1400 is in an open position (as in FIG. 14B), the first substrate 1406 and/or the second substrate 1412 may be loaded and positioned within the sample handling apparatus 1400 such as within the first member 1404 and the second member 1410, respectively. As noted, the hinge 1415 may allow the first member 1404 to close over the second member 1410 and form a sandwich configuration (e.g., the sandwich configuration shown in FIG. 3).

In some aspects, after the first member 1404 closes over the second member 1410, an adjustment mechanism (not shown) of the sample handling apparatus 1400 may actuate the first member 1404 and/or the second member 1410 to form the sandwich configuration for the permeabilization step (e.g., bringing the first substrate 1406 and the second substrate 1412 closer to each other and within a threshold distance for the sandwich configuration). The adjustment mechanism may be configured to control a speed, an angle, or the like of the sandwich configuration.

In some embodiments, the tissue sample (e.g., sample 302) may be aligned within the first member 1404 (e.g., via the first retaining mechanism 1408) prior to closing the first member 1404 such that a desired region of interest of the sample 302 is aligned with the barcoded array of the gene expression slide (e.g., the slide 304), e.g., when the first and second substrates are aligned in the sandwich configuration. Such alignment may be accomplished manually (e.g., by a user) or automatically (e.g., via an automated alignment mechanism). After or before alignment, spacers may be applied to the first substrate 1406 and/or the second substrate 1412 to maintain a minimum spacing between the first substrate 1406 and the second substrate 1412 during sandwiching. In some aspects, the permeabilization solution (e.g., permeabilization solution 305) may be applied to the first substrate 1406 and/or the second substrate 1412. The first member 1404 may then close over the second member 1410 and form the sandwich configuration. Analytes and/or mRNA transcripts 308 may be captured by the capture probes 306 and may be processed for spatial analysis.

In some embodiments, during the permeabilization step, the image capture device 1420 may capture images of the overlap area (e.g., overlap area 710) between the tissue 302 and the capture probes 306. If more than one first substrates 1406 and/or second substrates 1412 are present within the sample handling apparatus 1400, the image capture device 1420 may be configured to capture one or more images of one or more overlap areas 710.

The image capture device 1420 and the sample handling apparatus 1400 can be configured to capture images in one or more image capture modes. The image capture modes can include programmatic settings and parameters that can be applied by a user and can configure the image capture device 1420 and the sample handling apparatus 1400 to capture images in a variety of workflows or experimental conditions. The image capture modes can allow image capture and image data generation for a variety of use cases, including different sample stain conditions, different fluorescence conditions, and different illumination requirements. In this way, the sample handling apparatus 1400 can support a variety of imaging needs at varying resolutions that may be independent of a particular assay or experimental workflow.

In some embodiments, the image capture modes can include a free capture mode and an assay capture mode. The free capture mode may not be associates with capturing image data in regard to a particular assay or assay workflow. Instead, the free capture mode can enable users to acquire image data as they wish, in an ad hoc manner, or within a customized or alternate experimental workflow. For example, H&E stained tissue samples can be imaged prior to removing the hematoxylin and after removing the hematoxylin.

The assay capture mode can be associated with and performed within a particular assay or assay workflow. The assay or assay workflow can include capturing images of samples that have been stained. For example, H&E stained tissue samples that can be H&E stained with hematoxylin and eosin can be imaged in an assay or assay workflow to generate RGB image data. When configured in assay capture mode, the sample handling apparatus 1400 can capture image data before, during, or after permeabilization steps that can be performed during an assay as described herein.

The captured image data acquired in any one or the image capture modes can be used in the image registration methods performed by the sample handling apparatus 1400. In some embodiments, the image data acquired in assay capture more and/or the free capture mode can be acquired in an programmatically automated manner or in a manual manner defined by user inputs provided to the sample handling apparatus 1400.

In some embodiments, the image data captured in the image capture modes described herein can include image capture mode data. The image capture mode data can be a data such as a tag, a parameter, or an identifier identifying the particular image capture mode that the sample handling apparatus 1400 was operating in when the image data was captured using the image capture device 1420. In some embodiments, any of the sample handling apparatuses 400, 1400, and 3000 described herein can include software implementing any one of the image captured modes. When executed by a data processor, the software can cause the image capture device configured in any of sample handling apparatuses 400, 1400, and 3000 to acquire image data as described herein.

Figure 15:
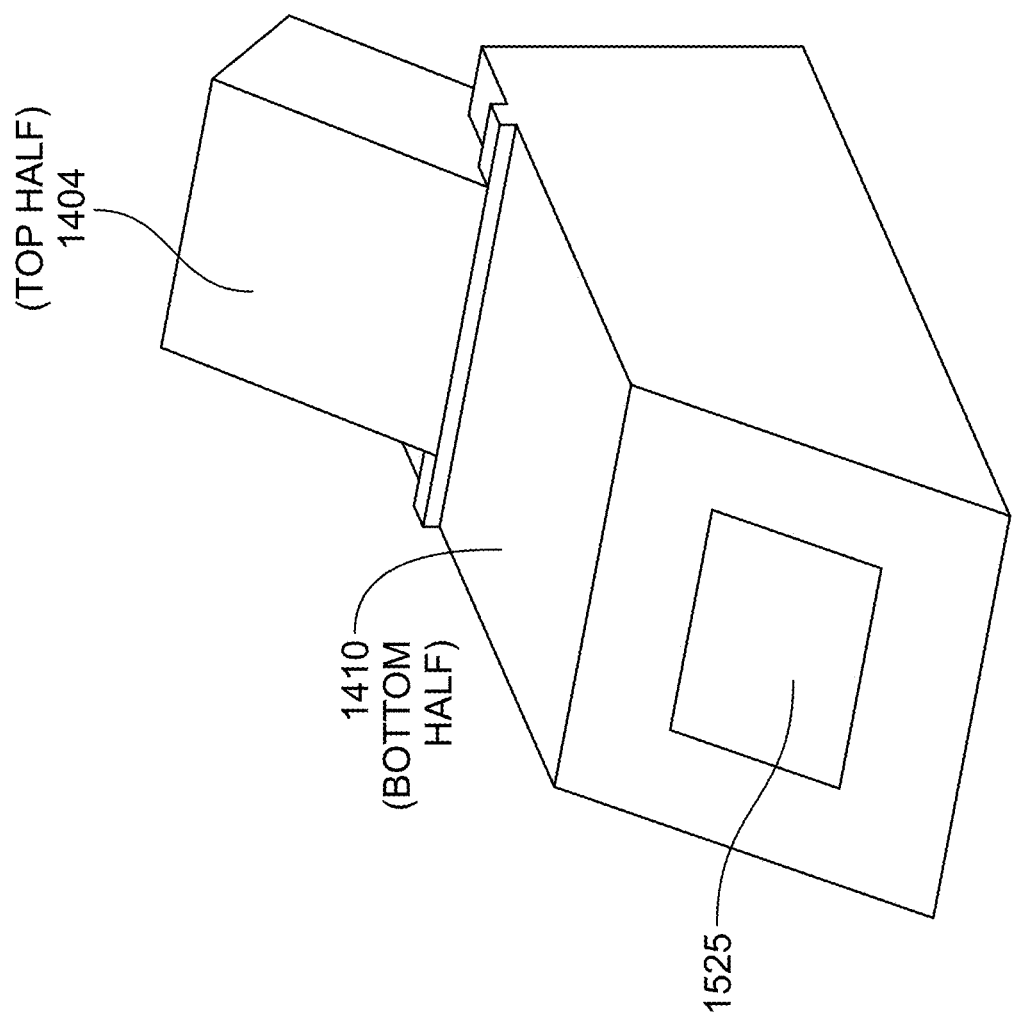
FIG. 15 is a perspective view of the example sample handling apparatus in accordance with some example implementations.

FIG. 15 is a perspective view of the example sample handling apparatus 1400 in accordance with some example implementations. As shown, the sample handling apparatus 1400 is in an open position with the first member 1404 disposed above (superior to) the second member 1410. As noted above, the first member 1404 and/or the second member 1410 may be configured to hold one or more substrates (e.g., first substrates 1406 and/or second substrates 1412, respectively). The sample handling apparatus 1400 further includes a user interface 1525. The user interface 1525 may include a touchscreen display for displaying information relating to the sample handling apparatus and receiving user input controls for controlling aspects or functions of the sample handling apparatus 1400.

FIG. 16A is a perspective view of the example sample handling apparatus 1400 in accordance with some example implementations.

FIG. 16B is a front view of the example sample handling apparatus 1400 showing example dimensions of the apparatus 1400 in accordance with some example implementations. As shown, the sample handling apparatus may have a width of 300 mm and a height of 255 mm, although other dimensions are possible. The second member 1410 may have a height of 150 mm and a width of 300 mm, although other dimensions are possible.

FIG. 16C is a side view of the example sample handling apparatus 1400 showing example dimensions of the apparatus 1400 in accordance with some example implementations. As shown, the sample handling apparatus may have a depth of 405 mm, although other dimensions are possible.

III. Sample and Array Alignment Devices and Methods

Spatial analysis workflows described herein generally involve contacting a sample with an array of features. With such workflows, aligning the sample with the array is an important step in performing spatialomic (e.g., spatial transcriptomic) assays. The ability to efficiently generate robust experimental data for a given sample can depend greatly on the alignment of the sample and the array. Traditional techniques require samples to be placed directly onto the array. This approach can require skilled personnel and additional experimental time to prepare a section of the sample and to mount the section of the sample directly on the array. Misalignment of the sample and the array can result in wasted resources, extended sample preparation time, and inefficient use of samples, which may be limited in quantity.

The systems, methods, and computer readable mediums described herein can enable efficient and precise alignment of samples and arrays, thus facilitating the spatialomic (e.g., spatial transcriptomic) imaging and analysis workflows or assays described herein. Samples, such as portions of tissue, can be placed on a first substrate. The first substrate can include a slide onto which a user can place a sample of the tissue. An array, such as a reagent array, can be formed on a second substrate. The second substrate can include a slide and the array can be formed on the second substrate. The use of separate substrates for the sample and the array can beneficially allow user to perform the spatialomic (e.g., spatial transcriptomic) assays described herein without requiring the sample to be placed onto an array substrate. The sample holder and methods of use described herein can improve the ease by which users provide samples for spatial transcriptomic analysis. For example, the systems and methods described herein alleviate users from possessing advanced sample or tissue sectioning or mounting expertise. Additional benefits of utilizing separate substrates for samples and arrays can include improved sample preparation and sample imaging times, greater ability to perform region of interest (ROI) selection, and more efficient use of samples and array substrates. The systems, methods, and computer readable mediums described herein can further enable users to select the best sections of a sample to commit to sequencing workflows. Some tissue samples or portions of the tissue samples can be damaged during mounting. For examples, the tissue samples or portions of the tissue samples can be folded over on themselves. The systems, methods, and computer readable mediums described herein can further enable users to confirm relevant pathology and/or biology prior to committing to sequencing workflows.

The sample substrate and the array substrate, and thus, the sample and the array, can be aligned using the instrument and processes described herein. The alignment techniques and methods described herein can generate more accurate spatialomic (e.g., spatial transcriptomic) assay results due to the improved alignment of samples with an array, such as a reagent array.

In some embodiments, a workflow described herein comprises contacting a sample disposed on an area of a first substrate with at least one feature array of a second substrate. In some embodiments, the contacting comprises bringing the two substrates into proximity such that the sample on the first substrate may be aligned with the barcoded array on the second substrate. In some instances, the contacting is achieved by arranging the first substrate and the second substrate in a sandwich assembly. In some embodiments, the workflow comprises a prior step of mounting the sample onto the first substrate.

Alignment of the sample on the first substrate with the array on the second substrate may be achieved manually or automatically (e.g., via a motorized alignment). In some aspects, manual alignment may be done with minimal optical or mechanical assistance and may result in limited precision when aligning a desired region of interest for the sample and the barcoded array. Additionally, adjustments to alignment done manually may be time-consuming due to the relatively small time requirements during the permeabilization step.

It may be desirable to perform real-time alignment of a tissue slide (e.g., the pathology slide 303) with an array slide (e.g., the slide 304 with barcoded capture probes 306). In some implementations, such real-time alignment may be achieved via motorized stages and actuators of a sample handling apparatus (e.g., the sample handling apparatus 400, the sample handling apparatus 1400, or the like).

Figure 17A:
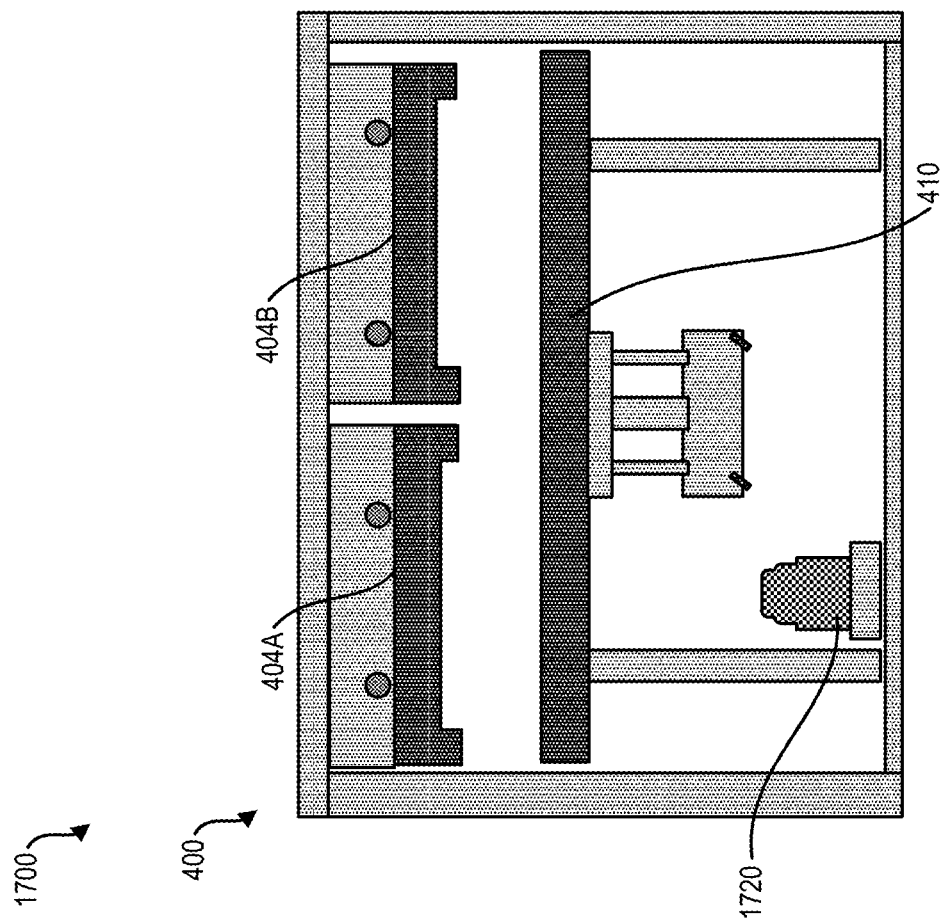
FIGS. 17A-17C depict a workflow for loading slides into a sample handling apparatus for later alignment in accordance with some example implementations.
Figure 17B:
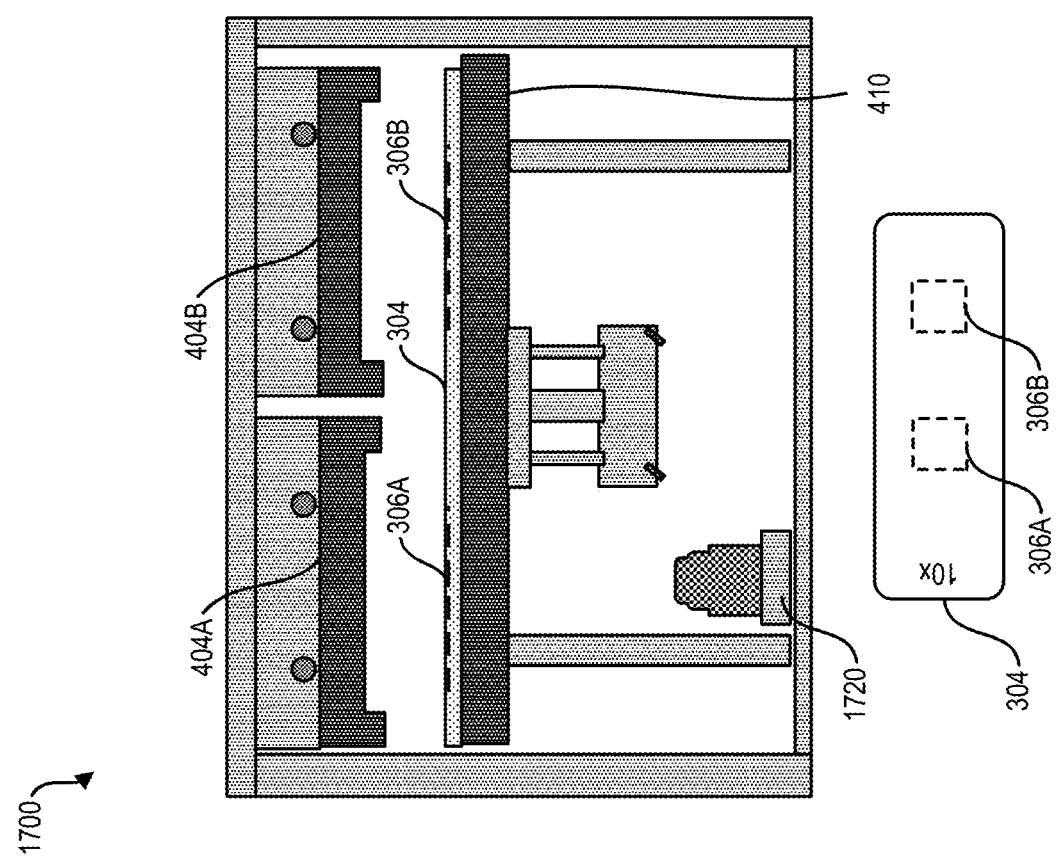
Figure 17C:
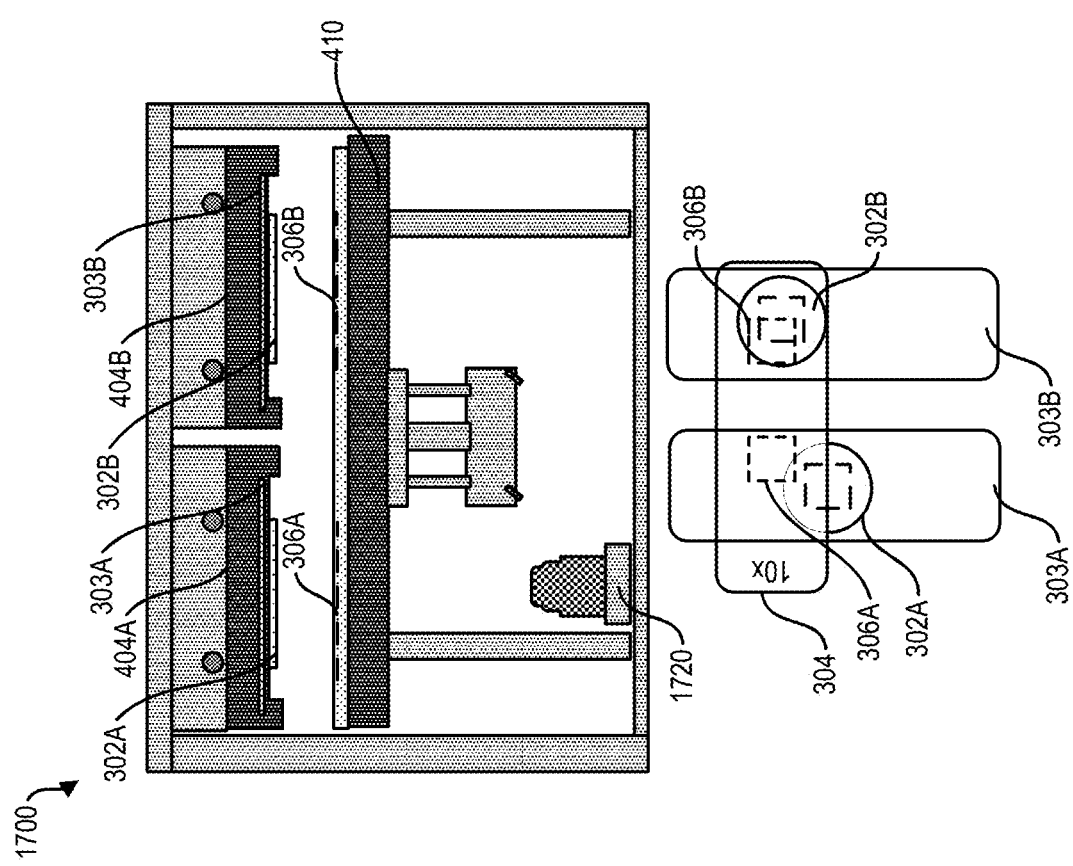

FIGS. 17A-17C depict a workflow 1700 for loading slides into a sample handling apparatus for later alignment in accordance with some example implementations.

FIG. 17A depicts the example sample handling apparatus 400 with no slides loaded into the apparatus 400. As shown, the sample handling apparatus 400 includes two first members 404, the second member 410, and an image capture device 1720. The image capture device 1720 can correspond to the image capture device 1420 shown and described in relation to FIGS. 14A-14B. While two first members 404 and a single second member 410 are shown in the FIGS. 17A-17C, it will be appreciated that more or fewer first members 404 and/or second members 410 are possible. While the image capture device 1720 is shown in a position inferior to the second member 410, other locations for the image capture device 1720 are possible and more or fewer image capture devices 1720 are also possible.

FIG. 17B depicts the sample handling apparatus 400 with a gene expression slide (e.g., slide 304 with barcoded capture probes 306) loaded into the second member 410. A bottom portion of the FIG. 17B shows a top view of the slide 304. As shown, the slide 304 includes two array regions with barcoded capture probes 306A and 306B, respectively.

FIG. 17C depicts the sample handling apparatus 400 with a histology slide 303A and a pathology slide 303B loaded into first members 404A and 404B, respectively. As shown, the histology slide 303A and the pathology slide 303B include tissue samples 302A and 302B, respectively. A bottom portion of FIG. 17C shows a top view of an initial alignment of the gene expression slide 304 with the histology slide 303A and the pathology slide 303B after loading.

Figure 18A:
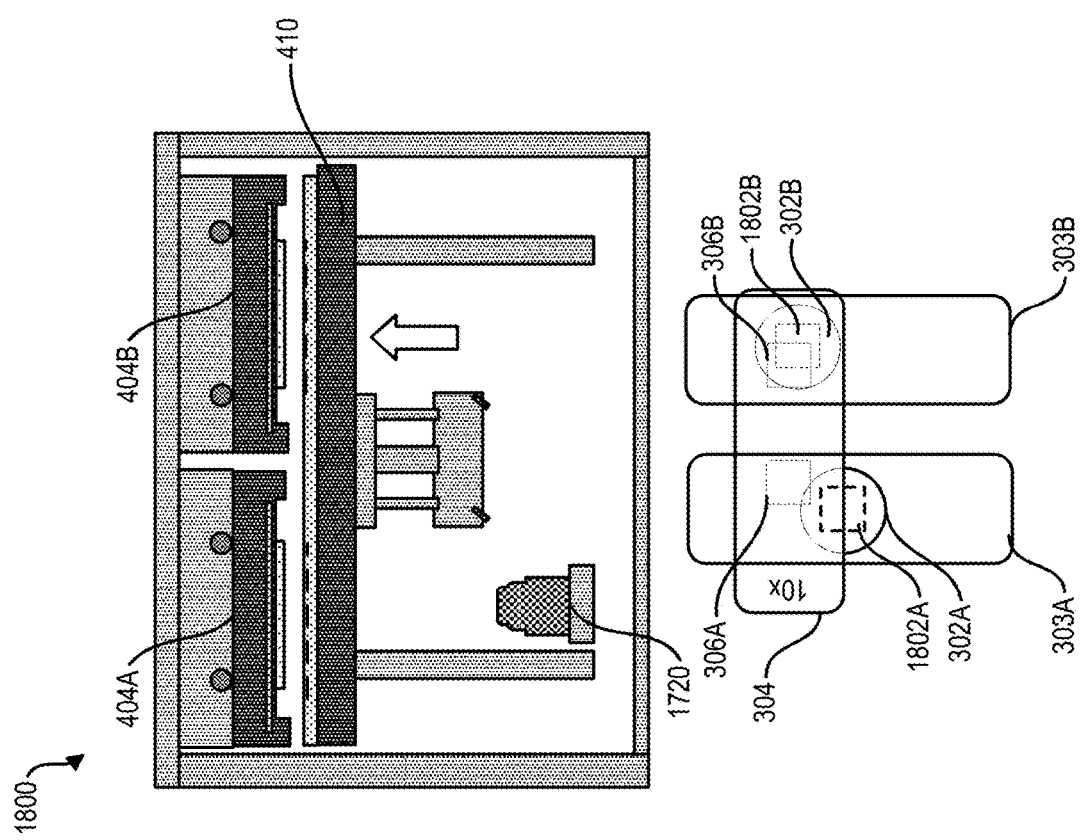
FIGS. 18A-18C depict a workflow for aligning the loaded slides of the sample handling apparatus in accordance with some example implementations.
Figure 18B:
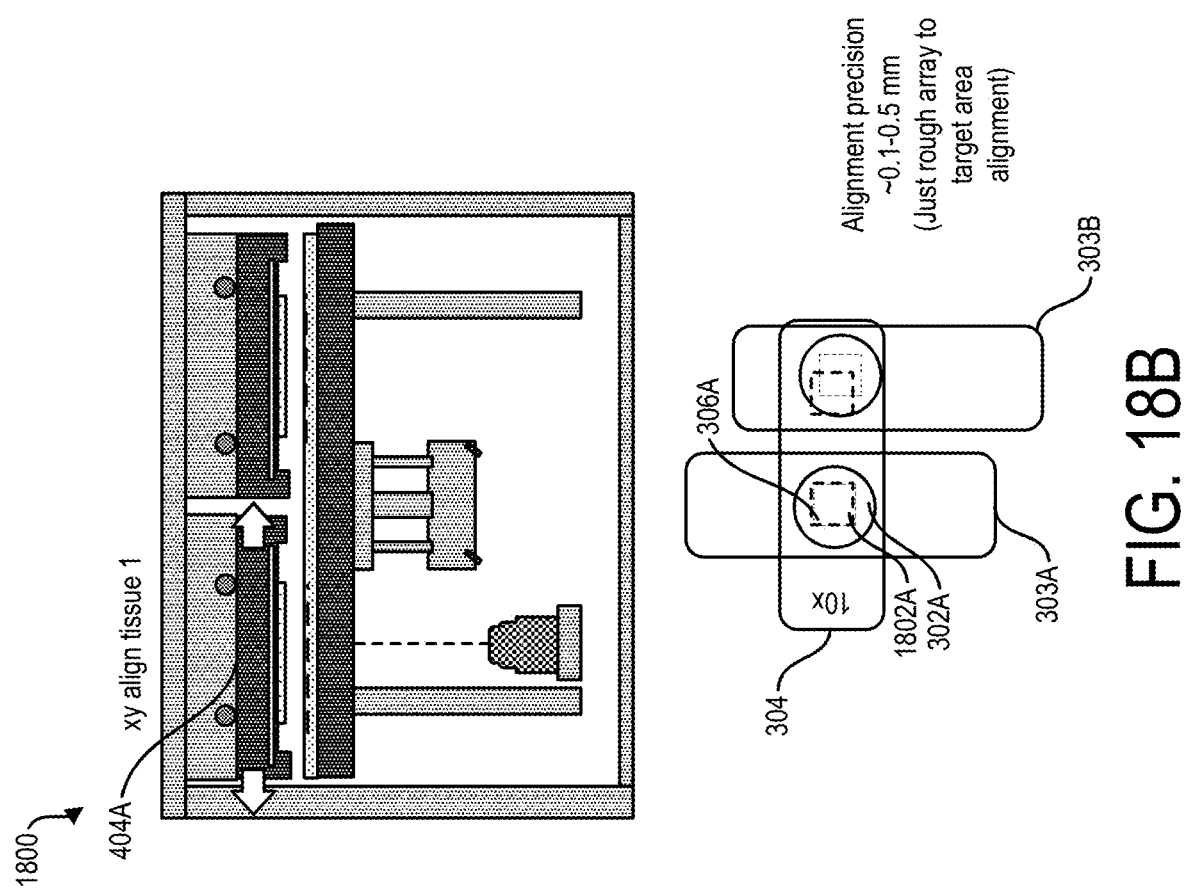
Figure 18C:
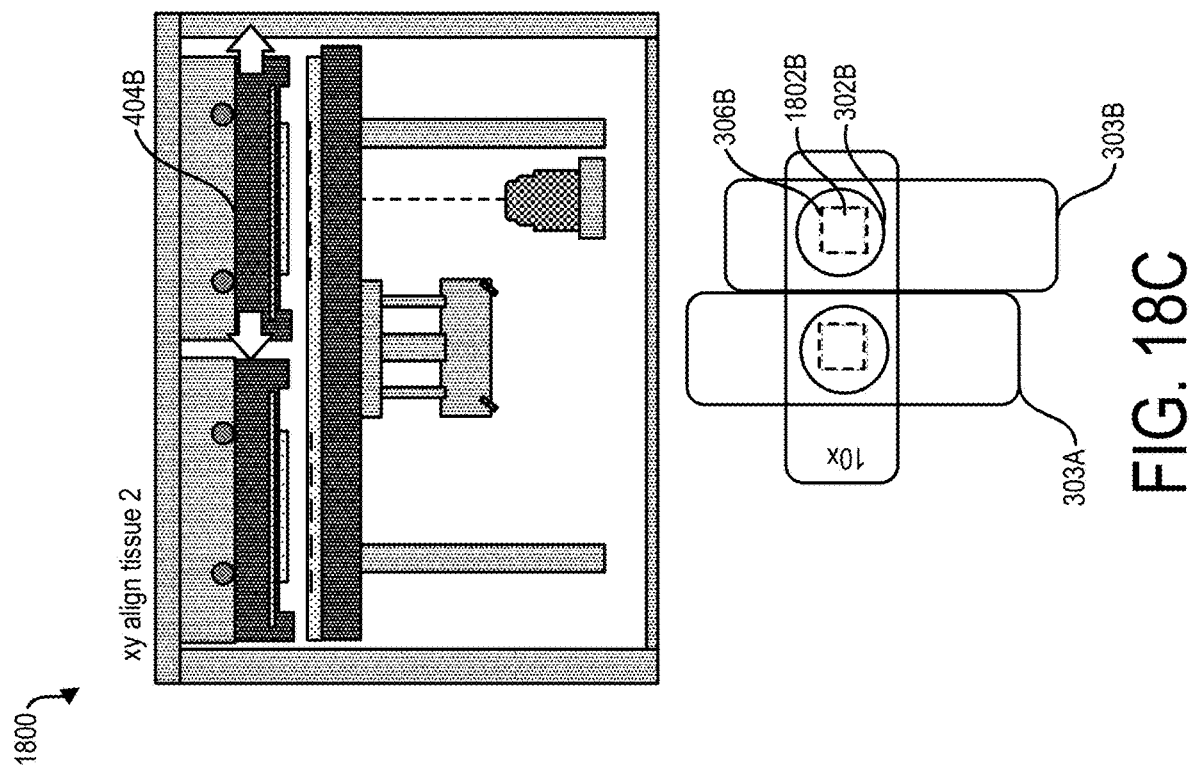

FIGS. 18A-18C depict a workflow 1800 for aligning the loaded slides of the sample handling apparatus 400. FIGS. 18A-18C are similar to and adapted from FIGS. 17A-17C and the workflow 1800 may occur after the workflow 1700.

FIG. 18A shows the sample handling apparatus 400 of FIG. 17C with the second member 410 moved up towards the first members 404A and 404B. In some aspects, bringing the second member 410 closer to the first members 404 may make alignment of the desired regions of the slides 303 and 304 easier to achieve. The movement of the second member 410 may be performed by an adjustment mechanism (e.g., adjustment mechanism 415) of the sample handling apparatus 400. The bottom portion of FIG. 18A shows a top view of the initial alignment of the slides 303A, 303B, and 304. As further shown, the tissue samples 302A and 302B include regions of interest 1802A and 1802B, respectively. The regions of interest 1802A and 1802B may be selected by a user prior to loading the slides 303 into the sample handling apparatus 400 or may be determined after imaging of the tissue samples 302A and 302B. In some embodiments, the regions of interests 1802 can be annotations that can be manually applied on the histology slide 303A, the pathology slide 303B, or the array slide 304 by a user. For example, the user can annotate the region of interest 1802 on the slides using a marker, a stamp, or a sticker. In some embodiments, the regions of interest 1802 can be manually applied on an image of the tissue samples 302A and/or 302B, or on an image of the tissue samples 302A or 302B that have been overlaid with the array slide 304 by a user.

In some embodiments, the regions of interest 1802 can be automatically applied on the histology slide 303A and/or the pathology slide 303B, or on the array slide 304 based on inputs provided to the sample handling apparatus 400 by a user. In some embodiments, the regions of interest 1802 can be selected and annotated on a display of a computing device coupled to the sample handling apparatus 400. In some embodiments, the sample handling apparatus 400 can align the histology slide 303A and/or the pathology slide 303B with the array slide 304 based on the selected regions of interest 1802. In some embodiments, the sample handling apparatus 400 can read or determine the annotations marking the regions of interest 1802 via image capture, such as using the image capture device 1720, and using image processing techniques. In some embodiments, the annotating the regions of interest 1802 can be performed by a dedicated machine, separate from the sample handling apparatus 400, such that the dedicated machine applies the annotation markings to the histology slide 303A, the pathology slide 303B, or the array slide 304 after the user has selected the regions of interest 1802 via an interface provided with the sample handling apparatus 400. FIG. 18B depicts an alignment of the barcoded capture probe area 306A with the tissue sample region of interest 1802A. The alignment may occur in an xy plane and by moving the first member 404A in an xy direction to optically and vertically align the capture probes 306A with the region of interest 1802A. For example, as shown in the bottom portion of FIG. 18B, the top view of the slides 303A and 304 show that the capture probes 306A are aligned with the region of interest 1802A of the tissue sample 302A (e.g., dashed lines). In some aspects, the image capture device 1720 may aid in the alignment of the slides 303 and 304 by providing images of the capture probes 306A, the sample 302A, and/or the region of interest 1802A. In some aspects, the alignment precision may be within approximately 0.1-0.5 mm. In some embodiments, the automated alignment described herein can enable alignment precision within 1-10 microns.

In some aspects, the movement of the first member 404A may be performed by an alignment mechanism configured to move the slide 303A (e.g., the first substrate 406, the first substrate 1406, or the like) along a first plane (e.g., the xy plane of the histology slide 303A). In some implementations, the alignment mechanism may be configured to move the gene expression slide 304 (e.g., the second substrate 412, the second substrate 1412, or the like) along a second plane (e.g., the xy plane of the slide 304).

FIG. 18C depicts an alignment of the barcoded capture probe area 306B with the tissue sample region of interest 1802B. The alignment may occur in an xy plane and by moving the first member 404B in an xy direction to optically and vertically align the capture probes 306B with the region of interest 1802B. For example, as shown in the bottom portion of FIG. 18C, the top view of the slides 303B and 304 show that the capture probes 306B are aligned with the region of interest 1802B of the tissue sample 302B. In some aspects, the image capture device 1720 may aid in the alignment of the slides 303 and 304 by providing images of the capture probes 306B, the sample 302B, and/or the region of interest 1802B.

In some aspects, the movement of the first member 404B may be performed by an alignment mechanism configured to move the slide 303B (e.g., the first substrate 406, the first substrate 1406, or the like) along a first plane (e.g., the xy plane of the slide 303B). In some implementations, the alignment mechanism may be configured to move the gene expression slide 304 (e.g., the second substrate 412, the second substrate 1412, or the like) along a second plane (e.g., the xy plane of the slide 304).

Figure 19:
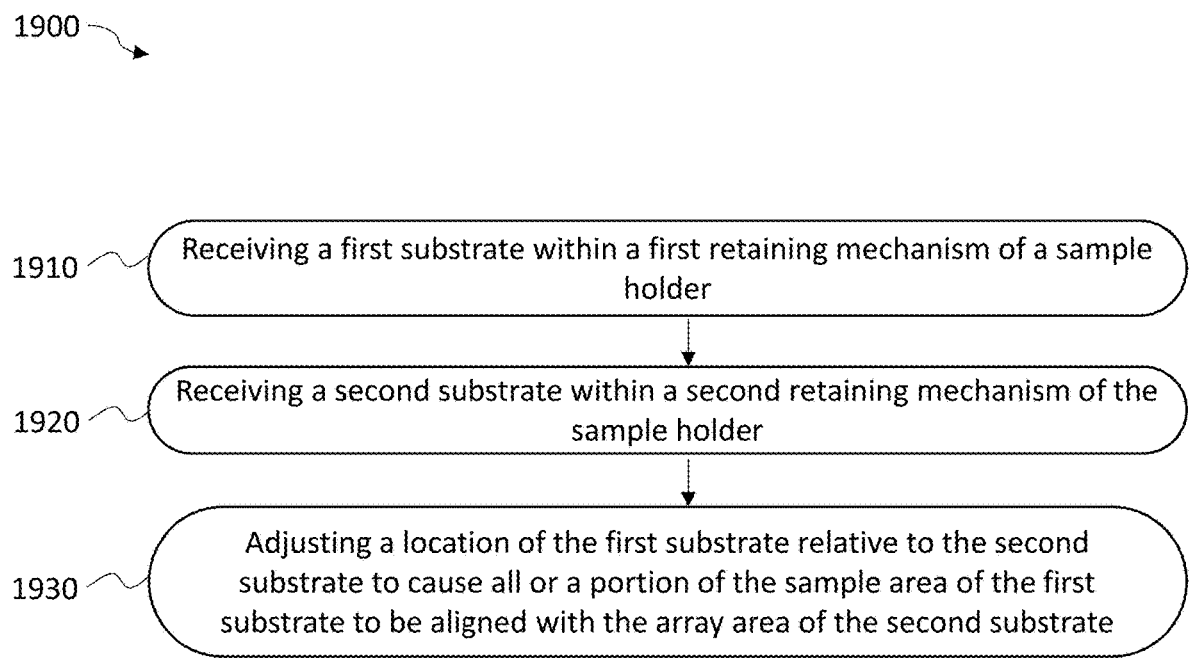
FIG. 19 is a process flow diagram illustrating an example process for aligning a sample area with an array area according to some implementations of the current subject matter.

FIG. 19 is a process flow diagram illustrating an example process 1900 for aligning a sample area with an array area according to some implementations of the current subject matter. At 1910, a first substrate can be received within a first retaining mechanism of a sample handling apparatus, such as sample handling apparatuses 400, 1400, or 3000. A user can provide or position the first substrate within the first retaining mechanism of the sample handling apparatus 400. The first substrate can include a sample applied to the first substrate by a user. The first substrate can also include a sample area into which the sample is to be placed. The first substrate can further include a sample area indicator identifying the sample area. In some embodiments, the first substrate can include a fiducial mark. The first retaining mechanism can include one or more spring members configured to apply a force to the first substrate to maintain contact between the first substrate and a first member of the sample handling apparatus 400 on which the first retaining mechanism is configured.

At 1920, a second substrate can be received within a second retaining mechanism of the sample handling apparatus 400. The second substrate can include an array of reagent medium formed within an array area indicator identifying the array on the second substrate. In some embodiments, the array area indicator can be provided on the sample handling apparatus 400. A user can provide or position the second substrate within the second retaining mechanism of the sample handling apparatus 400. The second retaining mechanism can include one or more spring members configured to apply a force to the second substrate to maintain contact between the second substrate and a second member of the sample holder on which the second retaining mechanism is configured.

At 1930, a location of the first substrate can be adjusted relative to the second substrate to cause all or a portion of the sample area of the first substrate to be aligned with the array area of the second substrate. In some embodiments, adjusting the location of the first substrate relative to the second substrate can be performed to cause the sample area indicator to be aligned with the array area indicator. In some embodiments, the location of the first substrate relative to the second substrate can be adjusted by a user. For example, the user can manually manipulate the first member and/or the second member of the sample holder so as to adjust a location of the first substrate and/or the second substrate within the sample holder to cause the sample area to be aligned with the array area. In some embodiments, the location of the first substrate can be adjusted relative to the second substrate, which can be fixed in position within the sample handling apparatus 400. In some embodiments, the location of the second substrate can be adjusted relative to the first substrate, which can be fixed in position within the sample handling apparatus 400. In some embodiments, the second substrate can be fixed in place within the sample handling apparatus 400 and the first retaining mechanism can be adjusted to cause all or a portion of the sample area to be aligned with the array area.

In some embodiments, a user can adjust the location of the first substrate and/or the second substrate while viewing the first substrate and/or the second substrate within the sample handling apparatus 400. For example, the user can view the first substrate and the second substrate via a microscope of the instrument configured to provide the sample holder within a field of view of the microscope. In some embodiments, the instrument can include a display providing a view of the first substrate and the second substrate within the sample handling apparatus.

In some embodiments, adjusting the location of the first substrate relative to the second substrate can further include viewing the first substrate and the second substrate within the sample holder and adjusting the first retaining mechanism and/or the second retaining mechanism to cause all or a portion of the sample area to be aligned with the array area. In this way, the sample handling apparatus 400 can advantageously support efficient and precise alignment by providing multiple, different ways to perform the alignment. In some embodiments, the adjusting can be performed in the absence of a sample area indicator configured on the first substrate and/or in the absence of an array area indicator configured on the second substrate.

In some embodiments, the location of the first substrate and/or the second substrate can be adjusted within the sample holder by a user interacting with a physical positioning device configured on the sample handling apparatus 400, or on the instrument while viewing the first substrate and the second substrate. The physical positioning device can include a joy stick, a pointing stick, a button, or the like. In some embodiments, the instrument can be configured with computer-readable, executable instructions stored in a memory of the instrument. The instructions, when executed, can perform the adjusting automatically based on image data associated with the sample handling apparatus 400, the first substrate, and/or the second substrate. In some embodiments, the instrument can be configured with a display providing a graphical user interface (GUI). A user can interact with the GUI to adjust the location of the first substrate relative to the second substrate to cause all or a portion of the sample area indicator to be aligned with respect to the array area indicator.

Figure 20:
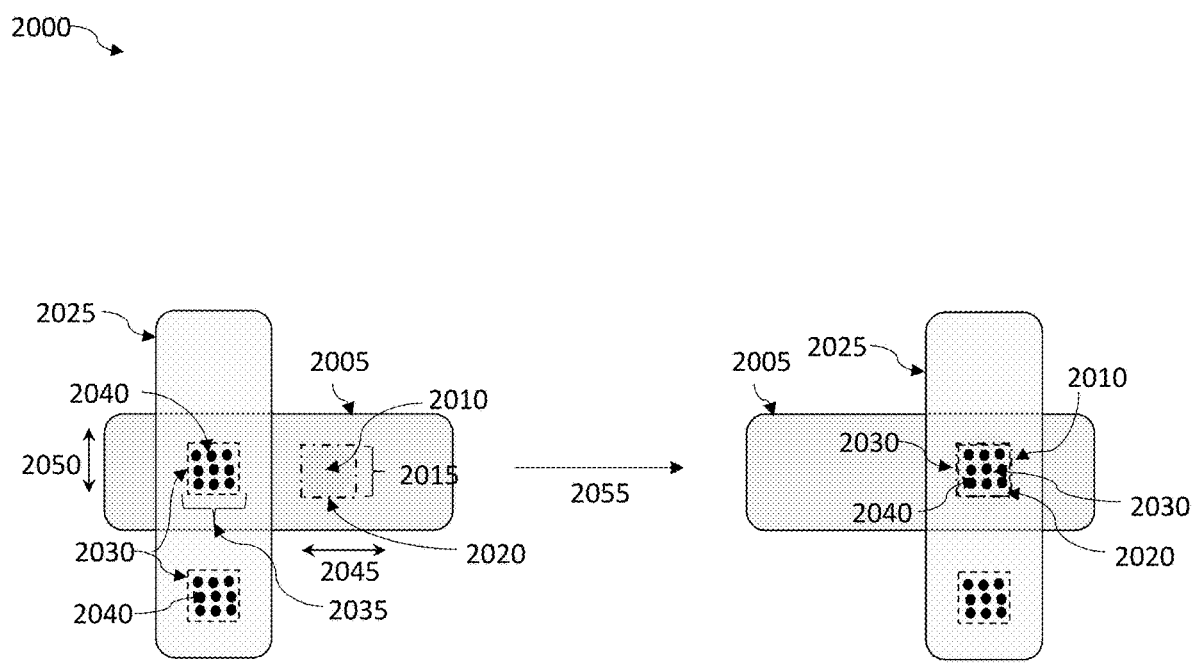
FIG. 20 depicts a workflow for adjusting a location of the first substrate relative to the second substrate to align all or a portion of a sample area with an array area according to some implementations of the current subject matter.

FIG. 20 depicts a workflow 2000 for adjusting a location of the first substrate relative to the second substrate to align all or a portion of a sample area with an array area. As shown in FIG. 20, and with reference to operation 1930 described in relation to FIG. 19, a first substrate 2005 can include a sample 2010 positioned by a user within a sample area 2015 identified by a sample area indicator 2020 of the first substrate 2005. In some embodiments, the first substrate 2005 may not include the sample area indicator 2020. The second substrate 2025 can include one or more array area indicators 2030 indicating a location of an array area 2035. Each array area 2035 can include an array 2040 therein.

The sample handling apparatus 400 can be configured to enable adjustment of the first substrate 2005 and/or the second substrate 2025 along a first axis 2045 and a second axis 2050. The first axis 2045 can be considered a later axis within a transverse plane corresponding to the mounting surface in which the first substrate 2005 and the second substrate 2025 are received within the sample handling apparatus 400. The second axis 2050 can be considered a longitudinal axis within the transverse plane corresponding to the mounting surface in which the first substrate 2005 and the second substrate 2025 are received within the sample handling apparatus 400.

As shown in FIG. 20, adjusting 2055 the first substrate 2005 relative to the second substrate 2025 can be performed to cause all or a portion of the sample area 2015 to be aligned with the array area 2035. Additionally, or alternatively, the adjusting 2055 (e.g., operation 1930 of FIG. 19) can further cause the sample area indicator 2020 to be aligned with respect to the array area indicator 2030. In this way, the adjusting 2055 can cause the sample 2010 to be aligned with the array 2040.

Figure 21A:
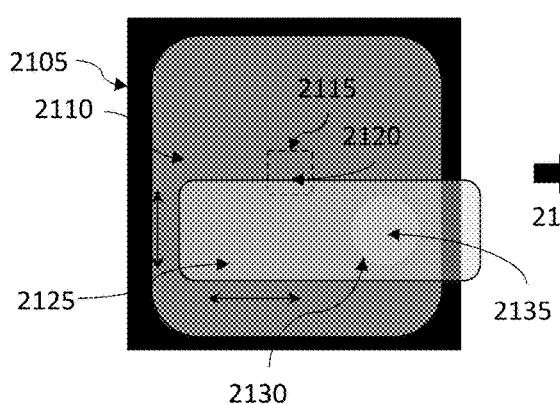
FIGS. 21A-21B depict a workflow for adjusting a location of the first substrate relative to the second substrate based on an array area indicator configured within a sample holder according to some implementations of the current subject matter.
Figure 21B:
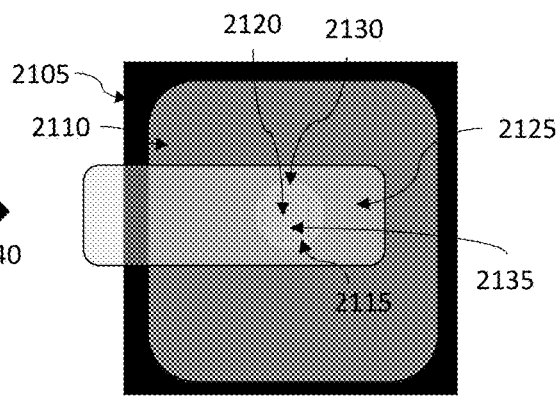

FIGS. 21A-21B depict a workflow 2100 for adjusting a location of the first substrate relative to the second substrate based on an array area indicator configured within a sample handling apparatus 400 according to some implementations of the current subject matter. As shown in FIG. 21A, a sample handling apparatus 400 can include a retaining mechanism 2105 configured with a surface 2110. The surface 2110 can include an array area indicator 2115 identifying an array area 2120. In some embodiments, part or all of the surface 2110 is transparent. In some embodiments, the array area indicator 2115 identifies the position of an array on the second substrate when the first and second substrates are brought into a sandwich configuration (e.g., the sandwich configuration depicted in FIG. 3). The array area indicator 2115 can be configured on a first surface of the retaining mechanism 2105, for example a first surface corresponding to the surface 2110. In some embodiments, the array area indicator 2115 can be configured on a second surface of the retaining mechanism 2105, the second surface opposite the surface 2110. In some embodiments, a portion of the retaining mechanism 2105 can include the surface 2110. In some embodiments, the array area indicator 2115 is transparent and can be backlit. In some embodiments, the surface 2110 can be frontlit instead of backlit. In some embodiments, the surface 2110 may not include lighting and can be lit via ambient lighting.

As shown in FIG. 21B, a first substrate 2125 including a sample 2130 positioned within a sample area 2135 can be received within the retaining mechanism 2105. Adjusting 2140 the substrate 2125 relative to the transparent surface 2110 can be performed to cause all or a portion of the sample area 2135 to be aligned with the array area 2120. The first and second substrates may be then brought into sandwich configuration (e.g., the sandwich configuration depicted in FIG. 3) such that the sample area 2135 is aligned with an array on the second substrate.

Figure 21C:
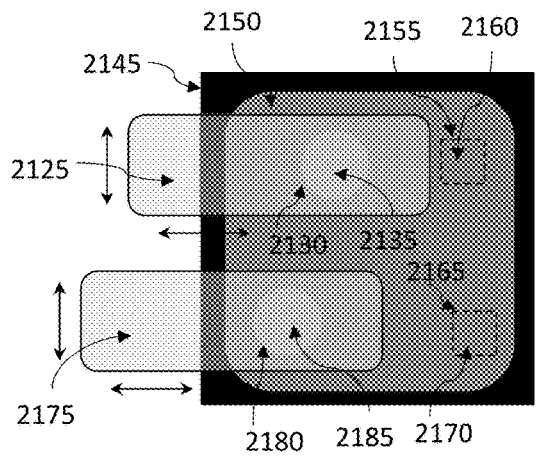
FIGS. 21C-21D depict a workflow for adjusting a location of multiple first substrates relative to the second substrate based on multiple array area indicators configured within a sample holder according to some implementations of the current subject matter.
Figure 21D:
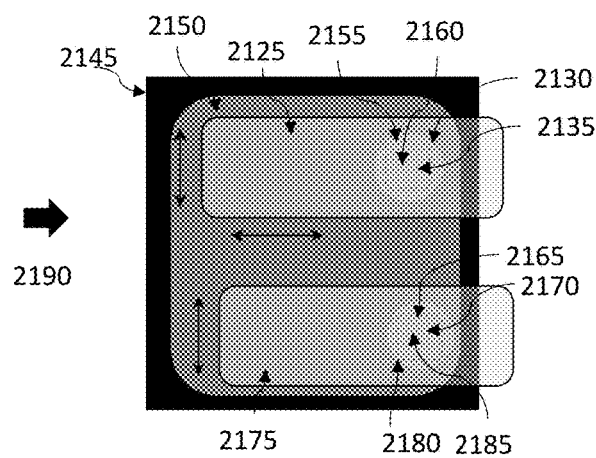

FIGS. 21C-21D depict a workflow for adjusting a location of multiple first substrates relative to the second substrate based on multiple array area indicators configured within a sample holder according to some implementations of the current subject matter. As shown in FIG. 21C, a sample handling apparatus 400 can include a retaining mechanism 2145 configured with a surface 2150. The surface 2150 can include a first array area indicator 2155 identifying a first array area 2160 and a second array area indicator 2165 identifying a second array area 2170. In some embodiments, part of all of the surface 2150 is transparent. In some embodiments, the array area indicators 2155 and 2165 identify the position of the arrays on the second substrate when the first and second substrates are brought into a sandwich configuration (e.g., the sandwich configuration depicted in FIG. 3). The array area indicators 2155 and 2165 can be configured on a first surface of the retaining mechanism 2145, for example a first surface corresponding to the surface 2150. In some embodiments, the array area indicators 2155 and 2165 can be configured on a second surface of the retaining mechanism 2145, the second surface opposite the surface 2150. As shown in FIG. 21C, a first substrate 2125 including a first sample 2130 positioned within a sample area 2135 can be received within the retaining mechanism 2145. A second substrate 2175 including second sample 2180 positioned within a second sample area 2185 can also be received within the retaining mechanism 2145.

As shown in FIG. 21C and FIG. 21D, adjusting 2190 the first substrate 2125 relative to the surface 2150 can be performed to cause all or a portion of the first sample area 2135 to be aligned with the first array area 2160. The second substrate 2175 can be also adjusted 2190 relative to the surface 2150 to cause all or a portion of the second sample area 2185 to be aligned with the second array area 2170. The first substrate 2125 and the second substrate 2175 may be then brought into sandwich configuration (e.g., the sandwich configuration depicted in FIG. 3) such that the first sample area 2135 is aligned with an array configured within the first array area 2160 and the second sample area 2185 is aligned with the an array configured within the second array area 2170.

Figure 22A:
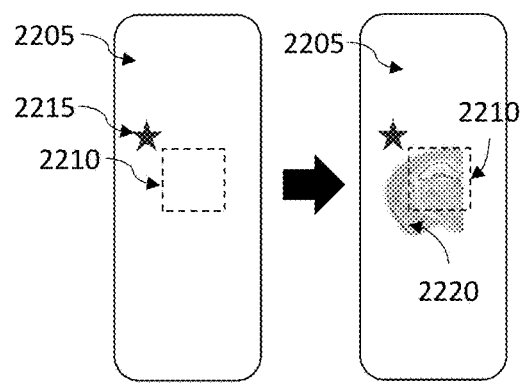
FIGS. 22A-22C depicts a workflow for indicating a sample area of a substrate according to some implementations of the current subject matter.
Figure 22B:
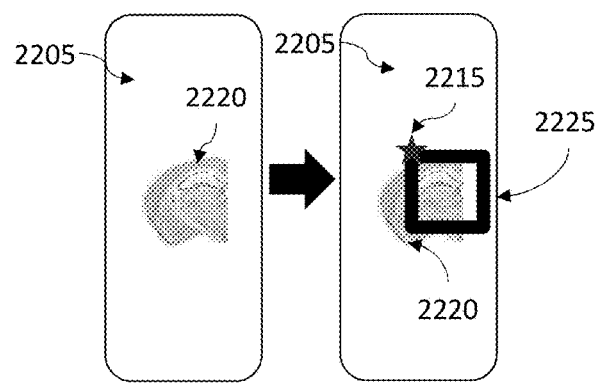
Figure 22C:
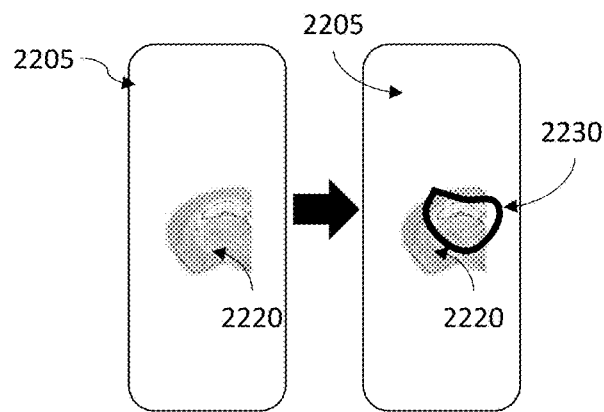

FIGS. 22A-22C depict a workflow 2200 for indicating a sample area of a substrate according to some implementations of the current subject matter. The substrate described in relation to FIGS. 22A-22C can be equivalent to the first substrate described in relation to FIGS. 19 and 20. To indicate a sample area of a substrate on to which a sample is placed a variety of embodiments can be considered.

As shown in FIG. 22A, a substrate 2205 can include a sample area indicator 2210. The sample area indicator 2210 can be provided by the manufacturer of the substrate such that the sample area indicator is provided on the substrate 2205 prior to a user placing a sample 2220 onto the substrate 2205. In some embodiments, the sample area indicator 2210 can be applied to a first side of the substrate 2205 prior to applying the sample 2220 to the first side of the substrate 2205. In some embodiments, the sample area indicator 2210 can be applied to a second side of the substrate 2205. The second side of the substrate 2205 can be opposite the first side of the substrate 2205. In some embodiments, the sample area indicator 2210 can be applied to the second side of the substrate 2205 after the sample 2220 has been applied to the first side of the substrate 2205.

As further shown in FIG. 22A, the substrate 2205 can include a fiducial mark 2215. The fiducial mark 2215 can be applied to the first side of the substrate 2205 or to the second side of the substrate 2205. The fiducial mark 2215 can be used to aid alignment of the sample area on a first substrate 2205 with an array area on second substrate, such as second substrate 2025 described in relation to FIG. 20. The fiducial mark 2215 can include a variety of non-limiting shapes and formats, such as variously shaped applied or embedded markings or etchings, suitable to provide a fiducial reference on the substrate 2205.

As shown in FIG. 22B, the sample area indicator can include a stamp or a sticker 2225. The stamp or sticker 2225 can be applied to the second side of the substrate 2205 after the sample 2220 has been applied to the first side of the substrate 2205 by a user.

As shown in FIG. 22C, the sample area indicator can be applied as a drawing 2230 on the second side of the substrate 2205 after the sample 2220 has been applied to the first side of the substrate 2205 by a user. In some embodiments, the drawing 2230 can be drawn by a user with a marker suitable for marking the substrate 2205.

In some embodiments, informational labels with printed guides can be provided to assist users in tissue placement onto slides. Fiducial markers (e.g., dots, numbers and letters) can provide a visual guide for the printed array location on the slide. Dots can indicate the center of an array while numbers and letters can identify individual wells. In some embodiments, informational labels with printed guides reduce surface smudging, and reduce direct contact with the cryostat surfaces by acting as a physical barrier between the slide and other surfaces. In some embodiments, informational labels are disposable.

In some embodiments, informational labels may be transparent. Informational labels may have printed guides that are printed with ink (e.g., white ink, black ink, color ink, or fluorescent ink). In some embodiments, informational labels may be printed using thermal printing which uses heat to transfer impressions to the informational label. In some embodiments, etching can be used to print guides on the informational label. Informational label texture can be altered by printing different patterns on the surface of the informational label. In some embodiments, an informational label has a matte finish. In some embodiments, an informational label has a glossy finish. Informational labels can have holes or cut-outs in the interior of the informational label. In some embodiments, an informational label occupies all of the retaining mechanism and/or transparent surface upon which sample substrates can be received within the sample handling apparatus 400, 1400, and 3000. In some embodiments, an informational label occupies a portion of the retaining mechanism and/or transparent surface of the sample handling apparatus 400, 1400, and 3000. In some embodiments, an informational label is capable of thermal and electrical conductivity. In some embodiments, an informational label is capable of thermal conductivity. In some embodiments, an informational label is capable of electrical conductivity. In some embodiments, an informational label contains metadata. Non-limiting examples of metadata include tissue placement guides, array/well identification, slide identification barcode, slide orientation, expiration date, type of slide, dimension of slide, or other instructions for the user. In some embodiments, a fixture could be used to hold the slide in place to apply the informational label and prevent damage to the slide. Using such fixture to apply the informational label can reduce surface smudging while applying the informational label to the slide.

Figure 23:
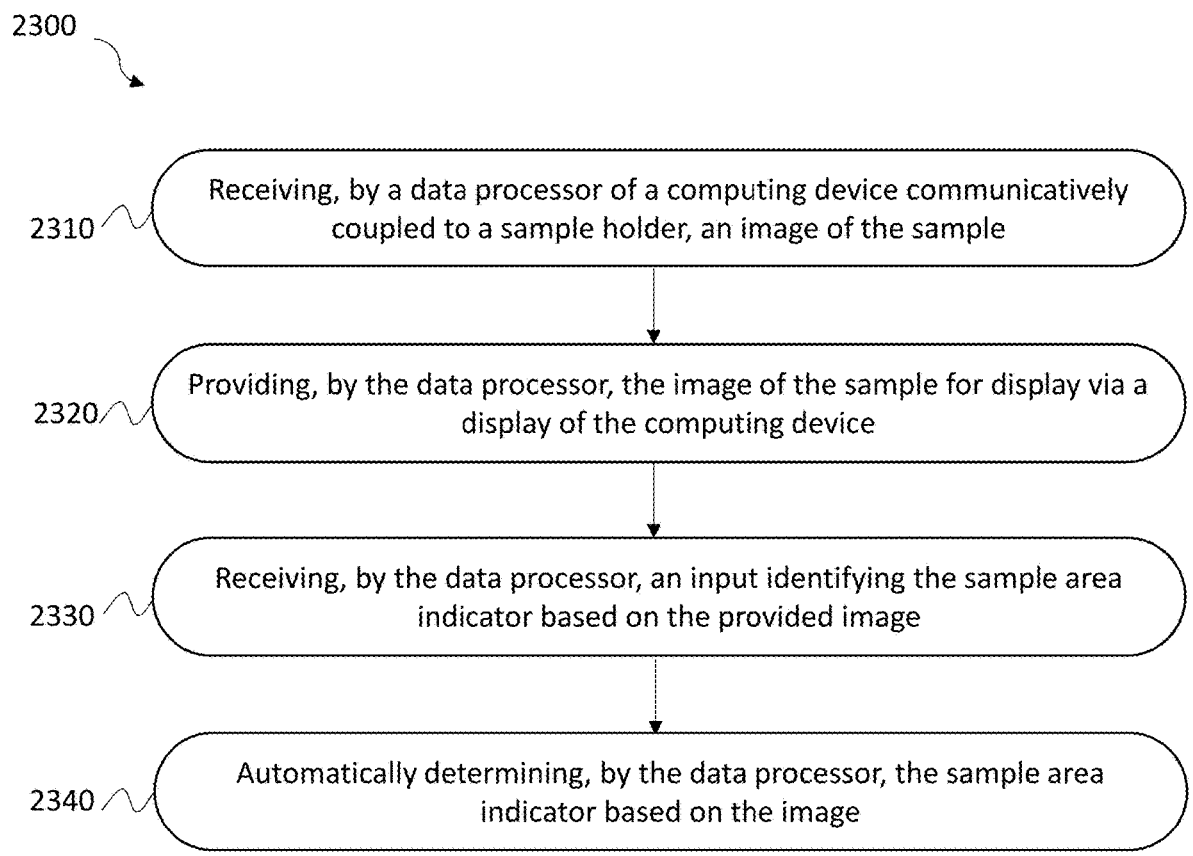
FIG. 23 is a process flow diagram illustrating an example process for automatically determining a sample area indicator based on a received image of the sample according to some implementations of the current subject matter.

FIG. 23 is a process flow diagram illustrating an example process 2300 for automatically determining a sample area indicator based on a received image of the sample according to some implementations of the current subject matter. The system, methods, and mediums described herein can be configured to determine a sample area indicator based on an image of a sample. At 2310, an image of a sample can be received by a data processor of a computing device communicatively coupled to a sample handling apparatus 400. The sample handling apparatus 400 can receive and retain a substrate including the sample therein. The computing device can be further communicatively coupled to an image capture device 1720, such as a microscope, a camera, an optical sensor, an imaging device, or the like configured to acquire and provide an image of the sample to the computing device. In some embodiments, the data processor of the computing device can be configured to receive the image of the sample from a data processor of a remote computing device communicatively coupled to the computing device at which the process 2300 is performed.

At 2320, the data processor can provide the image of the sample for display via a display of the computing device. In some embodiments, the image of the sample can be provided for display via a GUI configured within the display of the computing device.

At 2330, the data processor can receive an input identifying the sample area indicator based on the provided image. For example, the display of the computing device can include a touch-screen display configured to receive a user input identifying the sample area indicator on the displayed image. In some embodiments, the GUI can be configured to receive a user provided input identifying the sample area indicator.

At 2340, the data processor can automatically determine the sample area indicator based on the image. The data processor can be configured to access and execute computer-readable, executable instructions configured to automatically determine the sample area indicator based on a variety of features included in the image. For example, the data processor can automatically determine the sample area indicator based on an outline of the tissue present within the image. This approach can be used when the sample area is smaller than the array area. In some embodiments, the data processor can automatically determine the sample area indicator based on a stamp or a sticker that is visible in the image and was applied to the first substrate by a user. In some embodiments, the data processor can automatically determine the sample area indicator based on a fiducial mark located on the first substrate that is visible in the image. In some embodiments, the data processor can automatically determine the sample area indicator based on a drawing that is visible in the image and was applied to the first substrate by a user.

In some embodiments, the data processor can access and execute computer-readable, executable instructions configured to automatically determine the sample area indicator based on sample area indicator data which can be stored in a memory of the computing device. In some embodiments, the sample area indicator data can be imported into the computing device from a second computing device that is remote from and communicatively coupled to the computing device automatically determining the sample area indicator associated with the sample in the image.

In some embodiments, the data processor can access and execute computer-readable, executable instructions configured to automatically determine the sample area indicator based on processing the sample image using image segmentation functionality. In some embodiments, the data processor can access and execute computer-readable, executable instructions configured to automatically determine the sample area indicator based on a type of sample, a size of sample, a shape of the sample, and/or an area of the sample.

Figures 24A, 24B:
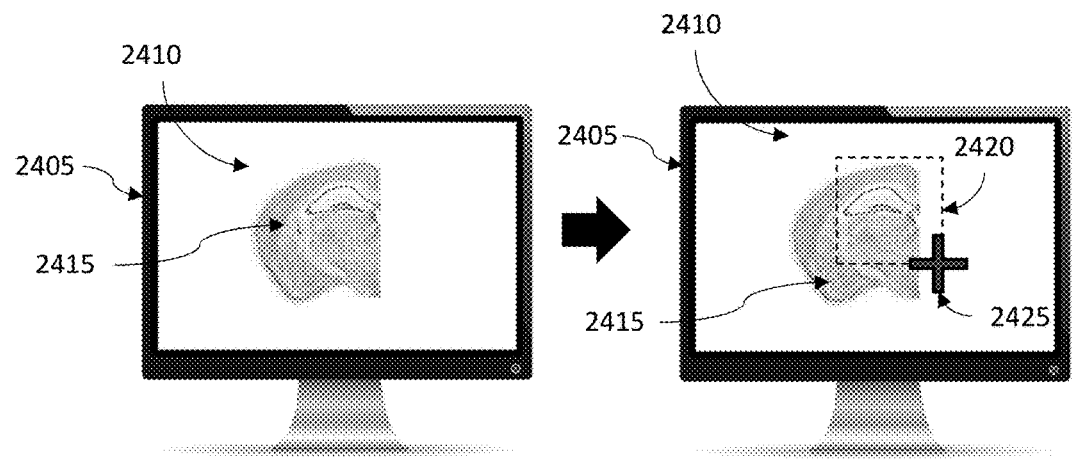
FIGS. 24A-24B depict a workflow for receiving an input identifying a sample area indicator based on an image of a sample.

FIGS. 24A-24B depict a workflow 2400 for receiving an input identifying a sample area indicator based on an image of a sample as described in relation to operation 2330 of FIG. 23. As shown in FIG. 24A, a computing device 2405 can include a display 2410. The display 2410 can be configured to provide an image 2415 of a sample. As shown in FIG. 24B, a user may interact with the display 2410 to provide an input identifying the sample area indicator 2420. For example, the user can manipulate a mouse or other input device in relation to the image 2415 of the sample so as to provide an input identifying the sample area indicator 2420. The user input can be provided to select all or a portion of the image 2415 to be associated with the sample area indicator 2420. The selection can be provided by the user dragging a cursor 2425 over the image 2415 to form the sample area indicator 2420. In some embodiments, the input can be provided by a user cropping the image 2415 such that the perimeter of the cropped image forms the sample area indicator 2420.

Figure 25:
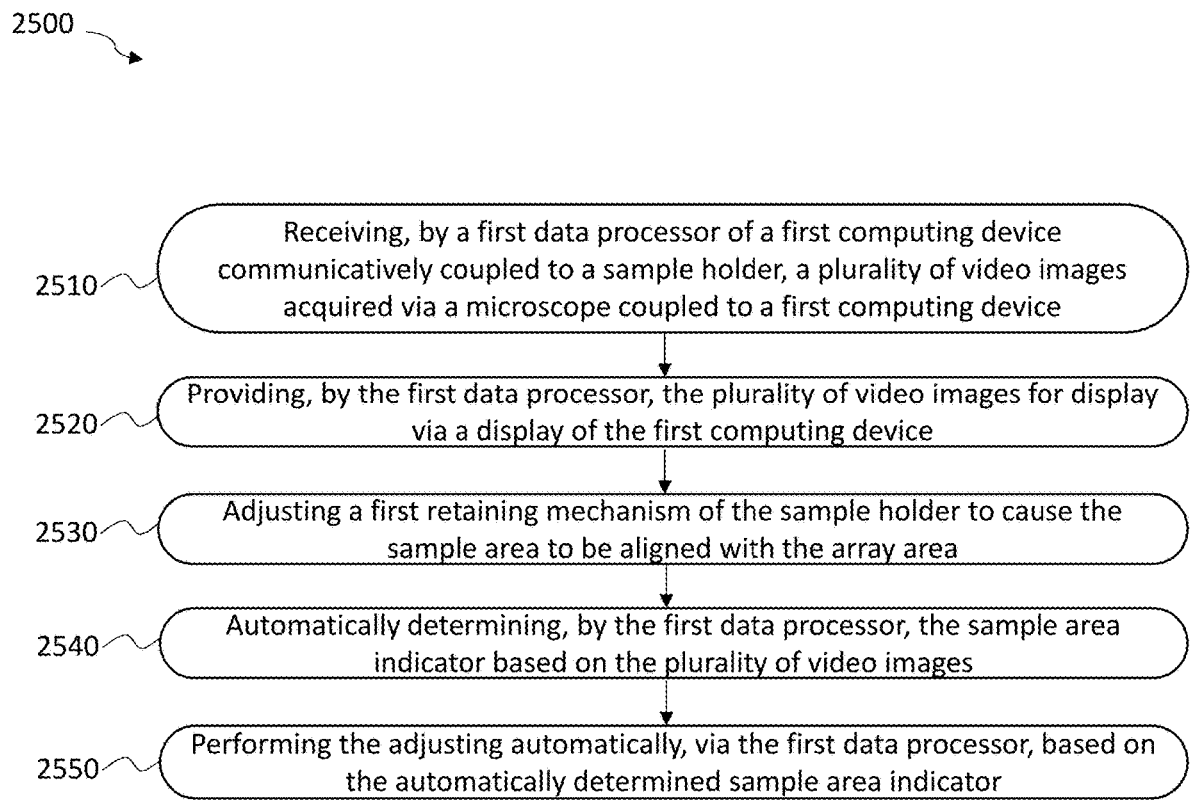
FIG. 25 is a process flow diagram illustrating an example process for automatically determining a sample area indicator based on a received plurality of video images according to some implementations of the current subject matter.

FIG. 25 is a process flow diagram illustrating an example process 2500 for automatically determining a sample area indicator based on a plurality of received video images according to some implementations of the current subject matter. At 2510, a data processor of a computing device communicatively coupled to a sample handling apparatus 400 can receive a plurality of video images. The plurality of video images can be acquired by and received from via an image capture device 1720, such as a microscope, a camera, an optical sensor, an imaging device, or the like, communicatively coupled to the data processor. The plurality of video images can include the sample positioned on a first substrate and the array located on the second substrate. The plurality of video images can include the second substrate overlaid atop the first substrate. In some embodiments, the data processor of the computing device can be configured to receive the image of the sample from a data processor of a remote computing device communicatively coupled to the computing device at which the process 2500 is performed.

At 2520, the data processor can provide the plurality of video images for display via a display of the computing device. In some embodiments, the plurality of video images can be provided for display via a GUI configured within the display of the computing device. In some embodiments, the plurality of video images can be provided to a data processor of a second computing device. The second computing device can be remote from the first computing device and can be communicatively coupled to the first computing device at which the plurality of video images were first received. The second computing device can be configured to provide the plurality of video images for display via a display of the second computing device. In some embodiments, the second computing device can be configured to receive an input from a user identifying a sample area indicator associated with the sample positioned on the first substrate. The user can provide the input identifying the sample area indicator to the second computing device as previously described above.

At 2530, a user can manually adjust a first retaining mechanism of the sample handling apparatus 400 to cause the sample area of the first substrate to be aligned with the array area of the second substrate. In some embodiments, the user can adjust the first retaining mechanism of the sample handling apparatus 400 to cause the sample area of the first substrate to be aligned with an array area configured within the sample handling apparatus 400. The user can adjust the first retaining mechanism based on viewing the plurality of video images provided by the first computing device or the second computing device.

At 2540, in addition, or in alternative, to the manual adjustment performed at 2530, the data processor of the first computing device can automatically determine the sample area indicator based on the plurality of video images. The data processor of the first computing device can be configured to access and execute computer-readable, executable instructions configured to automatically determine the sample area indicator based on a variety of features included in the plurality of video images. For example, the data processor can automatically determine the sample area indicator based on an outline of the tissue present within the plurality of video images. This approach can be used when the sample area is smaller than the array area. In some embodiments, the data processor can automatically determine the sample area indicator based on a stamp or a sticker that is visible in the plurality of video images and was applied to the first substrate by a user. In some embodiments, the data processor can automatically determine the sample area indicator based on a fiducial mark located on the first substrate that is visible in the plurality of video images. In some embodiments, the data processor can automatically determine the sample area indicator based on a drawing that is visible in the plurality of video images and was applied to the first substrate by a user.

In some embodiments, the data processor can access and execute computer-readable, executable instructions configured to automatically determine the sample area indicator based on sample area indicator data which can be stored in a memory of the computing device. In some embodiments, the sample area indicator data can be imported into the computing device from a second computing device that is remote from and communicatively coupled to the computing device automatically determining the sample area indicator associated with the sample in the plurality of video images.

At 2550, the data processor of the first computing device can perform the adjusting automatically based on the automatically determined sample area indicator. The computing device can be configured to automatically adjust the location of the first substrate relative to the second substrate to cause all or a portion of the sample area to be aligned with an array area of the second substrate via a controller that can be communicatively coupled to the sample handling apparatus 400 and to the first computing device. The controller can receive input signals from the data processor and can generate control signals causing the first retaining mechanism or the second retaining mechanism to translate within the sample handling apparatus 400 and there by adjust the location of the first substrate or the second substrate, respectively.

In some embodiments, the data processor of a second computing device, communicatively coupled to the data processor of the first computing device, can similarly be coupled to the controller and to the sample handling apparatus 400. The data processor of the second computing device can generate input signals to the controller and can cause the controller to generate control signals causing first retaining mechanism or the second retaining mechanism to translate within the sample handling apparatus 400. In this way, the location of the first substrate and/or the second substrate can be controlled and adjusted such that the sample area of the first substrate can be aligned with the array area of the second substrate.

Figure 26:
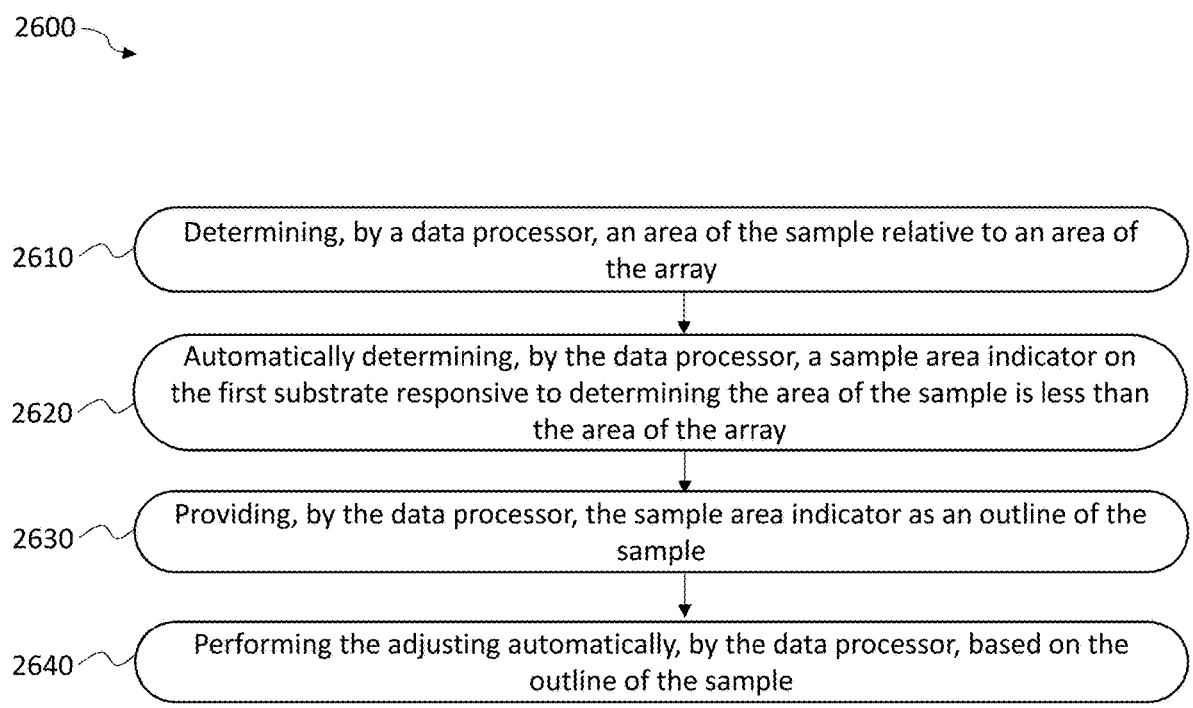
FIG. 26 is a process flow diagram illustrating an example process for automatically determining a sample area indicator responsive to determining an area of the sample according to some implementations of the current subject matter.

FIG. 26 is a process flow diagram illustrating an example process 2600 for automatically determining a sample area indicator responsive to determining an area of the sample according to some implementations of the current subject matter. At 2610, a data processor can determine an area of the sample relative to an area of the array, such as during alignment of the outline of the sample to the array area. For example, the data processor can be configured to determine an area of the sample relative to an area of the array in an automated manner. In some embodiments, the sample substrate would be imaged first and an outline of the sample could be determined using an image processing pipeline configured within the sample handling apparatus 400 or the data processor. If the sample size is determined to be larger than array size, the image processing pipeline can annotate the target sample area with an annotation detectable to the image processing pipeline.

In some embodiments, a user can manually align the outline of the sample to the array area. When the outline is not clear, or the sample is larger, the sample substrate or slide can be annotated by an expert indicating the sample area on the sample substrate with a marker, a stamp, a sticker, or the like. In some embodiments, the sample handling apparatus 400 can apply the annotation based on user provided inputs identifying the sample area or a region of interest in a display of the sample handling apparatus. In some embodiments, the inputs can be provided to the sample handling apparatus 400 or to a computing device communicatively coupled to the sample handling apparatus 400.

At 2620, the data processor can automatically determine a sample area indicator on the first substrate responsive to determining the area of the sample is less than the area of the array. For example, after the sample substrate is imaged and the outline of the sample is determined using the image processing pipeline, the outline may be compared to the area of the array to determine the area of the sample is less than the area of the array.

At 2630, the data processor can provide the sample area indicator as an outline of the sample. For example, the sample area indicator can be provided in a display of the computing device.

At 2640, the data processor can perform the adjusting automatically based on the outline of the sample. For example, the data processor can use the image processing pipeline of the sample handling apparatus 400 to fit the outline within the array area. The sample handling apparatus 400 can be configured to provide the actuation to cause the alignment via one or more actuators. In some embodiments, the alignment could be to the array itself, to a virtual outline provided in a graphical user interface of a display of the sample handling apparatus 400, or to alignment reference marks provided in the sample handling apparatus that indicate where the array will be located. As described above, the data processor of the computing device can be configured to automatically adjust the location of the first substrate relative to the second substrate to cause all or a portion of the sample area to be aligned with an array area of the second substrate via a controller that can be communicatively coupled to the sample handling apparatus 400 and to the computing device. The controller can receive input signals from the data processor and can generate control signals causing the first retaining mechanism or the second retaining mechanism to translate within the sample handling apparatus 400 and there by adjust the location of the first substrate or the second substrate, respectively.

Figure 27:
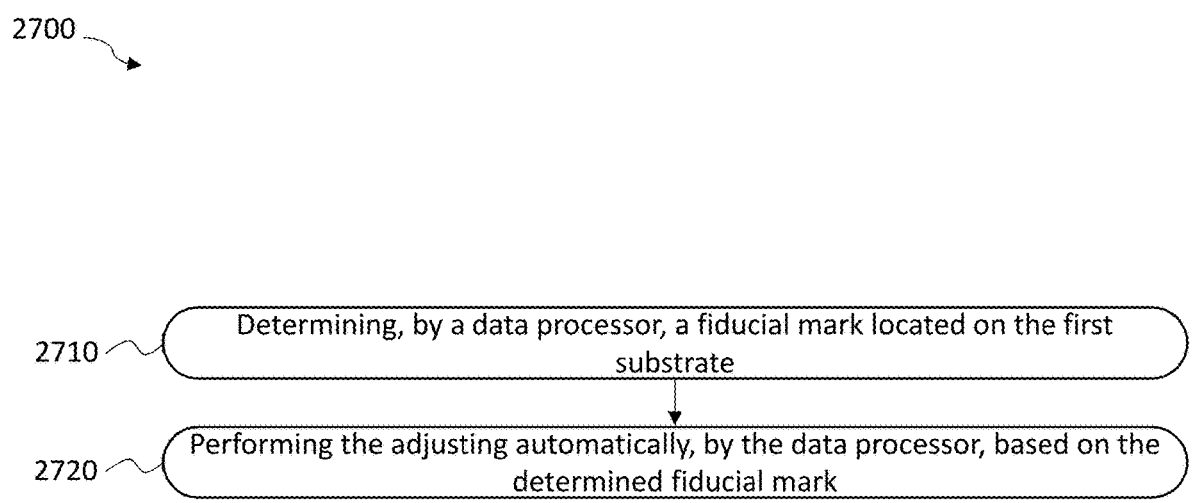
FIG. 27 is a process flow diagram illustrating an example process for determining a fiducial mark located on a first substrate according to some implementations of the current subject matter.

FIG. 27 is a process flow diagram illustrating an example process 2700 for determining a fiducial mark located on a first substrate according to some implementations of the current subject matter. At 2710, a data processor can determine a fiducial mark located on the first substrate. The fiducial marks can be determined using computer vision and/or image processing functionality provided in an image processing pipeline configured within the sample handling apparatus 400. The fiducial may include a high contrast or uniquely shaped mark to aid in determination of the fiducial via the computer vision and/or image processing functionality provided in an image processing pipeline, or other methods.

At 2720, the data processor can perform the adjusting automatically based on the determined fiducial mark. As described above, the data processor of the computing device can be configured to automatically adjust the location of the first substrate relative to the second substrate to cause all or a portion of the sample area to be aligned with an array area of the second substrate via a controller that can be communicatively coupled to the sample handling apparatus 400 and to the computing device. In some aspects, the adjusting may be based on the location of the determined fiducial. For example, the fiducial may provide a reference point for aligning the first substrate with the second substrate. The controller can receive input signals from the data processor and can generate control signals causing the first retaining mechanism or the second retaining mechanism to translate within the sample handling apparatus 400 and there by adjust the location of the first substrate or the second substrate, respectively.

Figure 28:
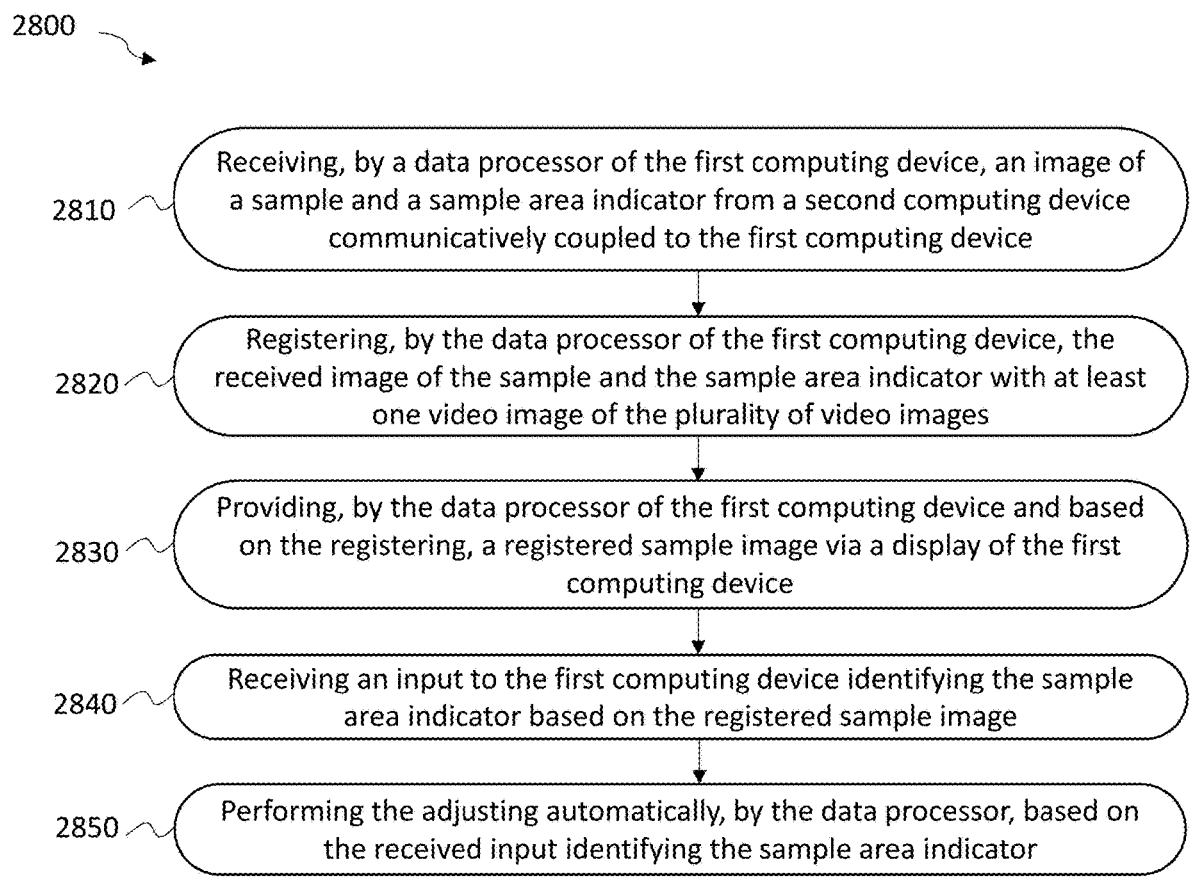
FIG. 28 is a process flow diagram illustrating an example process for identifying the sample area indicator based on a registered sample image according to some implementations of the current subject matter.

FIG. 28 is a process flow diagram illustrating an example process 2800 for identifying a sample area indicator based on a registered sample image according to some implementations of the current subject matter. At 2810, a data processor of a first computing device can receive an image of a sample and a sample area indicator from a second computing device communicatively coupled to the first computing device.

At 2820, the data processor of the first computing device can register the receive image of the sample and the sample area indicator with at least on video image of a plurality of video images. The plurality of video images can be acquired via an image capture device 1720, such as a microscope, a camera, an optical sensor, an imaging device, or the like, communicatively coupled to the data processor of the first computing device.

At 2830, the data processor of the first computing device can provide, based on the image registration, a registered sample image via a display of the first computing device. For example, the registered sample image can be provided in a display of the first computing device.

At 2840, an input identifying the sample area indicator in the registered sample image can be received at the first computing device. For example, a user can provide an input to a GUI provided in a display of the first computing device. In some embodiments, the display can receive the input directly from the user or via an input device, such as a mouse or a stylus, coupled to the display.

At 2850, the data processor can perform the adjusting automatically based on the received input identifying the sample area indicator. The computing device can be configured to automatically adjust the location of the first substrate relative to the second substrate to cause all or a portion of the sample area to be aligned with an array area of the second substrate via a controller that can be communicatively coupled to the sample handling apparatus 400 and to the first computing device. The controller can receive input signals from the data processor and can generate control signals causing the first retaining mechanism or the second retaining mechanism to translate within the sample handling apparatus 400 and there by adjust the location of the first substrate or the second substrate, respectively.

Figure 29:
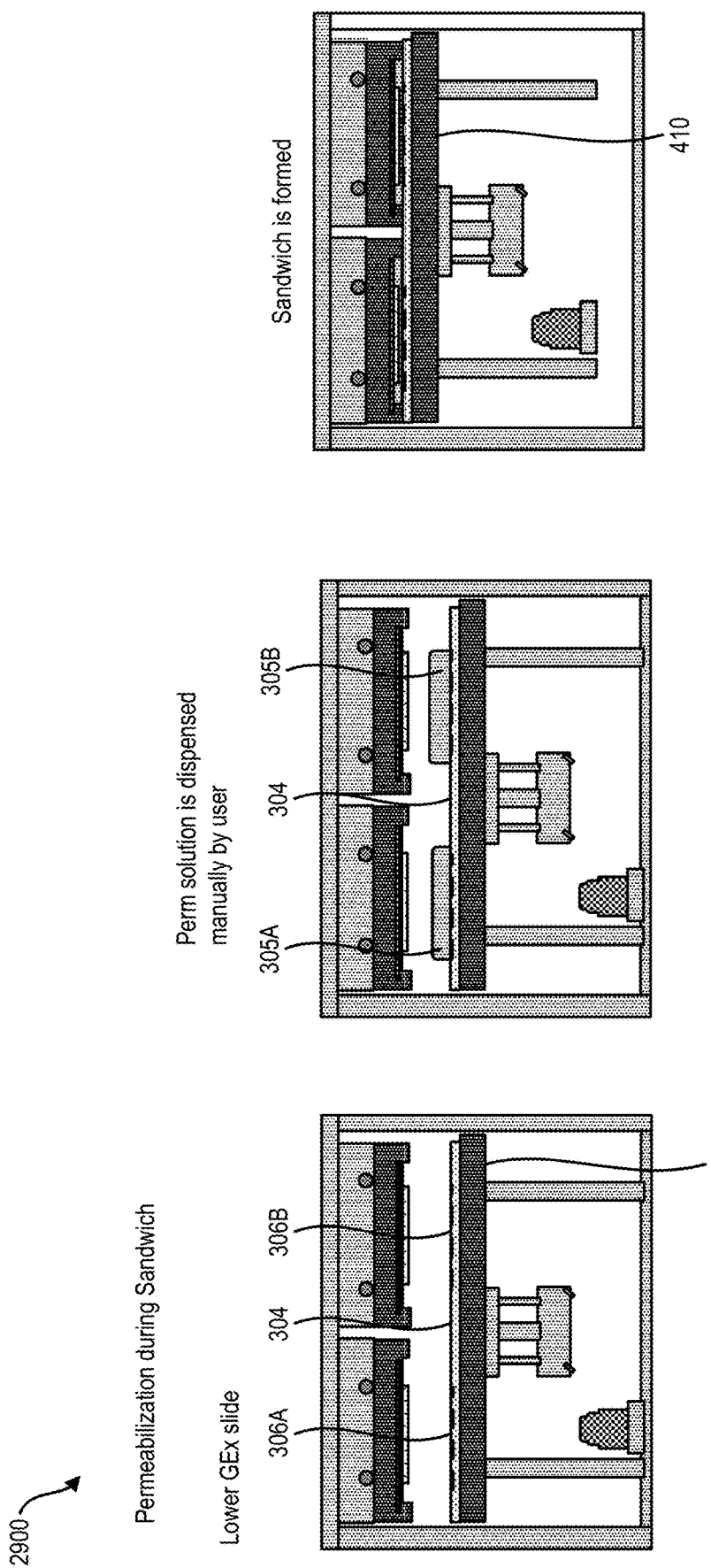
FIGS. 29A-29C depict a workflow for permeabilization of a sample of the sample handling apparatus in accordance with some example implementations.

FIGS. 29A-29C depict a workflow 2900 for permeabilization of a sample (e.g., sample 302) of the sample handling apparatus 400. FIGS. 29A-29C are similar to and adapted from FIGS. 18A-18C and the workflow 2900 may occur after the workflow 1800. In some embodiments, the workflow 2900 can occur after one or more of process 1900 described in relation to FIG. 19, process 2300 described in relation to FIG. 23, process 2500 described in relation to FIG. 25, process 2700 described in relation to FIG. 27, and process 2800 described in relation to FIG. 28.

After alignment of the slides 303 and 304 (e.g., as shown in FIG. 18C), a permeabilization solution (e.g., permeabilization solution 305) may be added. The permeabilization solution 305 may create a permeabilization buffer in the sandwich (e.g., within the gap 307) which permeabilizes or digests the tissue sample (e.g., sample 302). The analytes and/or mRNA transcripts of the tissue sample 302 may release, diffuse across the gap 307 toward the capture probes 306, and bind on the capture probes 306 (e.g., as shown in FIG. 3).

As shown in FIG. 29A, after alignment of the slides 303 and 304, the second member 410 may be lowered to facilitate in adding the permeabilization solution 305. In some embodiments, the alignment of the slides 303 and 304 may occur when second member 410 is in a lowered position to facilitate in adding the permeabilization solution 304.

FIG. 29B depicts the permeabilization solution 305 dispensed on the slide 304. As shown, the permeabilization solution is dispensed in two volumes 305A and 305B located in proximity to the capture probes 306A and 306B, respectively. In some aspects, the permeabilization solution 305 may be dispensed manually by a user or automatically via a component of the sample handling apparatus 400.

FIG. 29C depicts a sandwich formed by the slide 303, the slide 304, and the sample 302. During the sandwiching of the slides and sample, the permeabilization solution 305 may begin to digest the sample 302 and release analytes and or mRNA transcripts of the sample 302 for capture by the capture probes 306A and 306B. In some aspects, the sandwich may be formed by moving the second member 410 up towards the first members 404A and 404B such that the sample 302 contacts at least a portion of the permeabilization solution 305 and the slides 303 and 304 are within a threshold distance along an axis orthogonal to the slides (e.g., along a z axis). The movement of the second member 410 may be performed by an adjustment mechanism (e.g., the adjustment mechanism 415) of the sample handling apparatus 400.

IV. Image Registration Devices and Methods

Figure 30:
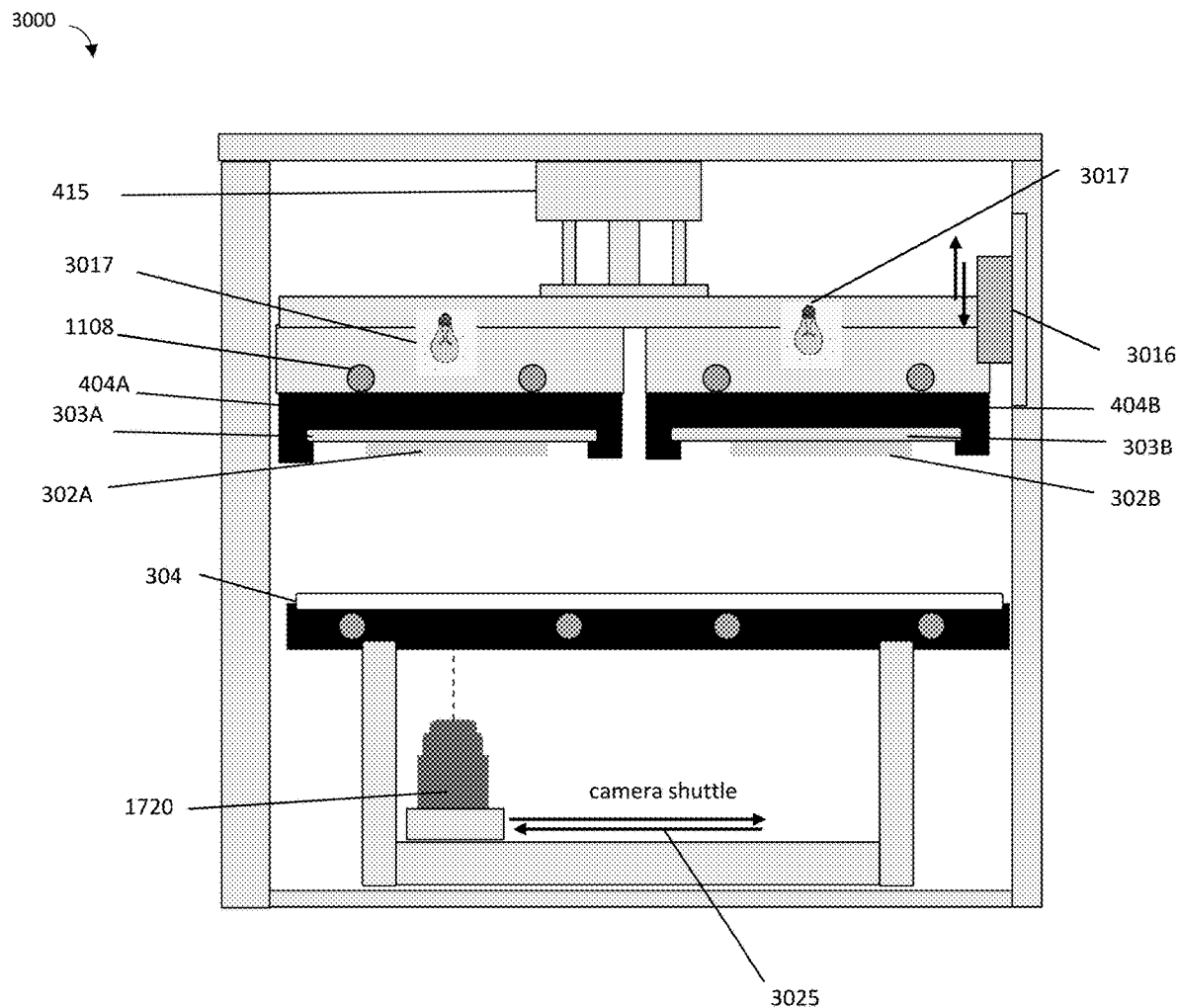
FIG. 30 is a diagram of an example sample handling apparatus in accordance with some example implementations.

FIG. 30 is a diagram of an example sample handling apparatus 3000 in accordance with some example implementations. The sample handling apparatus 3000 is similar to and adapted from the sample handling apparatus 400 of FIGS. 4-13C.

As shown, the sample handling apparatus 3000 includes an adjustment mechanism 415, a linear guide 3016, an illumination source 3017 (e.g., a trans-illumination source), one or more heaters 1108, first members 404A and 404B, tissue slides 303A and 303B, tissue samples 302A and 302B, a gene expression slide 304, and the image capture device 1720. In the example of FIG. 30, the adjustment mechanism 415 is configured to move one or more first members 404 along an axis orthogonal to the first members 404 (e.g., along a z axis). The linear guide 3016 may aid in the movement of the one or more first members 404 along the axis. As further shown, the image capture device 1720 may be mounted on a shuttle 3025 configured to move the image capture device 1720 laterally from a position inferior to the first member 404A to a position inferior to the first member 404B. The shuttle 3025 may allow the image capture device 1720 to capture images of the tissues 302A and 302B aligned with portions of the gene expression slide 304. In some embodiments, a second image capture device 1720 can be provided within the sample handling apparatus 400. Embodiments, including a second image capture device 1720 may not include the shuttle 3025 and instead, the first and second image capture devices may be fixed within the sample holding apparatus 400 in a position suitable for capturing image data associated with tissue sample 302A and 302B, respectively. The illumination source 3017 (e.g., trans-illumination source) may facilitate image capture of the aligned portions by providing sufficient illumination of the image capture area. In some embodiments, the illumination source 3017 can provide red light, green light, blue light, or combinations thereof.

In some embodiments, the illumination source 3017 can provide green, red or blue (e.g., RGB) illumination or light. The different illumination colors can be selected to prevent annotation marks from impacting the image data processing and image registration methods described herein. For example, green light can be used for tissue segmentation with eosin stains and tissue contrast will be maximized. Annotation marks, such as the regions of interest 1802 applied by a user, don't absorb green light and thus the annotation marks will have a lower contrast when imaged under green light.

In another example, red light can be used for fiducial detection with eosin stains and tissue contrast will be minimized. The fiducial frame can be visible in these conditions even when covered by tissue. Fiducial marks don't absorb red light and thus the fiducial marks will have a lower contrast when imaged under red light. In another example, blue light can be used during array alignment since annotation marks absorb blue light and thus have a higher contrast. The use of blue light during alignment can thus improve the accuracy of the alignment and results of the image registration methods.

Figure 31:
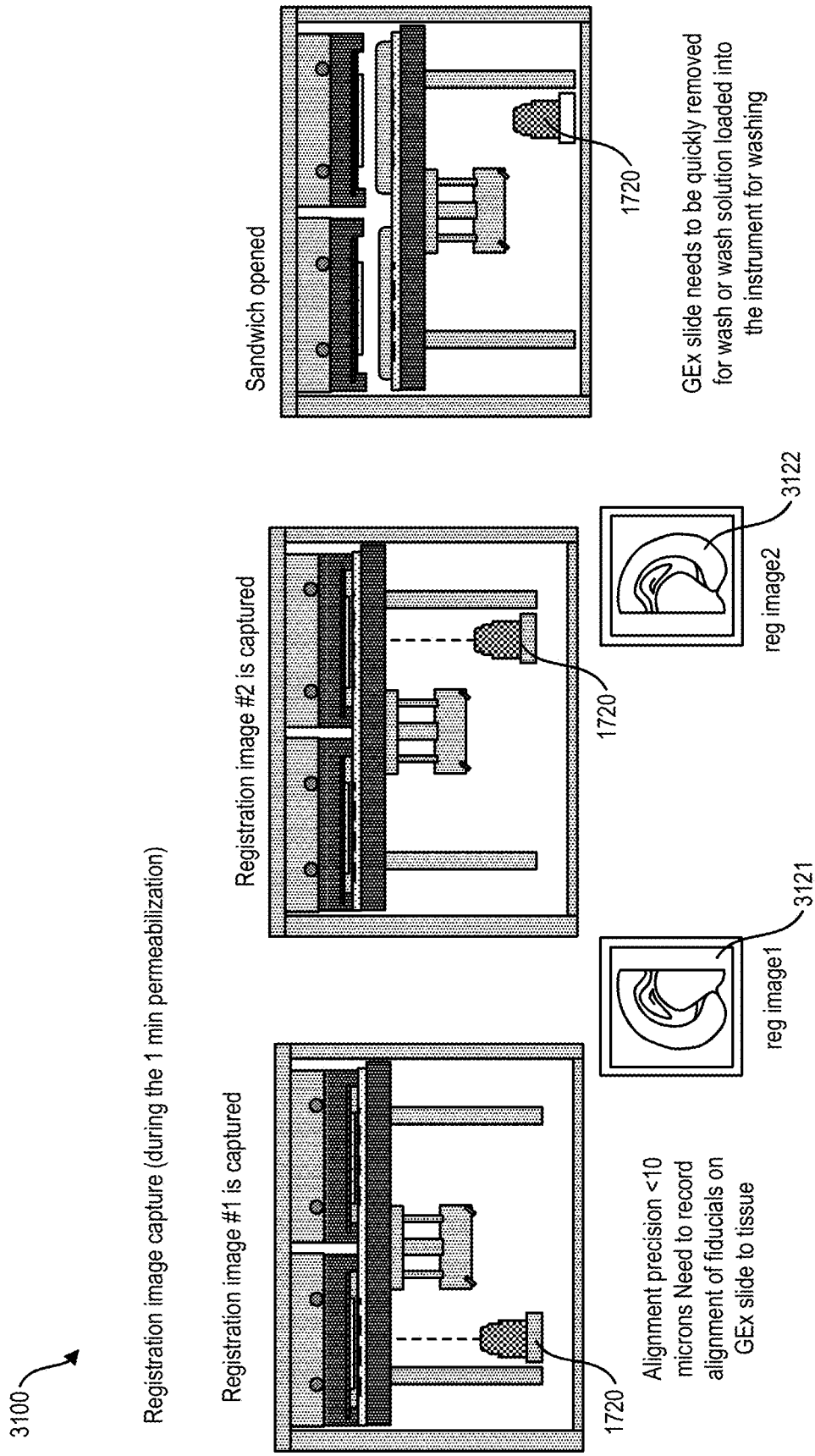
FIGS. 31A-31C depict a workflow for image capture of the sandwiched slides of the sample handling apparatus during a permeabilization step in accordance with some example implementations.

FIGS. 31A-31C depict a workflow 3100 for image capture of the sandwiched slides of the sample handling apparatus 400 during a permeabilization step in accordance with some example implementations. FIGS. 31A-31C are similar to and adapted from FIGS. 29A-29C and the workflow 3100 may occur after the workflow 2900. In some embodiments, the workflow 3100 can occur after one or more of process 1900 described in relation to FIG. 19, process 2300 described in relation to FIG. 23, process 2500 described in relation to FIG. 25, process 2700 described in relation to FIG. 27, and process 2800 described in relation to FIG. 28.

After adding the permeabilization solution (e.g., permeabilization solution 305) to the aligned slides, It may be beneficial to capture images of the aligned tissue sample 302 and/or the barcoded capture probes 306 to aid in mapping gene expressions to locations of the tissue sample 302. As such, the image capture device 1720 may be configured to capture images of the aligned tissue sample 302, regions of interest 1802, and/or the barcoded capture probes 306 during a permeabilization step.

FIG. 31A depicts the image capture device 1720 capturing a registration image of the aligned region of interest 1802A and the capture probes 306A during permeabilization. The bottom portion of FIG. 31A shows an example registration image 3121 captured by the image capture device 1720 of the tissue sample 302A. As further shown, it may be desirable that an alignment precision of the slides 303 and 304 be less than 10 microns. The registration image 3121 may record alignment of any fiducial's on the gene expression slide 304 with respect to the tissue 302.

FIG. 31B depicts the image capture device 1720 capturing a second registration image of the aligned region of interest 1802B with the capture probes 306B during permeabilization. The bottom portion of FIG. 31B shows an example second registration image 3122 captured by the image capture device 1720 of the tissue sample 302B.

In some aspects, the permeabilization step may occur within one minute and it may be beneficial for the image capture device 1720 to move quickly between the different sandwiched slides and regions of interest. Although a single image capture device 1720 is shown, more than one image capture device 1720 may be implemented.

FIG. 31C depicts the sample handling apparatus 400 after any registration images (e.g., registration images 3121 and/or 3122) are captured and the permeabilization step may be completed. As shown, the sandwich may be opened and any of the slides 303 and 304 may be removed for washing or a wash solution may be loaded into the instrument for washing. For example, the gene expression slide 303 may be removed for washing, library prep, gene sequencing, image registration, gene expression mapping, or the like.

In some aspects, the sandwich may be opened by moving the second member 410 away from the first members 404, or vice versa. The opening may be performed by the adjustment mechanism 415 of the sample handling apparatus 400.

While workflows 1700, 1800, 2900, and 3100 are shown and described with respect to the sample handling apparatus 400, the workflows 1700, 1800, 2900, and 3100 may also be performed with respect to the sample handling apparatus 1400, the sample handling apparatus 3000, or another sample handling apparatus in accordance with the implementations described herein. In some embodiments, the processes 1900, 2300, 2500, 3000, 2700, and 2800 may also be performed with respect to the sample handling apparatus 1400, the sample handling apparatus 3000, or another sample handling apparatus in accordance with the implementations described herein.

The spatialomic (e.g., spatial transcriptomic) processes and workflows described herein can be configured to display gene expression information over high-resolution sample images. Barcoded locations within a reagent array can capture transcripts from a sample that is in contact with the array. The captured transcripts can be used in subsequent downstream processing. Determining the location of the barcoded locations of the reagent array relative to the sample can be performed using fiducial markers placed on a substrate on which the reagent array is located. The barcoded locations can be imaged with the sample to generate spatialomic (e.g., spatial transcriptomic) data for the sample.

Generating image data suitable for spatialomic (e.g., spatial transcriptomic) analysis can be affected by the relative alignment of a sample with the barcoded regions of the reagent array. High-resolution arrays for spatialomic (e.g., spatial transcriptomic) can require resolution of the inferred barcoded locations overlaid atop a high-resolution sample image in order to properly associate the captured transcripts with the particular cell that the transcripts originated from. The sample handling apparatus 400 can be configured to perform the image registration processes and workflows described herein to provide a level of precision for aligning the sample image and the array image within +/−1-5 microns, +/−1-10 microns, +/−1-20 microns, or 1-30+/− microns.

Figure 32:
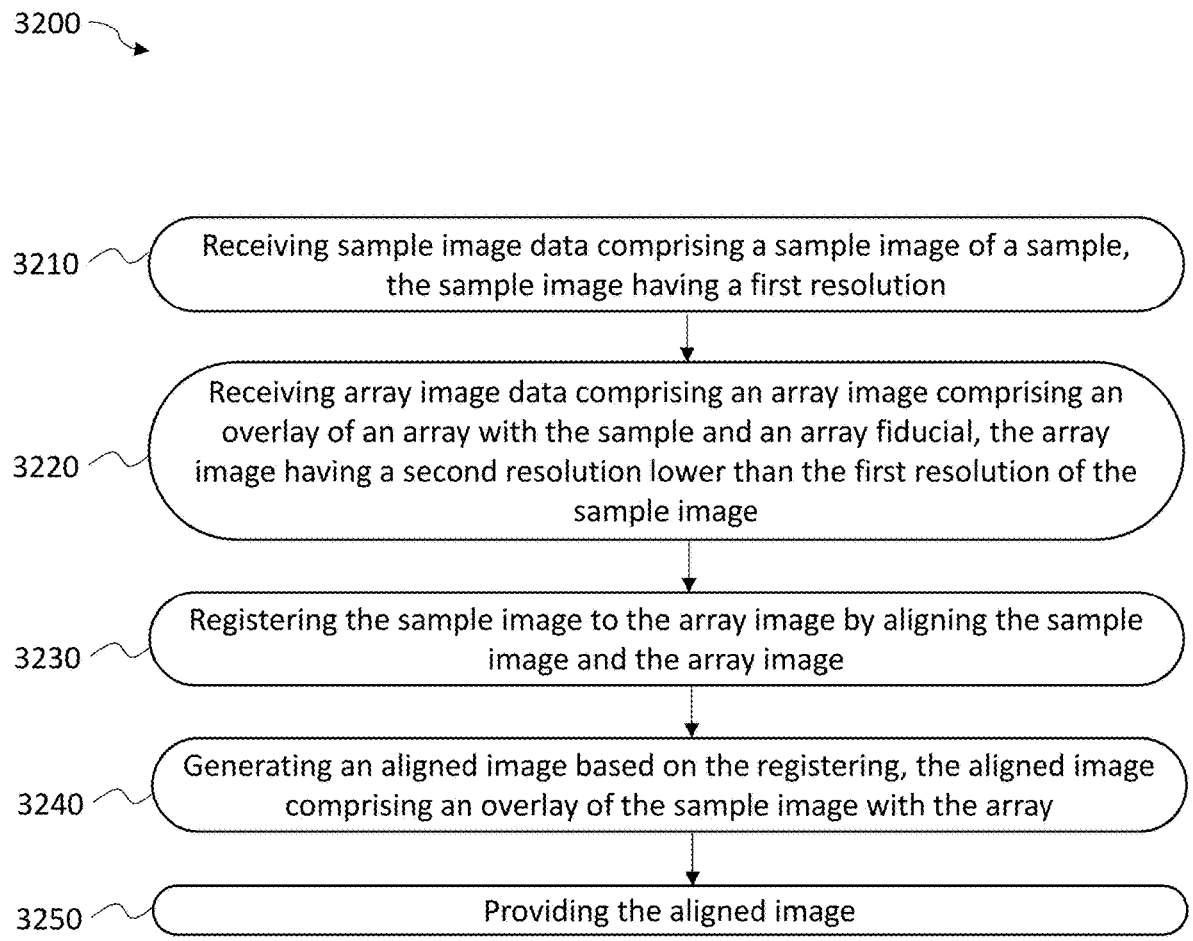
FIG. 32 is a process flow diagram illustrating an example process for generating an aligned image based on registering a sample image to an array image according to some implementations of the current subject matter.

FIG. 32 is a process flow diagram illustrating an example process 3200 for generating an aligned image based on registering a sample image to an array image according to some implementations of the current subject matter. At 3210, sample image data can be received by a data processor of the sample handling apparatus 400. In some embodiments, the sample image data can be received by the data processor from a user. In some embodiments, the sample image data can be received by the data processor from a computing device that is remotely located relative to the data processor.

The sample image data can include a sample image having a first resolution. For example, the resolution of the sample image can be the overall resolution of the image and can be based on the magnification, the numerical aperture, the resolution of the sensor or capture device in megapixels, and wavelength. For example, a capture device, such as the image capture device 1720 described in relation to FIGS. 17 and 30, can be configured to capture a sample image at a resolution of 0.8 microns using a 10× objective, a 0.45 numerical aperture at a wavelength of 575 nanometers. In some embodiments, the sample handling apparatus 400 can be configured to capture a sample image having a first resolution. For example, the sample apparatus 400 can be configured to capture the sample image having the first resolution via a high-resolution imaging module configured for brightfield and/or fluorescence modalities. The high-resolution imaging module can include high-resolution magnification image capture devices. In some embodiments, the high-resolution imaging module can also include a motorized stage configured to translate along horizontal and vertical planes (e.g., xy planes) so that multiple high-resolution images can be captured to form a single large image. In some embodiments, the sample image having the first resolution can be captured by an imaging system external to the sample handling apparatus 400 and prior to use of the sample handling apparatus 400. For example, a user may utilize a image capture device and/or system that is remote and external from the sample handling apparatus 400 to capture the sample image prior to using the sample handling apparatus 400 to perform the spatialomic (e.g., spatial transcriptomic) assay processes and workflows described herein. The sample image captured remotely or externally in this manner can be transmitted to the data processor of the sample handling apparatus 400, where it can be received for further processing as described in relation to operation 3210.

At 3220, the data processor can receive array image data comprising an array image. The array image can comprises an overlay of an array, such as a reagent array configured with the barcoded locations, with the sample. The array image can also include an array fiducial. The array fiducial can be used to infer the location of the array and the barcoded locations within the array so that coordinates of the barcoded locations can be determined relative to the array fiducial. The array image can have a second resolution lower than the first resolution of the sample image.

At 3230, the data processor can register the sample image to the array image by aligning the sample image and the array image. The registering can be performed as an intensity-based image registration process using a Matte's mutual information (entropy) or a mean differential metric. Preprocessing can be performed on the sample image and the array image. The preprocessing can include matching pixel-wise resolution (up-sampling), mirror image flipping, and angular rotation. An initial image transformation can be generated based on an initial transform type and an initial transformation matrix. The initial transformation matrix type can include a similarity transformation matrix based on translation, rotation, and scale. In some embodiments, the initial transformation matrix can include an affine transformation matrix based on translation, rotation, scale, and shear. The initial image transformation can be processed with respect to an initial moving image using bilinear interpolation to generate a transformed moving image. The transformed moving image can be registered with a fixed image to generate a registration metric, such as a measure of Matte's mutual information (entropy) or a mean differential metric value. The result can be provided to an optimizer for comparison against predetermined threshold values. Based on the comparison, the registration can continue using a new transformation matrix or can be completed to generate an aligned, registered image. In some embodiments, the sample image can further include a sample fiducial and the registering can further include aligning the array fiducial with the sample fiducial.

At 3240, the data processor, can generate the aligned image based on the registering performed at 3230. The aligned image can include an overlay of the sample image with the array. In some embodiments, the aligned image can include the array fiducial aligned with the sample.

At 3250, the data processor can provide the aligned image. For example, aligned image can be provided via a display of the sample handling apparatus 400, 1400, or 3000 described herein.

FIGS. 33A-33E depict a workflow 3300 for registering a sample image to an array image according to some implementations of the current subject matter. The image registration processes and workflows described herein can be enhanced by aligning a sample on a first substrate with a reagent array on a second substrate. To perform the aligning and image registration, the coordinates of the barcoded locations within the reagent array and the size of the barcoded reagent locations can be provided. In some embodiments, the coordinates of the barcoded locations and the size of the barcoded locations can be provided by the manufacturer of the substrate on which the reagent array is configured. In some embodiments, the coordinates of the barcoded locations and the size of the barcoded locations can be imaged and provided by the manufacturer of the sample handling apparatus 400, 1400, and 3000. In some embodiments, the coordinates of the barcoded locations and the size of the barcoded locations can be imaged and provided by a user of the sample handling apparatus 400, 1400, and 3000 prior to performing spatialomic (e.g., spatial transcriptomic) assays. To further perform the aligning and image registration, a high-resolution brightfield or fluorescence image of the sample can be provided. The high-resolution brightfield image can be registered to a lower resolution image comprising an overlay of the barcoded locations with the sample.

As shown in FIG. 33A, a substrate or slide can be provided and can include an array fiducial 3305 and an array of barcoded locations 3310. The array fiducial 3305 can be a micro-scale stamp or sticker with features dimensioned in microns. The diameter of the barcoded locations 3310 can be between 40-60 microns, such as 55 microns. In some embodiments, the diameter of the barcoded locations 3310 is less than 40 microns, e.g., less than 10 microns, e.g., around 5 microns. In FIG. 33B, a substrate or slide can be provided including a sample 3315. A user can provide the sample on the substrate. The sample can be provided at any location on the substrate. In FIG. 33C, a high-resolution image of the sample 3315 can be captured via an image capture device. The high-resolution image can typically include an image suitable for resolving subcellular histological and pathological features. The high-resolution image can include images having a resolution less than 5-10 microns. The image capture device can be configured to capture images at a resolution between 1000 and 3000 pixels. In FIG. 33D, the sample substrate can be brought into contact with the array substrate within the sample handling apparatus 400, 1400, and 3000 and a low-resolution image can be captured by the image capture device 1720. The low-resolution image can include an overlay of the array of barcoded locations 3310 and the sample 3315. The low-resolution image can also include the array fiducial 3305. The low-resolution image can include an image that has a lower resolution than the high-resolution image described above (e.g., an image having a resolution greater than 5-10 microns). In FIG. 33E, image registration can be performed between the high-resolution image of the sample 3315 shown in FIG. 33C and the lower resolution image of the overlay of the array of the barcoded locations 3310 and the sample 3315. The image registration can align the array fiducial 3305, such as the center of the array fiducial 3305, with the low-resolution image acquired in FIG. 33D, and the high-resolution image acquired in FIG. 33C can be aligned to the low-resolution image acquired in FIG. 33D to generate the overlay of barcoded locations 3310 displayed over the high-resolution image captured in FIG. 33C.

Figures 34A, 34B, 34C:
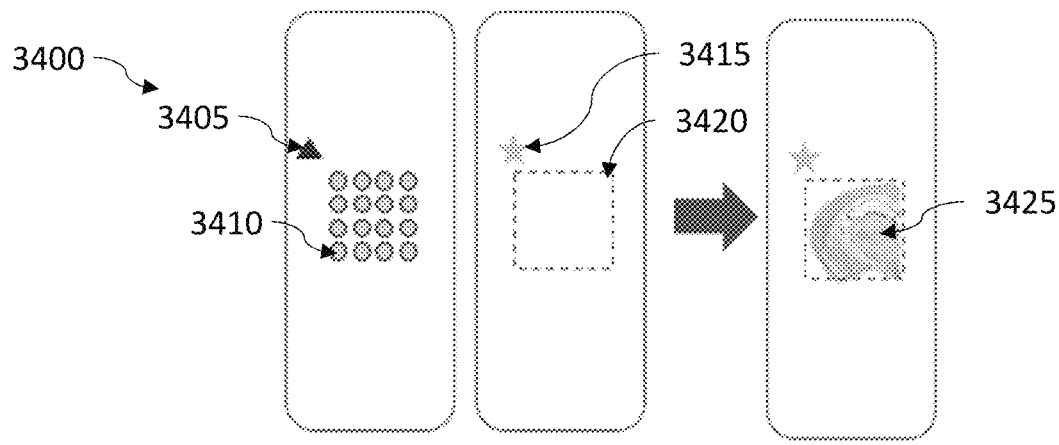
FIGS. 34A-34E depict a workflow for registering a sample image to an array image based on aligning a sample fiducial and an array fiducial according to some implementations of the current subject matter.
Figures 34D, 34E:
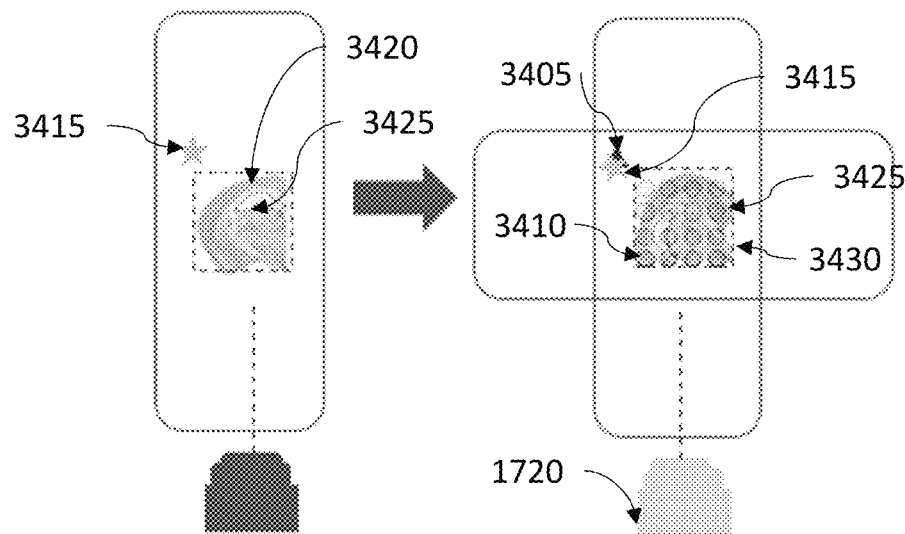

FIGS. 34A-34E depict a workflow 3400 for registering a sample image to an array image based on aligning a sample fiducial and an array fiducial according to some implementations of the current subject matter. In some embodiments, the manufacturer of the sample handling apparatus 400, 1400, and 3000 can provide a sample substrate or slide in addition to the array substrate on which an array fiducial and barcoded locations are provided. For example, as shown in FIG. 34A, the array substrate can include an array fiducial 3405 and barcoded locations 3410. In FIG. 34B, the sample substrate or slide can include a sample fiducial 3415 and a sample area indicator 3420. In FIG. 34C, a user can provide a sample 3425 onto the substrate within the sample area defined by the sample area indicator 3420. In FIG. 34D, an image capture device can acquire a high-resolution image of the sample 3425 and the sample fiducial 3415. In some embodiments, the high-resolution image can be acquired prior to the sample substrate being received within the sample handling apparatus 400, 1400, and 3000. Once the sample substrate is received, the sample substrate and the array substrate can be brought into contact within the sample handling apparatus 400, 1400, and 3000 and the image capture device 1720 can acquire a low-resolution image including the array fiducial 3405 aligned with the sample fiducial 3415 as shown in FIG. 34E. The alignment of the array fiducial 3405 with the sample fiducial 3415 can be used to generate an overlay of the array 3430 of barcoded locations 3410 atop the high-resolution image of the sample captured in FIG. 34D.

Figures 35A, 35B, 35C:
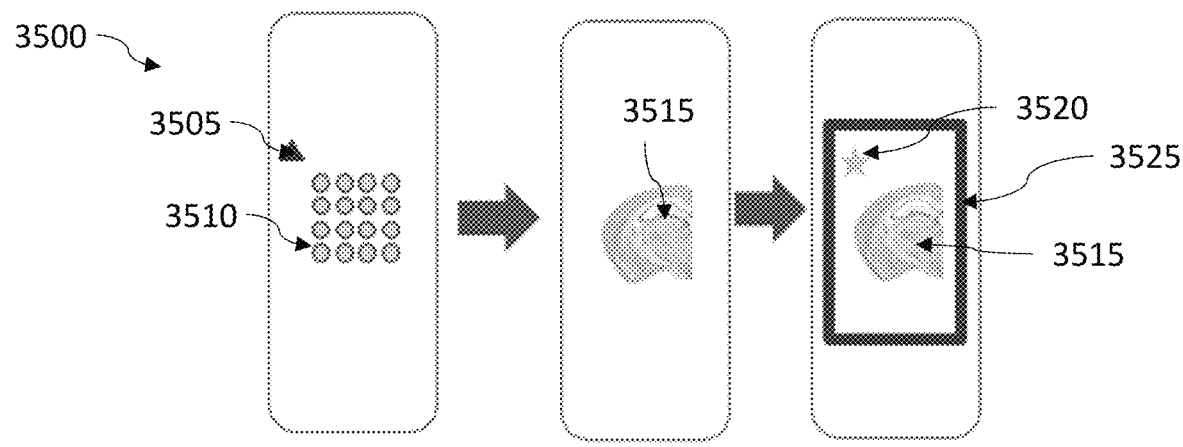
FIGS. 35A-35E depict a workflow for registering a sample image to an array image based on aligning a user-provided sample fiducial and an array fiducial according to some implementations of the current subject matter.
Figures 35D, 35E:
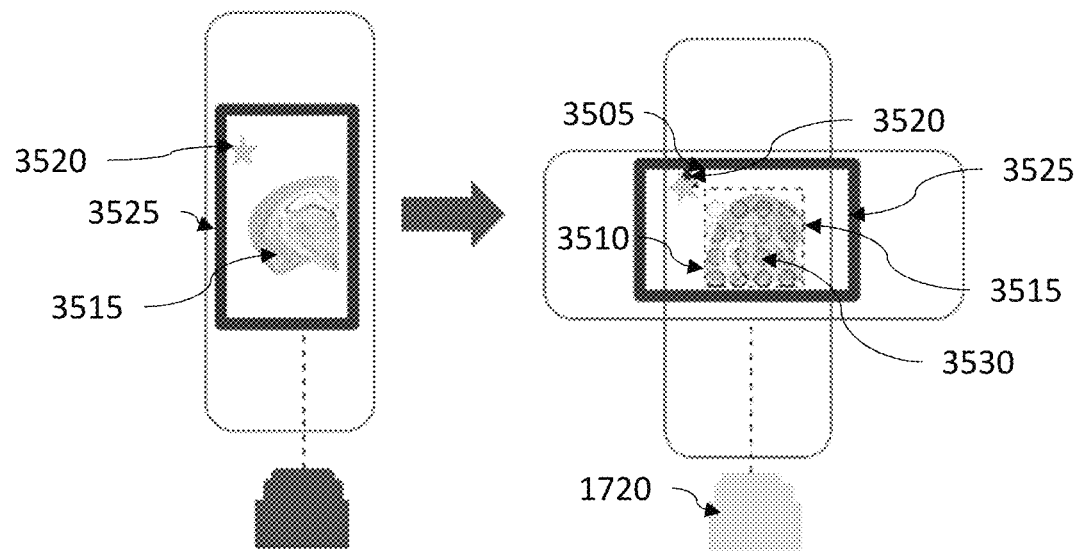

FIGS. 35A-35E depict a workflow 3500 for registering a sample image to an array image based on aligning a user-provided or system-provided sample fiducial and an array fiducial according to some implementations of the current subject matter. In some embodiments, the user of the sample handling apparatus 400, 1400, and 3000 or the sample handling apparatus itself can provide a sample fiducial on a substrate or slide intended for use as a sample substrate or slide. In such embodiments, any substrate or slide can be used as the sample substrate or slide for alignment and image registration. For example, as shown in FIG. 35A, the array substrate can include an array fiducial 3505 and barcoded locations 3510. In FIG. 35B, a user can provide a sample substrate or slide and the sample 3515 can be placed anywhere on the user-provided sample substrate or slide. In FIG. 35C, users or the sample handling apparatus 400, 1400, and 3000 can provide a sample fiducial 3520 and/or a sample area indicator 3525 to the user-provided sample substrate or slide on which the sample 3515 was placed. In some embodiments, the user-provided sample fiducial 3520 and/or the user-provided sample area indicator 3525 can include a stamp or a sticker applied to the sample substrate or slide. In some embodiments, the sample fiducial 3520 and/or the user-provided sample area indicator 3525 can be a mark on the sample handling instrument 400, 1400, and 3000. The mark on the instrument can be a high contrast mark including affordances to easily identify the center of the mark. In 35D, a high-resolution image of the sample 3515, the sample fiducial 3520, and the sample area indicator 3525 (if provided) can be acquired using the image capture device. In some embodiments, the high-resolution image can be acquired prior to the sample substrate being received within the sample handling apparatus 400, 1400, and 3000. The sample substrate and the array substrate can be brought into contact within the sample handling apparatus 400, 1400, and 3000 and the image capture device 1720 can acquire a low-resolution image including the array fiducial 3505 aligned with the sample fiducial 3520 as shown in FIG. 35E. The alignment of the array fiducial 3505 with the sample fiducial 3520 can be used to generate an overlay of the array 3530 of barcoded locations 3510 atop the high-resolution image of the sample captured in FIG. 34D.

FIGS. 36A-36B depict a workflow 3600 for registering a sample image to an array image based on aligning an edge of a sample substrate and an array fiducial according to some implementations of the current subject matter. In some embodiments, the alignment and image registration can be performed using an edge of a user-provided substrate or slide as the sample fiducial. In such embodiments, any substrate or slide can be used as the sample substrate or slide for alignment and image registration. For example, as shown in FIG. 36A, a sample 3610 can be placed at any location on a substrate or slide. An edge 3605 of the substrate or slide can be used as a sample fiducial. A high-resolution image of the sample and the edge 3605 can be captured via the image capture device In some embodiments, the high-resolution image can be acquired prior to the sample substrate being received within the sample handling apparatus 400, 1400, and 3000. In some embodiments, the high-resolution image can be acquired using macros or image acquisition/processing software configured to capture the edge 3605 within the high-resolution image. Once the sample substrate is received, the sample substrate and the array substrate can be brought into contact within the sample handling apparatus 400, 1400, and 3000 and the image capture device 1720 can acquire a low-resolution image including the array fiducial 3615 aligned with the edge 3605 as shown in FIG. 36B. The alignment of the array fiducial 3615 with the edge 3605 as the sample fiducial can be used to generate an overlay of the array 3620 of barcoded locations atop the high-resolution image of the sample captured in FIG. 36A.

Figures 37A, 37B:
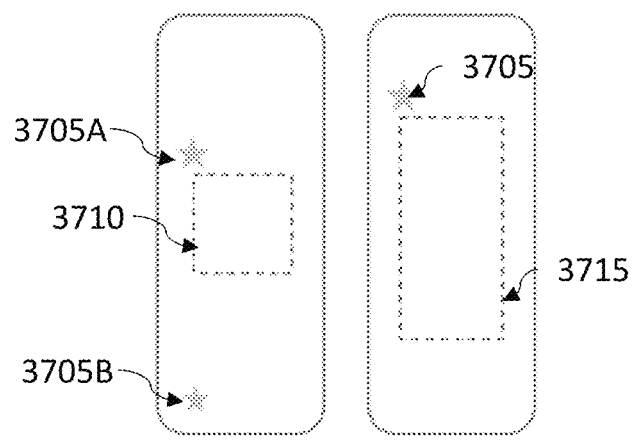
FIGS. 37A-37D are diagrams illustrating embodiments of sample fiducials according to some implementations of the current subject matter.
Figures 37C, 37D:
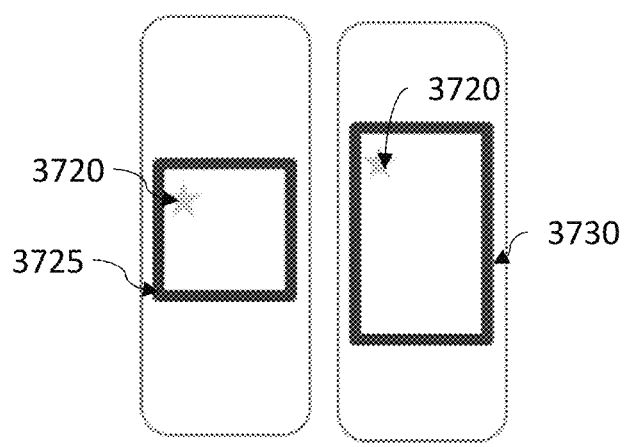

FIGS. 37A-37D are diagrams illustrating embodiments of sample fiducials according to some implementations of the current subject matter. A variety of non-limiting sample fiducial and sample area indicator sizes, shapes, and configurations can be contemplated for use with the sample handling apparatus 400, 1400, and 3000 without deviating from the intended use of the sample fiducial and/or sample area indicators described herein. The varying sizes, shapes, and configurations of sample fiducials and/or sample area indicators can be provided to accommodate varying sizes of samples. For example, as shown in FIG. 37A, the sample fiducial 3705A can be positioned relative to a sample area indicator 3710 provided as a square-shaped dashed line. In some embodiments, multiple sample fiducials can be provided on the sample substrate or slide as shown by the inclusion of a second sample fiducial 3705B. In some embodiments, the sample area indicator 3710 can include a square shape, a rectangular shape, a circular shape, an oval shape, or the like. The sample fiducial 3705 can be positioned in a variety of non-limiting locations in or around the sample area indicator 3710. As shown in FIG. 37B, the shape of the sample area indicator 3710 can be a rectangular shaped dashed line. As shown in FIG. 37C, the sample fiducial 3720 can be configured within the sample area indicator 3725. The sample area indicator 3725 can include a square shape provided as a thick solid line. In FIG. 37D, the sample area indicator 3730 can be provided as a rectangular shaped solid line and the sample fiducial 3720 can be provided within the sample area indicator 3730.

Figures 38A, 38B:
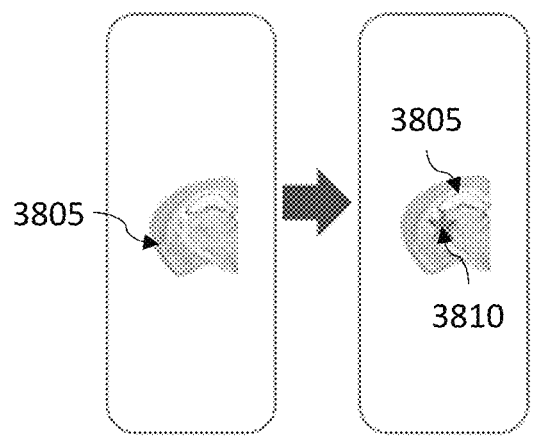
FIGS. 38A-38C are diagrams illustrating embodiments of a sample fiducial configured on a rear of a sample substrate according to some implementations of the current subject matter.
Figure 38C:
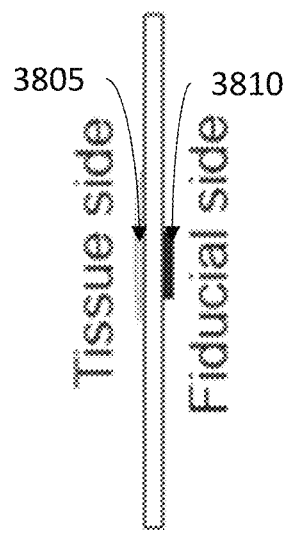

FIGS. 38A-38C are diagrams illustrating embodiments of a sample fiducial configured on a rear of a sample substrate according to some implementations of the current subject matter. Providing a sample fiducial on a rear surface of a sample substrate or slide can allow the sample fiducial to be placed anywhere on the sample substrate or slide, including a location that is within a location of the sample. For example, as shown in FIG. 38A, a sample substrate or slide can be provided and a sample 3805 can be placed on a surface of the substrate. In FIG. 38B, a sample fiducial 3810 can be placed on an opposite surface of the sample substrate on which the sample 3805 was applied in FIG. 38A. In FIG. 38C, a cross-section of the sample substrate or slide can be seen to further indicate the placement of the sample 3805 on a tissue or sample side of the sample substrate and the placement of the sample fiducial 3810 on a fiducial side of the sample substrate or slide. The fiducial side can be opposite to the tissue or sample side of the substrate or slide on which the sample 3805 is located.

An image capture device of the sample handling apparatus 400, 1400, and 3000 can be configured for capturing high-resolution images such that a sample substrate image and an array substrate image can be captured at two different focal points while keeping the xy location fixed. To capture the sample and the sample fiducial in the low-resolution image with the same focus, the image capture device 1720 can be configured with a low magnification object lens with a numerical aperture set to 0.02. This setting can provide a 1.5 mm field depth that is greater than a thickness of the sample substrate or slide (~1 mm). In some embodiments, the sample fiducial 3810 can be an opaque or transparent fiducial, such as when the high-resolution image is captured prior contacting the sample substrate with the array substrate within the sample handling apparatus 400, 1400, and 3000.

FIGS. 39A-39E are diagrams illustrating embodiments of configurations of array fiducials according to some implementations of the current subject matter. Similar to the placement of the sample fiducial on the sample substrate or slide, an array fiducial can be provided in a variety of non-limiting locations on the array substrate or slide without deviating from intended use of the array fiducial and/or the array as described herein. For example, as shown in FIG. 39A, an array substrate or slide can include an array fiducial 3905 located relative to the array 3910 of barcoded locations. The array fiducial 3905 can be located next to or in proximity of the array 3910. As shown in FIG. 39B, the array fiducial 3905 can be located within an area of the array 3910. As shown in FIG. 39C, multiple array fiducials 3905A and 3905B can be located on the array substrate or slide next to or in proximity of the array 3910. In some embodiments, multiple array fiducials 3905 can be located within an area of the array 3910. As shown in FIG. 39D, the array fiducial 3905 can be located on a rear surface of the array substrate or slide that is opposite the side on which the array 3910 is located. As shown in FIG. 39E, the array fiducial 3905 can be located on the same side of the array substrate or slide as the array 3910.

Figure 40A:
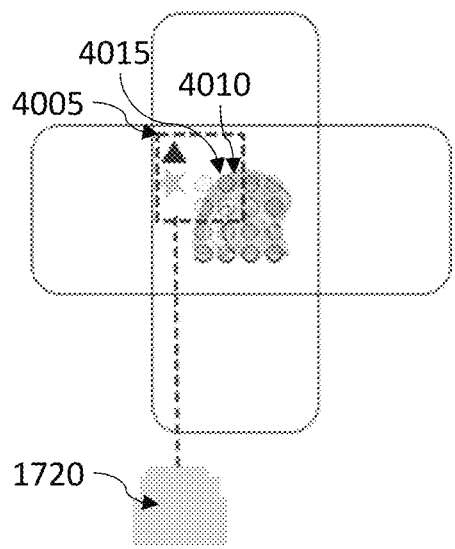
FIGS. 40A-40C are diagrams illustrating embodiments of locations at which a low-resolution image including an array overlaid atop a sample can be captured for registering a sample image to an array image according to some implementations of the current subject matter.
Figure 40B:
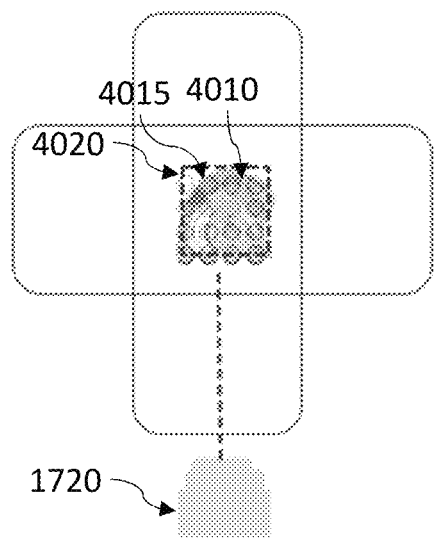
Figure 40C:
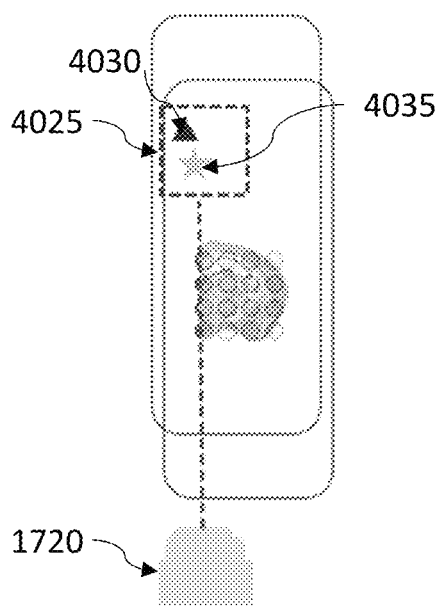

FIGS. 40A-40C are diagrams illustrating embodiments of locations at which a low-resolution image including an array overlaid atop a sample can be captured for registering a sample image to an array image according to some implementations of the current subject matter. The low-resolution image described in relation to operation 3220 of FIG. 32 by the image capture device 1720 can be captured on, near, or away from an area in which the sample and the array overlap depending on the location of the sample fiducial and the array fiducial. For example, as shown in FIG. 40A, the low-resolution image can be captured by the image capture device 1720 at a location 4005 in which at least a portion of the sample 4010 and the array 4015 overlap. As shown in FIG. 40B, the low-resolution image can be captures by the image capture device 1720 at a location 4020 in which the sample 4010 and the array 4015 overlap more completely. As shown in FIG. 40C, the low-resolution image can be captured by the image capture device 1720 at a location 4025 in which the array fiducial 4030 is aligned with or is in proximity of the sample fiducial 4035.

FIG. 41 is a process flow diagram illustrating an example process 4100 for generating an aligned image based on registering a sample image to an array image using multiple instrument fiducials according to some implementations of the current subject matter. In some embodiments, such as those described in relation to FIG. 21, the sample handling apparatus 400, 1400, and 3000 can include one or more instrument fiducials. The instrument fiducials can be provided on a transparent surface of the sample handling apparatus described herein. Image registration can be performed to provide an aligned image including the sample aligned with the array using the instrument fiducials.

At 4110, a data processor of the sample handling apparatus 400, 1400, and 3000 can receive sample image data comprising a sample image of a sample and a sample fiducial. The same image can have a first resolution. The sample image data can be received in accordance with operation 3210 of FIG. 32. At 4120, the data processor can receive instrument fiducial data comprising an instrument fiducial image of a first instrument fiducial and a second instrument fiducial. The instrument fiducials can include a variety of non-limiting sizes, shapes, and configurations on a suitable mounting or viewing surface of the sample handling apparatus 400, 1400, and 3000 as described in relation to FIG. 30.

At 4130, the data processor can receive array image data comprising an array image having a second resolution that is lower than the first resolution of the sample image. The array image can include an array and an array fiducial overlaid atop the sample and the sample fiducial. The array image data can be received in accordance with operation 3220 of FIG. 32. At 4140, the data processor can register the instrument fiducial image to the array image based on aligning the first instrument fiducial and the array fiducial. The registering can be performed analogously to the registering described in relation to operation 3230 of FIG. 32, except the registration is performed by registering the instrument fiducial image to the array image based on aligning the first instrument fiducial and the array fiducial. At 4150, the data processor can register the instrument fiducial image to the sample image by aligning the second instrument fiducial and the sample fiducial. The registering can be performed analogously to the registering described in relation to operation 3230 of FIG. 32, except the registration is performed by registering the instrument fiducial image to the sample image based on aligning the second instrument fiducial and the sample fiducial.

At 4160, the data processor can generate an aligned image based on registering the instrument fiducial image to the array image and registering the instrument fiducial to the sample image. At 4170, the data processor can provide the aligned image. For example, the data processor can provide the aligned image via a display of the sample handling apparatus 400, 1400, and 3000.

FIGS. 42A-42D depict a workflow 4200 for generating an aligned image based on registering a sample image to an array image using multiple instrument fiducials according to some implementations of the current subject matter. As shown in FIG. 42A, the sample handling apparatus 400, 1400, and 3000 can include a transparent viewing or mounting surface 4205 configured with a first instrument fiducial 4210 and a second instrument fiducial 4215. As shown in FIG. 42B, an array substrate or slide can include an array fiducial 4220 and an array 4225. As shown in FIG. 42C, a sample substrate or slide can include a sample fiducial 4230 and a sample 4235. As shown in FIG. 42D, the array substrate including the array fiducial 4220 can be aligned with the first instrument fiducial 4210 and the sample fiducial 4230 can be aligned with the second instrument fiducial 4215. The sample substrate and the array substrate can be brought into contact within the sample handling apparatus 400, 1400, and 3000 and the image capture device 1720 can acquire multiple low-resolution images. A first low-resolution image can be captured based on aligning the first instrument fiducial 4210 to the array fiducial 4220. A second low-resolution image can be captured based on aligning the second instrument fiducial 4215 to the sample fiducial 4230. The known coordinates of the barcoded locations within the array 4225 relative to the array fiducial 4225, the known location of the sample 4235 relative to the sample fiducial 4230, and the known location of the first instrument fiducial 4210 relative to the second instrument fiducial 4215 can be used with the sample image received at operation 4110 of FIG. 41 and the array image received at operation 4130 of FIG. 41 to align the array 4225 with the sample 4235.

The sample handling apparatus 400, 1400, and 3000 described herein can be configured to perform image registrations for sample images including multiple sample portion images which can be stitched together. When the high-resolution image of the sample is collected at a high magnification, it is typically obtained using image stitching of multiple fields of view of the sample. Image stitching can result in stitching artifacts. The stitching artifacts can generate errors during image registration when aligning the lower resolution image, which can be an unstitched lower resolution image of the array overlaid atop the sample, and the higher resolution stitched image of the sample.

Figure 43A:
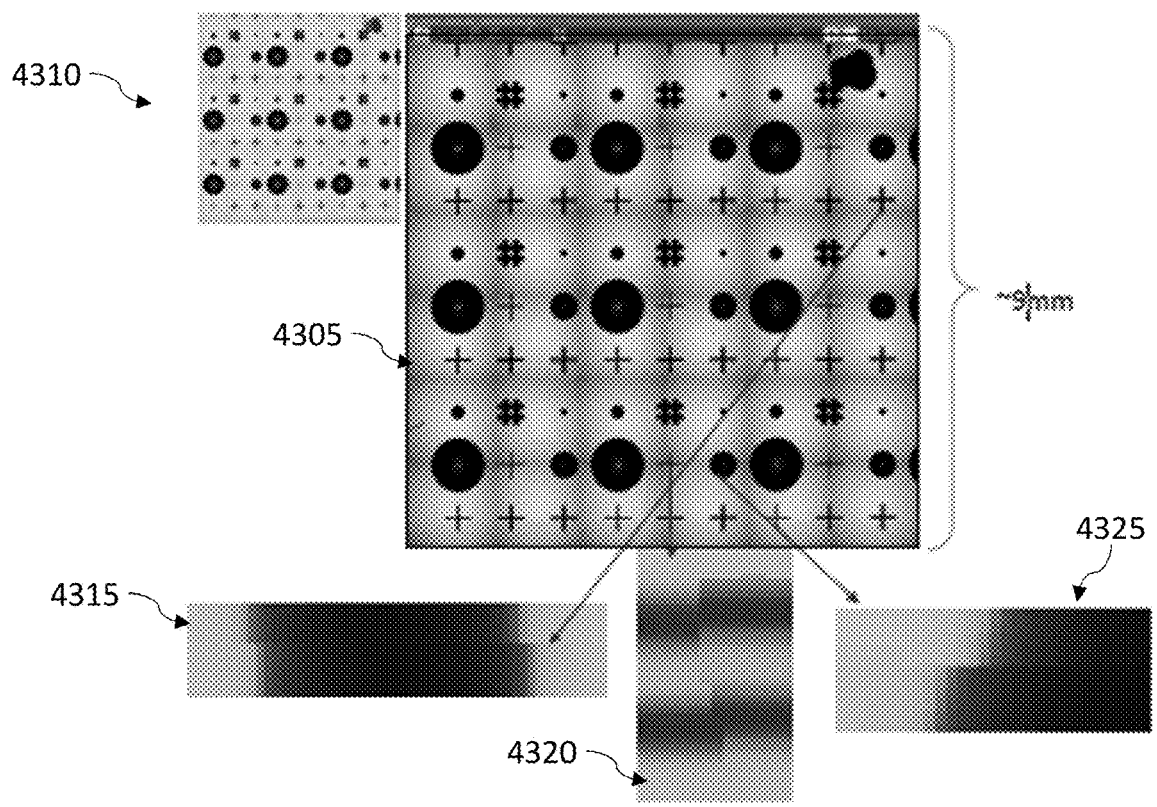
FIGS. 43A-43B illustrate stitching artifacts which can be present within stitched images including a plurality of individual image portions.
Figure 43B:
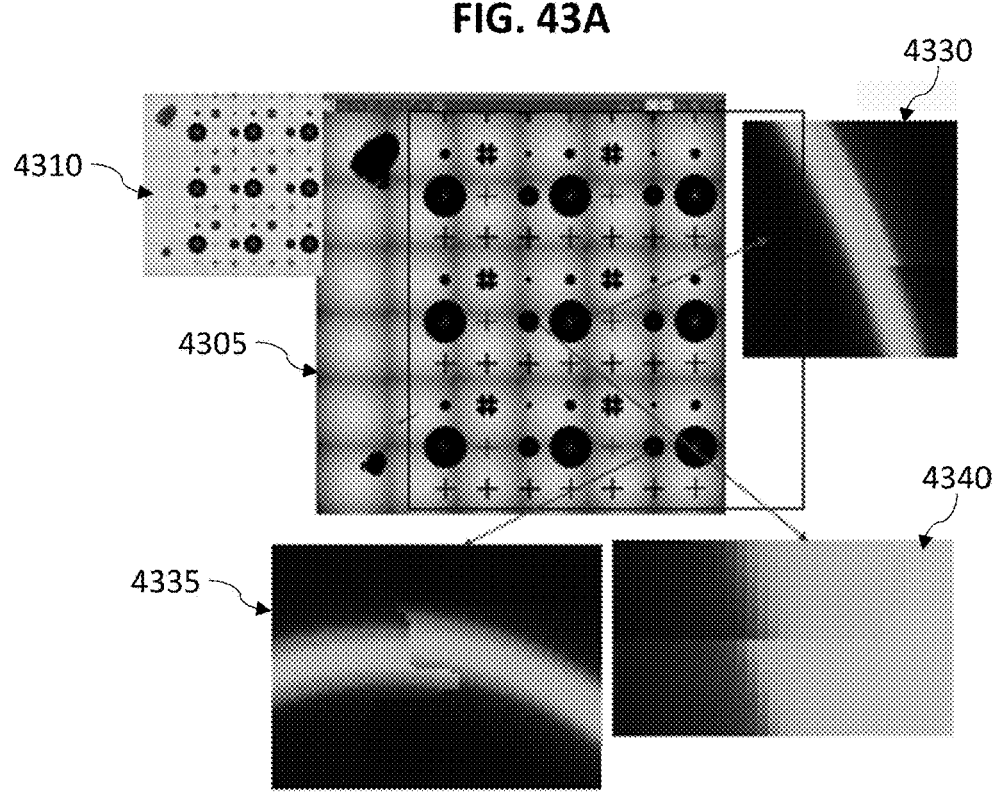

FIGS. 43A-43B illustrate stitching artifacts which can be present within stitched images including a plurality of individual image portions. Stitching artifacts can be present in high-resolution sample images including a plurality of sample portion images, and can also be present in low-resolution array images including a plurality of array portion images capturing one or more portions of an overlay of an array with the sample. The stitching artifacts can be present for horizontal, vertical, and curved features present within a stitched high-resolution image. As shown in FIG. 43A, a stitched high-resolution image 4305 can be acquired of an optical target 4310 of repeated patterns of a different shaped optical target marks, such as small and large circular-shaped marks, cross-shaped marks, and hash-shaped marks. For example, the stitched high-resolution image 4305 can be acquired at 10× magnification using an image capture device, such as a microscope, configured with a 150 megapixel resolution. Imaging functionality associated with the microscope can automatically stitch images together to build a larger composite image (e.g., image 4305). As shown in FIG. 43A, the stitched high-resolution image 4305 can include a single array that is 9 mm by 9 mm in size and is comprised of 81 individual portion images that are each 1 mm by 1 mm in size. The stitched high-resolution sample image 4305 can include the template marks of the stitched optical target 4310. As shown in 4315, the stitching artifacts can include vertical misalignment of a first cross-shaped template mark occurring across a horizontal stitching boundary between two of the individual portion images that the cross-shaped template mark spans. As shown in 4320, the stitching artifacts can include horizontal misalignment of the cross-shaped template mark occurring across a vertical stitching boundary between two of the individual portion images that a second cross-shaped template mark spans. As shown in 4315, the stitching artifacts can include misalignment of a curved feature of a small circular-shaped template mark occurring across a horizontal stitching boundary between two of the individual portion images that the small circular-shaped template mark spans.

As shown in 4330 of FIG. 43B, the stitching artifacts can include misalignment of a curved feature of a large circular-shaped template mark occurring across a horizontal stitching boundary between two of the individual portion images that the large circular-shaped template mark spans. As shown in 4335, the stitching artifacts can include misalignment of a curved feature of a small circular-shaped template mark occurring at an intersectional boundary of four individual portion images. As shown in 4340, the stitching artifacts can include misalignment of a curved feature of a small circular-shaped template mark occurring near an intersectional boundary of four individual portion images To mitigate and correct the image registration errors due to the stitching artifacts, the image registration can be performed using portions of the high-resolution sample image and registering the portions of the sample image to the whole lower resolution image. The stitching errors can also cause local registration errors. To mitigate and correct the local stitching errors, the image registration processes and workflows described herein can be performed using local sub images of the high-resolution stitched image. In this way, registration errors due to stitching artifacts can be mitigated and removed.

Figure 44:
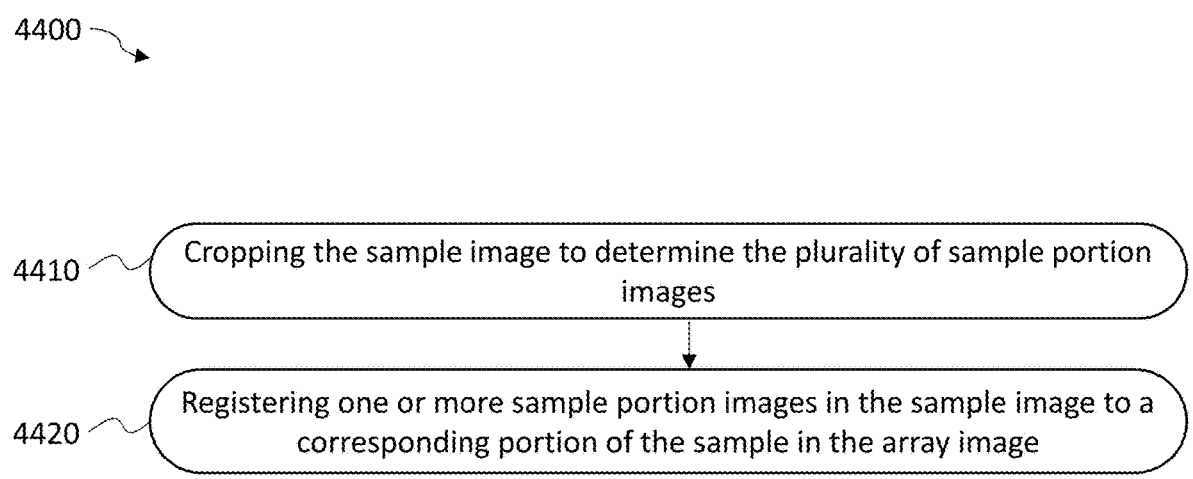
FIG. 44 is a process flow diagram illustrating an example process for registering sample portion images of a sample image to corresponding portions of the sample in an array image according to some implementations of the current subject matter.

FIG. 44 is a process flow diagram illustrating an example process 4400 for registering sample portion images of a sample image to corresponding portions of the sample in an array image according to some implementations of the current subject matter. In some embodiments, the high-resolution sample image can include multiple sample portion images that are stitched together to form the sample image. Each of the sample portion images can be associated with a portion of the sample. In some embodiments, each of the sample portion images can be sized such that the size of each sample portion image is less than a size of a single field of view of the sample image. In this way, the location registration errors due to stitching artifacts can be corrected.

As shown in FIG. 44, at 4410 the data processor of the sample handling apparatus 400, 1400, and 3000 can crop the high-resolution sample image to determine a plurality of sample portion images. The high-resolution sample image can be cropped to determine the plurality of sample portion images using computer vision and/or image processing functionality provided in an image processing pipeline configured within the sample handling apparatus 400, 1400, and 3000. At 4420, the data processor can register one or more of the sample portion images in the high-resolution sample image to a corresponding portion of the sample in the low-resolution array image. In some embodiments, registering the one or more sample portion images to a corresponding portion of the sample in the array image can be performed after initially registering the sample image to the array image in a pre-alignment operation.

Figure 45:
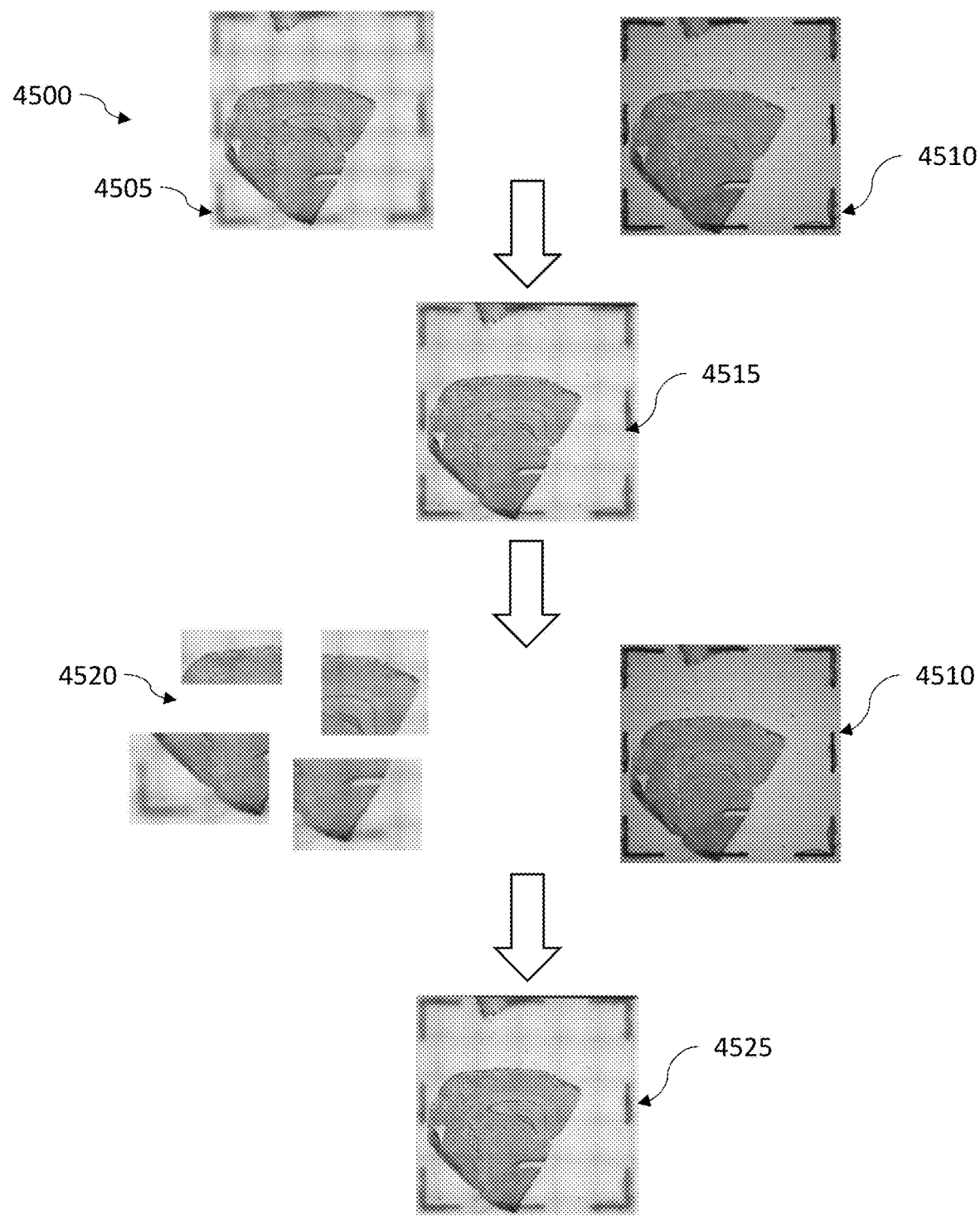
FIG. 45 depicts a workflow for registering sample portion images of a sample image to corresponding portions of the sample in an array image according to some implementations of the current subject matter.

FIG. 45 depicts a workflow 4500 for registering sample portion images of a sample image to corresponding portions of the sample in an array image according to some implementations of the current subject matter. A high-resolution stitched sample image 4405 can be received by a data processor of the sample handling apparatus 400, 1400, and 3000, such as the data processor 5320 described in relation to FIG. 53. In some embodiments, the data processor can be remote from or external to the sample handing apparatus 400, 1400, and 3000 and can be configured with the image processing pipelines and functionality described herein. In such embodiments, image data captured using the sample handling apparatus can be provided to the remote or externally configured data processor via a USB or network connection. In some embodiments, the high-resolution stitched sample image 4505 can include an overlay of the array with the sample and an array fiducial. A low-resolution sample image 4510 including a single field of view of the sample can also be received by the data processor of the sample handling apparatus 400, 1400, and 3000. An initial alignment image 4515 can be generated via a global whole image registration operation registering the high-resolution stitched sample image 4505 to the lower resolution sample image. In some embodiments, it may not be necessary to generate the initial alignment image 4515. In some embodiments, prior to generating the initial alignment image 4515, the sample substrate and the array substrate can be aligned manually or automatically by the data processor of the sample handling apparatus 400, 1400, and 3000. This preliminary alignment can be performed to specify the starting conditions of the image registration methods described herein.

The high-resolution stitched sample image 4505 can be cropped to determine a plurality of sample portion images 4520. The plurality of sample portion images 4520 can be locally registered with the low-resolution sample image 4510 to generate an locally aligned sample image 4525. Each sample portion image of the plurality of sample portion images can be smaller than a single field of view of the high-resolution stitched sample image 4505. In this way, local registration errors due to stitching artifacts can be corrected.

FIG. 46 is a process flow diagram illustrating an example process 4600 for registering array portion images of an array image to corresponding portions of the sample in a sample image according to some implementations of the current subject matter. In some embodiments, the low-resolution image of the array overlaid atop the sample described in relation to operation 3230 of FIG. 32 can include a plurality of array portion images. At 4610, the data processor of the sample handling apparatus 400, 1400, and 3000 can determine a plurality of array portion images in the low-resolution image of the array. The plurality of array portion images in the low-resolution image of the array can be determined using computer vision and/or image processing functionality provided in an image processing pipeline configured within the sample handling apparatus 400, 1400, and 3000. At 4620, the data processor can register one or more of the array portion images in the low-resolution array image to a corresponding portion of the sample in the high-resolution sample image.

Figure 47:
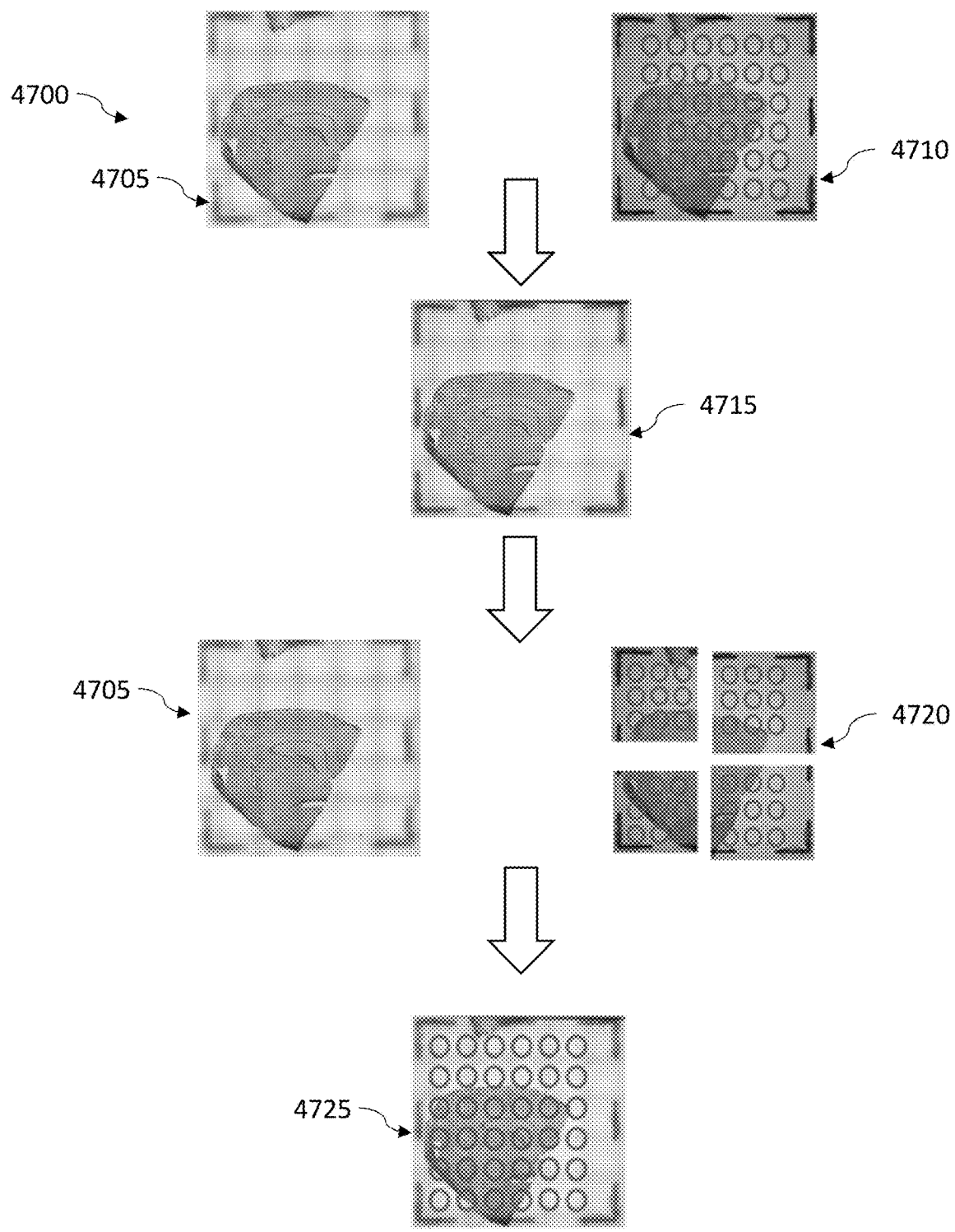
FIG. 47 depicts a workflow for registering array portion images of an array image to corresponding portions of the sample in a sample image according to some implementations of the current subject matter.

FIG. 47 depicts a workflow 4700 for registering array portion images of an array image to corresponding portions of the sample in a sample image according to some implementations of the current subject matter. A high-resolution stitched sample image 4705 can be received by a data processor of the sample handling apparatus 400, 1400, and 3000. A low-resolution array image 4710 including a single field of view of the array overlaid atop the sample can also be received by the data processor of the sample handling apparatus 400, 1400, and 3000. In some embodiments, the sample and the array can be located on a single substrate or slide. An initial alignment image 4715 can be generated via a global whole image registration operation registering the high-resolution stitched sample image 4705 to the lower resolution array image. In some embodiments, it may not be necessary to generate the initial alignment image 4715. In some embodiments, prior to generating the initial alignment image 4715, the sample substrate and the array substrate can be aligned manually or automatically by the data processor of the sample handling apparatus 400, 1400, and 3000. This preliminary alignment can be performed to specify the starting conditions of the image registration methods described herein.

The low-resolution array image 4710 can be processed to determine a plurality of array portion images 4720. The plurality of array portion images 4720 can be locally registered with the high-resolution stitched sample image 4705 to generate an locally aligned sample image 4725. Each array portion image of the plurality of array portion images can be smaller than a single field of view of the high-resolution stitched array image 4675. In this way, local registration errors due to stitching artifacts can be corrected.

High resolution arrays for spatialomic (e.g., spatial transcriptomic) can be configured to identify 5-10 micron features and single cell resolution. The alignment of the inferred barcoded locations of the array over the high-resolution sample image may require single cell resolution in order to properly associate the transcripts captured at the barcoded locations with the cell from which the transcripts originated. Typically the high-resolution sample image is acquired at a high magnification and can be stitched together using multiple fields of view. This manner of stitching images together can generate stitching artifacts. The stitching artifacts can cause errors when extrapolating the barcoded locations using fiducials. The stitching errors can be on the order of 5-10 microns. If left uncorrected, the gene expression data will be associated with the wrong location in the high-resolution sample image.

To correct or mitigate registration errors due to stitching artifacts, a single field of view low-resolution sample image can be captured in addition to the high-resolution sample image. The lower resolution sample image may not include stitching artifacts. Thus, no spot location errors may arise when extrapolating the barcoded locations using fiducials. Image registration can be performed between the high-resolution stitched sample image and the low-resolution unstitched sample image using portions of the high-resolution stitched sample image. In this way, errors associated with the barcoded locations due to stitching artifacts can be mitigated and/or removed.

Figure 48:
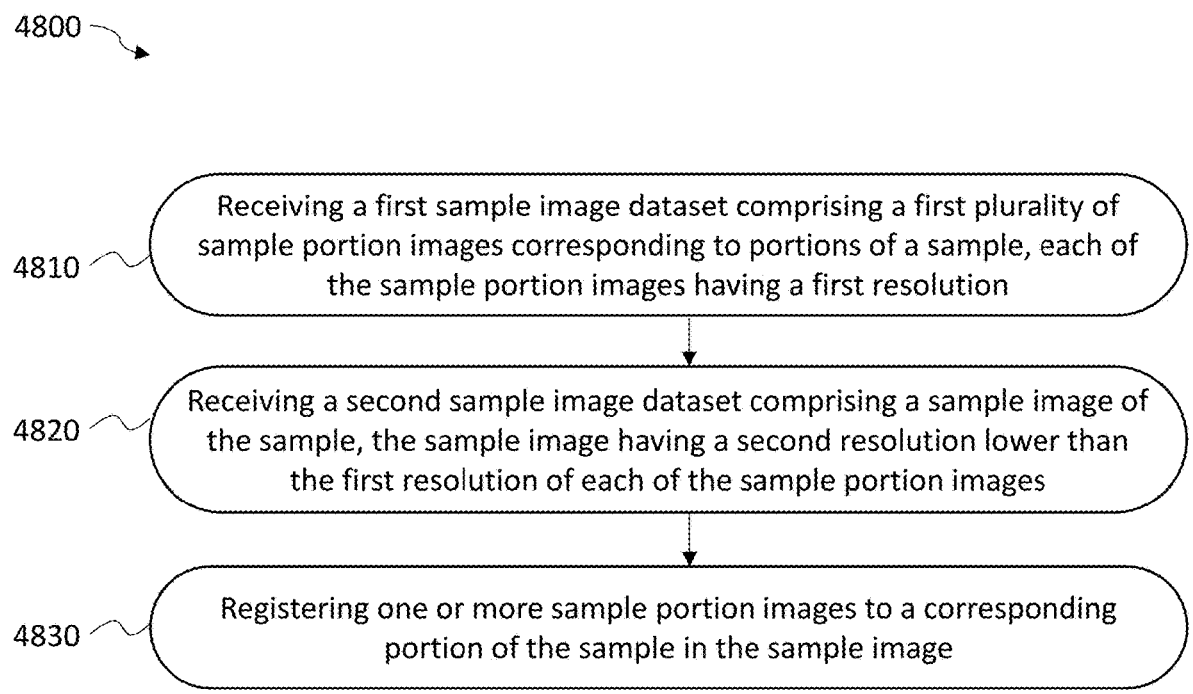
FIG. 48 is a process flow diagram illustrating an example process for registering stitched sample portion images to corresponding portions of the sample in a sample image according to some implementations of the current subject matter.

FIG. 48 is a process flow diagram illustrating an example process 4800 for registering stitched sample portion images to corresponding portions of the sample in a sample image according to some implementations of the current subject matter. At 4810, the data processor of the sample handling apparatus 400, 1400, and 3000 can receive a first sample image dataset including a first plurality of sample portion images corresponding to portions of a sample. Each of the sample portion images can have a first resolution.

At 4820, the data processor can receive a second sample image dataset including a sample image of the sample. The sample image can have a second resolution that is lower than the first resolution of each of the sample portion images in the first sample image dataset.

At 4830, the data processor can register one or more of the sample portion images to a corresponding portion of the sample in the sample image.

Figure 49:
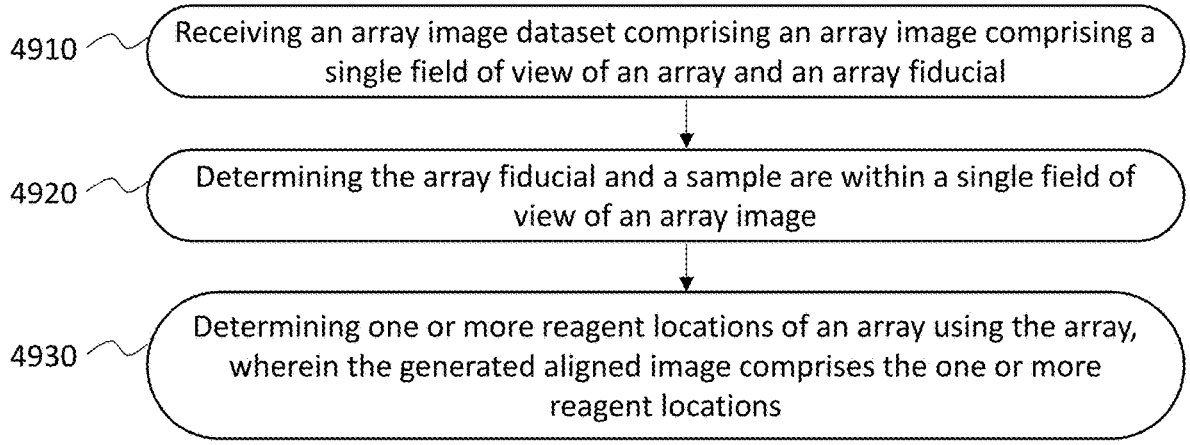
FIG. 49 is a process flow diagram illustrating an example process for registering stitched sample portion images to corresponding portions of the sample in a sample image based on determining one or more barcoded locations of an array in according to some implementations of the current subject matter.

FIG. 49 is a process flow diagram illustrating an example process 4900 for registering stitched sample portion images to corresponding portions of the sample in a sample image based on determining one or more barcoded locations of an array in according to some implementations of the current subject matter. In some embodiments, the sample image can include a plurality of sample portion images that are individually associated with a portion of the sample. In such embodiments, the registering can further include operations of the process 4900 shown in FIG. 49. For example, at 4910, the data processor can receive an array image dataset including an array image of a single field of view of an array. The array image can also include an array fiducial. At 4920, the data processor can determine the array fiducial are within a single field of view of the array image. The array fiducials can be determined using the computer vision and/or image processing functionality provided in an image processing pipeline configured within the sample handling apparatus 400, 1400, and 3000. In some embodiments, the array fiducials can be pre-defined and can be visible under field of view. The user or software can determine if all of the fiducial features are included in the field of view before the image is taken. In some embodiments, the array fiducials within a single field of view of the array image can be determined using computer vision and/or image processing functionality provided in an image processing pipeline configured within the sample handling apparatus 400, 1400, and 3000. At 4930, the data processor determines one or more barcoded locations of the array using the array image. The generated aligned image, described in relation to operation 3240 of FIG. 32, can include the one or more barcoded locations.

Figure 50:
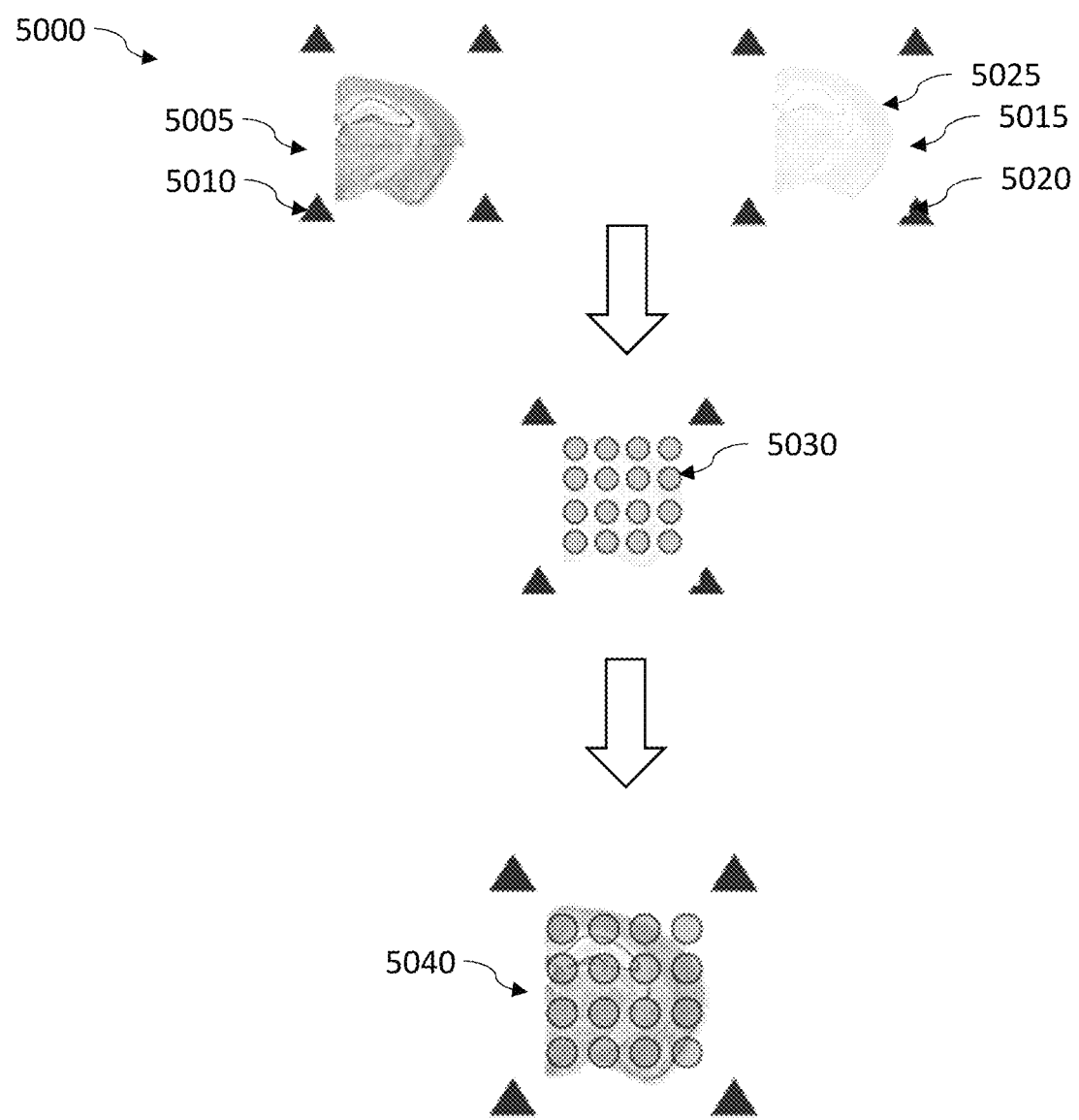
FIG. 50 depicts a workflow for registering stitched sample portion images to corresponding portions of the sample in a sample image according to some implementations of the current subject matter.

FIG. 50 depicts a workflow 5000 for registering stitched sample portion images to corresponding portions of the sample in a sample image according to some implementations of the current subject matter. A high-resolution stitched sample image 5005 including one or more fiducials 5010 can be received by the data processor of the sample handling apparatus 400, 1400, and 3000. A single field of view, unstitched, low-resolution image 5015 including one or more fiducials 5020 can also be received by the data processor of the sample handling apparatus 400, 1400, and 3000. The fiducials 5020 and the sample 5025 in the single field of view, unstitched, low-resolution image 5015 can be used to determine one or more barcoded locations 5030. Image registration can be performed between the single field of view, unstitched, low-resolution image 5015 and the high-resolution stitched sample image 5005 to provide as shown in 5040 high-resolution barcode location information with respect to the high-resolution stitched sample image 5005.

Figure 51:
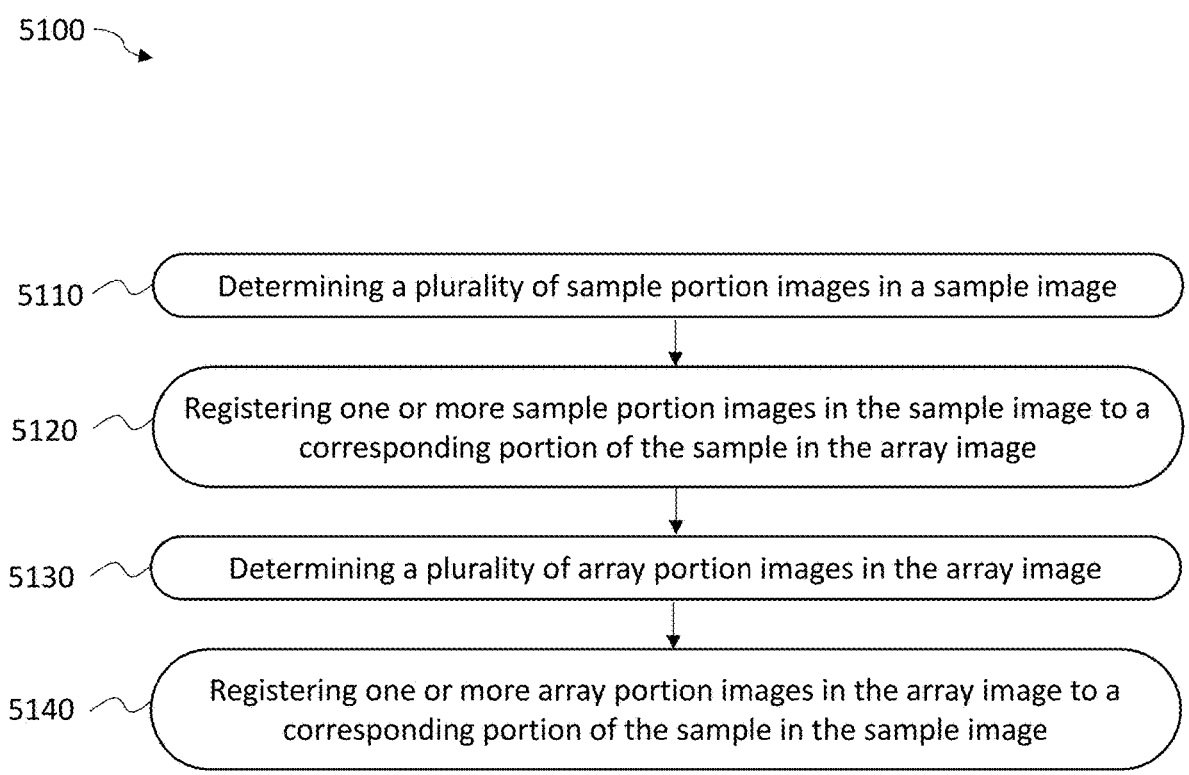
FIG. 51 is a process flow diagram illustrating an example process for registering stitched sample portion images to corresponding portions of the sample in a sample image and registering stitched array portion images to corresponding portions of the sample in the sample image according to some implementations of the current subject matter.

FIG. 51 is a process flow diagram illustrating an example process 5100 for registering stitched sample portion images to corresponding portions of the sample in a sample image and registering stitched array portion images to corresponding portions of the sample in the sample image according to some implementations of the current subject matter. In some embodiments, the high-resolution stitched sample image can include a plurality of sample portion images. Each of the sample portion images can be associated with a corresponding portion of the sample. The low-resolution array image can include a plurality of stitched array portion images. Each of the array portion images can be associated with a corresponding portion of the array and can include a single field of view.

At 5110, the data processor of the sample handling apparatus 400, 1400, and 3000 can determine a plurality of sample portion images in a high-resolution stitched sample image. The plurality of sample portion images can be determined using computer vision and/or image processing functionality configured within or accessible via the data processor. In some embodiments, the plurality of sample portion images can be known information recorded by the image capture device when the high-resolution stitched sample image was taken. At 5120, the data processor can register one or more of the sample portion images in the sample image to a corresponding portion of the sample in the low-resolution stitched array image. At 5130, the data processor can determine a plurality of array portion images in the low-resolution stitched array image. The plurality of array portion images can be determined using computer vision and/or image processing functionality configured within or accessible via the data processor. At 5140, the data processor can register one or more array portion images in the low-resolution stitched array image to a corresponding portion of the sample in the high-resolution stitched sample image.

Figure 52:
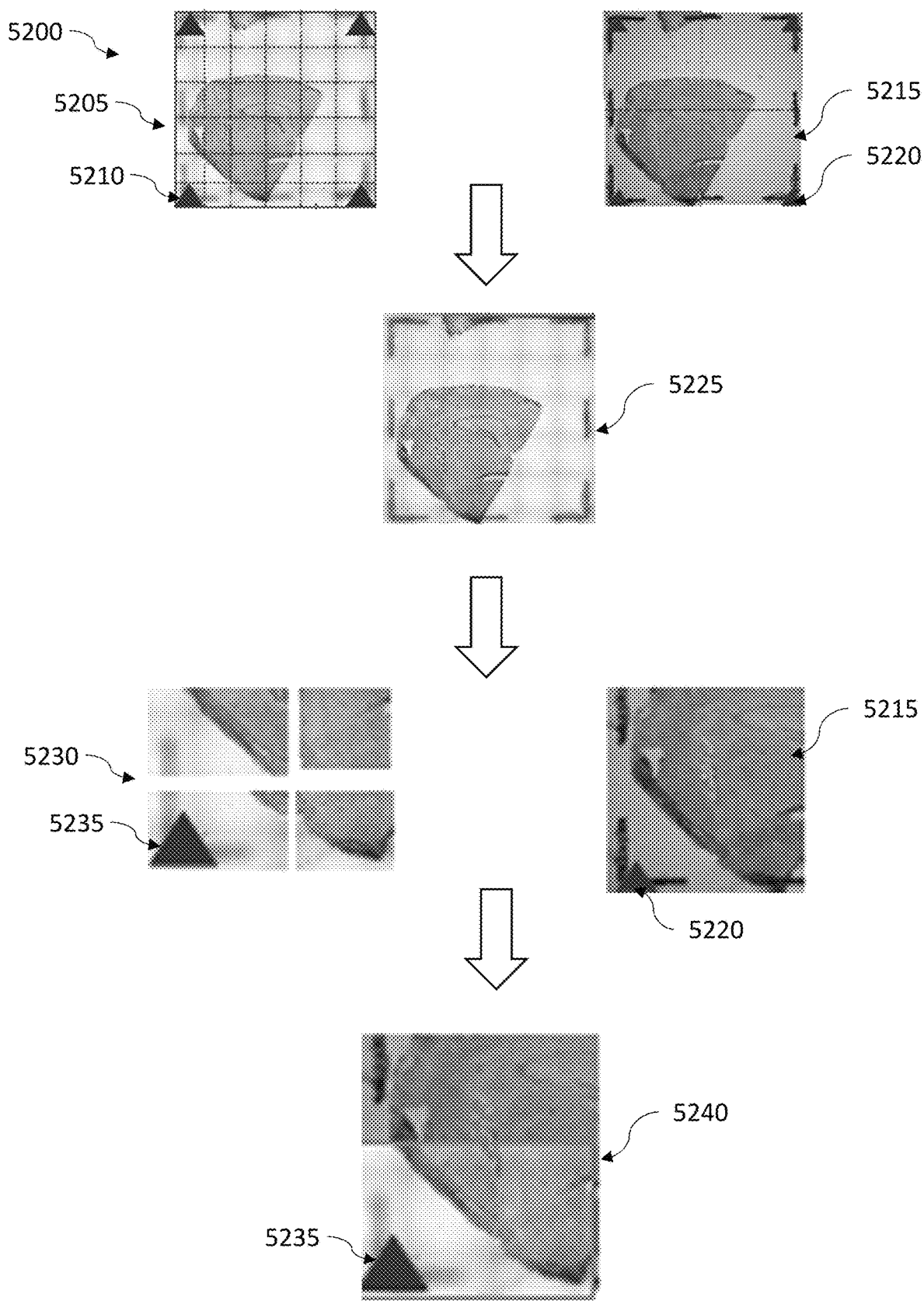
FIG. 52 depicts a workflow for registering stitched sample portion images to corresponding portions of the sample in a sample image and registering stitched array portion images to corresponding portions of the sample in the sample image according to some implementations of the current subject matter.

FIG. 52 depicts a workflow 5200 for registering stitched sample portion images to corresponding portions of the sample in a sample image and registering stitched array portion images to corresponding portions of the sample in the sample image according to some implementations of the current subject matter. A high-resolution stitched sample image 5205 can be received by a data processor of the sample handling apparatus 400, 1400, and 3000. The high-resolution stitched sample image 5205 can include one or more sample fiducials 5210. A low-resolution stitched array image 5215 including four single field of view array portion images can also be received by the data processor of the sample handling apparatus 400, 1400, and 3000. The low-resolution stitched array image 5215 can include one or more array fiducials 5220. An initial alignment image 5225 can be generated via a global whole image registration operation registering the high-resolution stitched sample image 5205 to the lower resolution stitched array image. In some embodiments, it may not be necessary to generate the initial alignment image 5215. In some embodiments, prior to generating the initial alignment image 5225, the sample substrate and the array substrate can be aligned manually or automatically by the data processor of the sample handling apparatus 400, 1400, and 3000. This preliminary alignment can be performed to specify the starting conditions of the image registration methods described herein.

A quarter of the low-resolution stitched sample image 5215 can be processed to determine a plurality of sample portion images 5230. Registration can be performed for each single field of view array portion images 5230. The fiducial 5235 can be used to facilitate mapping of the gene expression data to the high-resolution sample image. Since this quarter of the image 5215 can be a single field of view and unstitched, the location information between the tissue sample and fiducials can be determined to be accurate. The plurality of sample portion images 5230 can be locally registered with the low-resolution single field of view array image 5215 to generate a locally aligned sample image 5240. Each sample portion image of the plurality of array portion images can be smaller than a single field of view of the low-resolution stitched sample image 5215. In this way, local registration errors due to stitching artifacts in the high-resolution image can be corrected.

V. Image Registration System and Software Architecture

Figure 53:
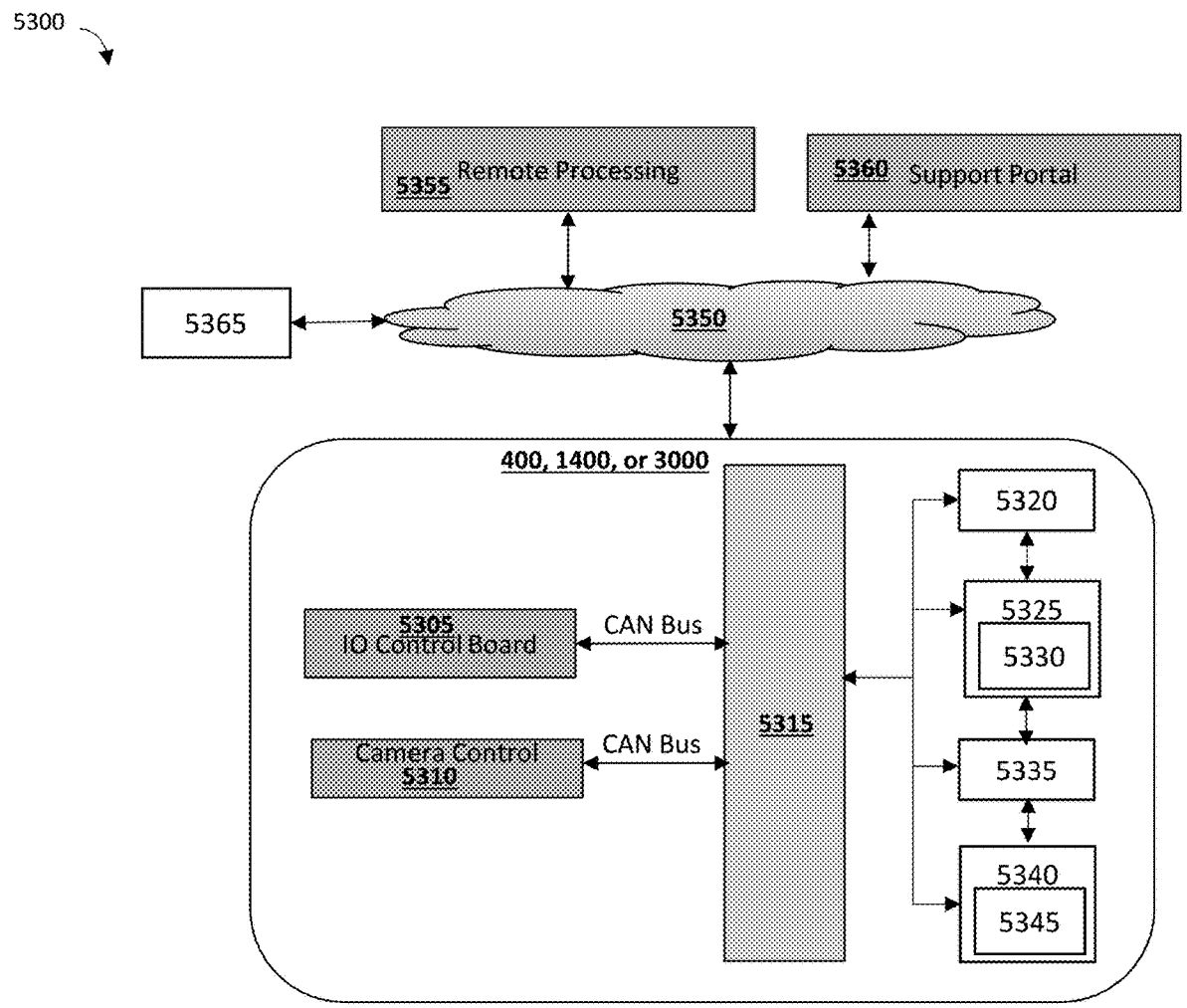
FIG. 53 is a diagram of an example system architecture for performing the image registration processes and workflows described herein in accordance with some example implementations.

FIG. 53 is a diagram of an example system architecture 5300 for performing the image registration processes and workflows described herein in accordance with some example implementations. For example, the system architecture 5300 be configured to operate with the sample handling apparatus 400, 1400, and 3000 to perform one or more of workflows and processes described herein. The system architecture 5300 can also include a remote processing service 5355, a support portal 5360, and a computing device 5365 that can be communicatively coupled to one another via a network 5350. The system architecture can be configured in a system and can perform image registration workflows described herein.

As shown in FIG. 53, the sample handling apparatus 400, 1400, and 3000 may include an input/output control board 5305 controlling operation of motors, pumps, fans, heaters, actuators, sensors, illuminations sources, fluid sources or the like that can be configured within the sample handling apparatus 400, 1400, and 3000. A camera control 5310, and a network interface 5315 can also be included in the sample handling apparatus 400, 1400, 3000. As shown, the input/output (I/O) controller 5305, the camera control 5310, and the network interface 5315 may be connected via a controller area network (CAN) bus. The camera control 5310 may be configured to control aspects or components of a camera (e.g., the image capture device 1420 or 1720). For example, the camera control 5310 may control a focus, a zoom, a position of the camera, an image capture, or the like.

The sample handling apparatus 400, 1400, and 3000 also includes a processor 5320, a memory 5325 storing one or more applications 5330, an input device 5335, and a display 5340. The processor 5320 can be configured to execute computer-readable instructions stored the memory 5325 to perform the workflows and processes associated with the applications 5330. The processor 5320 can also execute computer-readable instructions stored in the memory 5325, which cause the processor 5320 to control operations of the sample handling apparatus 400, 1400, and 3000 via the I/O controller 5305 and/or the image capture devices 1420, 1720 via the camera control 5310. In this way, the processor 5320 can control an operation of the sample handling apparatus 400, 1400, and 3000 to align a sample with an array. For example, the processor 5320 can execute instructions to cause either of the first retaining mechanism or the second retaining mechanism to translate within the sample handling apparatus 400, 1400, 3000 so as to adjust their respective locations and to cause a sample area of a first substrate to be aligned with an array area of a second substrate.

The input device 5335 can include a mouse, a stylus, a touch-pad, a joy stick, or the like configured to receive user inputs from a user. For example, a user can use the input device 5335 to provide an input indicating a sample area indicator for a first substrate. The display 5340 can include a graphical user interface 5345 displaying data associated with the one or more applications 5330.

The network interface 5315 may be configured to provide wired or wireless connectivity with a network 5350, such as the Internet, a local area network, a wide area network, a virtual private network, a cellular network or the like. In some embodiments, the network interface 5315 can be configured to communicate via Ethernet, Wi-Fi, Bluetooth, USB, or the like. The network 5350 may be connected to one or more distributed computing resources or remote processing services 5355. In some embodiments, the remote processing service 5355 can be a cloud computing environment, a software as a service (SaaS) pipeline. The remote processing service 5355 can be configured to aid, perform, or control automated image alignment and/or image registration of the sample handling apparatus 400, 1400, and 3000 described herein. The support portal 5360 can be configured to send share image data, image registration data, instrument calibration data or self-test data including images, videos, and logs or associated parameter data to the support portal 5655. In some embodiments, the remote processing service 5355 or the support portal 5360 can be configured as a cloud computing environment, a virtual or containerized computing environment, and/or a web-based microservices environment.

The sample handling apparatus 400 can also be communicatively coupled via the network 5350 to a computing device 5365. In some embodiments, the second computing device 5365 can be located remotely from the sample handling apparatus 400, 1400, and 3000.

The computing device 5365 can be configured to transmit and receive data with the sample handling apparatus 400, 1400, and 3000. The computing device 5365 can include a desktop, laptop, mobile, tablet, touch-screen computing device or the like. In some embodiments, the computing device 5365 can include a smart phone, such as a phone configured with an iOS or Android operating system.

Figure 54:
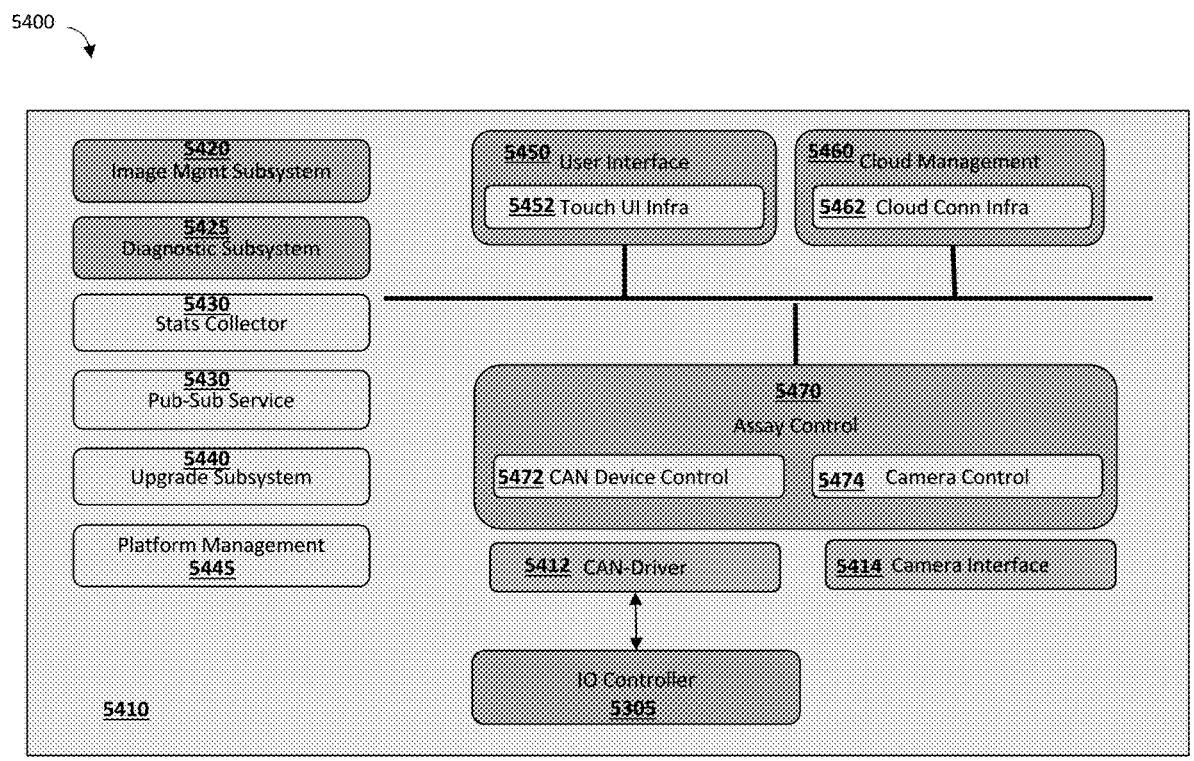
FIG. 54 is a diagram of an example software architecture for performing the processes and workflows described herein in accordance with some example implementations.

FIG. 54 is a diagram of an example software architecture 5400 for performing the processes and workflows described herein in accordance with some example implementations. The architecture 5400 can be configured in the memory 5325 of the sample handling apparatus 400, 1400, and 3000 described in relation to FIG. 53. Programmatic modules of the architecture can be implemented as an operating system 5410 (e.g., a Linux OS) of the sample handling apparatus 400, 1400, and 3000 and can be stored in memory 5325. The operating system 5410 may include the I/O controller 5305, a CAN driver 5412, a camera interface 5414, an image management subsystem 5420, a diagnostic subsystem 5425, a statistics collector 5430, a publication and subscription service 5435, and upgrade subsystem 5440, a platform management subsystem 5445, a user interface subsystem 5450, a cloud management subsystem 5460, and an assay control subsystem 5470. The user interface subsystem 5450 may include a touchscreen user interface infrastructure 5452. The cloud management subsystem 5460 may include a cloud connectivity infrastructure 5462. The assay control subsystem 5470 may include a controller area network (CAN) device control subsystem 5472 and a camera control subsystem 5474. The CAN device control subsystem 5472 may connect to other boards controlling other sensors, actuators, heaters, illumination sources, or other components of connected sample handling apparatuses 400, 1400, and 3000. The camera interface 5414 may be configured to control and record images/videos using the image capture device(s).

Figure 55:
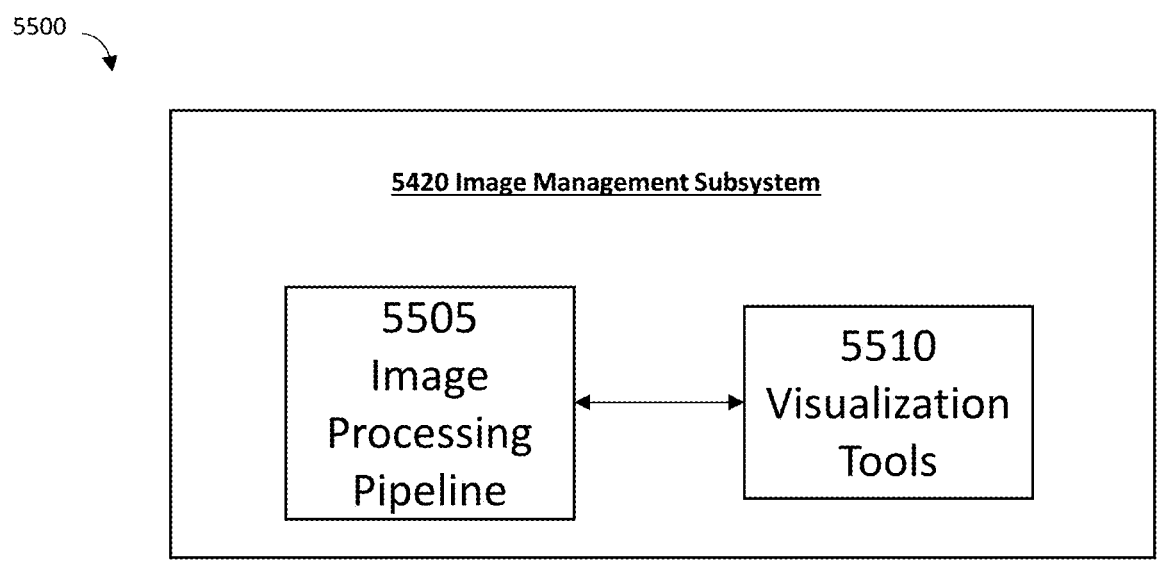
FIG. 55 is a diagram of an example architecture of the image management subsystem shown in FIG. 54 in accordance with some example implementations.

FIG. 55 is a diagram of an example architecture 5500 of the image management subsystem 5420 shown in FIG. 54. The image management subsystem 5420 can be configured to perform the image registration processes and workflows described herein in accordance with some example implementations. The image management subsystem 5420 can include an image processing pipeline 5505 and visualization tools 5510.

The image processing pipeline 5505 can include one or more analysis pipelines configured to process spatial RNA-seq output and brightfield and fluorescence microscope images in order to detect samples, align reads, generate feature-spot matrices, perform clustering and gene expression analysis, and place spots in spatial context on the substrate image. In some embodiments, the image processing pipeline 5505 can include functionality configured to correctly demultiplex sequencing runs and to convert barcode and read data to FASTQ formatted files. The FASTQ format is a text-based format for storing both a biological sequence (usually nucleotide sequence) and its corresponding quality scores. Both the sequence letter and quality score are each encoded with a single ASCII character for brevity. In some embodiments, the image processing pipeline 5505 can include functionality configured to receive a microscope slide image and FASTQ files and to perform alignment, tissue detection, fiducial detection, and barcode location counting. The image processing pipeline 5505 uses the spatial barcodes to generate feature-spot matrices, determine clusters, and perform gene expression analysis. In some embodiments, the image processing pipeline 5505 can include functionality configured to receive the output of multiple runs of counting barcode locations and/or unique molecular identifiers (UMI) from related samples and can aggregate the output, normalizing those runs to the same sequencing depth, and then recomputing the feature-barcode matrices and the analysis on the combined data. The image processing pipeline 5505 can combine data from multiple samples into an experiment-wide feature-barcode matrix and analysis.

The image processing pipeline 5505 can further include functionality configured to process brightfield and fluorescence imaging. For example, the image processing pipeline 5505 can be configured to receive a slide image as input to be used as an anatomical map on which gene expression measures are visualized. The image processing pipeline 5505 can be configured to receive at least two styles of images: a) a brightfield image stained with hematoxylin and eosin (H&E) with dark tissue on a light background or b) a fluorescence image with bright signal on a dark background. While brightfield input can comprises a single image, the fluorescence input can comprise one or more channels of information generated by separate excitations of the sample.

The image processing pipeline 5505 can further include functionality to automatically and/or manually perform image processing workflows described herein. For example, the image processing pipeline 5505 can include functionality configured to align a substrates barcoded spot pattern to an input substrate image for brightfield images. The image processing pipeline 5505 can further discriminate between tissue and background in a slide for brightfield images. The image processing pipeline 5505 can also be configured to prepare full-resolution slide images for use with the visualization tools 5510.

The image processing pipeline 5505 can be configured with one or more imaging algorithms. The imaging algorithms can be configured to determine where a sample, such as tissue, has been placed and aligning the printed fiducial spot pattern. Tissue detection can be used to identify which capture spots, and therefore which barcodes, will be used for analysis. Fiducial alignment can be performed to determine where in the image an individual barcoded spot resides, since each user may set a slightly different field of view when imaging the sample area. The image processing analysis pipeline 5505 can also be configured to support manual alignment and tissue selection via the visualization tools 5510.

The image processing pipeline 5505 can perform fiducial alignment by identifying the slide-specific pattern of invisible capture spots printed on each slide and how these relate to the visible fiducial spots that form a frame around each capture area. The fiducial frame can include unique corners and sides that the software attempts to identify. To determine alignment of fiducials, the image processing pipeline 5505 can extracts features that "look" like fiducial spots and then can attempt to align these candidate fiducial spots to the known fiducial spot pattern. The spots extracted from the image can necessarily contain some misses, for instance in places where the fiducial spots were covered by tissue, and some false positives, such as where debris on the slide or tissue features may look like fiducial spots.

After extraction of putative fiducial spots from the image, this pattern can be aligned to the known fiducial spot pattern in a manner that is robust to a reasonable number of false positives and false negatives. The output of this process can be a coordinate transform that relates the barcoded spot pattern to the user's tissue image. In some embodiments, the fiducial alignment algorithm can be executed for each of the possible fiducial frame transformations and choosing among those the alignment with the best fit.

The image processing pipeline 5505 can further include tissue detection functionality. Each area in a substrate or slide can contain a grid of capture spots populated with spatially barcoded probes for capturing poly-adenylated mRNA. Only a fraction of these spots can be covered by tissue. In order to restrict the image processing pipeline 5505 analysis to only those spots where tissue was placed, the image processing pipeline 5505 can use an algorithm to identify tissue in the input brightfield image. For example, using a grayscale, down-sampled version of an input image, multiple estimates of tissue section placement can be calculated and compared. These estimates can be used to train a statistical classifier to label each pixel within the capture area as either tissue or background. In order to achieve optimal results, the tissue detection algorithm can be configured to receive an image with a smooth, bright background and darker tissue with a complex structure.

As further shown in FIG. 55, the image management subsystem 5420 can also include visualization tools 5510. The visualization tools 5510 can be configured to provide the spatialomic (e.g., spatial transcriptomic) data in one or more visual formats. The visualization tools 5510 can provide the spatialomic (e.g., spatial transcriptomic) data for display in a display of the sample handling apparatus 400, 1400, and 3000. In some embodiments, the spatialomic (e.g., spatial transcriptomic) data can be provided in a GUI of the display of the sample handling apparatus 400, 1400, and 3000. In some embodiments, the visualization tools 5510 can be configured on a remote computing device that is communicatively coupled to the sample handling apparatus 400, 1400, and 3000, such that the spatialomic (e.g., spatial transcriptomic) data can be visualized and/or manipulated on the remote computing device.

The visualization tools 5510 can be configured to provide a user input system and user interface, such as a desktop application that provides interactive visualization functionality to analyze data from different spatialomic (e.g., spatial transcriptomic) processes and workflows described herein. The visualization tools 5510 can include a browser that can be configured to enable users to evaluate and interact with different views of the spatialomic (e.g., spatial transcriptomic) data to quickly gain insights into the underlying biology of the samples being analyzed. The browser can be configured to evaluate significant genes, characterize and refine clusters of data, and to perform differential expression analysis within the spatial context of a sample image.

The visualization tools 5510 can be configured to read from and write to files generated by the image processing pipeline 5505. The files can be configured to include tiled and untiled versions of sample images, gene expression data for all barcoded locations on a substrate or slide, alignment data associated with alignment of a sample or portions of the sample and the barcoded locations of an array, and gene expression-based clustering information for the barcoded locations. The gene expression-based clustering information can include t-Distributed Stochastic Neighbor Embedding (t-SNE) and Uniform Manifold Approximation and Projection (UMAP) projections.

Figure 56:
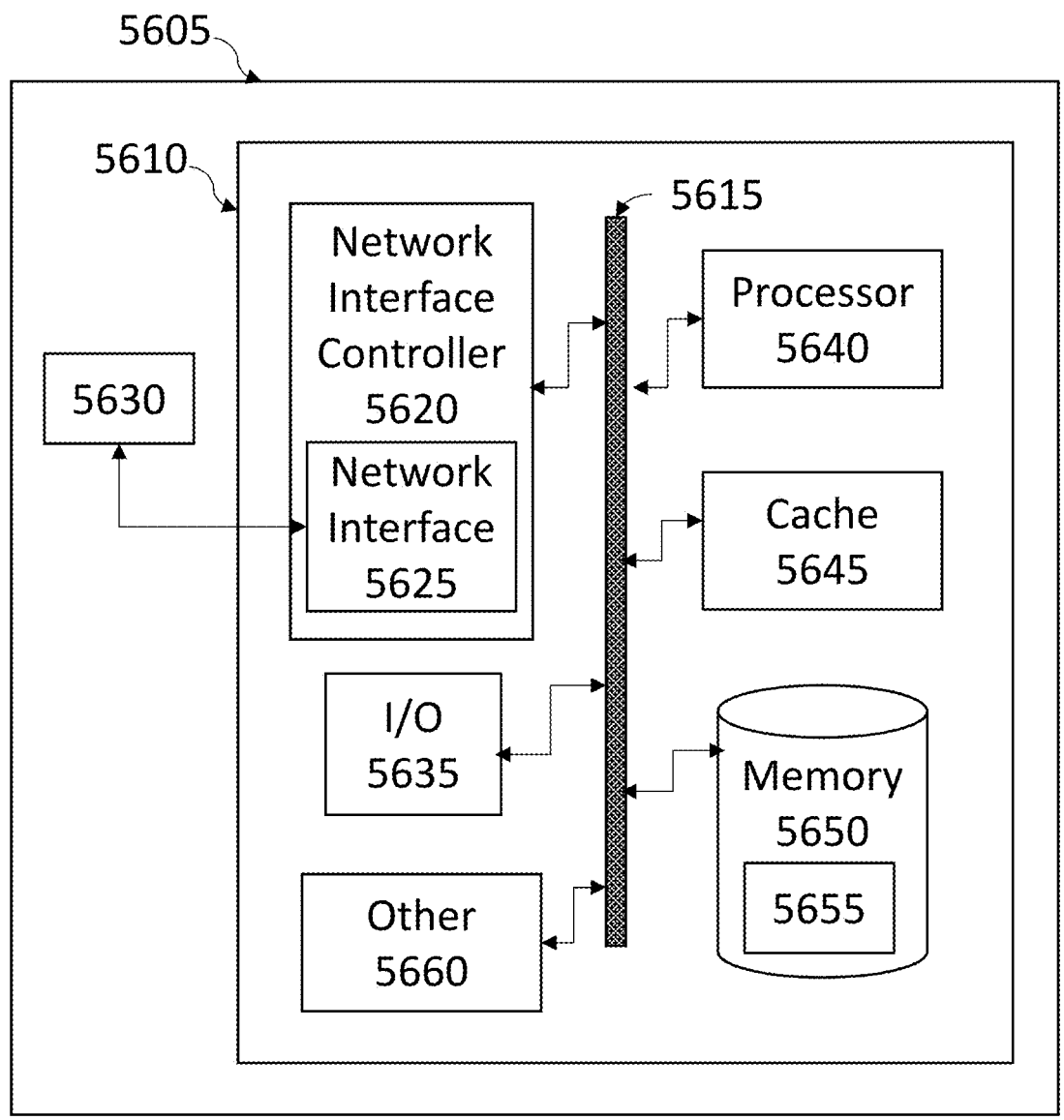
FIG. 56 is a diagram illustrating an example architecture of a computing device in accordance with some example implementations.

FIG. 56 is a diagram illustrating an example architecture of a computing system 5605. The computing system 5605 can include a first computing device 5610 and a second computing device 5630. In some embodiments, the computing device 5610 can be the same as computing device 5360 described in relation to FIG. 53. In some embodiments, the computing device 5610 can be communicatively coupled with the computing device 5630, for example when the computing device 5630 is configured as or within instrument 400, 1400, and 3000 described herein.

As shown in FIG. 56, the computing device 5610 includes at least one processor 5640 for performing actions in accordance with instructions, and one or more memory devices (e.g., cache 5645) and/or memory 5650 for storing instructions and data. The computing device 5610 includes one or more processors 5640 in communication, via a bus 5615, with memory 5650 and with at least one network interface controller 5620 with a network interface 5625 for connecting to external devices, such as computing device 5630, e.g., a computing device (such as the instrument 400, 1400, 3000 herein). The one or more processors 5640 are also in communication, via the bus 5615, with each other and with any I/O devices at one or more I/O interfaces 5625, and any other devices 5660. The processor 5640 illustrated can be incorporated, or can be directly connected to, cache memory 5645. Generally, a processor will execute instructions received from memory.

The network interface controller 5620 manages data exchanges via the network interface 5625. The network interface controller 5620 handles the physical and data link layers of the Open Systems Interconnect (OSI) model for network communication. In some implementations, some of the network interface controller's tasks are handled by the processor 5640. In some implementations, the network interface controller 5620 is part of the processor 5640. In some implementations, the computing device 5610 has multiple network interface controllers 5620. In some implementations, the network interface 5625 is a connection point for a physical network link, e.g., an RJ 45 connector. In some implementations, the network interface controller 5620 supports wireless network connections and an interface port 5625 is a wireless receiver/transmitter. Generally, the computing device 5610 can exchange data with other network devices 5630, such as the sampling handling apparatus 400, 1400, and 3000 described herein via physical or wireless links to a network interface 5625. In some implementations, the network interface controller 5620 implements a network protocol, such as Ethernet.

The other computing devices 5630 are connected to the computing device 5610 via a network interface port 5625. The other computing device 5630 can be a peer computing device, a network device, or any other computing device with network functionality. In some embodiments, the computing device 5630 can be a network device such as a hub, a bridge, a switch, or a router, connecting the computing device 5360 to a data network such as the Internet. In some embodiments, the computing device 5610 can be communicatively coupled to the computing device 5630 (e.g., the instrument 400, 1400, and 3000) via the I/O interface 5635. In some implementations an I/O device is incorporated into the computing device 5610, e.g., as would be configured on a touch screen computing device or a tablet computing device.

In some uses, the I/O interface 5635 supports an input device and/or an output device. In some uses, the input device and the output device are integrated into the same hardware, e.g., as in a touch screen. In some uses, such as in a server context, there is no I/O interface 5635 or the I/O interface 5635 is not used.

In more detail, the processor 5640 can be any logic circuitry that processes instructions, e.g., instructions fetched from the memory 5650 or cache 5645. In many embodiments, the processor 5640 is an embedded processor, a microprocessor unit or special purpose processor. In some embodiments, the functionality described in relation to computing device 5610 can be configured on any processor, e.g., suitable digital signal processor (DSP), or set of processors, capable of operating as described herein. In some embodiments, the processor 5640 can be a single core or multi-core processor. In some embodiments, the processor 5640 can be composed of multiple processors.

The cache memory 5645 is generally a form of high-speed computer memory placed in close proximity to the processor 5640 for fast read/write times. In some implementations, the cache memory 5645 is part of, or on the same chip as, the processor 5640.

The memory 5650 can be any device suitable for storing computer readable data. The memory 5650 can be a device with fixed storage or a device for reading removable storage media. Examples include all forms of non-volatile memory, media and memory devices, semiconductor memory devices (e.g., EPROM, EEPROM, SDRAM, flash memory devices, and all types of solid state memory), magnetic disks, and magneto optical disks. The computing device 5610 can have any number of memory devices 5650.

The memory 5650 can include one or more applications 5655. The applications 5655 can include programmatic instructions and user interfaces configured to transmit and receive data corresponding to image data and/or assay data generated by the sample handling apparatus 400, 1400, 3000. In some embodiments, the application 5655 can be configured to share data with the operating system 5410, the remote processing service 5355, and/or the support portal 5360.

The applications 5655 can allow a user to receive data regarding experimental workflows, samples, and settings of the sample handling apparatus 400, 1400, and 3000. The applications 5655 can include features and functionality for a user to visualize assay progress or results, or to monitor and control progress of an assay. In this way, the applications 5655 can provide monitoring such that in-person, on-site monitoring may not be required for some or all of an assay workflow. In some embodiments, the applications 5655 can include features or functionality to order consumables, such as reagents or stains, used in conjunction with assays performed using the sample handling apparatus 400, 1400, 3000.

In some embodiments, the applications 5655 can allow a user to annotate a region of interest on a slide or substrate. For example, the applications 5655 can provide a display of an image of a tissue sample on a substrate, an image of an array on a substrate, or an image of a tissue sample substrate overlaid with an array substrate in a sandwich configuration described herein. A user can interact with the applications 5655 to provide an input identifying a region of interest. The input can be provided with a mouse, a stylus, a touch-screen or the like. The input can be processed by the application 5655 and displayed on an image of the sample substrate, the array substrate, or the tissue sample substrate overlaid with an array substrate. In some embodiments, the sample handling apparatus 400, 1400, and 3000 can receive data associated with the user input annotation and can apply the annotate to the sample substrate, the array substrate, or the tissue sample substrate overlaid with an array substrate.

In some embodiments, the applications 5655 can provide features and functionality for a user to review assay results or image data, evaluate assay results or image data using additional processing techniques or components, as well as commenting on and sharing assay results and image data. The applications 5655 can also enable a user to report issues and track the status of issued about the operation of the sample handling apparatus 400, 1400, and 3000 to the support portal 5360. As such, the user's customer support experience can be elevated as the applications can enable direct access to an error without requiring the user to separately write lengthy emails and collect log files or operating parameters of the sample handling apparatus 400, 1400, 3000 to provide to the customer support team. In some embodiments, the applications 5360 can provide documentation, such as training materials, assay or reagent data, and user manuals for the sample handling apparatus 400, 1400, and 3000. For example, the applications 5655 can immediately inform the user of updated user guides and product improvements. In some embodiments, the applications 5655 can provide a user with easy access to tutorials and interactive instruction.

A user interacting with applications 5655 on computing device 5610, such a mobile phone, tablet, or personal computing device, can provide feedback about the sample handling apparatus 400, 1400, and 3000 to a customer support team, for example via the support portal 5360. The customer support team can interact back with the user to provide timely, actionable insights about the state and operations of the sample handling apparatus 400, 1400, and 3000 to improve the user's experience and the likelihood of more successful experimental outcomes. In this way, the customer support team can reduce diagnostic time and solution implementation time. In some embodiments, the applications 5655 can be configured to receive and install software updates or patches associated with the operating system 5410 or the applications 5655. In this way, the applications 5655 can help automatically or manually configure and initialize the sampling handling apparatus 400, 1400, and 3000. For example, the customer support team may access the sample handling apparatus via the applications 5655 and can directly access an error once notified of the issue by an application 5655. Thus, in some embodiments, the applications 5655 can generate alerts and notifications associated assays and configurations of the sample handling apparatus 400, 1400, and 3000. For example, in a customer support context, when a protocol or experimental workflow is determined or an addition to an assay is made, the applications 5655 can notify the user. The applications 5655 can instantiate the update on the sample handling apparatus 400, 1400, and 3000 such that the user can access the updates protocol immediately.

In some embodiments, other devices 5660 are in communication with the computing devices 5610 or 5630. In some embodiments, the other devices 5660 can include external computing or data storage devices connected via a universal serial bus (USB). The other devices 5660 can also include an I/O interface, communication ports and interfaces, and data processors. For example, the other devices can include a keyboard, microphone, mouse, or other pointing devices, output devices such as a video display, a speaker, or a printer. In some embodiments, the other devices 5660 can include additional memory devices (e.g., portable flash drive or external media drive). In some implementations, the other devices can include a co-processor. In some embodiments, the additional device 5660 can include an FPGA, an ASIC, or a GPU to assist the processor 5640 with high precision or complex calculations associated with the image processing and image registration methods described herein.

Figure 57:
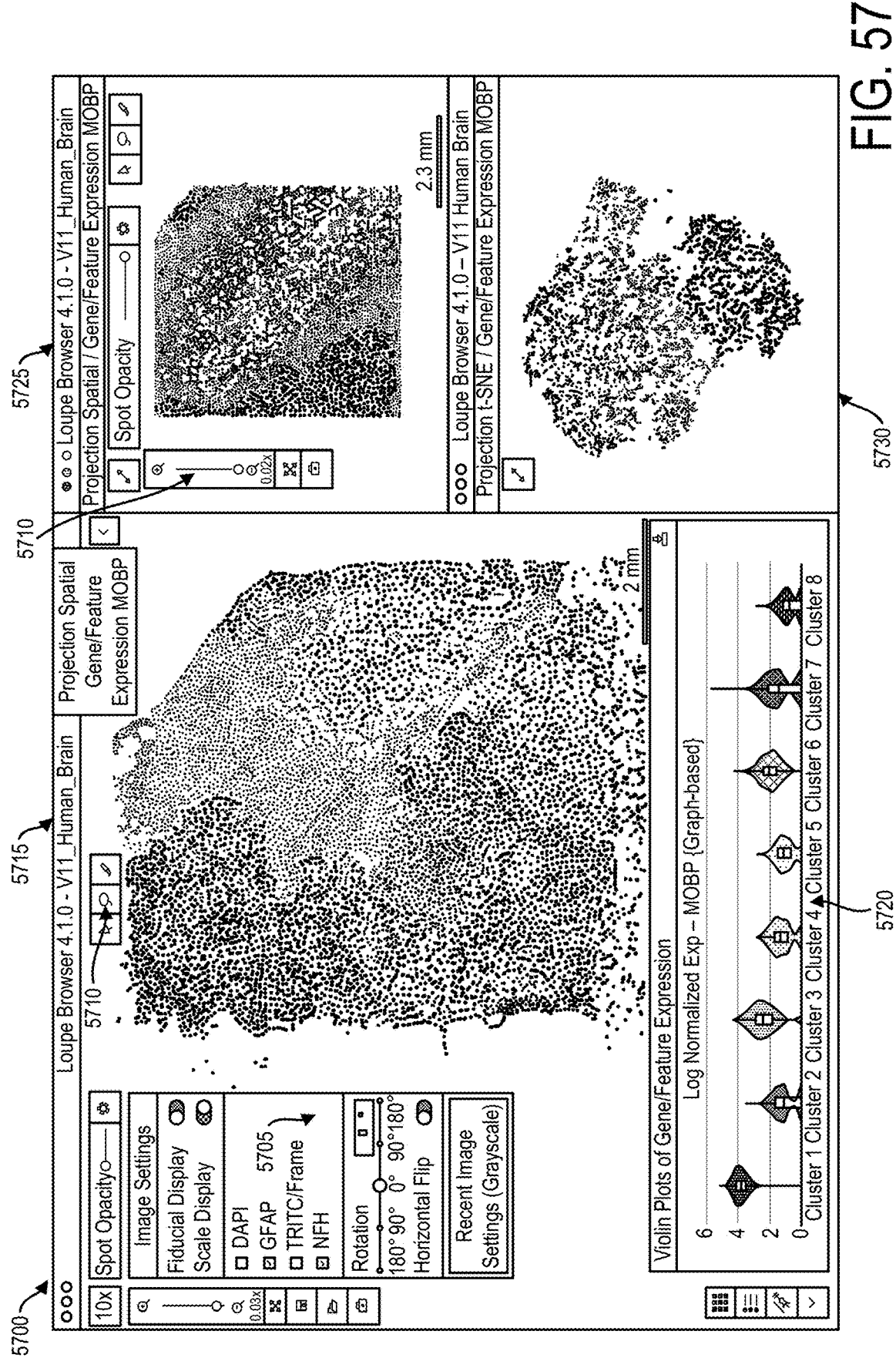
FIG. 57 is an example interface display provided by the visualization tools described herein in accordance with some example implementations.

FIG. 57 is an example interface display 5700 provided by the visualization tools 5410 described herein in accordance with some example implementations. The interface display 5700 can include image setting functionality 5705 configured to adjust or configured settings associated with fiducial display, scale display, rotation, and resetting the image data. The interface display 5700 can also include one or more image manipulation tools 5710, such as a pointer to select data or menu items, a lasso to select data, and a pen to annotate or mark data or a region of interest on a slide or an image of slide(s). The spatialomic (e.g., spatial transcriptomic) data can be provided in a primary viewing panel 5715.

As shown in FIG. 57, the interface display 5700 can include a presentation 5720 of gene/feature expression data organized with respect to clusters. In some embodiments, the presentation 5720 can provide representative clusters as violin plots, although a number of other non-limiting plot types can be envisioned. The interface display 5700 can also include secondary viewing panels 5725 and 5730. The secondary viewing panels 5725 and 5730 can provide one or more projections of the spatialomic (e.g., spatial transcriptomic) data provided in the primary viewing panel 5715. For example, the secondary viewing panel 5725 can provide a spatial projection of the spatialomic (e.g., spatial transcriptomic) data so that a user can interact with the spatial opacity and magnification settings of the data. The secondary viewing panel 5730 can provide an additional projection of the spatialomic (e.g., spatial transcriptomic) data, such as a t-SNE projection shown in FIG. 57. The primary viewing panel 5715 and secondary viewing panels 5725 and 5730 can each individually be configured with image manipulation tools 5510 including, but not limited to, image resize functionality, image cropping functionality, image zoom functionality, image capture functionality, tile view functionality, list view functionality, or the like.

VI. Fiducial Detection Using Image Registration System

For spatialomic (e.g., spatial transcriptomic) applications performed using the systems, methods, and computer readable mediums described herein, analyte information can be displayed over high resolution tissue images. An array of barcoded spots can capture analytes from a sample (e.g. a sample of a tissue section) for downstream sequencing. The location of the spots on an array substrate or slide relative to the location of the sample on a sample slide or substrate can be inferred using fiducial markers that can placed on the array substrate that can be imaged along with the tissue section on the sample substrate. The sample handling apparatuses, such as the sample handling apparatuses 400, 1400, or 3000 described herein can enable spatialomic (e.g., spatial transcriptomic) assays without having to first place a sample of a tissue selection directly on the array substrate that includes the array of barcoded spots. The sample handling apparatuses 400, 1400, or 3000 described herein can be configured to form an overlay or sandwich of a sample substrate and an array substrate. The overlay or sandwich can be formed and assembled during a permeabilization step in which a permeabilization solution can be introduced into the overlay or sandwich of the sample substrate and the array substrate. During permeabilization, the sample can be permeabilized or digested and can release transcripts that can diffuse across a gap formed between the sample substrate and the array substrate (e.g., from the tissue sample to the array of barcoded spots) and can bind on the barcoded oligos present within the barcoded spots. Because this transcript release and capture is done in the confined overlay or sandwich configuration of the sample substrate and the array substrate, it can be challenging to exchange reagents during this step to ensure sufficient fluid dispersal and control of reagent distribution so that spatial visualization of transcripts can be achieved under optimal conditions. When the sample overlaps the fiducials it can be difficult to visualize the fiducials for robust detection and subsequent image processing. This can affect the alignment of array images to sample images necessary to perform the spatialomic (e.g., spatial transcriptomic) workflows described herein.

Figure 58A:
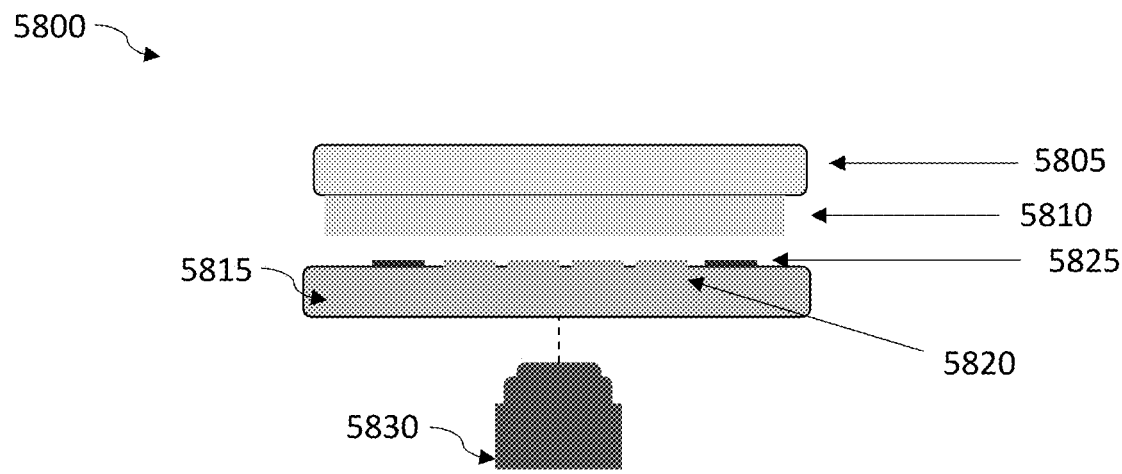
FIGS. 58A-58B depict a configuration of a sample and an array in which array fiducials are not overlapped with the sample in acquired image data in accordance with some example implementations.
Figure 58B:
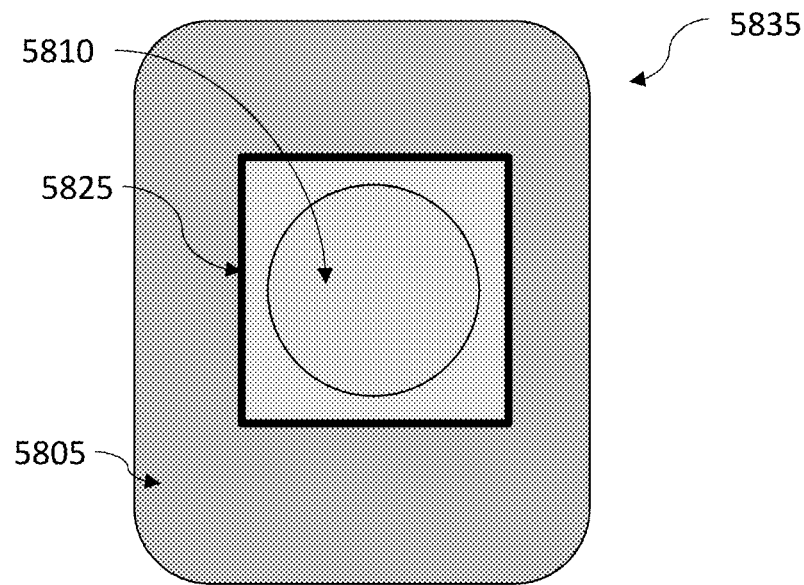

FIGS. 58A-58B depict a configuration of a sample and an array in which array fiducials are not overlapped with the sample in acquired image data in accordance with some example implementations. As shown in FIG. 58A, the sample handling apparatuses 400, 1400, or 3000 can acquire image data of a sample substrate 5805 including a sample 5810 thereon overlaid with an array substrate 5815. The array substrate 5815 can include an array 5820 and an array fiducial 5825. In some embodiments, a fiducial frame can include a plurality of individual array fiducials 5825 in a patterned arrangement that surrounds the array 5820. The array fiducial 5825 can delineate and identify a location of the array 5820 on the array substrate 5815. Images of the overlay can be acquired via image capture device 5830 (corresponding to image capture device 1720 described herein). The images and corresponding image data associated with the image can be acquired at one or more focal planes, illuminations, and frame rates as will be further described.

As shown in FIG. 58B, an image 5835 of the overlay can be acquired and can include the sample 5810 and the fiducial 5825. As shown, the sample 5810 has been provided such that it does not obscure or overlap the array fiducial 5825. In this way, the image 5835 includes both the sample 5810 and the array fiducial 5825 in the image. As the position of the array fiducial 5825 is known relative to the array 5820 of barcoded spots and the barcoded spots are not visible in the image 5835 of the overlay, the position of the array fiducial 5825 can be used to determine the location or position of the barcoded spots of the array 5820 relative to the location or position of the sample 5810.

In conditions in which the sample 5810 is not covering the array fiducial 5825, as shown in image 5835, the location of the array fiducials 5825 relative to the location of the sample 5810 can be determined using the sample handling apparatus 400, 1400, or 3000 by first loading the sample substrate and the array substrate into the sample handling apparatus and bringing the sample substrate 5805 in proximity of the array substrate 5815 to form the overlay or sandwich of the sample 5810 and the array 5820. Image data can be acquired via the image capture device 5830 of the overlay including the sample 5810, the array 5820, and the array fiducials 5825 as shown in image 5835. A computing device communicably coupled to the image capture device 5830 and the sample handling apparatus 400, 1400, or 3000 can receive image data including the image 5835 and can detect the location of the array fiducials 5825 with respect to a coordinate system determined and applied to the image data by the computing device. The computing device can further detect the location of the sample 5810 in the image 5835 using the coordinate system. Since the location of the sample 5810 and location of the array fiducials 5825 are determined by the computing device in the same image 5835 and using the same coordinate system, the location of the array fiducials 5825 relative to the location of the sample 5810 can be determined and provided by the computing device. However, in some conditions, the sample 5810 can overlap and obscure the array fiducials 5825 making it difficult to determine the location of the location of the array fiducials 5825 relative to the location of the sample 5810. The systems, methods, and computer readable mediums described herein provide improved detection of array fiducials.

Figure 59:
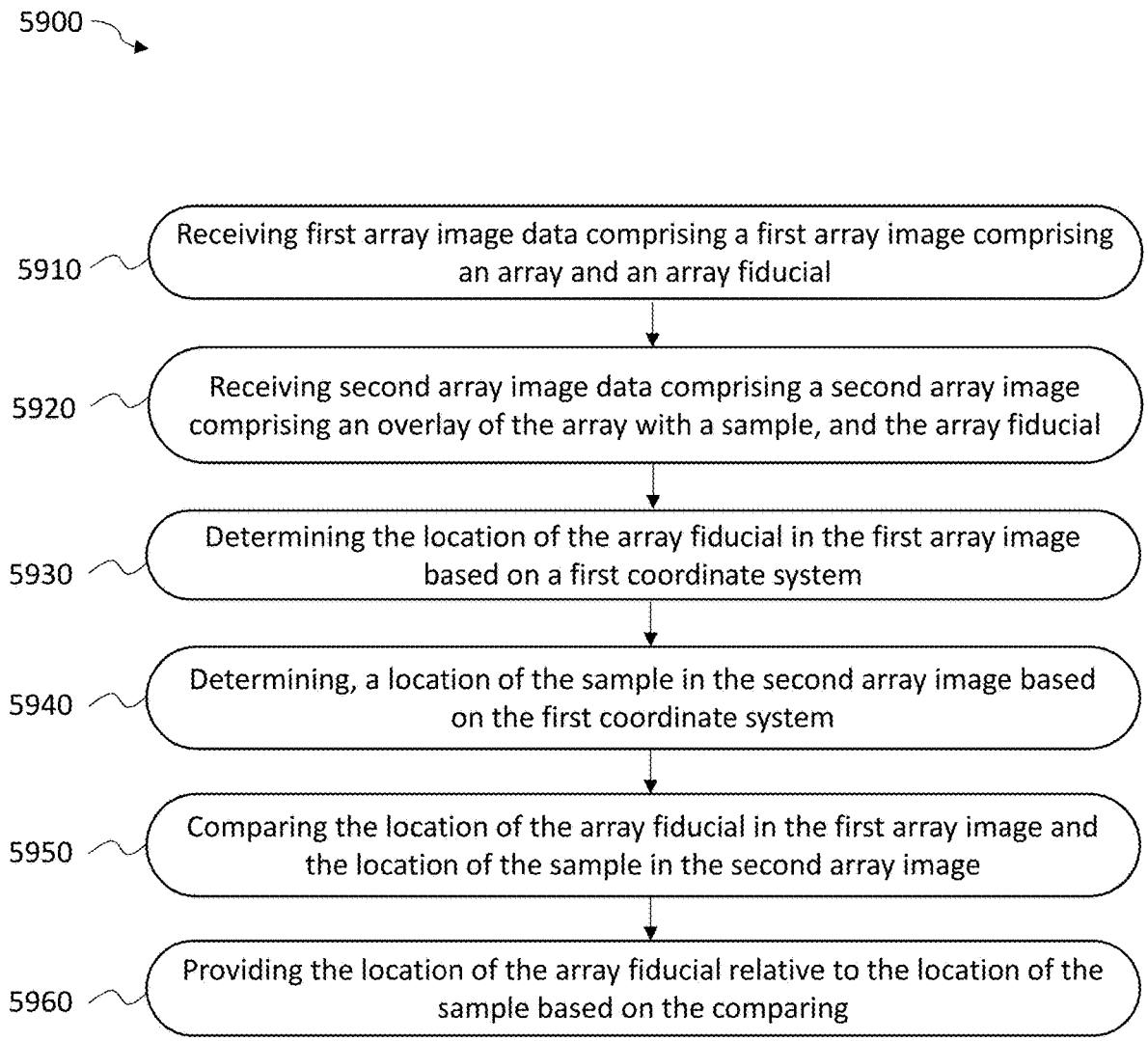
FIG. 59 is a process flow diagram illustrating an example process for detecting fiducials associated with an array in accordance with some example implementations.

FIG. 59 is a process flow diagram illustrating an example process 5900 for detecting fiducials associated with an array in accordance with some example implementations. The process 5900 can be performed by the system 5300 configured with the software architecture 5400 and the example architecture 5500 of the image management subsystem 5420.

For example, in operation 5910 the processor 5320 can receive image data acquired via an image capture device, such as image capture device 1720. The image data can include an image of an array and an array fiducial overlaid atop a sample.

In operation, 5920, the processor 5320 can receive image data, acquired via the image capture device 1720, including an image of an overlay of the array with the sample as described in relation to FIGS. 58A-58B after the sample substrate 5805 has been overlaid or sandwiched with respect to the array substrate 5815. The sample handling apparatus 400, 1400, and 3000 can prevent movement of the slide substrate relative to the array substrate as the overlay or sandwich is formed using the sample handling apparatus. The sample handling apparatus 400, 1400, and 3000 can also prevent movement of the array substrate relative to the image capture device 1720. The image of the overlay can also include the array fiducial. The sample can be located relative to the array such that the sample obscures the array fiducial in the overlay. The sample may not fully obscure the array fiducial, but instead may obscure a portion of the array fiducial so as to limit or reduce the improved array fiducial detection described herein.

In operation 5930, the processor 5320 can determine the location of the array fiducial based on the image data and the image including the array and the array fiducial. The processor 5320 can determine the location of the array fiducial based on a coordinate system. In some embodiments, image data includes the coordinate system, wherein pixel data is stored in the coordinate system. In some embodiments, the image data comprises data of pixel values stored in the coordinate system. In some embodiments, the image data comprises data of pixel values that are stored in a matrix coordinate system. In some embodiments, the coordinate system is stored within the memory 5320 or otherwise accessible to the operating system 5410 (such as the image management subsystem 5420, or the I/O control board 5305). In some embodiments, the memory 5320 or operating system 5410 can store or access one or more unique and different coordinate systems. In some embodiments, the coordinate systems can include one-, two-, or three-dimensional cartesian coordinate systems. The processor 5320 can apply the coordinate system coordinates to one or more features of the received image data so that locations of features in the image data, such as array fiducial locations and/or sample locations can be known with respect to the coordinate system coordinates.

In operation 5940, the processor 5320 can determine a location of the sample based on the image data and the image including the overlay of the array with the sample and further including the array fiducial. The array fiducials may be obscured in this image data by the sample and may not be visible. The location of the sample can be determined in the coordinate system by the data processor 5320 in a similar manner as described in relation to determining the location of the array fiducial in operation 5930.

In operation 5950, the data processor 5320 can compare the location of the array fiducial determined in operation 5930 and the location of the sample determined in operation 5940. Since there is no presumed shift in the sample substrate and the array substrate relative to each other or to one or more image capture device(s) 1720 between the capture of the first and second images, the locations can be considered within the same coordinate system and the processor 5320 can perform the comparison to confirm such. In operation 5960, based on the comparing, the processor 5320 can provide the location of the array fiducials relative to the location of the sample as defined by the coordinate system in which each have been determined to be located within. In some embodiments, the processor 5320 can provide the location of the array fiducial and the location of the sample in the display 5335 and/or the graphical user interface 5340.

Figure 60A:
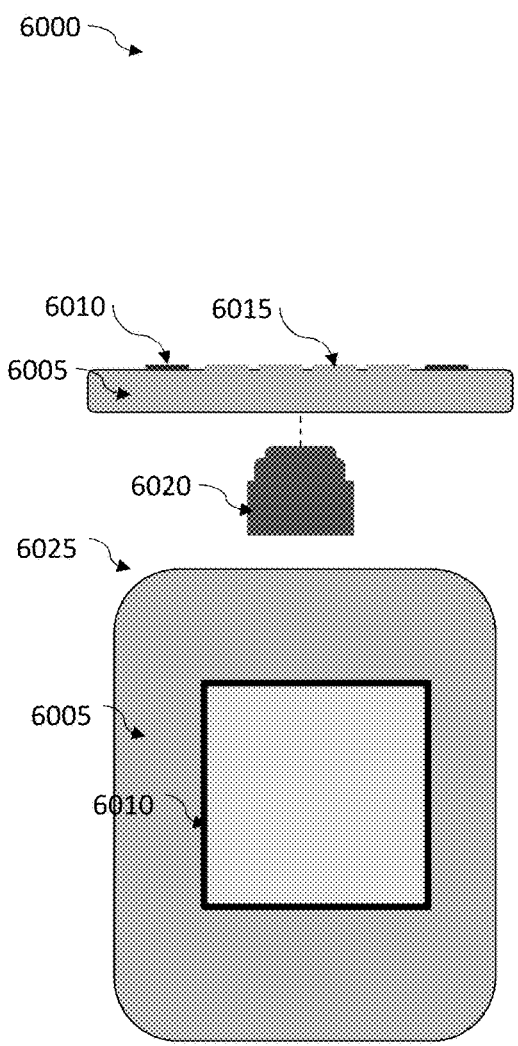
FIGS. 60A-60B depict a workflow for detecting array fiducials overlapped with a sample in acquired image data in accordance with some example implementations.
Figure 60B:
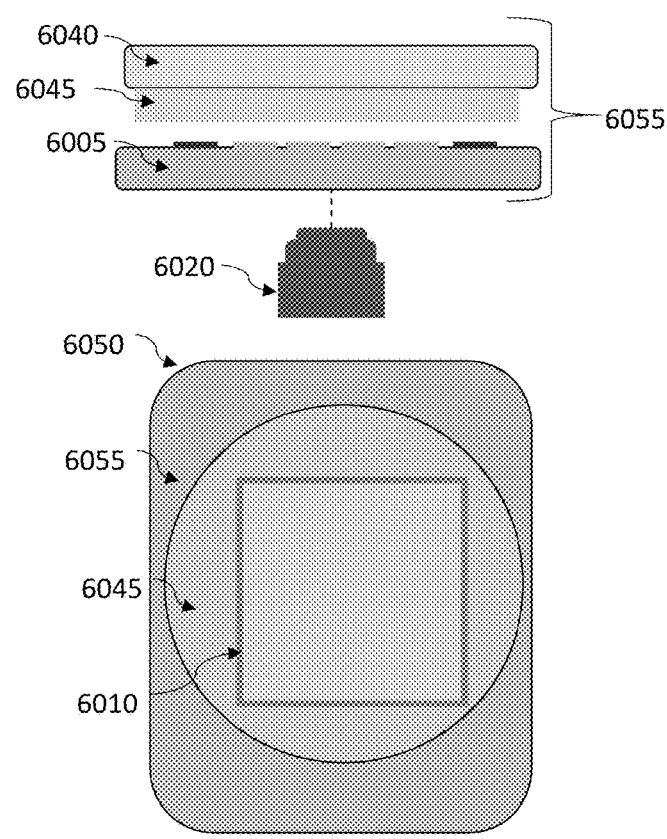

FIGS. 60A-60B depict a workflow 6000 for detecting array fiducials overlapped with a sample in acquired image data in accordance with some example implementations. The workflow 6000 can be performed with respect to embodiments of process 5900 described in FIG. 59. As shown in FIG. 60A, the image capture device 6020 (corresponding to image capture device 1720) can acquire an image 6025. The image 6025 can be of an array substrate 6005, which can include an array fiducial 6010 and an array 6015. The image 6025 can include the array substrate 6005 and the array fiducial 6010. As shown in FIG. 60B, an overlay 6055 of the sample substrate 6040 including a sample 6045 can be formed in the sample handling apparatus 400, 1400, or 3000 with the array substrate 6005. The image capture device 6020 can acquire an image 6050 of the overlay 6055. The image 6050 can include the array fiducial 6010 overlapped and obscured by the sample 6045.

Figures 61A, 61B:
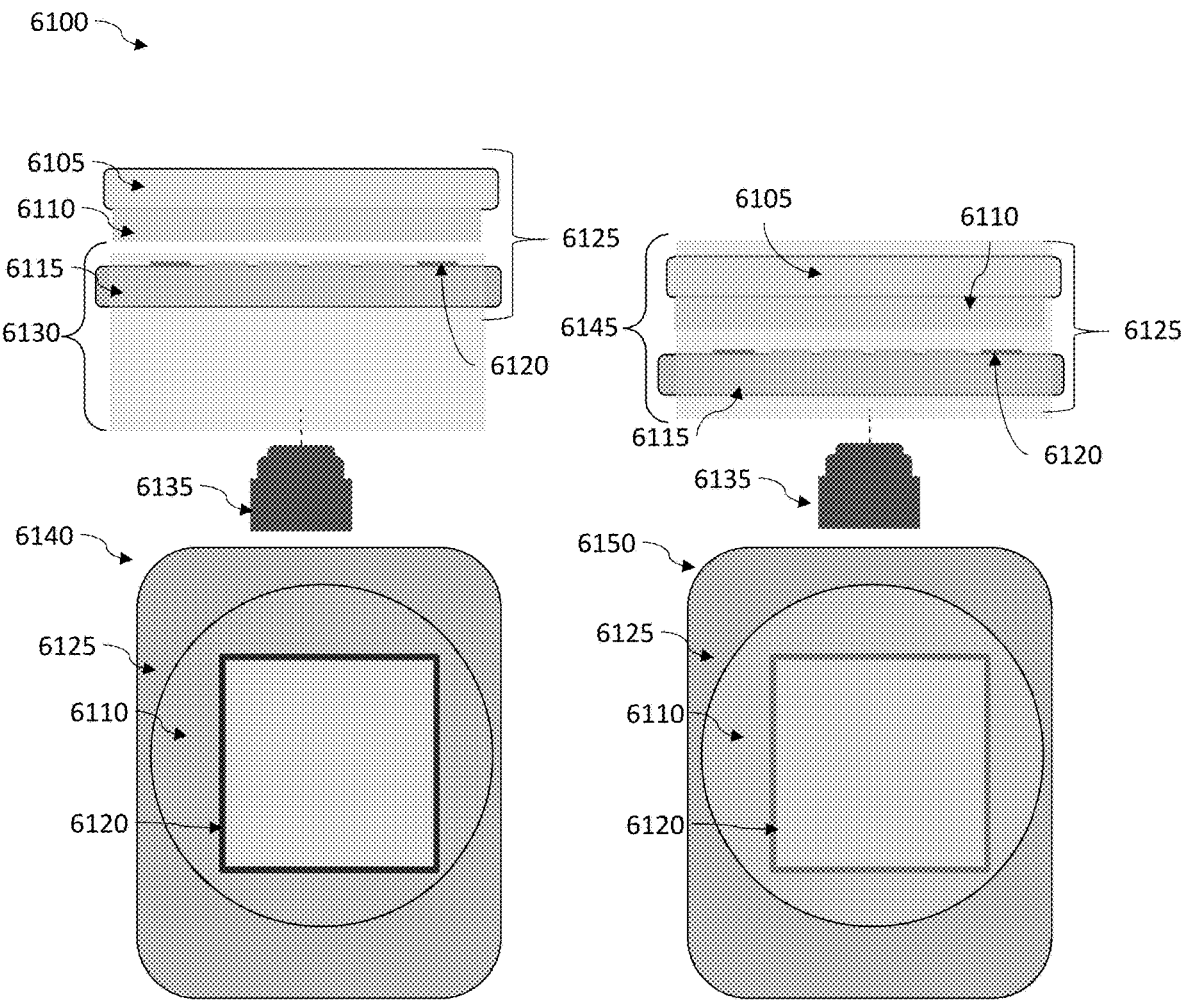
FIGS. 61A-61B depict a workflow for detecting array fiducials overlapped with a sample in image data acquired at different focal planes in accordance with some example implementations.

FIGS. 61A-61B depict a workflow 6100 for detecting array fiducials overlapped with a sample in image data acquired at different focal planes in accordance with some example implementations. The workflow 6100 can be performed with respect to embodiments of process 5900 of FIG. 59. The sample handling apparatus 400, 1400, and 3000 can be configured to move the image capture device 6135 in a vertical direction with respect to the z-axis, while remaining fixed in the x-, y-axes relative to the array substrate 6115.

As shown in FIG. 61A, image data can be acquired of an overlay 6125 of the sample substrate 6105 and the array substrate 6115. The sample substrate 6105 can include the sample 6110 and the array substrate can include the array fiducials 6120. The image data can be acquired by the image capture device 6135 (corresponding to image capture device 1720) at a focal plane 6130. The focal plane can correspond to a focal depth at which image data associated with the overlay 6125 is acquired. In the focal plane 6130 shown in FIG. 61A, the overlay 6125 may not be completely captured, for example the sample substrate 6105 and the sample 6110 may be out of focus, while the array substrate 6115 and the array fiducials 6120 can be more visible. The image 6140 captured by the image capture device 6135 of the overlay 6125 can reflect this suboptimal focal depth such that the array fiducials 6120 can be shown in the image 6140 in greater focus, while the sample 6110 is shown out of focus.

In FIG. 61B, the focal plane captures the overlay 6125 of the sample 6110 and the array fiducials 6120 more optimally. The image 6150 captured by image capture device 6135 can include the overlay 6125 and specifically, the sample 6110 and the array fiducials 6120, in focus. Image 6140 can be used detection of the array fiducials directly, or to aid detection of the array fiducials using image 6150. As there was is no presumed shift in the overlay 6125 relative to the image capture device 6135 in the x- and y-axes during formation of the overlay by sandwiching the sample substrate 6105 and the array substrate 6115, both substrates are present in the same coordinate system.

Figures 62A, 62B:
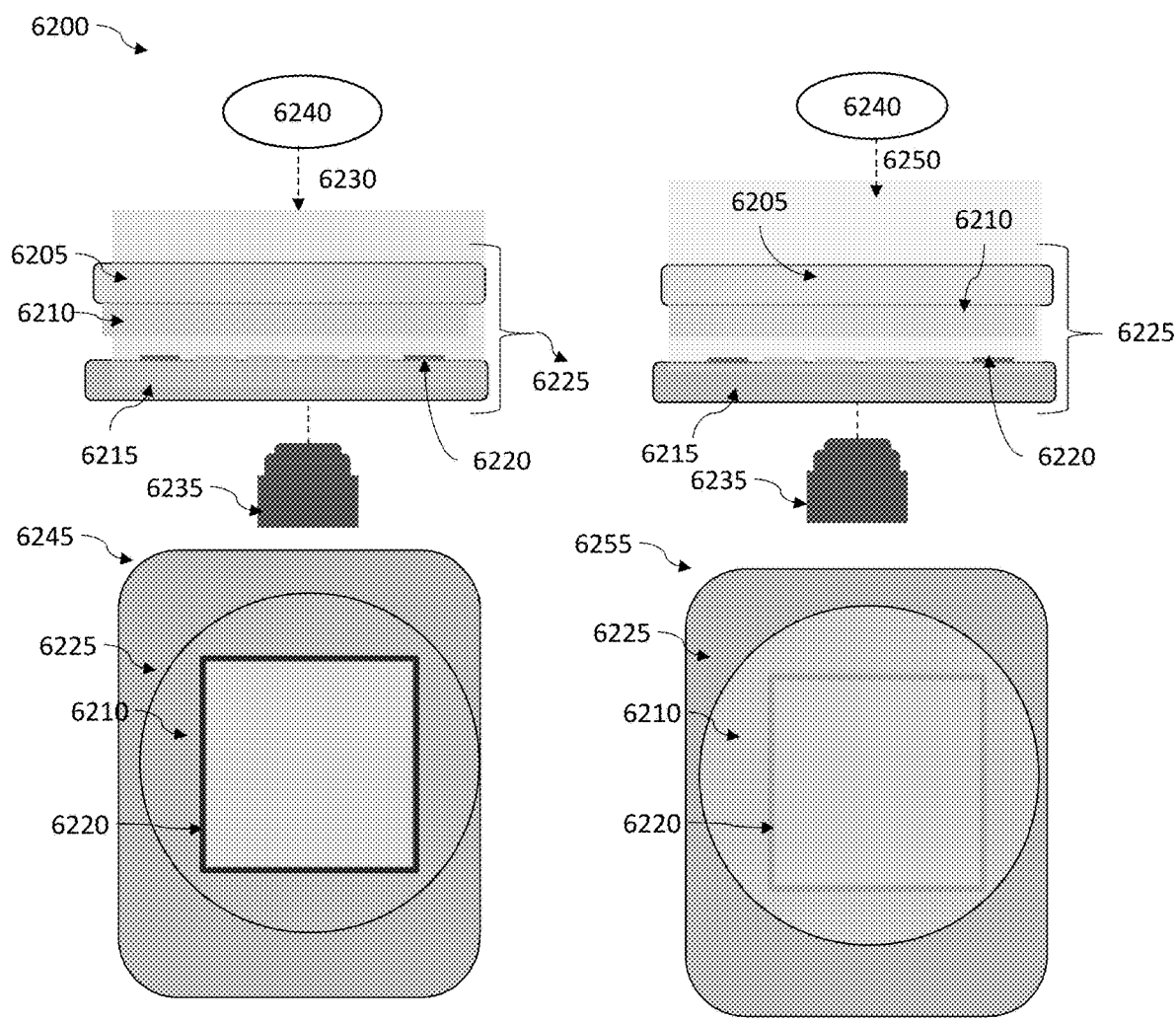
FIGS. 62A-62B depict a workflow for detecting array fiducials overlapped with a sample in image data acquired at different illuminations in accordance with some example implementations.

FIGS. 62A-62B depict a workflow 6200 for detecting array fiducials overlapped with a sample in image data acquired at different illuminations in accordance with some example implementations. The workflow 6200 can be performed with respect to embodiments of process 5900 described in relation to FIG. 59. The sample handling apparatus 400, 1400, and 3000 can be configured with a light source 6240 configured to provide light at one or more illumination setting during the image acquisition steps described in relation to the process 5900. Although the light source 6240 is shown oriented above the overlay 6225, a variety of non-limiting numbers, configurations, and orientations of the light source 6240 can be included in the sample handling apparatus 400, 1400, and 3000. For example, in some embodiments, the light source 6240 can be configured below the overlay 6225. The light source can emit colored RGB light in various wavelengths. In some embodiments, the light source and illumination settings can be associated with one or more wavelengths that are close to or match the absorbance wavelength of one or more dyes used to stain the sample, such as an eosin dye or a fluorescent dye. In some embodiments, the light source and illumination settings can be configured to improve array fiducial contrast and/or sample contrast. In some embodiments, the processor 5320 can select image data or filter the image data associated with one or more RGB channels of the light source 6240.

As shown in FIG. 62A, the light source 6240 can provide an illumination 6230 on to the overlay 6225. The illumination 6230 can correspond to a wavelength configured to improve a contrast of the array fiducials 6220. For example, an illumination between 550 nm and 1 μm can maximize contrast of the array fiducial relative to the contrast of an Eosin stained sample since the absorption band associated with the Eosin stain is 440 nm to ~550 nm. When the image 6245 is captured, the contrast of the array fiducial 6220 is improved with respect to the sample 6210 as shown in the image 6245 of the overlay 6225. For example, the illumination 6230 can include a red or an infrared (IR) illumination. As shown in FIG. 61B, the light source 6240 can provide an illumination 6250 on to the overlay 6225. The illumination 6250 can correspond to a wavelength configured to improve a contrast of the sample 6210 as shown in image 6255 of the overlay 6225. For example, the illumination 6250 can include a green illumination. In some embodiments, the illuminations 6230 and 6250 can include wavelengths between 500 nm and 1 mm. In some embodiments, the illuminations can include wavelengths between 500 nm and 530 nm, between 525 nm and 550 nm, between 540 and 570 nm, between 560 and 585 nm, between 580 nm and 700 nm, between 600 nm and 800 nm, between 700 nm and 1 mm, and between 850 nm and 1 μm. Image 6245 can be used directly for detection of the array fiducials 6220 or to aid detection of the array fiducials 6220 in image 6255. If there is no presumed shift in the sample substrate and the array substrate relative to each other or to one or more image capture device(s) 6235 between the capture of images at the different illuminations, the locations can be considered within the same coordinate system and the processor 5320 can perform the comparison to confirm such.

Figure 63A:
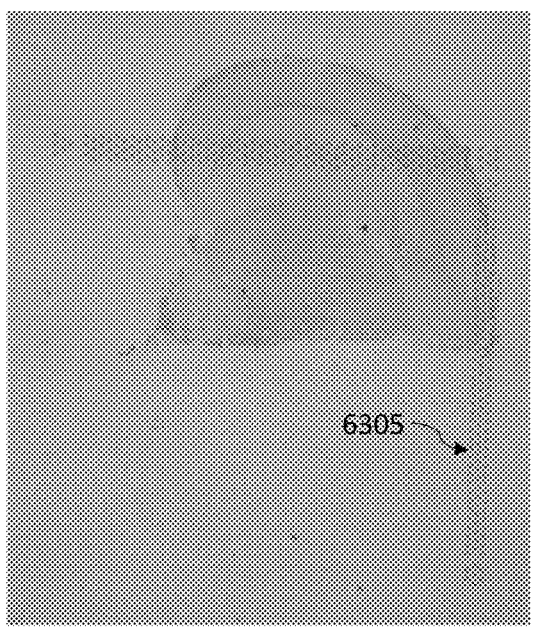
FIGS. 63A-63B are images illustrating image data acquired at different illuminations in accordance with some example implementations.
Figure 63B:
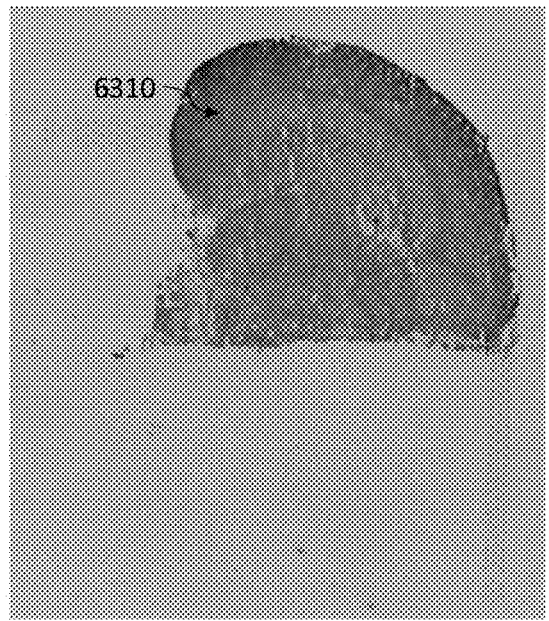

FIGS. 63A-63B are images illustrating image data acquired at different illuminations in accordance with some example implementations. As shown in FIG. 63A, an IR illumination can maximize contrast of the array fiducials 6305. As shown in FIG. 63B, a green illumination can maximize contrast of the sample of a tissue 6310.

Figure 64:
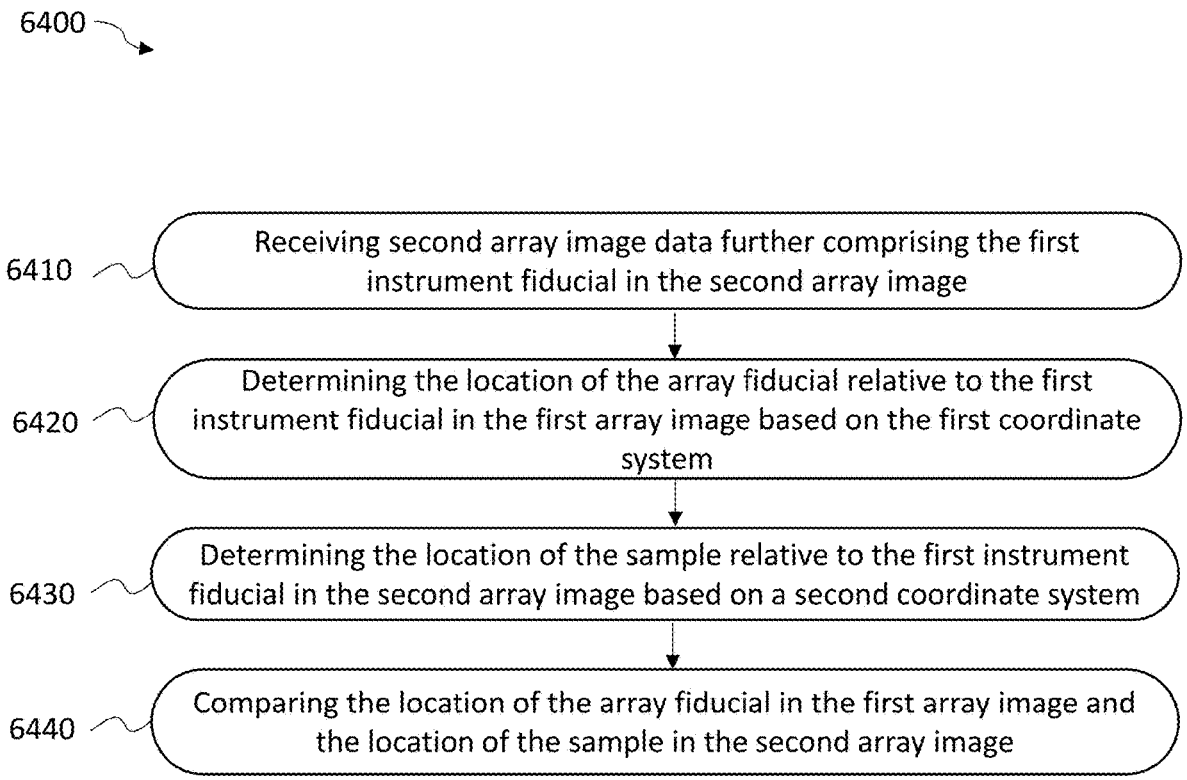
FIG. 64 is a process flow diagram illustrating an example process for detecting fiducials associated with an array using instrument fiducials provided in a sample handling apparatus in accordance with some example implementations.

FIG. 64 is a process flow diagram illustrating an example process 6400 for detecting fiducials associated with an array using instrument fiducials provided in a sample handling apparatus in accordance with some example implementations. The process 6400 can be performed with respect to embodiments described in relation to process 5900 of FIG. 59. The sample handling apparatus can include one or more instrument fiducials as described in relation to FIG. 41. The instrument fiducials can provide high contrast marks that are easily visible through samples of tissue. The array image data of the array image acquired in operation 5910 can further include an instrument fiducial configured on the sample handling apparatus. In this way, the location of the instrument fiducials relative to the array fiducials can be determined.

In operation 6410, the processor 5320 can receive array image data, such as in operation 5920, including an instrument fiducial in the image with the overlay of the sample, the array, and the array fiducial. The sample can obscure the array fiducial and the instrument fiducial in the overlay. In this way, the location of the instrument fiducials to the sample location can be determined. The array fiducials may not be easily visible if they are covered by the sample.

In operation 6420, the processor 5320 can determine the location of the array fiducial relative to the instrument fiducial in the array image data captured in operation 5910 and now including the instrument fiducial based on the coordinate system used in operation 5910.

In operation 6430, the processor 5320 can determine the location of the sample relative to the instrument fiducial captured in the array image data acquired in operation 5910. The location of the sample relative to the instrument fiducial can be determined using the array image data acquired in operation 6410. The location of the sample relative to the instrument fiducial can be determined using a second, or alternate coordinate system that is different than the coordinate system used to determine the location of the array fiducials relative to the instrument fiducials in operation 6420.

In operation 6440, the processor 5320 can compare the location of the array fiducial in the array image acquired in operation 5910 and further including the instrument fiducial with the location of the sample in the array image acquired in operation 6410. Since the location of the array fiducials are known relative to the location of the sample, and the location of the instrument fiducials are known relative to the location of the array fiducial, the location of the sample to the array fiducial can be determined based on the differences between the locations in the two coordinate systems.

Figure 65B:
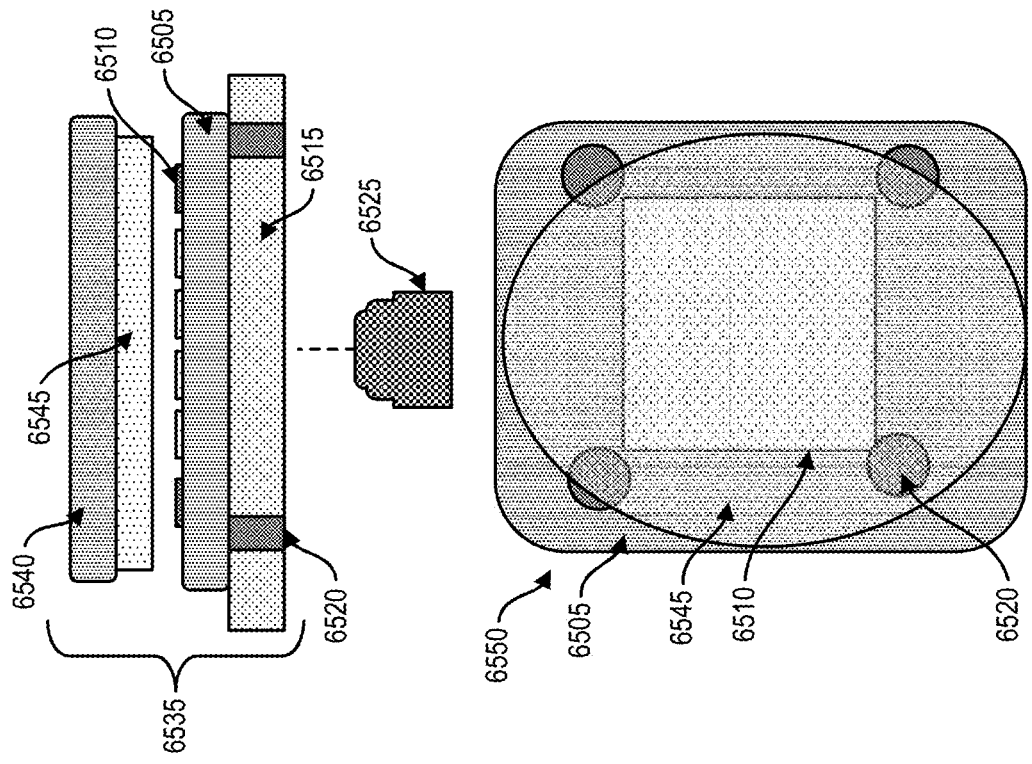
FIGS. 65A-65B depict a workflow for detecting array fiducials overlapped with a sample in image data including instrument fiducials provided in a sample handling apparatus in accordance with some example implementations.
Figure 65A:
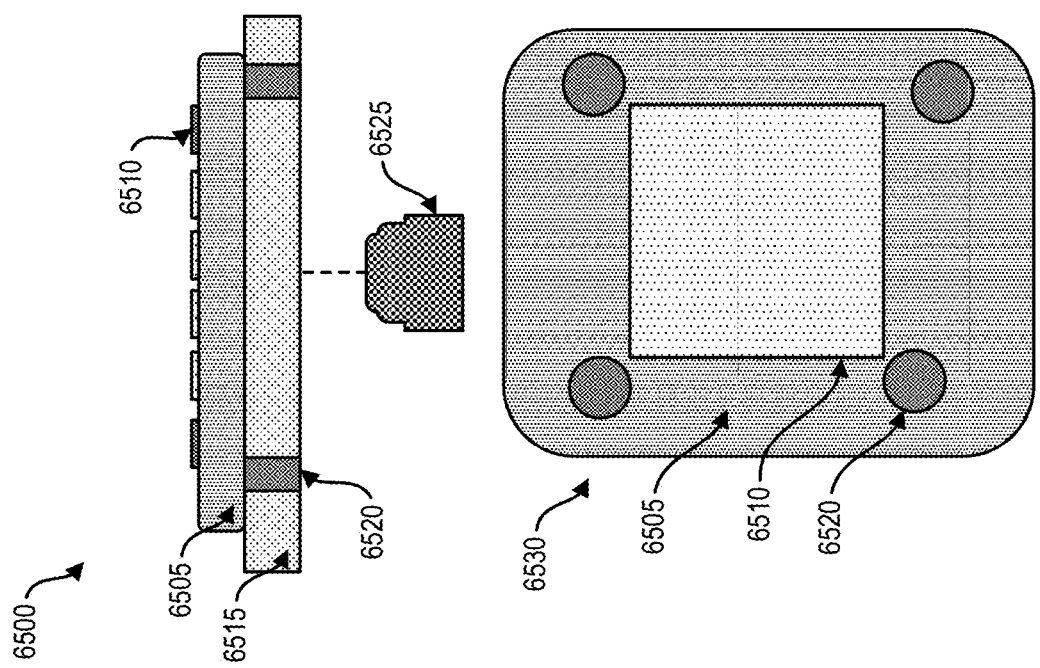

FIGS. 65A-65B depict a workflow 6500 for detecting array fiducials overlapped with a sample in image data including instrument fiducials provided in a sample handling apparatus in accordance with some example implementations. The workflow 6500 can be performed with respect to embodiments described in relation to process 5900 of FIG. 59. As shown in FIG. 65A, an array substrate 6505 including an array fiducial 6510 can be positioned in or on a holding member 6515 (corresponding to member 410). The holding member 6515 can include one more instrument fiducials 6520. Image capture device 6525 can acquire image 6530 including image data of the array fiducial 6510 and the instrument fiducial 6520. As shown in FIG. 65B, the image capture device 6525 can further acquire image data including image 6550 of the overlay 6535 including the sample 6545 overlaid with the array fiducial 6510 and the instrument fiducial 6520. The array fiducials 6510 can be obscured or covered by the sample 6545, however the location of the array fiducials 6510 can be determined using the instrument fiducials 6520 due to the high contrast and visibility of the instrument fiducials 6520 relative to the sample 6545.

Figure 66:
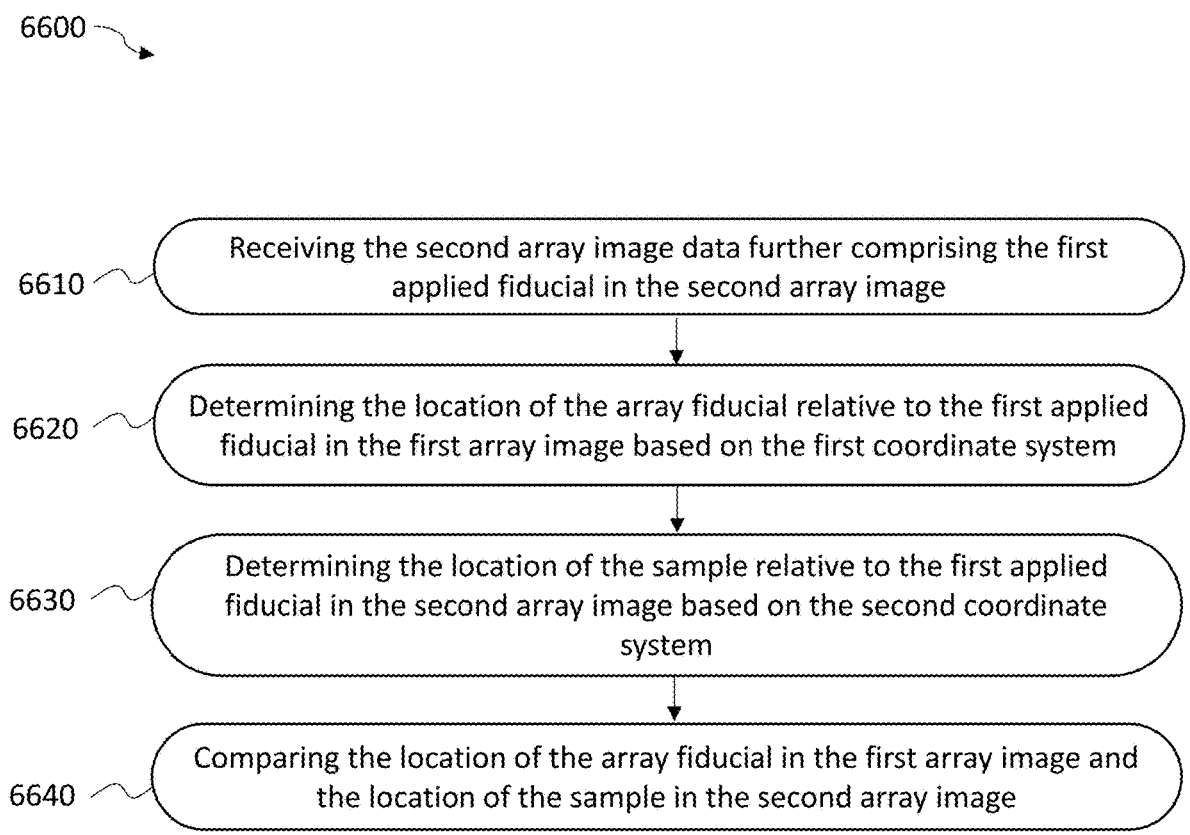
FIG. 66 is a process flow diagram illustrating an example process for detecting fiducials applied to a substrate on which an array is located in accordance with some example implementations.

FIG. 66 is a process flow diagram illustrating an example process 6600 for detecting fiducials applied to a substrate on which an array is located in accordance with some example implementations. The process 6600 can be performed with respect to embodiments described in relation to process 5900 of FIG. 59.

In some embodiments, applied fiducials can include a stamp, a sticker, a spacer, a drawing, printed spots, or a laser etching applied to and located on a substrate on which the array and the array fiducial can be located. Spacers can be applied to an array substrate to provide flow control of a permeabilization reagent used during the permeabilization processes described herein. The spacers can provide an amount of separation between an array substrate and a sample substrate such that when the array substrate and sample substrate are brought into contact, the spacer can function to maintain the amount of separation between the two substrates. The spacers can include high contrast materials that can be visible when covered or obscured by a sample of tissue. For example, in some embodiments, the spacers can include a graphite material formed from a graphite sheet. Graphite is a dark material and can provide a high contrast spacer without requiring additional high contrast finishes be applied to the spacer. In some embodiments, the spacers can include a high contrast finish applied to a spacer material. For example, a dark black finish can be applied to a transparent polyester material to create a high contrast spacer. The spacers can be fixed to the array substrate to prevent movement relative to the array substrate during the formation of the overlay formed by closing the substrate holding member 404 onto the substrate holding member 410. In some embodiments, the spacers can be opaque.

In some embodiments, applied fiducials can be formed from a material including a dye, a chemical, a contrast agent, or a nanoparticle. The applied fiducials can be configured to improve the contrast of the fiducial when obscured by a sample of tissue during imaging so that they are more readily visible to the human eye or to an image capture device when illuminated at specific wavelengths. For example, gold nanoparticles of different sizes and shapes can be used to provide different contrasts at different wavelengths. The array image data of the array image acquired in operation 5910 can further include an applied fiducial applied to the substrate on which the array and array fiducial are located. In this way, the location of the applied fiducials relative to the array fiducials can be determined.

In operation 6610, the processor 5320 can receive image data, such as in operation 5920, that further includes an applied fiducial that has been applied to the substrate on which the array and array fiducial are located. In this way, the location of the applied fiducials relative to the array fiducials can be determined. The array fiducials may not be easily visible if they are covered by the sample.

In operation 6620, the processor 5320 can determine the location of the array fiducial relative to the applied fiducial in the array image data captured in operation 5910 and now including the applied fiducial based on the coordinate system used in operation 5910.

In operation 6630, the processor 5320 can determine the location of the sample relative to the applied fiducial captured in the array image data acquired in operation 5910. The location of the sample relative to the applied fiducial can be determined using the array image data acquired in operation 6610. The location of the sample relative to the applied fiducial can be determined using a second, or alternate coordinate system that is different than the coordinate system used to determine the location of the array fiducials relative to the applied fiducials in operation 6620.

In operation 6640, the processor 5320 can compare the location of the array fiducial in the array image acquired in operation 5910 and further including the applied fiducial with the location of the sample in the array image acquired in operation 6610. Since the location of the array fiducials are known relative to the location of the sample, and the location of the applied fiducials are known relative to the location of the array fiducial, the location of the sample to the array fiducial can be determined based on the differences between the locations in the two coordinate systems.

Figure 67B:
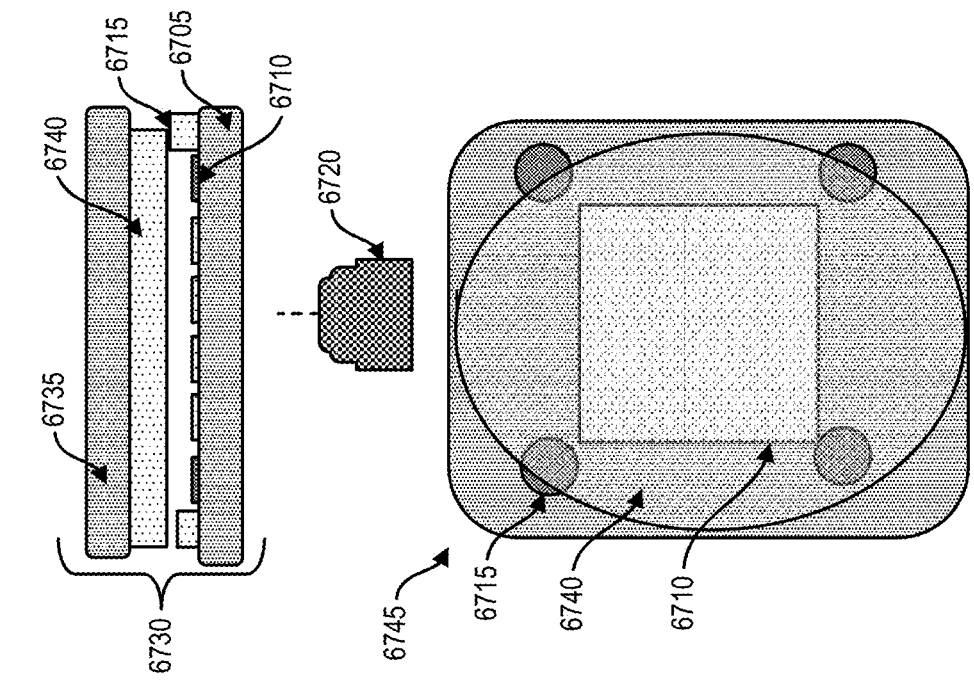
FIGS. 67A-67B depict a workflow for detecting array fiducials overlapped with a sample in image data including fiducials applied to a substrate on which an array is located in accordance with some example implementations.
Figure 67A:
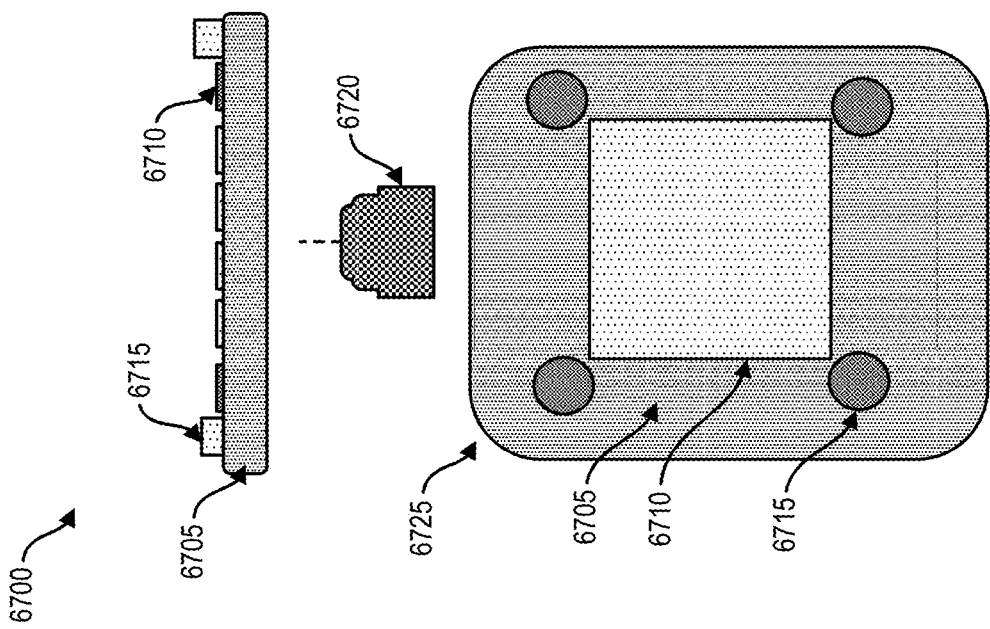

FIGS. 67A-67B depict a workflow 6700 for detecting array fiducials overlapped with a sample in image data including fiducials applied to a substrate on which an array is located in accordance with some example implementations. The workflow 6700 can be performed with respect to embodiments described in process 5900 of FIG. 59 and process 6600 of FIG. 66. As shown in FIG. 67A, image capture device 6720 (corresponding to image capture device 1720) can acquire image data including an image 6725. The image 6725 can include an array substrate 6705, an array fiducial 6710, and an applied fiducial 6715 that has been applied to the array substrate 6705. The image 6725 can be used to determine the position of the applied fiducials 6715 relative to the array fiducials 6710. In some embodiments, the applied fiducials 6715

As shown in FIG. 67B, image capture device 6720 can acquire image data of an image data including image 6745. The image 6745 can include an overlay 6730 of the sample 6740, the array fiducial 6710, and the applied fiducial 6715. The image 6745 can used to determine the location of the sample 6740 relative to the array fiducial 6710 since the location of the applied fiducial 6715 relative to the location of the sample 6740 is known and the location of the applied fiducial 6716 relative to the array fiducial 6710 is also known.

Figure 68B:
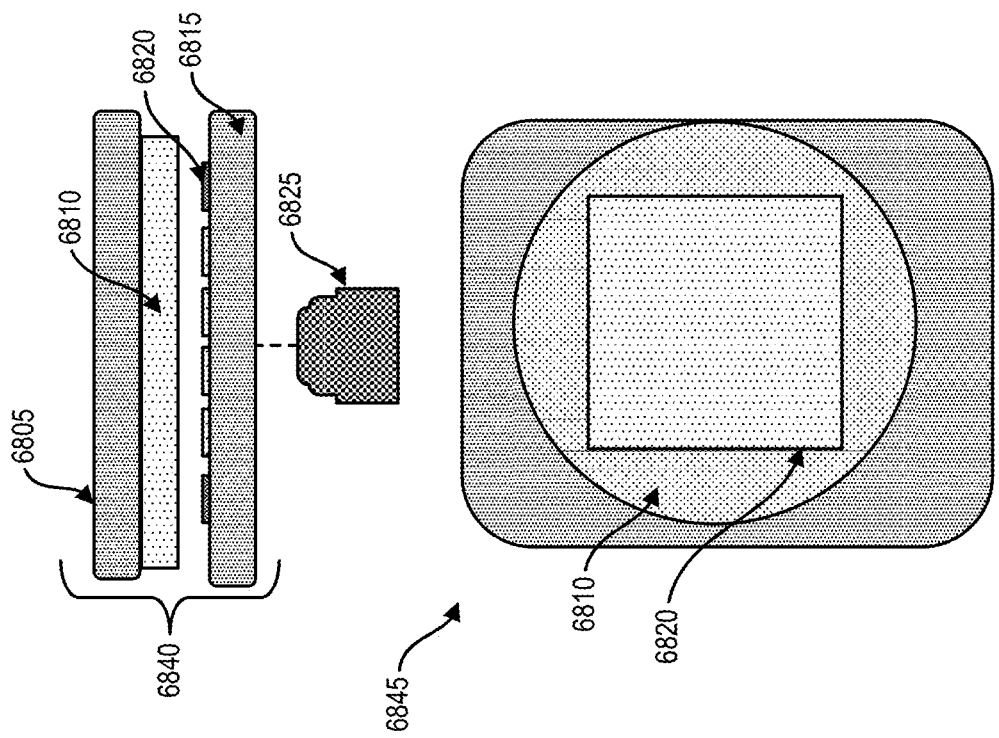
FIGS. 68A-68B depict a workflow for detecting array fiducials overlapped with a sample in image data acquired in relation to a permeabilization of the sample in accordance with some example implementations.
Figure 68A:
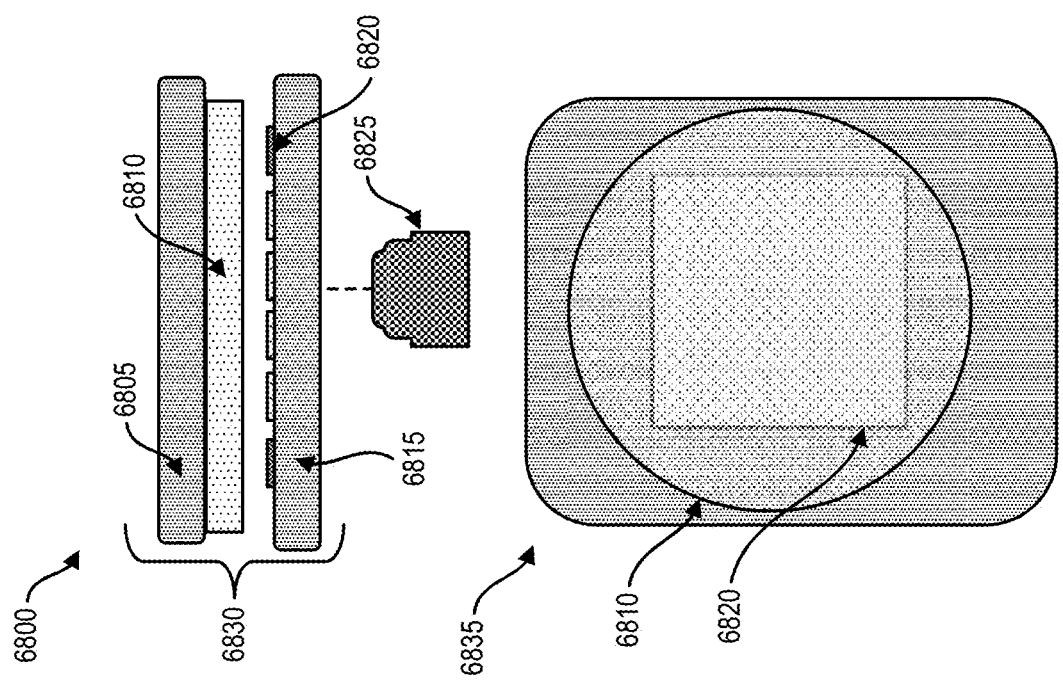

FIGS. 68A-68B depict a workflow 6800 for detecting array fiducials overlapped with a sample in image data acquired in relation to permeabilization of the sample in accordance with some example implementations. The workflow 6800 can be performed with respect to embodiments described in process 5900 of FIG. 59. Permeabilization of the sample using the sample handling apparatus described herein can be performed in accordance with the descriptions provided in relation to FIG. 3, FIGS. 29A-29C, and FIGS. 31A-31C. As shown in FIG. 68A, the image capture device 6825 (corresponding to image capture device 1720) can acquire image data of the overlay 6830 prior to the start or near the beginning of sample permeabilization when the overlay 6830 has been initially formed by closing the substrate holding member 404 onto the substrate holding member 410. The image 6835 can include the sample 6810 at high contrast obscuring the array fiducials 6820.

As shown in FIG. 68B, the image capture device 6825 can acquire image data including image 6845. Image 6845 can be acquired after a period of permeabilization of the sample 6810 has occurred in the overlay 6840. The period of permeabilization can cause the sample to be digested, which can result in the array fiducial 6820 becoming more visible at greater contrast in the image 6845.

Figure 69:
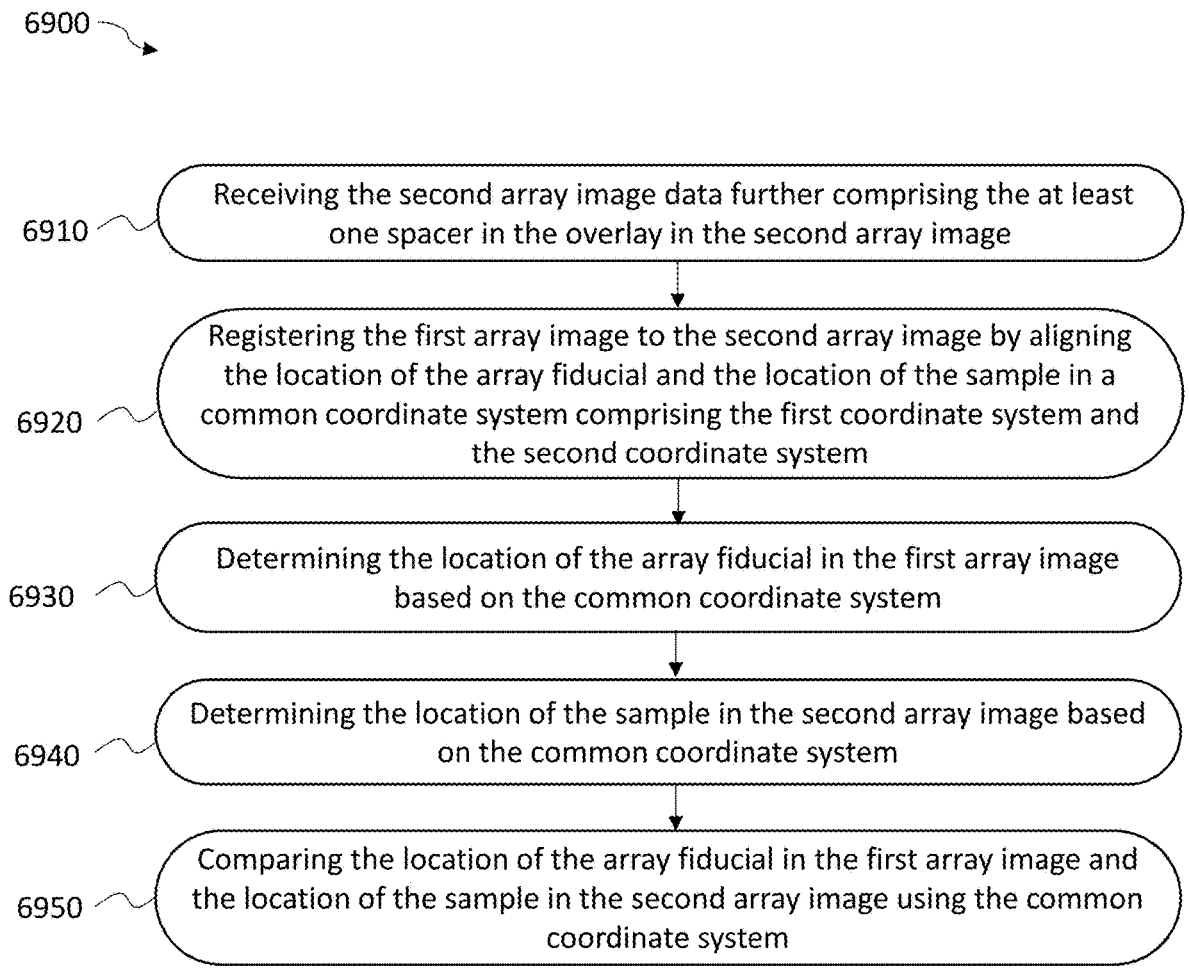
FIG. 69 is a process flow diagram illustrating an example process for detecting fiducials using image registration of sample image data and array image data acquired in a sample handling apparatus including spacers configured on an array substrate in accordance with some example implementations.

FIG. 69 is a process flow diagram illustrating an example process 6900 for detecting fiducials using image registration of sample image data and array image data acquired in a sample handling apparatus including spacers configured on an array substrate in accordance with some example implementations, such as those described in relation to FIG. 65. The process 6900 can be performed in relation to embodiments described in process 5900 of FIG. 59, process 6600 of FIG. 66, and workflow 6600 of FIGS. 66A-66B. Image registration methods and techniques can be performed in regard to the descriptions provided herein in Section IV: Image Registration Devices and Methods.

As shown in FIG. 69, in operation 6910 the processor 5320 can receive array image data acquired via the image capture device 1720 and including an image of the array fiducial as acquired in operation 5910, described in relation to FIG. 59, and further including at least one spacer. A variety of non-limiting numbers, shapes, and arrangements of spacers can be included on the array substrate and thus, in the array image data.

In operation 6920, the processor 5320 can perform image registration as described in relation to FIG. 53 to register the image acquired in operation 5910, described in relation to FIG. 59, to the image acquired in operation 6910 by aligning the location of the array fiducial and the location of the sample in a common coordinate system including the coordinate system applied by the processor 5320 to the image acquired in operation 5910 described in relation to FIG. 59 and the second coordinate system applied by the processor 5320 to the image acquired in operation 6910.

In operation 6930, the processor 5320 can determine the location of the array fiducial in the image acquired in operation 5910, described in relation to FIG. 59, based on the common coordinate system. In operation 6940, the processor 5320 can determine the location of the sample in the image acquired in operation 5910, described in relation to FIG. 59, based on the common coordinate system. In operation 6950, the processor 5320 can compare the location of the array fiducial in the image acquired in operation 5910 and the location of the sample in the image acquired in operation 6910 using the common coordinate system. Operations 6930-6950 can be performed as described in relation to operations 5930-5950 corresponding to the description of FIG. 59, except as noted otherwise herein.

Figure 70B:
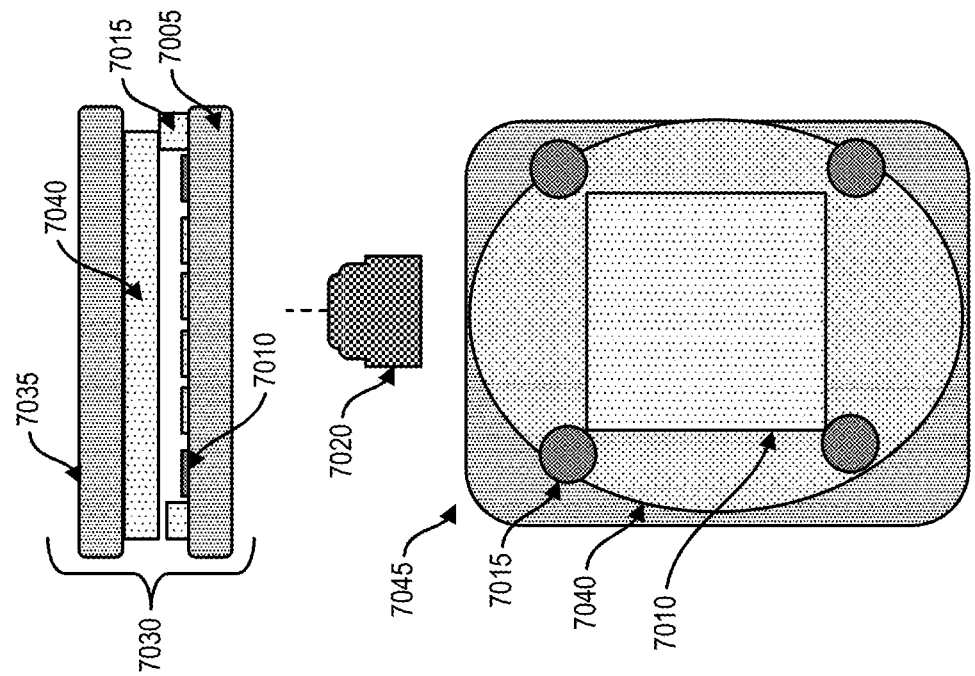
FIGS. 70A-70B depict a workflow for detecting array fiducials overlapped with a sample in image data acquired and registered using a sample handling apparatus including spacers in accordance with some example implementations.
Figure 70A:
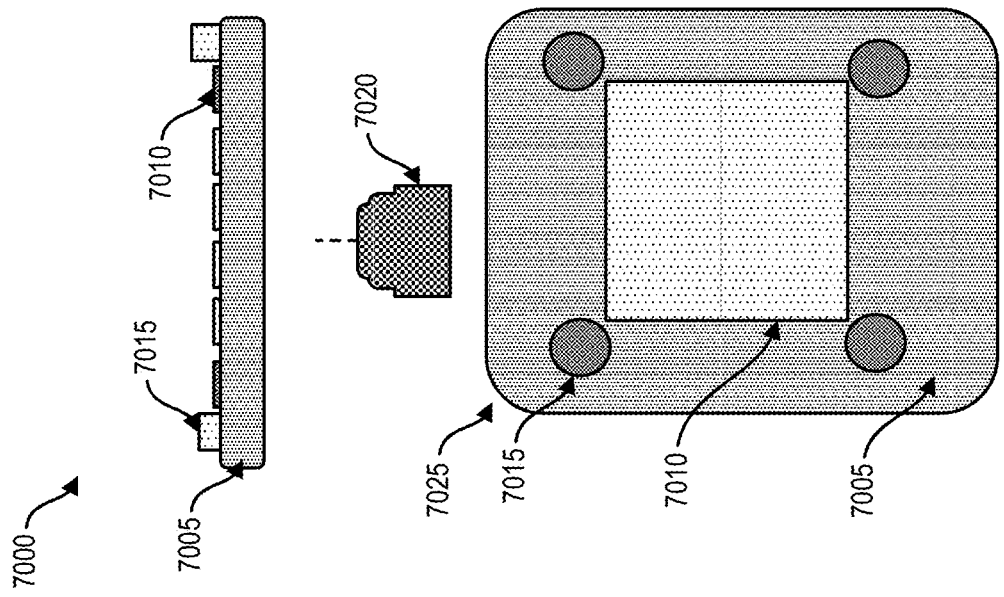

FIGS. 70A-70B depict a workflow 7000 for detecting array fiducials overlapped with a sample in image data acquired and registered using a sample handling apparatus including spacers in accordance with some example implementations. The workflow 7000 can be performed with respect to embodiments described in process 5900 described in relation to FIG. 59 and process 6900 described in relation to FIG. 69. As shown in FIG. 70A, the image capture device 7020 (corresponding to image capture device 1720) can acquire image data including an image 7025. The image 7025 can include the spacer 7015 in addition to the array fiducial 7010. The spacer 7015 can have a high contrast and can be visible when covered by the sample 7040.

As shown in FIG. 70B, the image capture device 7020 can acquire image data including an image 7045 of the overlay 7030. The image 7045 can include the spacer 7015 visible through the sample 7040 obscuring the array fiducials 7010. In this way, the processor 5320 can perform image registration between the image 7025 and the image 7045 to determine the location of the location of the array fiducial in image 7025 and the location of the sample in image 7045 in order to compare the location of the array fiducial 7010 and the location of the sample in image 7045 as described in relation to operations 6930-6950.

Figure 71:
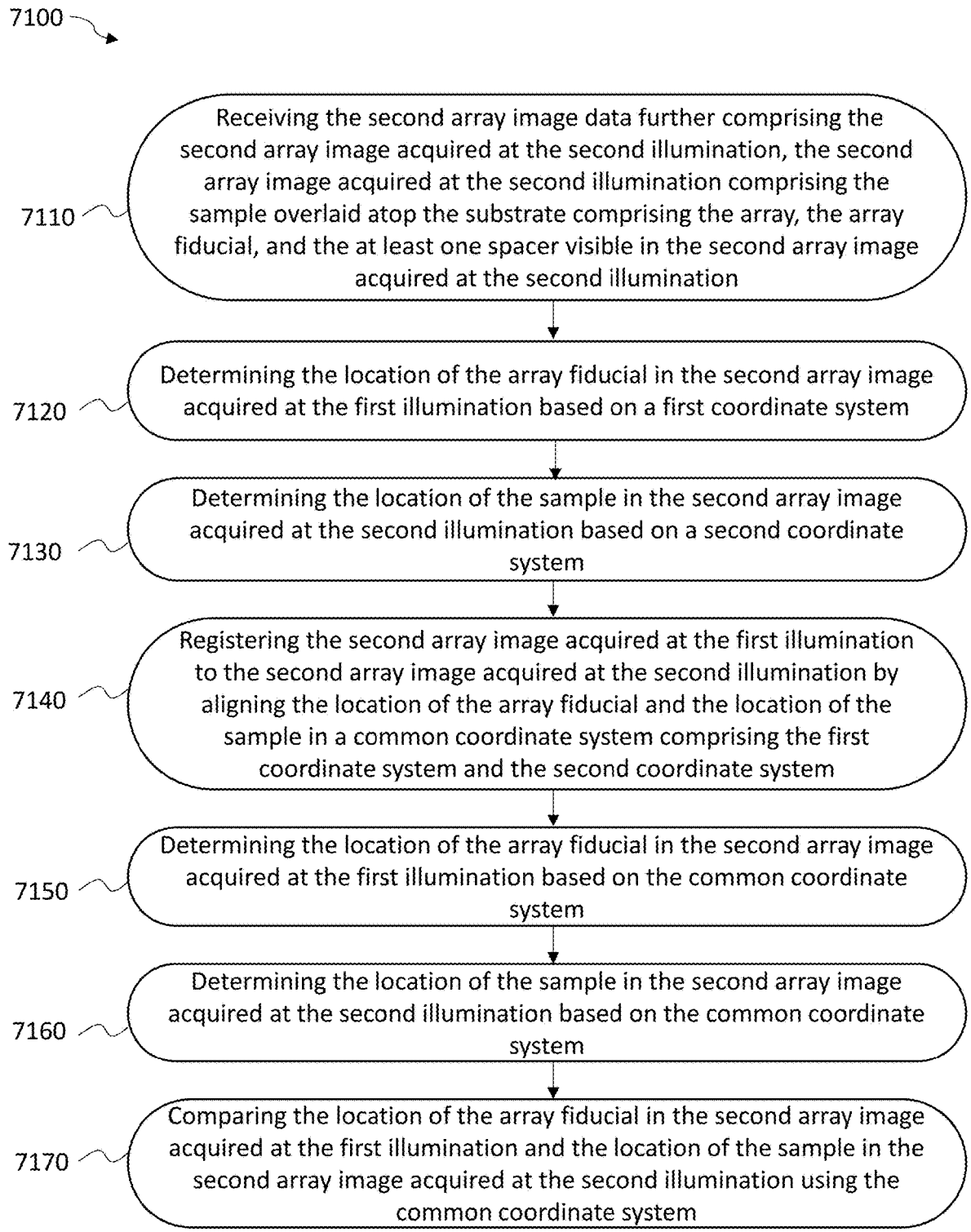
FIG. 71 is a process flow diagram illustrating an example process for detecting fiducials using image registration of sample image data and array image data acquired at multiple illuminations in a sample handling apparatus including spacers in accordance with some example implementations.

FIG. 71 is a process flow diagram illustrating an example process 7100 for detecting fiducials overlapped with a sample using image registration of sample image data and array image data acquired at multiple illuminations in a sample handling apparatus including spacers in accordance with some example implementations. The process 7100 can be performed with respect to embodiments described in process 5900 described in relation to FIG. 59, workflow 6200 described in relation to FIGS. 62A-62B, process 6600 described in relation to FIG. 66, and workflow 6700 described in relation to FIGS. 67A-67B. The process 7100 can be performed to confirm that sample location and fiducial locations remain unchanged when illumination conditions have changed. Performing image registration with respect to the spacer locations can help confirm the sample location and the fiducial location have not changed. If spacer positions have changed, image registration can be used to determine the location of the sample and the location of the fiducial in the received image data.

As shown in FIG. 71, in operation 7110 processor 5320 can receive the array image data acquired at a first illumination and received in operation 5920. The array image acquired at the first illumination and received in operation 5920 can include the sample overlaid atop a substrate including an array, an array fiducial, and at least a portion of a spacer visible in the array image acquired at the first illumination. The processor 5320 can further receive additional or subsequent array image data including an array image acquired at a second illumination and including the sample overlaid atop the substrate including the array, the array fiducial, and the spacer. In some embodiments, the spacers in the first array image and the second array image can be opaque. The spacer can be visible in the array image acquired at the second illumination due to its contrast properties. The comparison of the array image data of array images acquired at the first and the second illuminations can be used to determine locations of an array fiducial and a sample using a common coordinate system.

In some embodiments, the first and/or the second illumination can be selected to increase or decrease an amount of contrast between the sample and the array fiducial. For example, a first illumination can enhance the contrast of the sample compared to the contrast of the array fiducial. A second illumination can enhance the contrast of the array fiducial compared to the contrast of the sample. The illuminations can be also selected based on the illumination properties or characteristics described in relation to FIGS. 62A-62B and FIGS. 63A-63B herein.

In operation 7120, the processor 5320 can determine the location of the array fiducial in the array image acquired at the first illumination and received in operation 5920 and including the spacer visible in the array image acquired at the first illumination. The location of the array fiducial can be determined in the array image acquired at the first illumination based on a first coordinate system. In operation 7130, the processor can determine the location of the sample in the array image acquired at the second illumination and received in operation 7110 based on a second coordinate system. In some embodiments where there was no shift in the sample substrate, the spacer (or portion thereof) and the array substrate relative to each other or to one or more image capture device(s) between image capture at the first and second illuminations, the second coordinate system can be the same as the first coordinate system, e.g., can be a common coordinate system. In other words, the locations can be considered within the same coordinate system and the processor 5320 can perform the comparison to confirm such.

In some embodiments where a shift occurred in, e.g., the spacer or portion thereof relative to the image capture device(s) between image capture at the first and second illuminations, image registration may be performed to transform the second coordinate system to the first coordinate system. Alternatively, in some embodiments where a shift occurred in, e.g., the spacer or portion thereof relative to the image capture device(s) between image capture at the first and second illuminations, image registration may be performed to transform the first coordinate system to the second coordinate system. Alternatively, in some embodiments where a shift occurred in, e.g., the spacer or portion thereof relative to the image capture device(s) between image capture at the first and second illuminations, image registration may be performed to transform the first and second coordinate systems to a common coordinate system.

In operation 7140, the processor 5320 can register the array image acquired at the first illumination in operation 5920 including the spacer to the array image acquired at the second illumination and received in operation 7110 by aligning the location of the array fiducial and the location of the sample in the common coordinate system. The common coordinate system can include the first coordinate system and the second coordinate system and can also include the location of the array fiducial and the location of the sample. Alignment methods and techniques can be performed in regard to the descriptions provided herein in Section III: Sample and Array Alignment Devices and Methods. Image registration methods and techniques can be performed in regard to the descriptions provided herein in Section IV: Image Registration Devices and Methods.

In some embodiments, such as when there was no shift in the sample substrate, the spacer (or portion thereof) and the array substrate relative to each other or to one or more image capture device(s) between image capture at the first and second illuminations, and the second coordinate system can be the same as the first coordinate system, e.g., can be a common coordinate system, the operation 7140 can be optionally omitted as no image registration is needed. In other words, the first coordinate system and the second coordinate system can be considered as the same coordinate system because there is no change in the location of the array fiducial and/or the sample.

In operation 7150, the processor 5320 can determine the location of the array fiducial in the array image acquired at the first illumination and received in operation 5920 including the spacer based on the common coordinate system. In operation 7160, the processor 5320 can determine the location of the sample in the array image acquired at the second illumination and received in operation 7110 based on the common coordinate system. In operation 7170, the processor 5320 can compare the location of the array fiducial in the array image acquired at the first illumination and received in operation 5920 including the spacer and the location of the sample in the array image acquired at the second illumination and received in operation 7110 using the common coordinate system. In this way, the location of the array fiducials relative to the location of the sample can be provided.

In some embodiments, the operations of process 6900 described in relation to FIG. 69 and the operations of process 7100 described in relation to FIG. 71 can be combined.

FIGS. 72A-72B depict a workflow 7200 for detecting array fiducials overlapped with a sample in image data acquired and registered at multiple illuminations using a sample handling apparatus including spacers in accordance with some example implementations. The workflow 7200 can be performed with respect to embodiments of process 5900 described in relation to FIG. 59, embodiments of workflow 6200 described in relation to FIG. 62, and embodiments of process 7100 described in relation to FIG. 71.

As shown in FIG. 72A, the image capture device 7235 (corresponding to image capture device 1720) can acquire image data including image 7250. Image 7250 can include an overlay 7230 of the sample 7210, the array fiducial 7220, and the spacer 7225. The image 7250 can be illuminated by light source 7240 providing an illumination 7245. For example, illumination 7245 can include a red or an infrared (IR) wavelength to maximize the contrast of the array fiducials 7220. For example, an illumination between 550 nm and 1 μm can maximize contrast of the array fiducial relative to the contrast of an Eosin stained sample since the absorption band associated with the Eosin stain is 440 nm to ~550 nm. The high contrast spacer 7220 can also be visible in the image 7250.

As shown in FIG. 72B, the image capture device can acquire image data including image 7265. Image 7265 can include an overlay of the sample 7210, the array fiducial 7220, and the spacer 7225. The image 7265 can be illuminated by light source 7240 providing illumination 7260. For example, illumination 7260 can include a green wavelength to maximize contrast of the sample 7210. In some embodiments, more than one light source 7240 can be configured in the sample handling apparatus 400, 1400, and 3000. In the image 7265, the spacer 7225 and the sample 7210 are visible, while the array fiducials 7220 are not visible when covered by the sample 7210. In some embodiments, the illuminations 7245 and 7260 can include wavelengths between 500 nm and 1 mm. In some embodiments, the illuminations can include wavelengths between 500 nm and 530 nm, between 525 nm and 550 nm, between 540 and 570 nm, between 560 and 585 nm, between 580 nm and 700 nm, between 600 nm and 800 nm, between 700 nm and 1 mm, and between 850 nm and 1 μm.

Figure 73A:
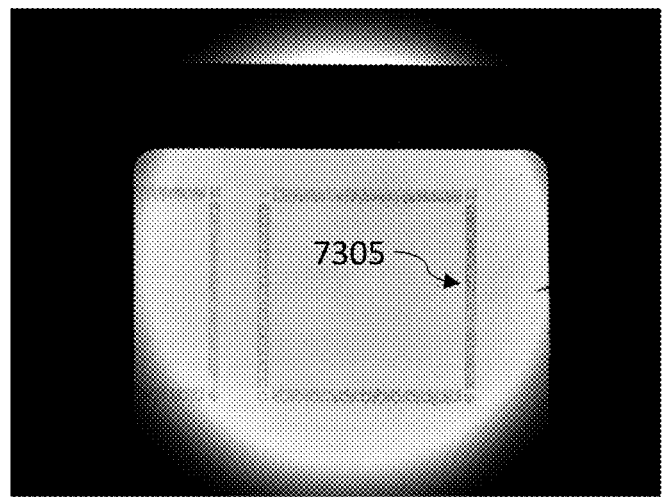
FIGS. 73A-73C are images illustrating embodiments of image data acquired at different illuminations by a sample handling apparatus for use in image registration processes and techniques according to some example implementations.
Figure 73B:
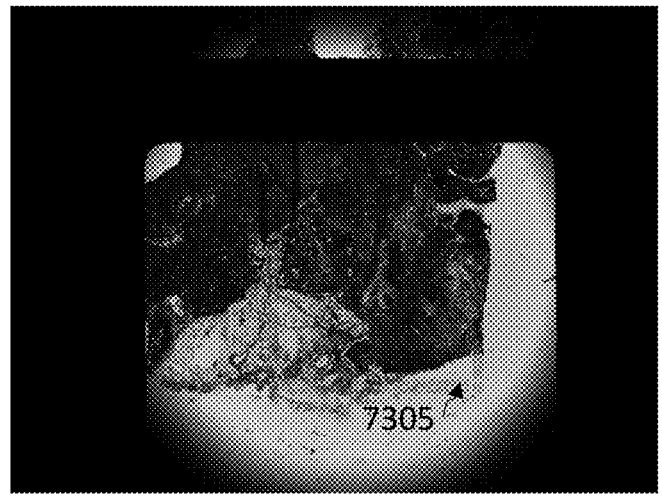
Figure 73C:
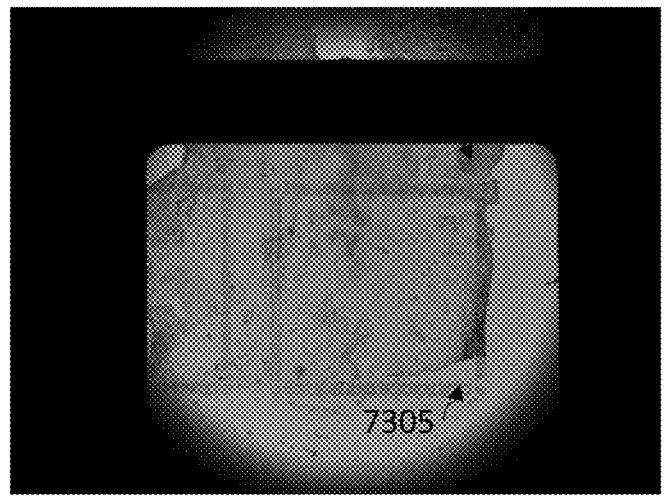

FIGS. 73A-73C are images illustrating embodiments of image data acquired at different illuminations by the sample handling apparatus 400, 1400, and 300 for use in image registration processes and techniques described in relation to embodiments described in FIGS. 62A-62B and FIGS. 72A-72B in accordance with some example implementations. As shown in FIG. 73A, an image can be acquired including an array fiducial 7305. In FIG. 73B, an image can be acquired at a green illumination to maximize a contrast between the sample 7310 and the array fiducial 7305. In FIG. 73C, an image can be acquired at a red or infrared (IR) illumination to maximize a contrast of the array fiducials 7305.

Figure 74A:
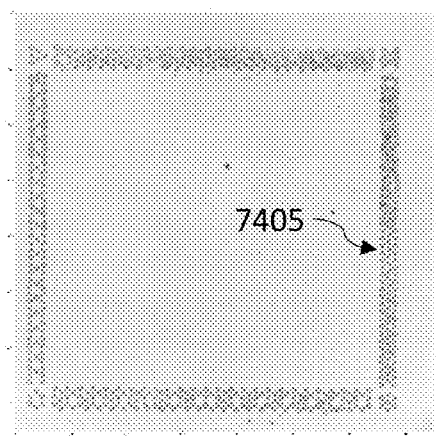
FIGS. 74A-74C are images illustrating additional embodiments of image data acquired at different illuminations by a sample handling apparatus for use in image registration processes and techniques according to some example implementations.
Figure 74B:
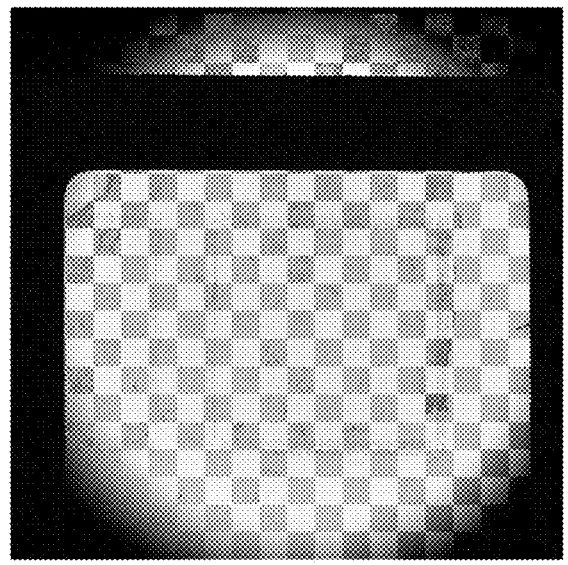
Figure 74C:
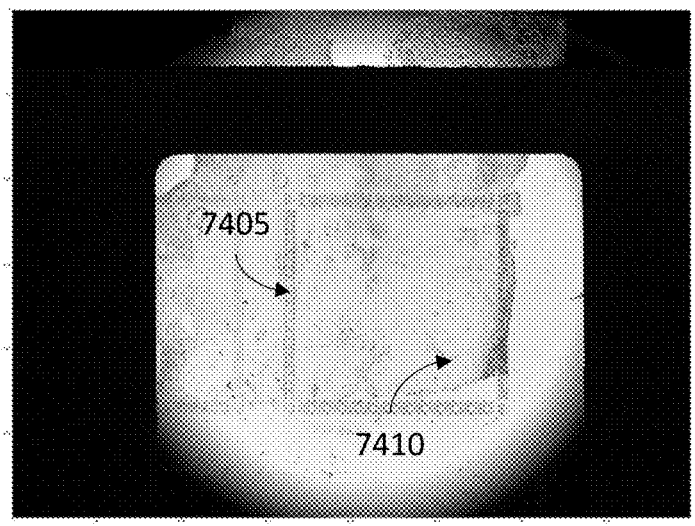

FIGS. 74A-74B are images illustrating additional embodiments of image data acquired at different illuminations by the sample handling apparatus 400, 1400, and 300 for use in image registration processes and techniques described in relation to embodiments described in FIGS. 62A-62B and FIGS. 72A-72B in accordance with some example implementations. As shown in FIG. 74A, array fiducials can be detected in an image where the array fiducials 7405 are visible within the image. In FIG. 74B, image registration can be performed on image data including images that contain a spacer. In FIG. 74C, a frame of array fiducials 7405 can be superimposed over a sample 7410.

In some embodiments, detected array fiducial locations in acquired image data can be registered with locations of array fiducials identified in a data file, such as a .gpr file. Based on the image registration, a registration error can be assigned for each array fiducial. In some embodiments, detected array fiducial locations in acquired low resolution image data can be registered with detected array fiducial locations in acquired high resolutions image data. Based on the image registration, a registration error can be assigned for each array fiducial. Monochromatic illuminations can be used for acquired image data without contributing to registration errors.

Figure 75A:
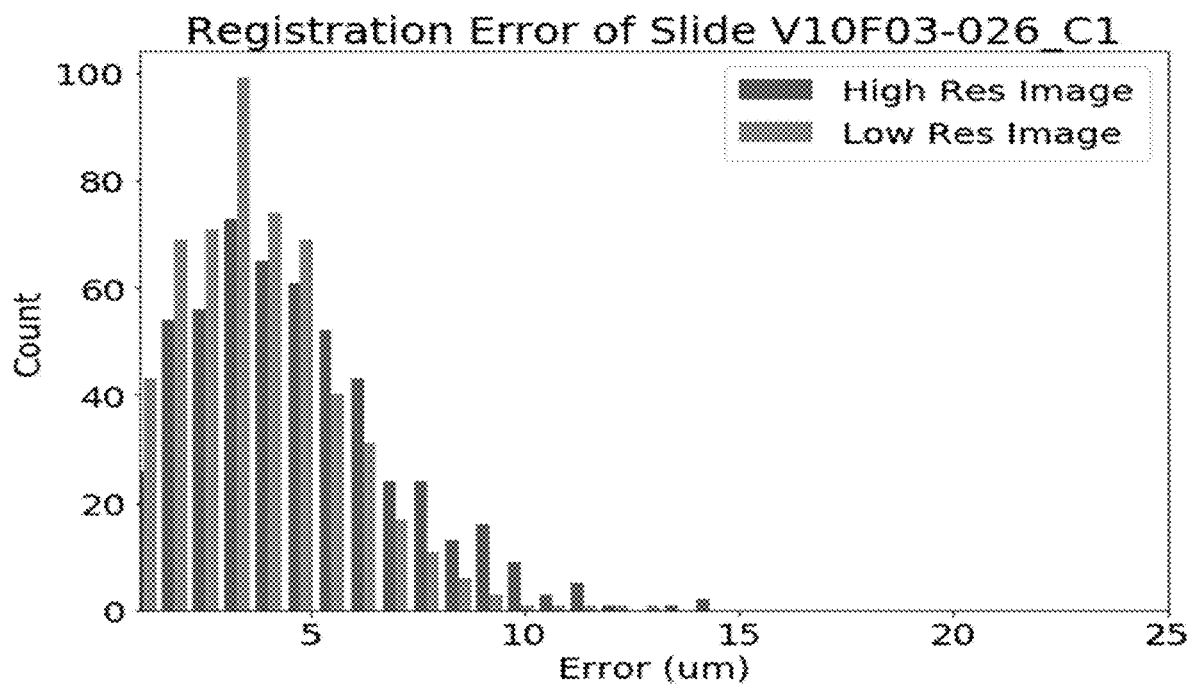
FIGS. 75A-75D are plots illustrating example data associated with registration and position errors used in verifying the image registration processes and techniques described herein according to some example implementations.
Figure 75B:
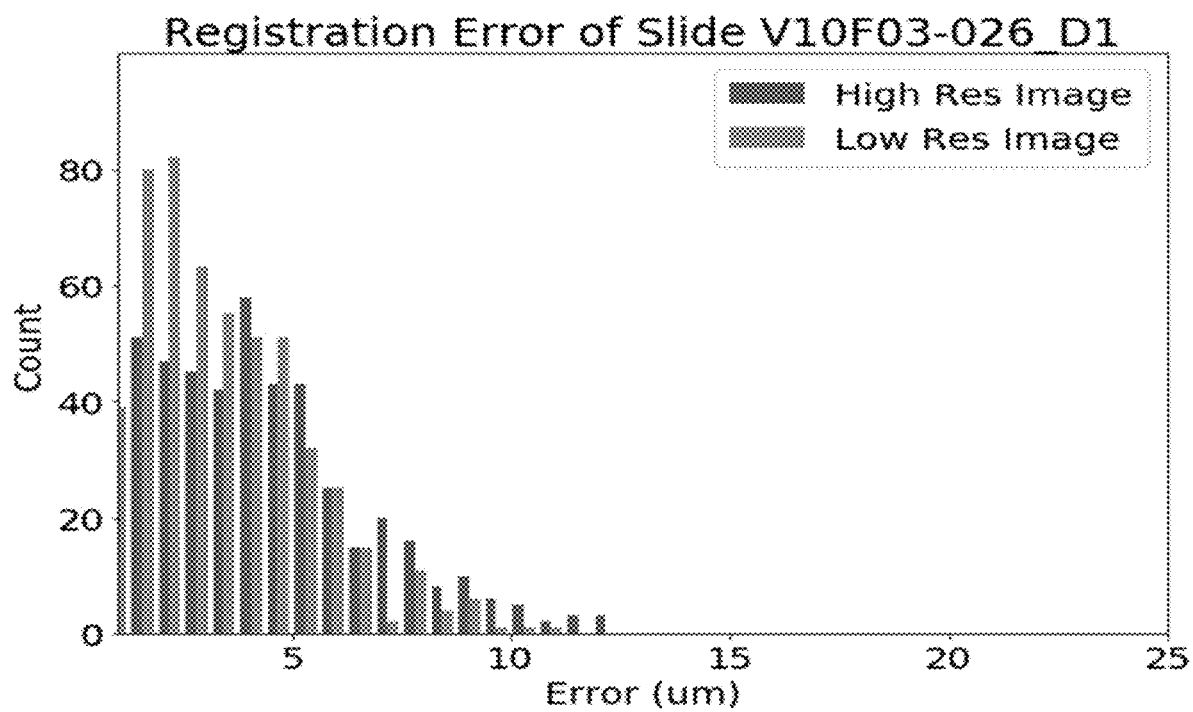

FIGS. 75A-75D are plots illustrating example data associated with registration and position errors used in verifying the image registration processes and techniques described herein according to some example implementations. As shown in FIGS. 75A-75B, plots for two different samples of image data (e.g., "C1" and "D1") illustrate registration error counts (x-axis) as a function of the size of the registration error (y-axis) in μm for high resolution images and low resolution images. As shown in FIGS. 75A-75B, registration error counts are similar for high and low resolution images when using a monochromatic 12M sensor (e.g., a 3k sensor) with 0.4 magnification.

Figure 75C:
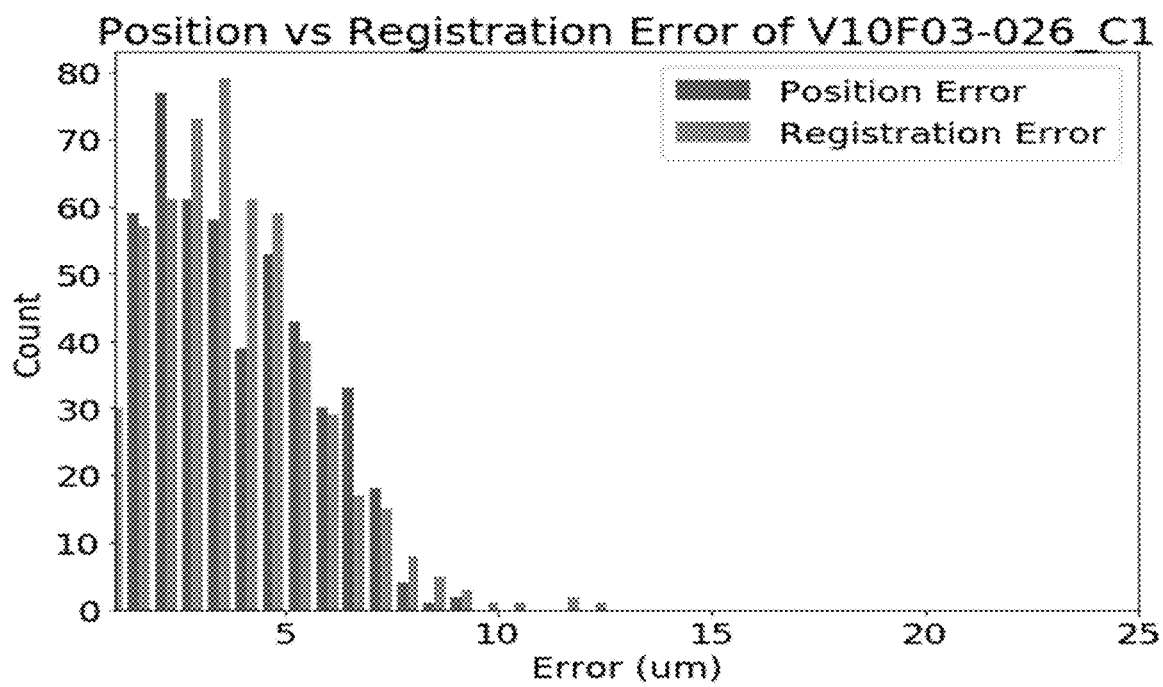
Figure 75D:
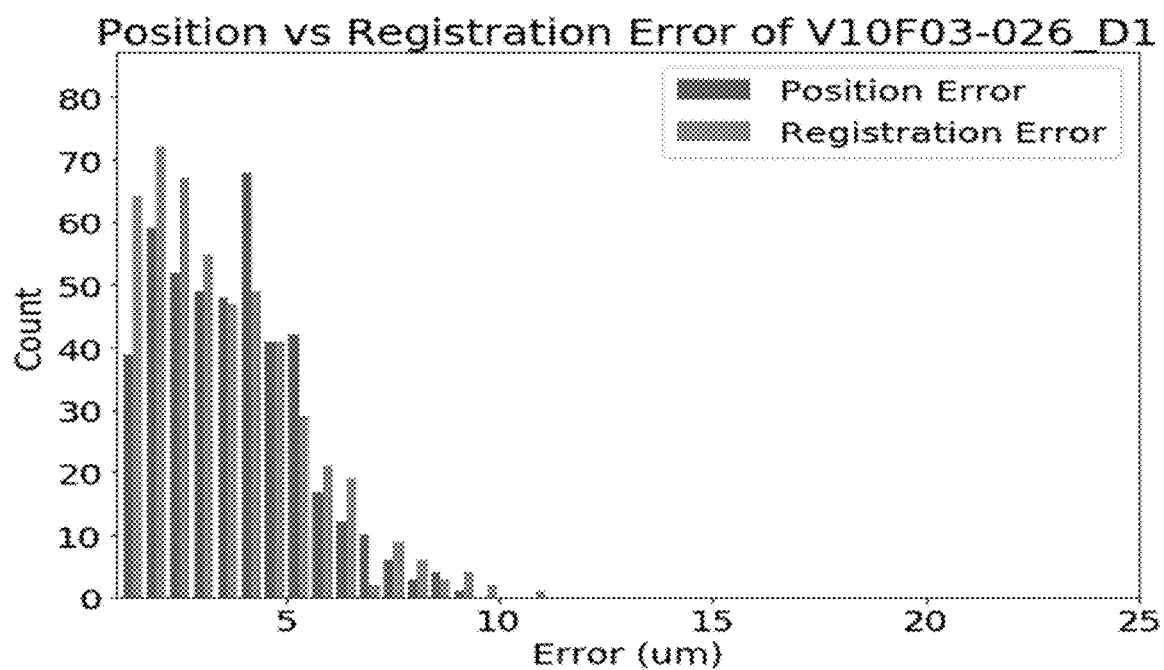

As shown in FIGS. 75C-75D, plots for two different samples of image data (e.g., "C1" and "D1") illustrate registration vs. position errors counts (x-axis) as a function of the size of the error (y-axis) in μm for high resolution images and low resolution images. As shown in FIGS. 75C-75D, the majority of the errors are less than or equal to 1 pixel (e.g., ~4.5 μm) at 0.4 magnification for image data acquired at high resolution and low resolution using the monochromatic 12M sensor.

Figure 76:
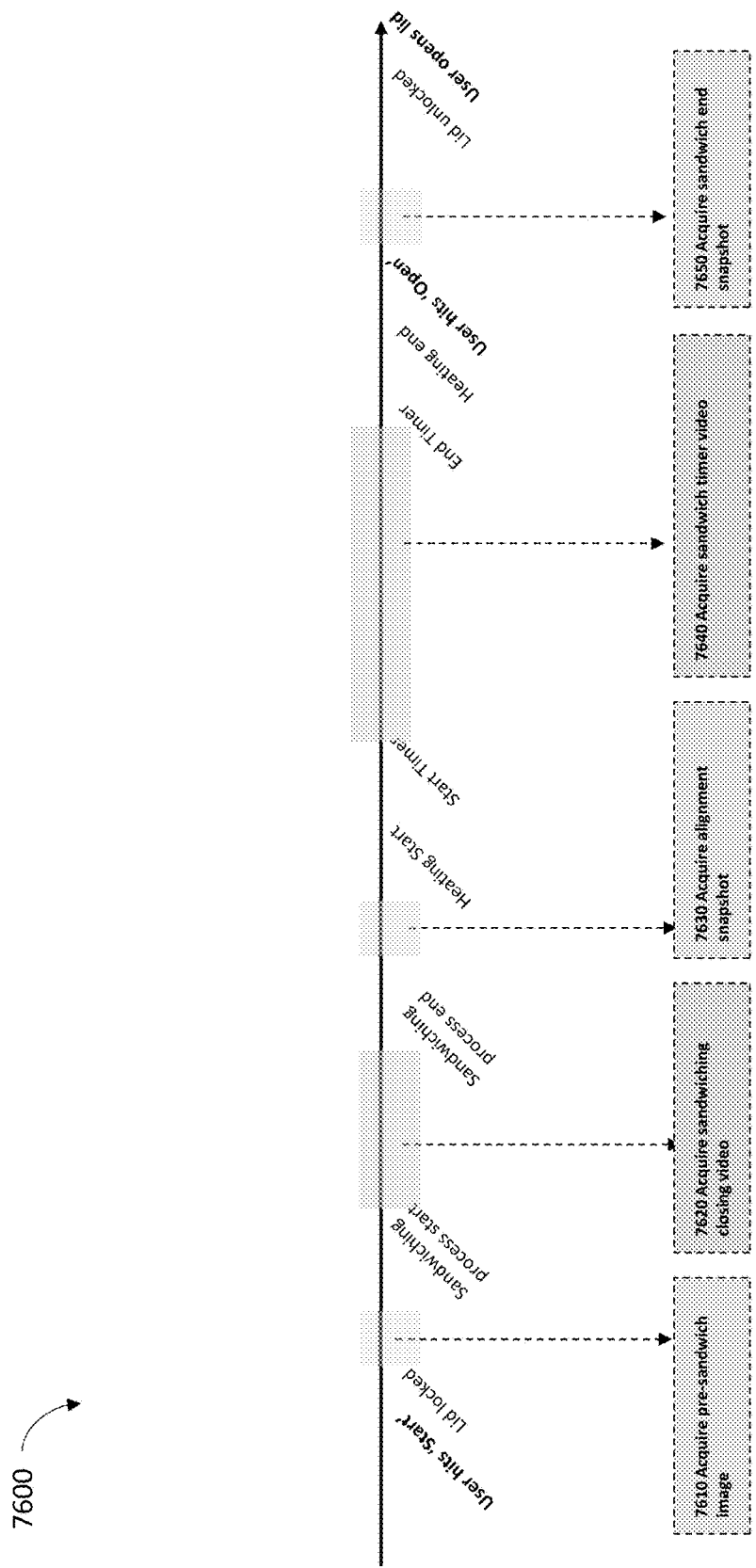
FIG. 76 depicts an exemplary workflow for image and video capture by a sample handling apparatus described herein according to some example implementations.

FIG. 76 depicts an exemplary workflow 7600 for image and video capture by a sample handling apparatus described herein. The workflow 7600 commences once substrates including a sample and an array are loaded in the sample handling apparatus. A user can initiate the workflow by pressing a "start" button on the sample handling apparatus. In some embodiments, the initiation of the workflow 7600 can be programmatically controlled by a computing device communicatively coupled to the sample handling apparatus.

At 7610, after lid closure, a pre-sandwich image of the array slide is captured. Multiple images can be captured at this time. In some embodiments, images of the sample on the first substrate overlaid atop the array on the second substrate are acquired at one or more illuminations, such as illuminations including wavelengths associated with red, green, or blue light. In some embodiments, the images are acquired at one or more resolutions, such as a full resolution. For example, a full resolution can include a resolution associated with the as-designed resolution capabilities of the device acquiring the image, such as a 3000×3000 pixel resolution.

In some embodiments, the images are acquired at one or more magnifications, such as 0.4 magnification. A 0.4 magnification can be interpreted to indicate a 1 cm object can be imaged as a 0.4 cm object in the plane of the sensor acquiring the image. In some embodiments, the images are acquired in a multilayer tag image file format (TIFF). In some embodiments, the images are acquired over a period of time, such as 3-5 seconds. Acquiring images during 7610 can enable determination of serviceability of the sample handling apparatus, and proper slide loading, as well as identification and recording of pre-sandwich starting conditions. Following 7610, the sample handling apparatus commences to bring the first substrate including a sample together with the second substrate including the array to initiate the start of the sandwiching process.

At 7620, the sandwich closure and sandwich alignment processes begins. A video of the sandwich closure process is acquired. In some embodiments, the video is acquired at a pre-determined frame rate, such as 30 frames per second (fps). In some embodiments, the video is acquired at one or more illuminations, such as an illumination including a wavelength associated with a green light. In some embodiments, the video is acquired at one or more resolutions, such as 1000 pixel×1000 pixel resolution, which may be a resolution that is less than the as-designed resolution capabilities of the sensor acquiring the images. In some embodiments, the video is acquired in one or more video formats, such as an audio video interleave (AVI) format. The AVI formatted video file can include video data that is compressed using one or more compression schemes, such as a compressed JPEG scheme. In some embodiments, the video is acquired for a period of time, such as 10 seconds. Acquiring video during 7620 can help determine the serviceability of the sample handling apparatus.

At 7630, images of the aligned slides can be acquired. In some embodiments, images of the sample on the first substrate aligned atop the array on the second substrate are acquired at one or more illuminations, such as illuminations including wavelengths associated with red, green, or blue light. In some embodiments, the images are acquired at one or more resolutions, such as a full resolution as described above in relation to 7610. In some embodiments, the images are acquired in a multilayer TIFF format. In some embodiments, the images are acquired over a period of time, such as 3-5 seconds. Acquiring images during 7630 can enable determination of the output of the assay being performed.

At 7640, a video capturing the period of time in which the first substrate including the sample is sandwiched with the second substrate including the array is acquired. The sandwich timer video can be associated with a period of permeabilization performed during the assay. In some embodiments, the video is acquired at a pre-determined frame rate, such as 0.5 fps. In some embodiments, the video is acquired at one or more illuminations, such as an illumination including a wavelength associated with a green light. In some embodiments, the video is acquired at one or more resolutions, such as 1000 pixel×1000 pixel resolution as described above in relation to 7520. In some embodiments, the video is acquired in one or more video formats, such as an AVI format. The AVI formatted video file can include video data that is compressed using one or more compression schemes, such as a compressed JPEG scheme. In some embodiments, the video is acquired for a period of time, such as ~30 minutes. In some embodiments, the video is acquired for a period of time between 1-90 minutes. Acquiring video during 7640 can help determine the serviceability of the sample handling apparatus.

At 7650, images can be acquired at the end of the sandwich process. Multiple images can be captured at this time. In some embodiments, images of the sample on the first substrate overlaid atop the array on the second substrate are acquired at one or more illuminations, such as illuminations including wavelengths associated with red, green, or blue light. In some embodiments, the images are acquired at one or more resolutions, such as a full resolution as described above in relation to 7610. In some embodiments, the images are acquired at one or more magnifications, such as 0.4 magnification as described above in relation to 7610. In some embodiments, the images are acquired in a multi-layer TIFF. In some embodiments, the images are acquired over a period of time, such as 3-5 seconds. Acquiring images during 7650 can enable determination of serviceability of the sample handling apparatus, and identification and recording sandwich conditions before opening the sandwich.

While workflows 1700, 1800, 2900, 3100, and 7600 are shown and described with respect to the sample handling apparatus 400, the workflows 1700, 1800, 2900, 3100, and 7600 may also be performed with respect to the sample handling apparatus 1400, the sample handling apparatus 3000, or another sample handling apparatus in accordance with the implementations described herein. In some embodiments, the processes 1900, 2300, 2500, 2700, 2800, and 3000 may also be performed with respect to the sample handling apparatus 1400, the sample handling apparatus 3000, or another sample handling apparatus in accordance with the implementations described herein.

The spatialomic (e.g., spatial transcriptomic) processes and workflows described herein can be configured to display gene expression information over high-resolution sample images. Barcoded locations within a reagent array can capture transcripts from a sample that is in contact with the array. The captured transcripts can be used in subsequent downstream processing. Determining the location of the barcoded locations of the reagent array relative to the sample can be performed using fiducial markers placed on a substrate on which the reagent array is located. The barcoded locations can be imaged with the sample to generate spatialomic (e.g., spatial transcriptomic) data for the sample.

Generating image data suitable for spatialomic (e.g., spatial transcriptomic) analysis can be affected by the relative alignment of a sample with the barcoded regions of the reagent array. High-resolution arrays for spatialomics (e.g., spatial transcriptomics) can require resolution of the inferred barcoded locations overlaid atop a high-resolution sample image in order to properly associate the captured transcripts with the particular cell that the transcripts originated from. The sample handling apparatus 400, 1400, and 3000 can be configured to perform the image registration processes and workflows described herein to provide a level of precision for aligning the sample image and the array image within +/−1-5 microns, +/−1-10 microns, +/−1-20 microns, or 1-30+/− microns.

One or more aspects or features of the subject matter described herein may be realized in digital electronic circuitry, integrated circuitry, specially designed ASICs, field programmable gate arrays (FPGAs) computer hardware, firmware, software, and/or combinations thereof. These various aspects or features may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which may also be referred to as programs, software, software applications, applications, components, or code, include machine instructions for a programmable processor, and may be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium may store such machine instructions non-transitorily, such as for example as would a non-transient solid-state memory or a magnetic hard drive or any equivalent storage medium. The machine-readable medium may alternatively or additionally store such machine instructions in a transient manner, such as for example, as would a processor cache or other random access memory associated with one or more physical processor cores.

To provide for interaction with a user, one or more aspects or features of the subject matter described herein may be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices may be used to provide for interaction with a user as well. For example, feedback provided to the user may be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein may be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

The invention claimed is:

1. A method for aligning a sample to an array, the method comprising:
   receiving, by a data processor, sample image data comprising a sample image of the sample on a first substrate, the sample image having a first resolution;
   receiving, by the data processor, array image data comprising an array image having a second resolution lower than the first resolution, wherein the array image comprises an overlay of the array and an array fiducial on a second substrate with the sample on the first substrate, the array fiducial comprising a plurality of array fiducial elements separated from the array and forming a fiducial frame surrounding a perimeter of the array;
   registering, by the data processor, the sample image to the array image by aligning the sample image and the array image using the array fiducial;
   generating, by the data processor, an aligned image based on the registering, the aligned image comprising an overlay of the sample image with the array image; and
   providing, by the data processor, the aligned image.

2. The method of claim 1, wherein the sample image data is received from a user or from a computing device remote from the data processor.

3. The method of claim 1, wherein the aligned image further comprises the array fiducial aligned with the sample.

4. The method of claim 1, wherein the sample image further comprises a sample fiducial delineating a sample area into which the sample is placed.

5. The method of claim 1, wherein the sample image is of the sample on the first substrate.

6. The method of claim 1, wherein the sample on the first substrate is a tissue section disposed on a slide and the array on the second substrate is a reagent array formed on the second substrate.

7. The method of claim 1, wherein the array and the array fiducial are located on a first side of the second substrate.

8. The method claim 7, wherein the array fiducial is located on the second substrate adjacent to, within, or distanced from a reagent configured on the second substrate.

9. The method of claim 1, wherein a location of the array fiducial is used to determine positions of a plurality of barcoded spots comprised in the array relative to a location of the sample.

10. The method of claim 1, wherein the sample image comprises a plurality of sample portion images, each sample portion image associated with a portion of the sample, wherein a size of each sample portion image is less than a size of a single field of view of the sample image.

11. The method of claim 10, wherein registering the sample image to the array image further comprises
   cropping, by the data processor, the sample image to determine the plurality of sample portion images; and
   registering one or more sample portion images in the sample image to a corresponding portion of the sample in the array image.

12. The method of claim 11, wherein registering the one or more sample portion images in the sample image to the corresponding portion of the sample in the array image is performed after registering the sample image to the array image.

13. The method of claim 1, wherein the array image comprises a plurality of array portion images, each array portion image associated with a portion of the array, wherein a size of each array portion image is less than a size of a single field of view of the array image.

14. The method of claim 13, wherein the registering further comprises:
   determining, by the data processor, the plurality of array portion images in the array image; and
   registering, by the data processor, one or more array portion images in the array image to a corresponding portion of the sample in the sample image.

15. The method of claim 1, wherein the array image data is generated by adjusting a location of the first substrate comprising the sample relative to the second substrate comprising the array and the array fiducial, to cause all or a portion of the sample to be aligned with the array and the array fiducial, and acquiring an image of the overlay of the sample on the first substrate aligned to the array and array fiducial on the second substrate.

16. The method of claim 1, wherein the array fiducial comprising the plurality of array fiducial elements is affixed to the second substrate comprising the array.

17. The method of claim 1 wherein the first substrate and the second substrate are distinct substrates.

18. A system for aligning a sample to an array, the system comprising: a sample holder comprising:
   a first retaining mechanism configured to retain a first substrate received within the first retaining mechanism, the first substrate comprising a sample, and
   a second retaining mechanism configured to retain a second substrate received within the second retaining mechanism, the second substrate comprising an array and an array fiducial comprising a plurality of array fiducial elements separated from the array and forming a fiducial frame surrounding a perimeter of the array, the sample holder configured to adjust a location of the first substrate relative to the second substrate to cause all or a portion of the sample to be aligned with the array;
   a microscope operatively coupled to the sample holder, the microscope configured to view the first substrate and the second substrate within the sample holder; and acquire image data associated with the sample and/or the array; and a first computing device communicatively coupled to the microscope and to the sample holder, the computing device comprising a display, a data processor, and a non-transitory computer readable storage medium storing computer readable and executable instructions, which when executed cause the data processor to perform operations comprising receiving sample image data comprising a sample image of the sample on the first substrate, the sample image having a first resolution;

receiving array image data comprising an array image having a second resolution lower than the first resolution of the sample image, wherein the array image comprises an overlay of the sample on the first substrate with the array and the array fiducial on the second substrate;

registering the sample image to the array image by aligning the sample image and the array image using the array fiducial;

generating an aligned image based on the registering, the aligned image comprising the sample image aligned with the array image; and providing the aligned image.

19. The system of claim 18, wherein the sample image data is received from a user or from a computing device remote from the data processor.

20. The system of claim 18, wherein the aligned image further comprises the array fiducial aligned with the sample.

21. The system of claim 18, wherein the sample image further comprises a sample fiducial delineating a sample area into which the sample is placed on the first substrate.

22. The system of claim 18, wherein the sample image of the sample on the first substrate is a tissue sample fixed, stained and/or permeabilized on a slide.

23. The system of claim 18, wherein the array fiducial is located on the second substrate adjacent to, within, or distanced from a reagent configured on the second substrate.

24. The system of claim 18, wherein the sample image comprises a plurality of sample portion images, each sample portion image associated with a portion of the sample, wherein a size of each sample portion image is less than a size of a single field of view of the sample image.

25. The system of claim 24, wherein the registering further comprises cropping, by the data processor, the sample image to determine the plurality of sample portion images; and registering one or more sample portion images in the sample image to a corresponding portion of the sample in the array image.

26. The system of claim 18, wherein the array image comprises a plurality of array portion images, each array portion image associated with a portion of the array, wherein a size of each array portion image is less than a size of a single field of view of the array image.

27. The system of claim 26, wherein the registering further comprises:

determining the plurality of array portion images in the array image; and registering one or more array portion images in the array image to a corresponding portion of the sample in the sample image.

* * * * *

UNITED STATES PATENT AND TRADEMARK OFFICE
CERTIFICATE OF CORRECTION

| | |
|---|---|
| PATENT NO. | : 12,249,085 B2 |
| APPLICATION NO. | : 18/185599 |
| DATED | : March 11, 2025 |
| INVENTOR(S) | : Augusto Manuel Tentori et al. |

It is certified that error appears in the above-identified patent and that said Letters Patent is hereby corrected as shown below:

In the Claims

Column 71, Line 65, in Claim 8, after "method" insert -- of --.

Column 72, Line 29, in Claim 14, delete "comprises:" and insert -- comprises --.

Column 72, Lines 48-62, in Claim 18, delete
"A system for aligning a sample to an array, the system comprising: a sample holder comprising:
a first retaining mechanism configured to retain a first substrate received within the first retaining mechanism, the first substrate comprising a sample, and
    a second retaining mechanism configured to retain a second substrate received within the
    second retaining mechanism, the second substrate comprising an array and an array fiducial
    comprising a plurality of array fiducial elements separated from the array and forming a
    fiducial frame surrounding a perimeter of the array, the sample holder configured to adjust a
    location of the first substrate relative to the second substrate to
    cause all or a portion of the sample to be aligned with the array;" and insert
-- A system for aligning a sample to an array, the system comprising:
    a sample holder comprising:
        a first retaining mechanism configured to retain a first substrate received
within the first retaining mechanism, the first substrate comprising a sample, and
        a second retaining mechanism configured to retain a second substrate
received within the second retaining mechanism, the second substrate comprising an array and an array fiducial comprising a plurality of array fiducial elements separated from the array and forming a fiducial frame surrounding a perimeter of the array, the sample holder configured to adjust a location of the first substrate relative to the second substrate to cause all or a portion of the sample to be aligned with the array; --.

Column 74, Line 25, in Claim 27, delete "comprises:" and insert -- comprises --.

Signed and Sealed this
Twenty-ninth Day of July, 2025

Coke Morgan Stewart
*Acting Director of the United States Patent and Trademark Office*